US012612642B2

(12) United States Patent
Manjunath et al.

(10) Patent No.: US 12,612,642 B2
(45) Date of Patent: \*Apr. 28, 2026

(54) METHODS AND COMPOSITIONS FOR INCREASING HARVESTABLE YIELD VIA EDITING GA20 OXIDASE GENES TO GENERATE SHORT STATURE PLANTS

(71) Applicant: MONSANTO TECHNOLOGY LLC, St. Louis, MO (US)

(72) Inventors: Sivalinganna Manjunath, Chesterfield, MO (US); Linda A. Rymarquis, High Ridge, MO (US); Thomas L. Slewinski, Chesterfield, MO (US)

(73) Assignee: MONSANTO TECHNOLOGY LLC, St. Louis, MO (US)

( \* ) Notice: Subject to any disclaimer, the term of this patent is extended or adjusted under 35 U.S.C. 154(b) by 225 days.

This patent is subject to a terminal disclaimer.

(21) Appl. No.: 16/967,039

(22) PCT Filed: Feb. 15, 2019

(86) PCT No.: PCT/US2019/018133
§ 371 (c)(1),
(2) Date: Aug. 3, 2020

(87) PCT Pub. No.: WO2019/161149
PCT Pub. Date: Aug. 22, 2019

(65) Prior Publication Data
US 2021/0040498 A1 Feb. 11, 2021

Related U.S. Application Data

(60) Provisional application No. 62/631,412, filed on Feb. 15, 2018, provisional application No. 62/631,416, filed on Feb. 15, 2018.

(51) Int. Cl.
*C12N 15/82* (2006.01)

(52) U.S. Cl.
CPC ..... *C12N 15/8297* (2013.01); *C12N 15/8213* (2013.01); *C12N 15/8242* (2013.01)

(58) Field of Classification Search
None
See application file for complete search history.

(56) References Cited

U.S. PATENT DOCUMENTS

| | | | | |
|---|---|---|---|---|
| 7,138,567 | B2 * | 11/2006 | Okawa | C12N 9/0071 |
| | | | | 536/23.6 |
| 10,724,047 | B2 | 7/2020 | Allen et al. | |
| 11,319,550 | B2 | 5/2022 | Allen | |
| 11,414,670 | B2 | 8/2022 | Allen | |
| 11,441,153 | B2 | 9/2022 | Dietrich | |
| 11,472,852 | B2 | 10/2022 | Alves-Junior | |
| 11,702,670 | B2 | 7/2023 | Dietrich | |
| 12,024,711 | B2 | 7/2024 | Manjunath et al. | |

| | | | |
|---|---|---|---|
| 2004/0250315 | A1 | 12/2004 | Okawa et al. |
| 2011/0145940 | A1 | 6/2011 | Voytas et al. |
| 2011/0301051 | A1 | 12/2011 | Gregory |
| 2013/0117869 | A1 | 5/2013 | Duchateau et al. |
| 2016/0208272 | A1 | 7/2016 | Cigan et al. |
| 2016/0230183 | A1 | 8/2016 | Abad et al. |
| 2017/0114356 | A1 | 4/2017 | Li et al. |
| 2022/0298527 | A1 | 9/2022 | Dietrich et al. |

OTHER PUBLICATIONS

Song et al. (Gene 482.1-2 (2011): 34-42). (Year: 2011).*
Kusaba, Makoto. "RNA interference in crop plants." Current opinion in Biotechnology 15.2 (2004): 139-143. (Year: 2004).*
Small, Ian. "RNAi for revealing and engineering plant gene functions." Current Opinion in Biotechnology 18.2 (2007): 148-153. (Year: 2007).*
Altschul, S.F. et al. (Oct. 5, 1990). "Basic Local Alignment Search Tool," J. Mol. Biol. 215(3):403-410.
Ashikari, M. et al. (2002). "Loss-of-function of a Rice Gibberellin Biosynthetic Gene, GA20 oxidase (GA20ox-2), Led to the Rice 'Green Revolution'," Breeding Science 52: 143-150.
Beurdeley, M. et al. (Apr. 23, 2013). "Compact Designer TALENs for Efficient Genome Engineering," Nat. Commun. 4: 1762, 8 pages.
Cermak, T. et al. (Jul. 2011, e-pub. Apr. 14, 2011). "Efficient Design and Assembly Of Custom TALEN and Other TAL Effector-Based Constructs For DNA Targeting," Nucleic Acids Research 39(12):e82, 11 pages.
Chen, Y. et al. (Dec. 2014). "The Maize DWARF1 Encodes a Gibberellin 3-Oxidase and is Dual Localized to the Nucleus and Cytosol," Plant Physiology 166(4): 2028-2039.
Chenna, R. et al. (Jul. 1, 2003). "Multiple Sequence Alignment with the Clustal Series of Programs," Nucleic Acids Research 31(13): 3497-3500.
Colbert, T. et al. (Jun. 2001). "High-Throughput Screening for Induced Point Mutations," Plant Physiol, 126(2): 480-484.
Coles, J. P. et al. (1999). "Modification of Gibberellin Production and Plant Development in *Arabidopsis* by Sense and Antisense Expression of Gibberellin 20-Oxidase Genes," The Plant Journal, 17(5): 547-556.
Depalma, A. (Feb. 13, 2018). "Reaping Better Crops with Plant Genome Editing. Biocompare: The Buyer's Guide for Life Scientists", located at https://www.biocompare.com/Editorial-Articles/346955-Reaping-Better-Crops-with-Plant-Genome-Editing, last visited on Dec. 17, 2021, 13 pages.

(Continued)

*Primary Examiner* — Charles Logsdon
(74) *Attorney, Agent, or Firm* — Morrison & Foerster LLP

(57) ABSTRACT

The present disclosure provides compositions and methods for the editing or mutating of specific subtypes of GA20 oxidase genes and specific zygosity combinations of those edits or mutations. Modified plants, and plant parts and cells thereof, having mutations reducing the expression or activity of GA20 oxidase genes are further provided with improved characteristics, such as reduced plant height and increased lodging resistance, but without off-types. Methods are further provided for making modified plants, and plant parts and cells thereof, having one or more mutations in specific subtypes of GA20 oxidase genes.

38 Claims, 1 Drawing Sheet

Specification includes a Sequence Listing.

(56) References Cited

OTHER PUBLICATIONS

Doyle, E.L. et al. (Jun. 12, 2012). "TAL Effector-Nucleotide Targeter (TALE-NT) 2.0: Tools for TAL Effector Design and Target Prediction," Nucleic Acids Research, 40: W117-W122.

Gabsalilow, L. et al. (Feb. 13, 2013). "Site- and Strand-specific Nicking of DNA by Fusion Proteins Derived from MutH and I-SceI or TALE Repeats," Nucleic Acids Research 41(7): e83, 11 pages.

Gaj, T. et al. (Jul. 2013, e-pub. May 9, 2013). "ZFN, TALEN, and CRISPR/Cas-Based Methods For Genome Engineering," Trends Biotechnol. 31(7):397-405.

GenBank Accession No. AC191666, last updated Sep. 24, 2013, located at https://www.ncbi.nlm.nih.gov/nuccore/AC191666, last visited on Jun. 10, 2022, forty four pages.

GenBank Accession No. AC209074, last updated Sep. 13, 2014, located at https://www.ncbi.nlm.nih.gov/nuccore/AC209074, last visited on Jun. 10, 2022, forty one pages.

GenBank Accession No. BT068785, last updated Jun. 15, 2012 located at https://www.ncbi.nlm.nih.gov/nuccore/BT068785.2/, last visited on Jun. 10, 2022, two pages.

GenBank Accession No. EF030816, last updated Sep. 28, 2006 located at https://www.ncbi.nlm.nih.gov/nuccore/EF030816.1/, last visited on Jun. 13, 2022, two pages.

GenBank Accession No. EF030817, last updated Sep. 28, 2006 located at https://www.ncbi.nlm.nih.gov/nuccore/EF030817.1/, last visited on Jun. 13, 2022, two pages.

Helliwell , C. et al. (Aug. 2003). "Constructs and Methods for High-Throughput Gene Silencing in Plants" Methods in Enzymology 30(4): 289-295.

International Search Report mailed on Jul. 16, 2019, for PCT Patent Application No. PCT/US2019/018133 filed on Feb. 15, 2019, eighteen pages.

International Search Report mailed on Jun. 17, 2019, for PCT Patent Application No. PCT/US2019/018131, filed on Feb. 15, 2019, nineteen pages.

International Search Report mailed on Jun. 25, 2019, for PCT Patent Application No. PCT/US2019/018128 filed on Feb. 15, 2019, twelve pages.

Arkin, M. A. et al. (Nov. 1, 2007). "Clustal W and Clustal X Version 2.0," Bioinformatics 23(21): 2947-2948.

McCallum, C. M. et al. (Apr. 2000). "Targeted Screening for Induced Mutations," Nature Biotechnology 18: 455-457.

Plackett, A. R. G., et al. (Mar. 2012) "Analysis of the Developmental Roles of the *Arabidopsis* Gibberellin 20-Oxidases Demonstrates That GA20ox1, -2, and -3 Are the Dominant Paralogs" The Plant Cell, 24:941-960.

Qiao, F. et al. (Jun. 19, 2013). "Alteration of Rice Growth and Development Via Antisense Expression of OsGA20ox2 gene," African Journal of Biotechnology. 12(25): 3898-3904.

Spielmeyer, W. et al. (2002) "Semidwarf (sd-1), 'Green Revolution' Rice, Contains a Defective Gibberellin 20-oxidase Gene," PNAS, 99(13): 9043-9048.

Thompson, J.D. (Nov. 11, 1994). "CLUSTAL W: Improving the Sensitivity of Progressive Multiple Sequence Alignment Through Sequence Weighting, Position-Specific Gap Penalties and Weight Matrix Choice," Nucleic Acids Res. 22(22):4673-4680.

Tomita, M. (2012), Combining Two Semidwarfing Genes d60 and sd1 for Reduced Height in 'Minihikari', a New Rice Germplasm in the 'Koshihikari' Genetic Background, Genetics Research 94: 235-244.

Wu, X. et al. (Jun. 2014). "Target Specificity of the CRISPR-Cas9 System," Quant Biol., 2(2): 59-70.

Williams, J. et al. (1998). "Function and Substrate Specificity of the Gibberellin 3beta-Hydroxylase Encoded by the *Arabidopsis* GA4 Gene1," Plant Physiology 117:559-563.

Chiang, H. H. et al. (Feb. 1995). "Isolation of the *Arabidopsis* GA4 Locus," The Plant Cell 7:195-201.

Uniprot Accession No. A0A1D6N5E5, last updated Nov. 30, 2016 located at https://www.uniprot.org/uniprot/A0A1D6N5E5, last visited Jun. 13, 2022, 6 pages.

Uniprot Accession No. A0A3L6FA55, last updated Feb. 13, 2019 located at https://www.uniprot.org/uniprot/A0A3L6FA55, last visited Jun. 13, 2022, 5 pages.

Uniprot Accession No. C0HFM9, last updated May 9, 2009 located at https://www.uniprot.org/uniprot/C0HFM9, last visited Jun. 13, 2022, 4 pages.

Uniprot Accession No. K7VMU4, last updated Feb. 6, 2013 located at https://www.uniprot.org/uniprot/K7VMU4, last visited Jun. 13, 2022, 6 pages.

Xu, Y. L. et al. (Jul. 3, 1995). "The GA5 Locus of *Arabidopsis thaliana* Encodes a Multifunctional Gibberellin 20-oxidase: Molecular Cloning and Functional Expression," Proc Natl Acad Sci USA 92(14):6640-6644.

Yanik, M. et al. (Dec. 5, 2013). "TALE-PvuII Fusion Proteins—Novel Tools for Gene Targeting," PLoS One 8(12): e82539, 22 pages.A 92(14):6640-6644.

Unterseer, S. et al. (Jan. 27, 2017). "European Flint reference sequences complement the maize pan-genome," BioRxiv 103747, 3 pages.

Mani, D. (Aug. 2008). "Characterization and Genetic Analysis of a Very High Tillering and Dwarf Rice (*Oryza sativa* L.) Mutant, " Master's Thesis at Texas A&M University, 96 pages.

Petti, C. et al. (Sep. 2015). "Mapping of a Cellulose-Deficient Mutant Named dwarf1-1 in Sorghum Bicolor in the Green Revolution Gene Gibberellin20-oxidase Reveals a Positive Regulatory Association between Gibberellin and Cellulose Biosynthesis," Plant Physiology 169(1):705-716.

Arora, L. et al. (Nov. 8, 2017). "Gene Editing and Crop Improvement Using CRISPR-Caas 9 System," Frontiers in Plant Science 8:1-21.

Bunton-Stasyshyn, R. K. A. et al. (Feb. 1, 2019, e-pub. Jan. 2, 2019). "Prominent Role of Forebrain Excitatory Neurons in SCN8A Encephalopathy," Brain 142(2):362-375.

Guerrero-Mendez, C. et al. (2024, e-pub. Nov. 15, 2023). "Factors Specifying Sex Determination in Maize," Plant Reproduction 37:171-178.

Izawa, T. et al. (Mar. 1996). "Becoming a Model Plant: The Importance of Rice to Plant Science," Trends In Plant Science 1(3):95-99.

Schnable, J. A. et al. (Mar. 8, 2011, e-pub. Feb. 22, 2011). "Differentiation of the Maize Subgenomes by Genome Dominance and Both Ancient and Ongoing Gene Loss," Proc Natl Acad Sci U S A. 108(10):4069-4074.

Slewinski, T. L. et al. (Nov. 2012, e-pub. Aug. 29, 2012). "Tie-dyed2 Encodes a Callose Synthase That Functions in Vein Development and Affects Symplastic Trafficking within the Phloem of Maize Leaves," Plant Physiology 160(3): 1540-1550.

Unniyampurath, U. et al. (Feb. 26, 2016). "RNA Interference in the Age of CRISPR: Will CRISPR Interfere with RNAi?" Int. J. Mol. Sci. 17(3):291, 15 pages.

* cited by examiner

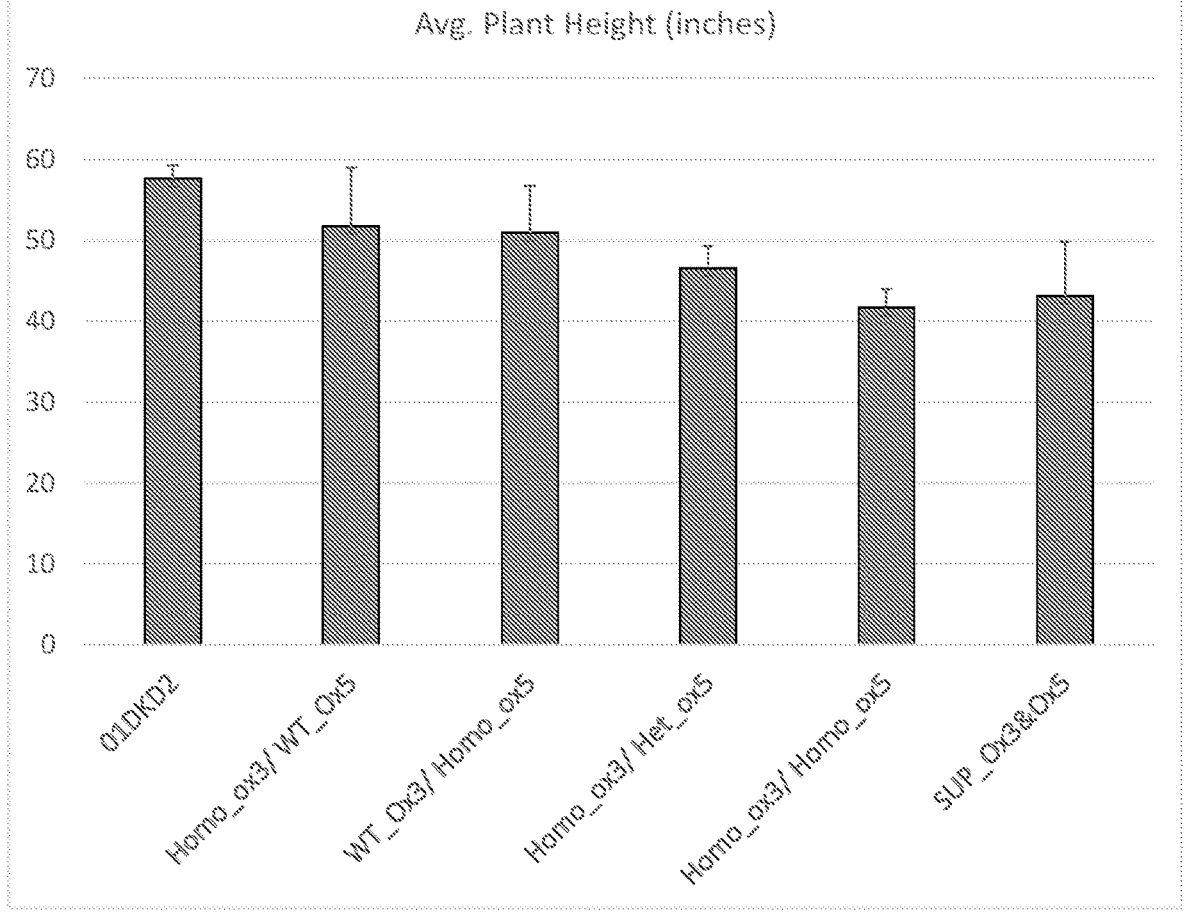

SEQUENCE LISTING

<160> NUMBER OF SEQ ID NOS: 261

<210> SEQ ID NO 1
<211> LENGTH: 1741
<212> TYPE: DNA
<213> ORGANISM: Zea mays

<400> SEQUENCE: 1

```
gacggtagtt ttcatctaaa gtttattctt cgtcacatgg gatggccgtt tgcttgtttg      60
ttgcttccgg gaggcggtgg tgaattgaag cagatcgaca agcatggctg cccactggtc     120
tcgatcgatc ggcctgccat gccatgccat gccactagag tccgtcctga ctggccgccc     180
gttcccccgt ataaaaaggc aggcaggcag gcagagcggg gacgagcaag caagcagttg     240
cagttgcagc ggcctcctcc tctgcttcct ccctcctcct cctcaccatg gtgctggctg     300
cgcacgatcc ccctcccctt gtgttcgacg ctgcccgcct gagcggcctc tccgacatcc     360
cgcagcagtt catctggccg gcggacgaga gccccacccc ggactccgcc gaggagctgg     420
ccgtgccgct catcgacctc tccggggacg ccgccgaggt ggtccggcag gtccggcgcg     480
cctgcgacct gcacggcttc ttccaggtgg tggggcacgg catcgacgcg gcgctgacgg     540
cggaggccca ccgctgcatg gacgccttct tcacgctgcc gctcccggac aagcagcgcg     600
cgcagcgccg ccaggggggac agctgcggct acgccagcag cttcacgggc cggttcgcgt     660
ccaagctgcc ctggaaggag acgctgtcgt tccgctacac cgacgacgac gacgcgaca     720 agtccaagga cgtcgtggcg tcctacttcg tggacaagct gggcgagggg taccggcacc     780
```

-continued

```
acggggaggt gtacgggcgc tactgctctg agatgagccg tctgtcgctg gagctcatgg      840
aggtgctagg cgagagcctg ggcgtgggcc ggcgccactt ccggcgcttc ttccagggga      900
acgactccat catgcgcctc aactactacc cgccgtgcca gcggccctac gacacgctgg      960
gcacggggcc gcattgcgac cccacgtcgc tcaccatcct gcaccaggac gacgtgggcg     1020
gactccaggt gttcgacgcc gccacgctcg cgtggcgctc catcaggccc cgcccgggcg     1080
ccttcgtcgt caacatcggc gacaccttca tggcgctctc caacgggcgc tacaggagct     1140
gcctccaccg cgccgtcgtc aacagccggg tggcacgccg ctcgctcgcc ttcttcctgt     1200
gcccggagat ggacaaggtg gtcaggccgc ccaaggagct ggtggacgac gccaacccga     1260
gggcgtaccc ggacttcacg tggaggacgc tgctggactt caccatgagg cactacaggt     1320
cggacatgag gacgctcgag gccttctcca actggctcag caccagtagc aatggcggac     1380
agcacctgct ggagaagaag taggcatgct atttgggtat ggaagatggt ggatgtaagc     1440
aaacaaagcc aaattaagca gagtaggtta attaaggttg gctgatgatc catttaggga     1500
aggagctgat ctccctgact ccctcctcca attttctcaa ccaaatttat atagtataat     1560
aataataata aaatagcaag taatagttgt atcgtattat tattaattaa tttattagct     1620
ggtaggcaag tagtattaaa taccatttgt agtacgatgg gcgtatttct attttggcgt     1680
tttgctctgt gttttttgac gtttcctttg gatttggggg gacctcagat cagctcggcc     1740
t                                                                     1741

<210> SEQ ID NO 2
<211> LENGTH: 1116
<212> TYPE: DNA
<213> ORGANISM: Zea mays

<400> SEQUENCE: 2
atggtgctgg ctgcgcacga tcccctccc cttgtgttcg acgctgcccg cctgagcggc        60
ctctccgaca tcccgcagca gttcatctgg ccggcggacg agagccccac cccggactcc       120
gccgaggagc tggccgtgcc gctcatcgac ctctccgggg acgccgccga ggtggtccgg       180
caggtccggc gcgcctgcga cctgcacggc ttcttccagg tggtggggca cggcatcgac       240
gcggcgctga cggcggaggc ccaccgctgc atggacgcct tcttcacgct gccgctcccg       300
gacaagcagc gcgcgcagcg ccgccagggg gacagctgcg ctacgccag cagcttcacg        360 ggccggttcg cgtccaagct gccctggaag gagacgctgt cgttccgcta caccgacgac       420
gacgacggca caagtccaa ggacgtcgtg gcgtcctact tcgtggacaa gctgggcgag        480
gggtaccggc accacgggga ggtgtacggg cgctactgct ctgagatgag ccgtctgtcg       540
ctggagctca tggaggtgct aggcgagagc ctgggcgtgg gccggcgcca cttccggcgc       600
ttcttccagg ggaacgactc catcatgcgc ctcaactact acccgccgtg ccagcggccc       660
tacgacacgc tgggcacggg gccgcattgc gaccccacgt cgctcaccat cctgcaccag       720
gacgacgtgg gcggactcca ggtgttcgac gccgccacgc tcgcgtggcg ctccatcagg       780
ccccgcccgg gcgccttcgt cgtcaacatc ggcgacacct tcatggcgct ctccaacggg       840
cgctacagga gctgcctcca ccgcgccgtc gtcaacagcc gggtggcacg ccgctcgctc       900
gccttcttcc tgtgcccgga gatggacaag gtggtcaggc cgcccaagga gctggtggac       960
gacgccaacc cgagggcgta cccggacttc acgtggagga cgctgctgga cttcaccatg      1020
aggcactaca ggtcggacat gaggacgctc gaggccttct ccaactggct cagcaccagt      1080
agcaatggcg gacagcacct gctggagaag aagtag                               1116
```

-continued

```
<210> SEQ ID NO 3
<211> LENGTH: 371
<212> TYPE: PRT
<213> ORGANISM: Zea mays

<400> SEQUENCE: 3

Met Val Leu Ala Ala His Asp Pro Pro Leu Val Phe Asp Ala Ala
1               5                   10                  15

Arg Leu Ser Gly Leu Ser Asp Ile Pro Gln Gln Phe Ile Trp Pro Ala
            20                  25                  30

Asp Glu Ser Pro Thr Pro Asp Ser Ala Glu Glu Leu Ala Val Pro Leu
            35                  40                  45

Ile Asp Leu Ser Gly Asp Ala Ala Glu Val Val Arg Gln Val Arg Arg
    50                  55                  60

Ala Cys Asp Leu His Gly Phe Phe Gln Val Val Gly His Gly Ile Asp
65                  70                  75                  80

Ala Ala Leu Thr Ala Glu Ala His Arg Cys Met Asp Ala Phe Phe Thr
                85                  90                  95

Leu Pro Leu Pro Asp Lys Gln Arg Ala Gln Arg Arg Gln Gly Asp Ser
            100                 105                 110

Cys Gly Tyr Ala Ser Ser Phe Thr Gly Arg Phe Ala Ser Lys Leu Pro
            115                 120                 125

Trp Lys Glu Thr Leu Ser Phe Arg Tyr Thr Asp Asp Asp Gly Asp
            130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
            180                 185                 190

Val Gly Arg Arg His Phe Arg Arg Phe Phe Gln Gly Asn Asp Ser Ile
            195                 200                 205

Met Arg Leu Asn Tyr Tyr Pro Pro Cys Gln Arg Pro Tyr Asp Thr Leu
    210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Thr Leu Ala Trp
                245                 250                 255

Arg Ser Ile Arg Pro Arg Pro Gly Ala Phe Val Val Asn Ile Gly Asp
            260                 265                 270

Thr Phe Met Ala Leu Ser Asn Gly Arg Tyr Arg Ser Cys Leu His Arg
            275                 280                 285

Ala Val Val Asn Ser Arg Val Ala Arg Arg Ser Leu Ala Phe Phe Leu
            290                 295                 300

Cys Pro Glu Met Asp Lys Val Val Arg Pro Pro Lys Glu Leu Val Asp
305                 310                 315                 320

Asp Ala Asn Pro Arg Ala Tyr Pro Asp Phe Thr Trp Arg Thr Leu Leu
                325                 330                 335

Asp Phe Thr Met Arg His Tyr Arg Ser Asp Met Arg Thr Leu Glu Ala
            340                 345                 350

Phe Ser Asn Trp Leu Ser Thr Ser Ser Asn Gly Gly Gln His Leu Leu
            355                 360                 365

Glu Lys Lys
```

-continued

370

```
<210> SEQ ID NO 4
<211> LENGTH: 1517
<212> TYPE: DNA
<213> ORGANISM: Zea mays

<400> SEQUENCE: 4
caggaataaa ataagcctcc gcccggcttc gttgcatcca cgcacgcagc aagcgatcgg      60
atttcgccag catggcggcg gcggccgtgg tgttcgacgc cgaggcgctg agccgggagg     120
agcacatccc ggcgcagttc gtgtggccca ccgaggagcg ggcgccggcg ggcggcgtgg     180
aggaggtcgc catccccgtg gtcgacctcg gcgagttcct ccgccgcggg gtgctcccgc     240
gcggcgtggc ggaggcgtgc gagcgccacg gcgtcttcca ggtggtgaac cacggcgtgg     300
gcgccgcgct gctcgccgag gcctaccgct gttgcgacgc ctttttacgcg ctcccgctcg     360 cggacaagca gcgcgcgcag cgccggcacg gggagaacca cggctacgcc agcagcttca     420
cgggccgctt ccactgctgc ctgccgtgga aggagacgct gtccttcaac tgccccgccg     480
gtgccgggac tgcgcgcgcc gtcgtcggct acttcgtcga cgtcctcggc gaggactacc     540
gccacatggg ggaggtgtac caggagtact gcgacgcgat gacgcgtctg gcgctggacg     600
tgacggaggt gctggcggca gcgctggggc tggaccgcgg cgcactgcgc ggcttcttcg     660
agggcggcga ctccgtcatg cggctgaacc actaccggc gtgccggcag ccgcacctga     720
cgctggggac gggcccgcac cgggacccga cgtcgctgac gctgctgcac caggacgacg     780
tgggcgggct gcaggtgcgc gccggcggcg ggccgtggcg cgcggtgcgg ccccgcgcgg     840
acgcgttcgt ggtcaacatt ggcgacacct cgccgcgct caccgacggg cgtcacacca     900
gctgcctgca ccgcgccgtg gtgaccggcg gcggctcccg ccggtcgctc gccttcttcc     960
tcaacccgcc gctggaccgc gtcgtccgcc cgccgggcgc gctcctccag gagaacaagc    1020
aggcgggccg cccgcgcgcg ttcccggact tcacgtggcg cgagttcctc gagttcacgc    1080
agaagcacta ccggtcggac gcgggcacca tggacgcctt cgtgtcgtgg atcgcgggag    1140
gccgccgcca ccatggcgga caggaggagg gcaactgaga tcgatgcatc tctagctgta    1200
ggcagcagcg cagcagctac caagaataat ggccggcgac ggagatgcag ctacgacgca    1260
caaataaatt gagtgtttgt ggtacaataa ggacgaggac gatcaatggc gacctgtaac    1320
cggtgcagtt ttagttaatc tttcatggcg atatggcatt aaccaatcgt tggtgtaaaa    1380
tgcgtgcatg ctttgcatgc caatgttggc catgtgatgg cacagcgtga gtgtagctca    1440
cccaccgtga caacgtgcta atttcgtgtg gtcctagata ccaaggtcgt ctaatgaact    1500
tgatggattg atgattt                                                   1517
```

```
<210> SEQ ID NO 5
<211> LENGTH: 1107
<212> TYPE: DNA
<213> ORGANISM: Zea mays

<400> SEQUENCE: 5
atggcggcgg cggccgtggt gttcgacgcc gaggcgctga gccgggagga gcacatcccg      60
gcgcagttcg tgtggcccac cgaggagcgg gcgccggcgg cggcgtgga ggaggtcgcc     120 atccccgtgg tcgacctcgg cgagttcctc cgccgcgggg tgctcccgcg cggcgtggcg     180
gaggcgtgcg agcgccacgg cgtcttccag gtggtgaacc acggcgtggg cgccgcgctg     240
ctcgccgagg cctaccgctg ttgcgacgcc ttttacgcgc tcccgctcgc ggacaagcag     300
```

-continued

```
cgcgcgcagc gccggcacgg ggagaaccac ggctacgcca gcagcttcac gggccgcttc       360
cactgctgcc tgccgtggaa ggagacgctg tccttcaact gccccgccgg tgccgggact       420
gcgcgcgccg tcgtcggcta cttcgtcgac gtcctcggcg aggactaccg ccacatgggg       480
gaggtgtacc aggagtactg cgacgcgatg acgcgtctgg cgctggacgt gacggaggtg       540
ctggcggcag cgctgggggct ggaccgcggc gcactgcgcg gcttcttcga gggcggcgac       600
tccgtcatgc ggctgaacca ctacccggcg tgccggcagc cgcacctgac gctggggacg       660
ggcccgcacc gggacccgac gtcgctgacg ctgctgcacc aggacgacgt gggcgggctg       720
caggtgcgcg ccggcggcgg gccgtggcgc gcggtgcggc cccgcgcgga cgcgttcgtg       780
gtcaacattg gcgacacctt cgccgcgctc accgacgggc gtcacaccag ctgcctgcac       840
cgcgccgtgg tgaccggcgg cggctcccgc cggtcgctcg ccttcttcct caacccgccg       900
ctggaccgcg tcgtccgccc gccgggcgcg ctcctccagg agaacaagca ggcgggccgc       960
ccgcgcgcgt ccccggactt cacgtggcgc gagttcctcg agttcacgca gaagcactac      1020
cggtcggacg cgggcaccat ggacgccttc gtgtcgtgga tcgcgggagg ccgccgccac      1080
catggcggac aggaggaggg caactga                                         1107
```

```
<210> SEQ ID NO 6
<211> LENGTH: 368
<212> TYPE: PRT
<213> ORGANISM: Zea mays

<400> SEQUENCE: 6

Met Ala Ala Ala Ala Val Val Phe Asp Ala Glu Ala Leu Ser Arg Glu
1               5                   10                  15

Glu His Ile Pro Ala Gln Phe Val Trp Pro Thr Glu Glu Arg Ala Pro
            20                  25                  30

Ala Gly Gly Val Glu Glu Val Ala Ile Pro Val Val Asp Leu Gly Glu
        35                  40                  45

Phe Leu Arg Arg Gly Val Leu Pro Arg Gly Val Ala Glu Ala Cys Glu
    50                  55                  60

Arg His Gly Val Phe Gln Val Val Asn His Gly Val Gly Ala Ala Leu
65                  70                  75                  80

Leu Ala Glu Ala Tyr Arg Cys Cys Asp Ala Phe Tyr Ala Leu Pro Leu
                85                  90                  95

Ala Asp Lys Gln Arg Ala Gln Arg Arg His Gly Glu Asn His Gly Tyr
            100                 105                 110

Ala Ser Ser Phe Thr Gly Arg Phe His Cys Cys Leu Pro Trp Lys Glu
        115                 120                 125

Thr Leu Ser Phe Asn Cys Pro Ala Gly Ala Gly Thr Ala Arg Ala Val
    130                 135                 140

Val Gly Tyr Phe Val Asp Val Leu Gly Glu Asp Tyr Arg His Met Gly
145                 150                 155                 160

Glu Val Tyr Gln Glu Tyr Cys Asp Ala Met Thr Arg Leu Ala Leu Asp
                165                 170                 175

Val Thr Glu Val Leu Ala Ala Ala Leu Gly Leu Asp Arg Gly Ala Leu
            180                 185                 190

Arg Gly Phe Phe Glu Gly Gly Asp Ser Val Met Arg Leu Asn His Tyr
        195                 200                 205

Pro Ala Cys Arg Gln Pro His Leu Thr Leu Gly Thr Gly Pro His Arg
    210                 215                 220
```

```
Asp Pro Thr Ser Leu Thr Leu Leu His Gln Asp Asp Val Gly Gly Leu
225             230             235             240

Gln Val Arg Ala Gly Gly Gly Pro Trp Arg Ala Val Arg Pro Arg Ala
            245             250             255

Asp Ala Phe Val Val Asn Ile Gly Asp Thr Phe Ala Ala Leu Thr Asp
            260             265             270

Gly Arg His Thr Ser Cys Leu His Arg Ala Val Val Thr Gly Gly Gly
            275             280             285

Ser Arg Arg Ser Leu Ala Phe Phe Leu Asn Pro Pro Leu Asp Arg Val
            290             295             300

Val Arg Pro Pro Gly Ala Leu Leu Gln Glu Asn Lys Gln Ala Gly Arg
305             310             315             320

Pro Arg Ala Phe Pro Asp Phe Thr Trp Arg Glu Phe Leu Glu Phe Thr
                325             330             335

Gln Lys His Tyr Arg Ser Asp Ala Gly Thr Met Asp Ala Phe Val Ser
            340             345             350

Trp Ile Ala Gly Gly Arg Arg His His Gly Gly Gln Glu Glu Gly Asn
            355             360             365
```

<210> SEQ ID NO 7
<211> LENGTH: 1522
<212> TYPE: DNA
<213> ORGANISM: Zea mays

<400> SEQUENCE: 7

```
gcacactcgc agctcgcaca tctcatggtg tcctaagaac ggcaagagcc agctctgcct      60
agcagcagcg cacagccaca tccatggacg ccagcccgac cccaccgctc cccctccgcg     120
ccccaactcc cagcattgac ctccccgctg gcaaggacag ggccgacgcg gcggctaaca     180
aggccgcggc tgtgttcgac ctgcgccggg agcccaagat cccggagcca ttcctgtggc     240
cgcacgaaga ggcgcggccg acctcggccg cggagctgga ggtgccggtg gtggacgtgg     300
gcgtgctgcg caatggcgac ggcgcggggc tccgccgcgc cgcggcgcaa gtggcggcgg     360
cgtgcgcgac gcacgggttc ttccaggtgt gcgggcacgg cgtggacgcg cgctgggggc     420
gcgccgcgct ggacggcgcc agcgacttct tccggctgcc gctggctgag aagcagcggg     480
cccggcgcgt ccccggcacc gtgtccgggt acacgagcgc gcacgccgac cggttcgcgt     540
ccaagctccc ctggaaggag accctgtcct tcggcttcca cgacggcgcc gcggcgcccg     600
tcgtcgtgga ctacttcacc ggcaccctcg gccaagattt cgagccagtg gggcgggtgt     660
accagaggta ctgcgaggag atgaaggagc tgtcgctgac gatcatggag ctgctggagc     720
tgagcctggg cgtggagcgc ggctactacc gggagttctt cgaggacagc cgctccatca     780
tgcggtgcaa ctactacccg ccgtgccggg tgccggagcg cacgctgggc acgggccgc     840 actgcgaccc cacggcgctg accatcctcc tgcaggacga cgtcggcggg ctggaggtcc     900
tggtggacgg cgagtggcgc cccgtccggc cgtcccagg cgccatggtc atcaacatcg     960
gcgacacctt catggcgctg tccaacgggc ggtacaagag ctgcctgcac cgcgcggtgg    1020
tgaaccggcg gcaggagcgg caatcgctgg ccttcttcct gtgcccgcgc gaggaccggg    1080
tggtgcgccc gccggccagc gccgcgccgc ggcagtaccc ggacttcacc tgggccgacc    1140
tcatgcgctt cacgcagcgc cactaccgcg ccgacacccg cacgctggac gccttcaccc    1200
gctggctctc ccacgcccg gcggcggcgg ctccctgcac ctaacgagcc ggccgtctct    1260
ttcgccgggg cccgcgcggg gttcgcccac gtggtgatca ggtggcagac atgtggccca    1320
```

-continued cgggccccgc gccgccttcc ccatttttgg acgaccctac tgctactact actagtgtac    1380
atatgcaaaa aaatacatat atatataggt actttctcta atattttat atataagcaa    1440 ggcggcctgg tgttctttc tttgttttgt cgacaactgt ttgatcccat cctatggacg    1500
atggatagtt caatgtttgt ac    1522

<210> SEQ ID NO 8
<211> LENGTH: 1161
<212> TYPE: DNA
<213> ORGANISM: Zea mays

<400> SEQUENCE: 8
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg acgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctgtccttcg gcttccacga cggcgccgcg gcgcccgtcg tcgtggacta cttcaccggc    540
accctcggcc aagatttcga gccagtgggg cgggtgtacc agaggtactg cgaggagatg    600
aaggagctgt cgctgacgat catggagctg ctggagctga gcctgggcgt ggagcgcggc    660
tactaccggg agttcttcga ggacagccgc tccatcatgc ggtgcaacta ctacccgccg    720
tgcccggtgc cggagcgcac gctgggcacg ggccgcact gcgaccccac ggcgctgacc    780
atcctcctgc aggacgacgt cggcgggctg gaggtcctgg tggacggcga gtggcgcccc    840
gtccggcccg tcccaggcgc catggtcatc aacatcggcg acaccttcat ggcgctgtcc    900
aacgggcggt acaagagctg cctgcaccgc gcggtggtga accggcggca ggagcggcaa    960
tcgctggcct cttcctgtg cccgcgcgag accgggtgg tgcgcccgcc ggccagcgcc   1020
gcgccgcggc agtacccgga cttcacctgg gccgacctca tgcgcttcac gcagcgccac   1080
taccgcgccg acaccgcac gctggacgcc ttcacccgct ggctctccca cggcccggcg   1140
gcggcggctc cctgcaccta a    1161

<210> SEQ ID NO 9
<211> LENGTH: 386
<212> TYPE: PRT
<213> ORGANISM: Zea mays

<400> SEQUENCE: 9

Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
    50                  55                  60

Leu Glu Val Pro Val Val Asp Val Gly Val Leu Arg Asn Gly Asp Gly
65                  70                  75                  80

-continued

```
Ala Gly Leu Arg Arg Ala Ala Ala Gln Val Ala Ala Ala Cys Ala Thr
                85              90              95

His Gly Phe Phe Gln Val Cys Gly His Gly Val Asp Ala Ala Leu Gly
            100             105             110

Arg Ala Ala Leu Asp Gly Ala Ser Asp Phe Phe Arg Leu Pro Leu Ala
        115             120             125

Glu Lys Gln Arg Ala Arg Arg Val Pro Gly Thr Val Ser Gly Tyr Thr
    130             135             140

Ser Ala His Ala Asp Arg Phe Ala Ser Lys Leu Pro Trp Lys Glu Thr
145             150             155             160

Leu Ser Phe Gly Phe His Asp Gly Ala Ala Ala Pro Val Val Val Asp
            165             170             175

Tyr Phe Thr Gly Thr Leu Gly Gln Asp Phe Glu Pro Val Gly Arg Val
        180             185             190

Tyr Gln Arg Tyr Cys Glu Glu Met Lys Glu Leu Ser Leu Thr Ile Met
        195             200             205

Glu Leu Leu Glu Leu Ser Leu Gly Val Glu Arg Gly Tyr Tyr Arg Glu
    210             215             220

Phe Phe Glu Asp Ser Arg Ser Ile Met Arg Cys Asn Tyr Tyr Pro Pro
225             230             235             240

Cys Pro Val Pro Glu Arg Thr Leu Gly Thr Gly Pro His Cys Asp Pro
            245             250             255

Thr Ala Leu Thr Ile Leu Leu Gln Asp Asp Val Gly Gly Leu Glu Val
            260             265             270

Leu Val Asp Gly Glu Trp Arg Pro Val Arg Pro Val Pro Gly Ala Met
        275             280             285

Val Ile Asn Ile Gly Asp Thr Phe Met Ala Leu Ser Asn Gly Arg Tyr
    290             295             300

Lys Ser Cys Leu His Arg Ala Val Val Asn Arg Arg Gln Glu Arg Gln
305             310             315             320

Ser Leu Ala Phe Phe Leu Cys Pro Arg Glu Asp Arg Val Val Arg Pro
            325             330             335

Pro Ala Ser Ala Ala Pro Arg Gln Tyr Pro Asp Phe Thr Trp Ala Asp
            340             345             350

Leu Met Arg Phe Thr Gln Arg His Tyr Arg Ala Asp Thr Arg Thr Leu
        355             360             365

Asp Ala Phe Thr Arg Trp Leu Ser His Gly Pro Ala Ala Ala Ala Pro
    370             375             380

Cys Thr
385
```

```
<210> SEQ ID NO 10
<211> LENGTH: 1457
<212> TYPE: DNA
<213> ORGANISM: Zea mays

<400> SEQUENCE: 10
taatcacctc atcacaggtc cccccagcct cactctcgcg ccggctcaag gtacattgcg      60
tgtcctagcc aagacacgca gctcatctca gcctcacacg cacagcaaga gcgaggcgtg     120
attcgccatg ggcggcctca ctatggacca ggccttcgtg caggcccccg agcaccgccc     180
caagcccatc gtcaccgagg ccaccggcat ccctctcatc gacctctcgc ctctggccgc     240
cagcggcggc gccgtggacg cgctggccgc cgaggtgggc gcggcgagcc gggactgggg     300
cttcttcgtg gtcgtgggcc acggcgtgcc cgcagagacc gtggcgcgcg cgacggaggc     360
```

-continued

```
gcagcgagcg ttcttcgcgc tgccggcaga gcggaaggcc gccgtgcgga ggaacgaggc      420
ggagccgctc gggtactacg agtcggagca caccaagaac gtgagggact ggaaggaggt      480
gtacgacctc gtgccgcgcg agccgccgcc gccggcagcc gtggccgacg gcgagcttgt      540
gttcgataac aagtggcccc aggatctacc gggcttcaga gaggcgctgg aggagtacgc      600
gaaagcgatg gaagagctgg cgttcaagct gctggagctg atcgcccgga gcctgaagct      660
gaggcccgac cggctgcacg gcttcttcaa ggaccagacg accttcatcc ggctgaacca      720
ctaccctcct tgcccgagcc ccgacctggc cctcggcgtg gggcggcaca aggacgccgg      780
cgccctgacc atcctgtacc aggacgacgt cggggggctc gacgtccggc ggcgctccga      840
cggcgagtgg gtccgcgtca ggcccgtgcc cgactcgttc atcatcaacg tcggcgacct      900
catccaggta cgagagcgcg gagcaccggg tgtcggtgaa ctcggcgagg agaggttct      960 ccatgcccta cttcttcaac ccggcgacct acaccatggt ggagccggtg gaggagctgg     1020
tgagcaagga cgatccgccc aggtacgacg cctacaactg gggcgacttc ttcagcacca     1080
ggaagaacag caacttcaag aagctcaacg tggagaacat tcagatcgcg catttcaaga     1140
agagcctcgt cctcgcctaa ctactgctac tgctaggatc catgccattg ccatgtcgtc     1200
ttcagattca gagcacgcca tgtcgtcgct agcttcgtgg tagaacaaat aatgatgtgc     1260
gtgctgtgtg taagcatgga tatggatgtg aatatgtaat atgatgagca ctcctactt      1320 ggtatgtttg ggaataacag acttgtgttg gtctggttca ttatttgtaa gaaaatcaaa     1380
aagagttagt agggcaggag gctaaccaca gtcatgctgc accacatccc tggtggaaag     1440
ctggccgggt tacgcta                                                    1457
```

<210> SEQ ID NO 11
<211> LENGTH: 1116
<212> TYPE: DNA
<213> ORGANISM: Zea mays

<400> SEQUENCE: 11

```
atgggcggcc tcactatgga ccaggccttc gtgcaggccc ccgagcaccg ccccaagccc       60
atcgtcaccg aggccaccgg catccctctc atcgacctct cgcctctggc cgccagcggc      120
ggcgccgtgg acgcgctggc cgccgaggtg ggcgcggcga ccgggactg gggcttcttc       180 gtggtcgtgg ccacggccgt gcccgcagag accgtggcgc gcgcgacgga ggcgcagcga      240
gcgttcttcg cgctgccggc agagcggaag gccgccgtgc ggaggaacga ggcggagccg      300
ctcgggtact acgagtcgga gcacaccaag aacgtgaggg actggaagga ggtgtacgac      360
ctcgtgccgc gcgagccgcc gccgccggca gccgtggccg acggcgagct tgtgttcgat      420
aacaagtggc cccaggatct accgggcttc agagaggcgc tggaggagta cgcgaaagcg      480
atggaagagc tggcgttcaa gctgctggag ctgatcgccc ggagcctgaa gctgaggccc      540
gaccggctgc acggcttctt caaggaccag acgaccttca tccggctgaa ccactaccct      600
ccttgcccga gccccgacct ggccctcggc gtggggcggc acaaggacgc cggcgccctg      660
accatcctgt accaggacga cgtcgggggg ctcgacgtcc ggcggcgctc cgacggcgag      720
tgggtccgcg tcaggcccgt gcccgactcg ttcatcatca cgtcggcga cctcatccag      780 gtacgagagc gcggagcacc gggtgtcggt gaactcggcg agggagaggt tctccatgcc      840
ctacttcttc aacccggcga cctacaccat ggtggagccg gtggaggagc tggtgagcaa      900
ggacgatccg cccaggtacg acgcctacaa ctggggcgac ttcttcagca ccaggaagaa      960
```

```
cagcaacttc aagaagctca acgtggagaa cattcagatc gcgcatttca agaagagcct    1020
cgtcctcgcc taactactgc tactgctagg atccatgcca ttgccatgtc gtcttcagat    1080
tcagagcacg ccatgtcgtc gctagcttcg tggtag                              1116
```

```
<210> SEQ ID NO 12
<211> LENGTH: 371
<212> TYPE: PRT
<213> ORGANISM: Zea mays

<400> SEQUENCE: 12

Met Gly Gly Leu Thr Met Asp Gln Ala Phe Val Gln Ala Pro Glu His
1               5                   10                  15

Arg Pro Lys Pro Ile Val Thr Glu Ala Thr Gly Ile Pro Leu Ile Asp
                20                  25                  30

Leu Ser Pro Leu Ala Ala Ser Gly Gly Ala Val Asp Ala Leu Ala Ala
            35                  40                  45

Glu Val Gly Ala Ala Ser Arg Asp Trp Gly Phe Phe Val Val Val Gly
        50                  55                  60

His Gly Val Pro Ala Glu Thr Val Ala Arg Ala Thr Glu Ala Gln Arg
65                  70                  75                  80

Ala Phe Phe Ala Leu Pro Ala Glu Arg Lys Ala Ala Val Arg Arg Asn
                85                  90                  95

Glu Ala Glu Pro Leu Gly Tyr Tyr Glu Ser Glu His Thr Lys Asn Val
            100                 105                 110

Arg Asp Trp Lys Glu Val Tyr Asp Leu Val Pro Arg Glu Pro Pro
            115                 120                 125

Pro Ala Ala Val Ala Asp Gly Glu Leu Val Phe Asp Asn Lys Trp Pro
        130                 135                 140

Gln Asp Leu Pro Gly Phe Arg Glu Ala Leu Glu Glu Tyr Ala Lys Ala
145                 150                 155                 160

Met Glu Glu Leu Ala Phe Lys Leu Leu Glu Leu Ile Ala Arg Ser Leu
                165                 170                 175

Lys Leu Arg Pro Asp Arg Leu His Gly Phe Phe Lys Asp Gln Thr Thr
                180                 185                 190

Phe Ile Arg Leu Asn His Tyr Pro Pro Cys Pro Ser Pro Asp Leu Ala
            195                 200                 205

Leu Gly Val Gly Arg His Lys Asp Ala Gly Ala Leu Thr Ile Leu Tyr
        210                 215                 220

Gln Asp Asp Val Gly Gly Leu Asp Val Arg Arg Arg Ser Asp Gly Glu
225                 230                 235                 240

Trp Val Arg Val Arg Pro Val Pro Asp Ser Phe Ile Ile Asn Val Gly
                245                 250                 255

Asp Leu Ile Gln Val Arg Glu Arg Gly Ala Pro Gly Val Gly Glu Leu
            260                 265                 270

Gly Glu Gly Glu Val Leu His Ala Leu Leu Leu Gln Pro Gly Asp Leu
        275                 280                 285

His His Gly Gly Ala Gly Gly Ala Gly Glu Gln Gly Arg Ser Ala
        290                 295                 300

Gln Val Arg Arg Leu Gln Leu Gly Arg Leu Leu Gln His Gln Glu Glu
305                 310                 315                 320

Gln Gln Leu Gln Glu Ala Gln Arg Gly Glu His Ser Asp Arg Ala Phe
                325                 330                 335

Gln Glu Glu Pro Arg Pro Arg Leu Thr Thr Ala Thr Ala Arg Ile His
            340                 345                 350
```

```
Ala Ile Ala Met Ser Ser Ser Asp Ser Glu His Ala Met Ser Ser Leu
        355                 360                 365

Ala Ser Trp
    370
```

<210> SEQ ID NO 13
<211> LENGTH: 1733
<212> TYPE: DNA
<213> ORGANISM: Zea mays

<400> SEQUENCE: 13

```
atgaggccgc gcctccctcc aaatgttccc tccctgcctt cgtctttgtc gttgctcgca      60
aactccctgt cctcccctgt tacaaatacc cccacccgcc cggacagctt ccctgcatac     120
ttgcagctcg cacatctcat ggtgtcgcag gaacgacaag agccagctgt gcctagcagc     180
agcagcagca gcgccaagcg cgcagccacg tccatggacg ccagcccggc cccgccgctc     240
ctcctccgcg cccccactcc cagccccagc attgacctcc ccgctggcaa ggacaaggcc     300
gacgcggcgg ccagcaaggc cggcgcggcc gtgttcgacc tgcgccggga gcccaagatc     360
cccgcgccat tcctgtggcc gcaggaagag gcgcggccgt cctcggccgc ggagctggag     420
gtgccgatgg tggacgtggg cgtgctgcgc aatggcgacc gcgcggggct gcggcgcgcc     480
gcggcgcagg tggccgcggc gtgcgcgacg cacgggttct tccaggtgtg cgggcacggc     540
gtggacgcgg cgctggggcg cgccgcgctg gacgcgccca gcgacttctt ccggctgccg     600
ctcgccgaga agcagcgcgc ccggcgcgtc cccggcaccg tgtccgggta cacgagcgcg     660
cacgccgacc ggttcgcggc caagctcccc tggaaggaga ccctgtcgtt cggctaccac     720 gacgcgccg cgtcgcctgt cgtcgtggac tacttcgtcg gcaccctcgg ccaggatttc     780
gagccaatgg ggtgggtgta ccagaggtac tgcgaggaga tgaaggagct gtcgctgacg     840
atcatggagc tgctggagct gagcctgggc gtggagctgc gcggctacta ccgggagttc     900
ttcgaggaca gccggtccat catgcggtgc aactactacc cgccgtgccc ggagccggag     960
cgcacgctgg gcacgggccc gcactgcgac cccacggcgc tcaccatcct cctgcaggac    1020
gacgtgggcg ggctggaggt gctggtggac ggtgagtggc cccgtccg gcccgtcccg       1080 ggcgccatgg tcatcaacat cggcgacacc ttcatggcgc tgtcgaacgg gaggtacaag    1140
agctgcctgc accgcgcggt ggtgaaccag cggcgggcg gcggtcgct ggccttcttc       1200 ctgtgcccgc gcgaggaccg ggtggtgcgc ccgccggcca gtgctgcgcc gcggcgctac    1260
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct agcgagccgg gccaaggcg tctctttcgc cccacgtgcg cgcccagctg       1440
ggcaggtggc cagacacgcg gcccgcgggc cccgcgccgc cttgccattt tttgacgctg    1500
gccctactgc tgtgctacta gtgtacatat gcaagagtac atatatatat atatatatac    1560
gtattttcta tatattatat ataaaagcaa ggcggcccgg tgcccttctc ttgttttgtc    1620
cacaactgtt tgatcccatt attctatgga ccatggatac ttcaatgttt gtactaagac    1680
cgtgaacgtg ggattctttt ccttcctctg tgttttttct gagaaaaatt aaa          1733
```

<210> SEQ ID NO 14
<211> LENGTH: 1392
<212> TYPE: DNA
<213> ORGANISM: Zea mays

```
<400> SEQUENCE: 14
atgaggccgc gcctccctcc aaatgttccc tccctgcctt cgtctttgtc gttgctcgca      60
aactccctgt cctccctgt tacaaatacc cccacccgcc cggacagctt ccctgcatac     120
ttgcagctcg cacatctcat ggtgtcgcag aacgacaag agccagctgt gcctagcagc     180
agcagcagca gcgccaagcg cgcagccacg tccatggacg ccagcccggc cccgccgctc     240
ctcctccgcg cccccactcc cagccccagc attgacctcc ccgctggcaa ggacaaggcc     300
gacgcggcgg ccagcaaggc cggcgcggcc gtgttcgacc tgcgccggga gcccaagatc     360
cccgcgccat tcctgtggcc gcaggaagag gcgcggccgt cctcggccgc ggagctggag     420
gtgccgatgg tggacgtggg cgtgctgcgc aatggcgacc gcgcggggct cgcggcgcgcc     480 gcggcgcagg tggccgcggc gtgcgcgacg cacgggttct tccaggtgtg cgggcacggc     540
gtggacgcgg cgctggggcg cgccgcgctg gacgcgcca gcgacttctt ccggctgccg     600
ctcgccgaga agcagcgcgc ccggcgcgtc cccggcaccg tgtccgggta cacgagcgcg     660
cacgccgacc ggttcgcggc caagctcccc tggaaggaga ccctgtcgtt cggctaccac     720
gacggcgccg cgtcgcctgt cgtcgtggac tacttcgtcg gcaccctcgg ccaggatttc     780
gagccaatgg ggtgggtgta ccagaggtac tgcgaggaga tgaaggagct gtcgctgacg     840
atcatggagc tgctggagct gagcctgggc gtggagctgc gcggctacta ccgggagttc     900
ttcgaggaca gccggtccat catgcggtgc aactactacc gccgtgccc ggagccggag     960 cgcacgctgg gcacgggccc gcactgcgac cccacggcgc tcaccatcct cctgcaggac    1020
gacgtgggcg ggctggaggt gctggtggac ggtgagtggc gccccgtccg gcccgtcccg    1080
ggcgccatgg tcatcaacat cggcgacacc ttcatggcgc tgtcgaacgg gaggtacaag    1140
agctgcctgc accgcgcggt ggtgaaccag cggcggcgc ggcggtcgct ggccttcttc    1200
ctgtgcccgc gcgaggaccg ggtggtgcgc ccgccggcca gtgctgcgcc gcggcgctac    1260
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct ag                                                        1392

<210> SEQ ID NO 15
<211> LENGTH: 463
<212> TYPE: PRT
<213> ORGANISM: Zea mays

<400> SEQUENCE: 15

Met Arg Pro Arg Leu Pro Pro Asn Val Pro Ser Leu Pro Ser Ser Leu
1               5                   10                  15

Ser Leu Leu Ala Asn Ser Leu Ser Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly
                85                  90                  95

Lys Asp Lys Ala Asp Ala Ala Ala Ser Lys Ala Gly Ala Ala Val Phe
            100                 105                 110
```

```
Asp Leu Arg Arg Glu Pro Lys Ile Pro Ala Pro Phe Leu Trp Pro Gln
        115             120             125

Glu Glu Ala Arg Pro Ser Ser Ala Ala Glu Leu Glu Val Pro Met Val
        130             135             140

Asp Val Gly Val Leu Arg Asn Gly Asp Arg Ala Gly Leu Arg Arg Ala
145             150             155             160

Ala Ala Gln Val Ala Ala Ala Cys Ala Thr His Gly Phe Phe Gln Val
                165             170             175

Cys Gly His Gly Val Asp Ala Ala Leu Gly Arg Ala Ala Leu Asp Gly
            180             185             190

Ala Ser Asp Phe Phe Arg Leu Pro Leu Ala Glu Lys Gln Arg Ala Arg
        195             200             205

Arg Val Pro Gly Thr Val Ser Gly Tyr Thr Ser Ala His Ala Asp Arg
        210             215             220

Phe Ala Ala Lys Leu Pro Trp Lys Glu Thr Leu Ser Phe Gly Tyr His
225             230             235             240

Asp Gly Ala Ala Ser Pro Val Val Val Asp Tyr Phe Val Gly Thr Leu
                245             250             255

Gly Gln Asp Phe Glu Pro Met Gly Trp Val Tyr Gln Arg Tyr Cys Glu
            260             265             270

Glu Met Lys Glu Leu Ser Leu Thr Ile Met Glu Leu Leu Glu Leu Ser
        275             280             285

Leu Gly Val Glu Leu Arg Gly Tyr Tyr Arg Glu Phe Phe Glu Asp Ser
        290             295             300

Arg Ser Ile Met Arg Cys Asn Tyr Tyr Pro Pro Cys Pro Glu Pro Glu
305             310             315             320

Arg Thr Leu Gly Thr Gly Pro His Cys Asp Pro Thr Ala Leu Thr Ile
                325             330             335

Leu Leu Gln Asp Asp Val Gly Gly Leu Glu Val Leu Val Asp Gly Glu
            340             345             350

Trp Arg Pro Val Arg Pro Val Pro Gly Ala Met Val Ile Asn Ile Gly
        355             360             365

Asp Thr Phe Met Ala Leu Ser Asn Gly Arg Tyr Lys Ser Cys Leu His
        370             375             380

Arg Ala Val Val Asn Gln Arg Arg Ala Arg Arg Ser Leu Ala Phe Phe
385             390             395             400

Leu Cys Pro Arg Glu Asp Arg Val Val Arg Pro Pro Ala Ser Ala Ala
                405             410             415

Pro Arg Arg Tyr Pro Asp Phe Thr Trp Ala Asp Leu Met Arg Phe Thr
            420             425             430

Gln Arg His Tyr Arg Ala Asp Thr Arg Thr Leu Asp Ala Phe Thr Arg
        435             440             445

Trp Leu Ser His Gly Pro Ala Gln Ala Ala Ala Pro Pro Cys Thr
    450             455             460
```

<210> SEQ ID NO 16
<211> LENGTH: 1510
<212> TYPE: DNA
<213> ORGANISM: Zea mays

<400> SEQUENCE: 16

```
aaagagcgcg cgacggcggc ccctgggaga gccatgcgag actggaggcg gaaccgcgca        60
cgacaccaag ctgccgcgcc ggactgctgc acgcaagcgc agcgcaggac cgaccgacct       120
ccgtaggcac gcacggcgcc ggcggcatgg cggagcacct cctgtcgacg gccgtgcacg       180
```

-continued

```
acacgctgcc ggggagctac gtgcggccgg agccggagcg cccgcgcctc gcggaggtcg      240
tgaccggcgc gcgcatcccc gtcgtggacc tgggcagccc cgaccgcggc gcggtcgtgg      300
ccgccgtcgg cgacgcctgc cgctcgcacg gcttcttcca ggtcgtcaac cacgggatac      360
acgccgccct ggtcgcggcg gtgatggccg cggggcgcgg cttcttccgg ctgccccccg      420
aggagaaggc caagctctac tccgacgacc ccgccaggaa gatccggctg tccaccagct      480
tcaacgtgcg caaggagacg gtgcacaact ggcgcgacta cctccgcctg cactgccatc      540
ccctcgacga gttcctgccc gattggccgt ccaacccgcc cgatttcaag gagaccatgg      600
gcacctactg caaggaggtc cgggagctcg ggttcaggct gtacgccgcg atctcggaga      660
gcctgggcct agaggcgagc tacatgaagg aagcgctggg ggagcaggag cagcacatgg      720
cggtcaactt ctacccgccg tgcccggagc cggagctcac ctacggcctc ccggcgcaca      780
ccgaccccaa cgcgctcacc atcctgctca tggacccgga cgtcgccggc ctgcaggtgc      840
tccacgccgg ccagtgggtc gccgtcaacc cgcagcccgg cgcgctcatc atcaacatcg      900
gcgaccagct gcaggcgctg agcaacgggc agtaccggag cgtgtggcac cgcgcggtgg      960
tgaactcgga ccgggagcgc atgtccgtgg cgtcgttcct gtgcccgtgc aaccacgtcg     1020
tgctcggccc cgcgcggaag ctcgtcaccg aggacacccc ggccgtgtac aggaactaca     1080
cgtacgacaa gtactacgcc aagttctgga gcaggaacct ggaccaggag cactgcctcg     1140
agctcttcag aacctagcga atcggatacg gatggatgga tacattacat acgcgccctc     1200 tgttttttctc catgacgtta gaagaacacg ttctgcaatg tttgtccatt caaggtggta     1260
tcaatcaagg ctgtggtcgt tgcaattctt ccgctccata tacatgatta aatgctttga     1320
aagaaaaaga aaaaaaagaa acacaagtat tatggcacta ctagtgtttt taggaacaag     1380
gaaagagggg ttgcccctgc tggctatata tattaaatat aaataaaggt aaggctgtag     1440
acattggtga ataagagaaa gtatttgagt ttctctattg tcactccaga acagactcct     1500
ttgcctcgat                                                           1510
```

```
<210> SEQ ID NO 17
<211> LENGTH: 1011
<212> TYPE: DNA
<213> ORGANISM: Zea mays

<400> SEQUENCE: 17
atggcggagc acctcctgtc gacggccgtg cacgacacgc tgccggggag ctacgtgcgg       60
ccggagccgg agcgcccgcg cctcgcggag gtcgtgaccg gcgcgcgcat ccccgtcgtg      120
gacctgggca gccccgaccg cggcgcggtc gtggccgccg tcggcgacgc ctgccgctcg      180
cacggcttct tccaggtcgt caaccacggg atacacgccg ccctggtcgc ggcggtgatg      240
gccgcggggc gcggcttctt ccggctgccc cccgaggaga aggccaagct ctactccgac      300
gaccccgcca ggaagatccg gctgtccacc agcttcaacg tgcgcaagga cgcggtgcac      360
aactggcgcg actacctccg cctgcactgc catcccctcg acgagttcct gcccgattgg      420
ccgtccaacc cgcccgattt caaggagacc atgggcacct actgcaagga ggtccgggag      480
ctcgggttca ggctgtacgc cgcgatctcg gagagcctgg gcctagaggc gagctacatg      540
aaggaagcgc tggggggagca ggagcagcac atggcggtca acttctaccc gccgtgcccg      600
gagccggagc tcacctacgg cctcccggcg cacaccgacc ccaacgcgct caccatcctg      660
ctcatggacc cggacgtcgc cggcctgcag gtgctccacg ccggccagtg ggtcgccgtc      720
```

```
aacccgcagc ccggcgcgct catcatcaac atcggcgacc agctgcaggc gctgagcaac      780
gggcagtacc ggagcgtgtg caccgcgcg gtggtgaact cggaccggga gcgcatgtcc       840
gtggcgtcgt tcctgtgccc gtgcaaccac gtcgtgctcg ccccgcgcg gaagctcgtc       900 accgaggaca ccccggccgt gtacaggaac tacacgtacg acaagtacta cgccaagttc      960
tggagcagga acctggacca ggagcactgc ctcgagctct tcagaaccta g             1011
```

<210> SEQ ID NO 18
<211> LENGTH: 336
<212> TYPE: PRT
<213> ORGANISM: Zea mays

<400> SEQUENCE: 18

```
Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
                20                  25                  30

Thr Gly Ala Arg Ile Pro Val Val Asp Leu Gly Ser Pro Asp Arg Gly
            35                  40                  45

Ala Val Val Ala Ala Val Gly Asp Ala Cys Arg Ser His Gly Phe Phe
        50                  55                  60

Gln Val Val Asn His Gly Ile His Ala Ala Leu Val Ala Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
                100                 105                 110

Asn Val Arg Lys Glu Thr Val His Asn Trp Arg Asp Tyr Leu Arg Leu
            115                 120                 125

His Cys His Pro Leu Asp Glu Phe Leu Pro Asp Trp Pro Ser Asn Pro
        130                 135                 140

Pro Asp Phe Lys Glu Thr Met Gly Thr Tyr Cys Lys Glu Val Arg Glu
145                 150                 155                 160

Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
                180                 185                 190

Val Asn Phe Tyr Pro Pro Cys Pro Glu Pro Glu Leu Thr Tyr Gly Leu
            195                 200                 205

Pro Ala His Thr Asp Pro Asn Ala Leu Thr Ile Leu Leu Met Asp Pro
        210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
                260                 265                 270

Asn Ser Asp Arg Glu Arg Met Ser Val Ala Ser Phe Leu Cys Pro Cys
            275                 280                 285

Asn His Val Val Leu Gly Pro Ala Arg Lys Leu Val Thr Glu Asp Thr
        290                 295                 300

Pro Ala Val Tyr Arg Asn Tyr Thr Tyr Asp Lys Tyr Tyr Ala Lys Phe
305                 310                 315                 320

Trp Ser Arg Asn Leu Asp Gln Glu His Cys Leu Glu Leu Phe Arg Thr
```

-continued

```
            325              330              335
```

```
<210> SEQ ID NO 19
<211> LENGTH: 1387
<212> TYPE: DNA
<213> ORGANISM: Zea mays

<400> SEQUENCE: 19
gttttctttt tgaacgtaac tgacagaagc tatctgccta gctacggcgt gtcggttgct    60
tgtctcacca aagcagcgac atggaagcct gacagctcgt cgcgtcgcgc catttccacc    120
caacaaagcg gcggcgccag cacgcactgc ttctgcttgt gcgtgctcct ccgttccggg    180
cacgcctcta aagtctatac agcctcgaat ccatcccggc cgccgctcct gggggatact    240
acagcgagcc gaagcgggga tggcggagat ccctgtgatc gacctgcgcg tcgccggctc    300
ggcggccgag gagtccgcgc ggctgcgggc cgcgtgcgag cgcctgggct gcttccgggt    360
gaccggccac ggcgtgccct cggtgctcct ggcagagatg aaggccgccg tgcgcgcgct    420
cttcgacctc cccgacgacg ccaagcgccg caacgccgac gtcatcaccg gcagcggcta    480
cgtcgccccc agcccgacca acccgctcta cgaggccttc gggctcctcg acgccgccgt    540
gcccaccgac gtcgacgcct tttgcgcgct cctcgacgcg ccgcccaaca tcagggagac    600
cgtcaaggcc tacgcggaga agatgcacga tgtgatcgtt ggcgtcgccc gcgagctggc    660
gtctagcctg gggctagtcg aggagcactc gttccaggac tggccgtgcc agttccgcat    720
caacaggtac aactacacgc gggagacggt gggctcctcc ggcgtgcaga cccacacgga    780
ctcgggcttc ctcaccgtgc tccatgagga cgagtgtgtc ggcggcctcg aggtcctgga    840
cccgggcacc ggcgagttcg tgcccgtgga ccccgtcgcg ggctcctttc tcgtaaacat    900
cggcgacgtc ggcacggcgt ggagcaacgg gaggctgcac aacgtgaagc accgggtgcg    960
gtgcgtcgca cccgtgccgc gcatctccat cgccatgttc ctgctcgcac ccaaggacga    1020
cagcgtgagc gcaccggcgg cgttcgtgga cgcggaccac ccgcgcaggt acaaggtgtt    1080
caactacaac gactatcgga ggctcagact gtccaccggc gagcacgcag gcgaggcgct    1140
cgcacggatg gcggcgtgac gtggctggag ctgcaaattg gattggaagc cgagacaagc    1200
cgttagttat ttaccatgcc cgtgcgttca ccgcacacaa tcatattcaa aagccataaa    1260
ataaaaaata attttaatat cagtcaacat atggtttaaa tatcatatgg agtacaatat    1320
tccgaatttt tttttgtaat ttagtctgtc ttttgaaaaa aatgcacatc tagacctccg    1380
gatgact                                                             1387

<210> SEQ ID NO 20
<211> LENGTH: 900
<212> TYPE: DNA
<213> ORGANISM: Zea mays

<400> SEQUENCE: 20
atggcggaga tccctgtgat cgacctgcgc gtcgccggct cggcggccga ggagtccgcg    60
cggctgcggg ccgcgtgcga gcgcctgggc tgcttccggg tgaccggcca cggcgtgccc    120
tcggtgctcc tggcagagat gaaggccgcc gtgcgcgcgc tcttcgacct ccccgacgac    180
gccaagcgcc gcaacgccga cgtcatcacc ggcagcggct acgtcgcccc cagcccgacc    240
aacccgctct acgaggcctt cgggctcctc gacgccgccg tgcccaccga cgtcgacgcc    300
ttttgcgcgc tcctcgacgc gccgcccaac atcagggaga ccgtcaaggc ctacgcggag    360
aagatgcacg atgtgatcgt tggcgtcgcc cgcgagctgg cgtctagcct ggggctagtc    420
```

```
gaggagcact cgttccagga ctggccgtgc cagttccgca tcaacaggta caactacacg    480
cgggagacgg tgggctcctc cggcgtgcag acccacacgg actcgggctt cctcaccgtg    540
ctccatgagg acgagtgtgt cggcggcctc gaggtcctgg acccgggcac cggcgagttc    600
gtgcccgtgg accccgtcgc gggctccttt ctcgtaaaca tcggcgacgt cggcacggcg    660
tggagcaacg ggaggctgca caacgtgaag caccgggtgc ggtgcgtcgc acccgtgccg    720
cgcatctcca tcgccatgtt cctgctcgca cccaaggacg acagcgtgag cgcaccggcg    780
gcgttcgtgg acgcggacca cccgcgcagg tacaaggtgt tcaactacaa cgactatcgg    840
aggctcagac tgtccaccgg cgagcacgca ggcgaggcgc tcgcacggat ggcggcgtga    900
```

<210> SEQ ID NO 21
<211> LENGTH: 299
<212> TYPE: PRT
<213> ORGANISM: Zea mays

<400> SEQUENCE: 21

```
Met Ala Glu Ile Pro Val Ile Asp Leu Arg Val Ala Gly Ser Ala Ala
1               5                   10                  15

Glu Glu Ser Ala Arg Leu Arg Ala Ala Cys Glu Arg Leu Gly Cys Phe
            20                  25                  30

Arg Val Thr Gly His Gly Val Pro Ser Val Leu Leu Ala Glu Met Lys
        35                  40                  45

Ala Ala Val Arg Ala Leu Phe Asp Leu Pro Asp Asp Ala Lys Arg Arg
    50                  55                  60

Asn Ala Asp Val Ile Thr Gly Ser Gly Tyr Val Ala Pro Ser Pro Thr
65                  70                  75                  80

Asn Pro Leu Tyr Glu Ala Phe Gly Leu Leu Asp Ala Ala Val Pro Thr
                85                  90                  95

Asp Val Asp Ala Phe Cys Ala Leu Leu Asp Ala Pro Pro Asn Ile Arg
            100                 105                 110

Glu Thr Val Lys Ala Tyr Ala Glu Lys Met His Asp Val Ile Val Gly
        115                 120                 125

Val Ala Arg Glu Leu Ala Ser Ser Leu Gly Leu Val Glu Glu His Ser
    130                 135                 140

Phe Gln Asp Trp Pro Cys Gln Phe Arg Ile Asn Arg Tyr Asn Tyr Thr
145                 150                 155                 160

Arg Glu Thr Val Gly Ser Ser Gly Val Gln Thr His Thr Asp Ser Gly
                165                 170                 175

Phe Leu Thr Val Leu His Glu Asp Glu Cys Val Gly Gly Leu Glu Val
            180                 185                 190

Leu Asp Pro Gly Thr Gly Glu Phe Val Pro Val Asp Pro Val Ala Gly
        195                 200                 205

Ser Phe Leu Val Asn Ile Gly Asp Val Gly Thr Ala Trp Ser Asn Gly
    210                 215                 220

Arg Leu His Asn Val Lys His Arg Val Arg Cys Val Ala Pro Val Pro
225                 230                 235                 240

Arg Ile Ser Ile Ala Met Phe Leu Leu Ala Pro Lys Asp Asp Ser Val
                245                 250                 255

Ser Ala Pro Ala Ala Phe Val Asp Ala Asp His Pro Arg Arg Tyr Lys
            260                 265                 270

Val Phe Asn Tyr Asn Asp Tyr Arg Arg Leu Arg Leu Ser Thr Gly Glu
        275                 280                 285
```

```
His Ala Gly Glu Ala Leu Ala Arg Met Ala Ala
   290                 295

<210> SEQ ID NO 22
<211> LENGTH: 1496
<212> TYPE: DNA
<213> ORGANISM: Zea mays

<400> SEQUENCE: 22
gtcggtctct tgtctcacca aaccggcgac atggtacatg gaggccagcc cgtcgcttgg      60
cgccacaagt ctcggtgccg tccgtccgac aagcggcgcc agcgcacgct ggctgctcgt     120
gcacgcctct aaatacggcc ccggacccgc caccaagcga aggccaatcc cgtccgccgc     180
cccccaccaa ccacgaacca cgcaagcgaa cccggccggc gcggggcagc ggcgatggcg     240
gagatcccgg tgatcgacct cgccctcgcc ggctcgtcgc ccgacgagtc ggcgcggctg     300
cgcgacgcgt gcgagcgcct gggctgcttt cgggtgaccg gccacggcgc gcccgcgggg     360
ctcctggccg acatgaaggc cgccgtgcgc gcgctcttcg acctccccga cgacgccaag     420
cgccgcaacg ccgacgtcat ccccggcagc ggctacgtcg cgccctgccc cgccaacccg     480
ctctacgagg ccttcgggct cctcgacgcc gccgcgcccg ccgacgtcga cgccttctgc     540
gcgcgcctcg acgcgccgcc caaagtcagg gagaccgtca agacctacgc ggagaagatg     600
cacgacgtga tcgtcggcgt cgccggcgag ctggccacca gcctggggct gggcctggag     660
gagcactcgt tccaggactg gccgtgccag ttccgcatca acaggtacaa ctacacgcag     720
gagacggtgg gctcctccgg cgtgcagacc cacacggact cgggcttcct caccgtgctc     780
caggaggacg agtgcgtcgg cggcctcgag gtgctggacc ccgccgccgg tgagttcgtg     840
cccgtggacc ccgtcgccgg ctccttcctc gtcaacatcg cgacgtcgg cacggcgtgg      900 agcaacggga ggctccacaa cgtgaagcac cgggtgcggt gcgtcgcgcc cgtgccgcgc     960
atctccatcg ccatgttcct gctggcgccc aaggacgacc gcgtgagcgc cccggaggcg    1020
ttggtcgacg cgggccaccc gcgtcggtac aagccgttca actacgacga ctaccggagg    1080
ctccggctgt ccaccggcga gcgcgcaggc gaggcgctcg cgcggatggc ggcgtgatgt    1140
cgtcacgcac gtgcaagccg ttaattatag gctcgcgcat gcatacgcct acacgagagg    1200
ttgtctcgtt aagccgttct attaaaatgt gtgggggaga aagatgacta ccgtggtgcc    1260
atgtggattg ctatcgggtc tgatcaataa aatcttgcaa cacttgcacg tgcgattcca    1320
tatcctagca cgggtgggcg ccacgctagt aggtagagac cggagcggcc aaaaaatggc    1380
tacagcacca gtaggtgaac tctcaagcaa cactggctat cccacttctg acgttgtctc    1440
tctcatcact atgtatgacc agcgaatgaa gtgtttaaaa atctgacgcc gtgaaa        1496

<210> SEQ ID NO 23
<211> LENGTH: 903
<212> TYPE: DNA
<213> ORGANISM: Zea mays

<400> SEQUENCE: 23
atggcggaga tcccggtgat cgacctgcgc ctcgccggct cgtcgcccga cgagtcggcg      60
cggctgcgcg acgcgtgcga gcgcctgggc tgctttcggg tgaccggcca cggcgcgccc     120
gcggggctcc tggccgacat gaaggccgcc gtgcgcgcgc tcttcgacct ccccgacgac     180
gccaagcgcc gcaacgccga cgtcatcccc ggcagcggct acgtcgcgcc ctgccccgcc     240
aacccgctct acgaggcctt cgggctcctc gacgccgccg cgcccgccga cgtcgacgcc     300
```

-continued

```
ttctgcgcgc gcctcgacgc gccgcccaaa gtcagggaga ccgtcaagac ctacgcggag      360
aagatgcacg acgtgatcgt cggcgtcgcc ggcgagctgg ccaccagcct ggggctgggc      420
ctggaggagc actcgttcca ggactggccg tgccagttcc gcatcaacag gtacaactac      480
acgcaggaga cggtgggctc ctccggcgtg cagacccaca cggactcggg cttcctcacc      540
gtgctccagg aggacgagtg cgtcggcggc ctcgaggtgc tggaccccgc cgccggtgag      600
ttcgtgcccg tggaccccgt cgccggctcc ttcctcgtca acatcggcga cgtcggcacg      660
gcgtggagca cgggaggct ccacaacgtg aagcaccggg tgcggtgcgt cgcgcccgtg       720
ccgcgcatct ccatcgccat gttcctgctg gcgcccaagg acgaccgcgt gagcgccccg      780
gaggcgttgg tcgacgcggg ccacccgcgt cggtacaagc cgttcaacta cgacgactac      840
cggaggctcc ggctgtccac cggcgagcgc gcaggcgagg cgctcgcgcg gatggcggcg      900
tga                                                                   903
```

```
<210> SEQ ID NO 24
<211> LENGTH: 300
<212> TYPE: PRT
<213> ORGANISM: Zea mays

<400> SEQUENCE: 24

Met Ala Glu Ile Pro Val Ile Asp Leu Arg Leu Ala Gly Ser Ser Pro
1               5                   10                  15

Asp Glu Ser Ala Arg Leu Arg Asp Ala Cys Glu Arg Leu Gly Cys Phe
            20                  25                  30

Arg Val Thr Gly His Gly Ala Pro Ala Gly Leu Leu Ala Asp Met Lys
        35                  40                  45

Ala Ala Val Arg Ala Leu Phe Asp Leu Pro Asp Asp Ala Lys Arg Arg
    50                  55                  60

Asn Ala Asp Val Ile Pro Gly Ser Gly Tyr Val Ala Pro Cys Pro Ala
65                  70                  75                  80

Asn Pro Leu Tyr Glu Ala Phe Gly Leu Leu Asp Ala Ala Ala Pro Ala
                85                  90                  95

Asp Val Asp Ala Phe Cys Ala Arg Leu Asp Ala Pro Pro Lys Val Arg
            100                 105                 110

Glu Thr Val Lys Thr Tyr Ala Glu Lys Met His Asp Val Ile Val Gly
        115                 120                 125

Val Ala Gly Glu Leu Ala Thr Ser Leu Gly Leu Gly Leu Glu Glu His
    130                 135                 140

Ser Phe Gln Asp Trp Pro Cys Gln Phe Arg Ile Asn Arg Tyr Asn Tyr
145                 150                 155                 160

Thr Gln Glu Thr Val Gly Ser Ser Gly Val Gln Thr His Thr Asp Ser
                165                 170                 175

Gly Phe Leu Thr Val Leu Gln Glu Asp Glu Cys Val Gly Gly Leu Glu
            180                 185                 190

Val Leu Asp Pro Ala Ala Gly Glu Phe Val Pro Val Asp Pro Val Ala
        195                 200                 205

Gly Ser Phe Leu Val Asn Ile Gly Asp Val Gly Thr Ala Trp Ser Asn
    210                 215                 220

Gly Arg Leu His Asn Val Lys His Arg Val Arg Cys Val Ala Pro Val
225                 230                 235                 240

Pro Arg Ile Ser Ile Ala Met Phe Leu Leu Ala Pro Lys Asp Asp Arg
                245                 250                 255

Val Ser Ala Pro Glu Ala Leu Val Asp Ala Gly His Pro Arg Arg Tyr
```

```
                260              265              270
Lys Pro Phe Asn Tyr Asp Asp Tyr Arg Arg Leu Arg Leu Ser Thr Gly
        275              280              285

Glu Arg Ala Gly Glu Ala Leu Ala Arg Met Ala Ala
        290              295              300

<210> SEQ ID NO 25
<211> LENGTH: 1614
<212> TYPE: DNA
<213> ORGANISM: Zea mays

<400> SEQUENCE: 25
accacacgaa ttgcacatct ccacagctca cgattccaac actagctaca tatatatgta      60
gctttctagg ctactatata cactcaccac caagtgtgaa gtgtgtatat atagtgacag     120
ctactgcaat atatacatac gcgtcaccta tatattagcc aagctagcta tatgagcttg     180
gttgcggcgc caatggcgat cgtcgacgtg gccaacgccc agctgcagca agcagcagca     240
gcagctgcca agaaagacga ggacggccat gagcagcagg agtcgtccta cgactacggc     300
gcgctgatga aaggcgtgag gcacctgtcg gacagcggca ttaccaggct gcccgacagg     360
tacgtcctgc ccgcgtccga ccgccccggc gtccttgccg tctcgtcgtc cgtggcgggc     420
agcggcaggg tcaagctccc tgtcgtcaac ctcgccggcc tccgcgaccc ctgccagcgc     480
gccgccgtgc tggccacgct cgacgccgcg tgccgggagt acggcttctt tcaggtggta     540
aaccacgggt tcgggagcga cgtgagcggc gggatgctgg acgtggcgca gcgcttcttc     600
gagctgccgc tggccgagcg agcgcggcac atgtcggcgg acgtgcgggc gccggtgcgc     660
tacggcacca gcttcaacca ggccaaggac gacgtgctct gctggcgcga cttcctcaag     720
ctcgtctgcc agccgctgca ggcggtgctc ccgtactggc cccagcagcc ggcggacctc     780
agggacgtgg ccaccaggta cgccacggcg agccaccggc tgttcatgga ggtcatggag     840
gcggcgctgg aggccctggg catccccacg gccggcggcg tgctcgggga gctggcagcg     900
tcgtcgtcgc acatgatgac ggtgaactgc tacccggcgt gcccgcagcc tgagctcacg     960
ctggggatgc cctcgcactc ggactacggc ctcttcacgt tcgtcctgca ggaccacgtc    1020
gagggcctcc aggtcatgca cgacggccgc tggctcacca tcgaccccat cccgggatcg    1080
ttcgtcgtca acgtcggcga ccacctagag atctacagca acgggcggta caagagcgcg    1140
ctgcaccggg tgcacgtgaa ctccacgcgg ccgcgcatct cggtggcgtc gttccacagc    1200
ctgccggcgg agcgagtgat cgggccggcg ccggagctgg tggacgacga ggccggcaac    1260
ccgcggcggt acatggacac cgacttcgct accttcctcg cctacctcgc atccgcggac    1320
ggcaagaaca agaccttcct ccagtcaagg aagctgcctg ctgctgctcc tccatgcctc    1380
tagctaacta gatagctgct tattaatctg acagaataaa attaatcagt tcagcgcaca    1440
attccacaag cgaaacaaa cctggatttg ttttaattag ctctgccctt cattattaca    1500
ttcaagctag ctcttggtca acgcatgcac acaagcttga gcattgactg gtcccttttc    1560
aatcggttgc attgtactcc ctccgtacca aaattggttg tcgctatagt attt          1614

<210> SEQ ID NO 26
<211> LENGTH: 1212
<212> TYPE: DNA
<213> ORGANISM: Zea mays

<400> SEQUENCE: 26
atgagcttgg ttgcggcgcc aatggcgatc gtcgacgtgg ccaacgccca gctgcagcaa      60
```

```
gcagcagcag cagctgccaa gaaagacgag gacggccatg agcagcagga gtcgtcctac        120
gactacggcg cgctgatgaa aggcgtgagg cacctgtcgg acagcggcat taccaggctg        180
cccgacaggt acgtcctgcc cgcgtccgac cgccccggcg tccttgccgt ctcgtcgtcc        240
gtggcgggca gcggcagggt caagctccct gtcgtcaacc tcgccggcct ccgcgacccc        300
tgccagcgcg ccgccgtgct ggccacgctc gacgccgcgt gccgggagta cggcttcttt        360
caggtggtaa accacgggtt cgggagcgac gtgagcggcg ggatgctgga cgtggcgcag        420
cgcttcttcg agctgccgct ggccgagcga gcgcggcaca tgtcggcgga cgtgcgggcg        480
ccggtgcgct acggcaccag cttcaaccag gccaaggacg acgtgctctg ctggcgcgac        540
ttcctcaagc tcgtctgcca gccgctgcag gcggtgctcc cgtactggcc ccagcagccg        600
gcggacctca gggacgtggc caccaggtac gccacggcga gccaccggct gttcatggag        660
gtcatggagg cggcgctgga ggccctgggc atccccacgg ccggcggcgt gctcggggag        720
ctggcagcgt cgtcgtcgca catgatgacg gtgaactgct accgggcgtg cccgcagcct        780
gagctcacgc tggggatgcc ctcgcactcg gactacggcc tcttcacgtt cgtcctgcag        840
gaccacgtcg agggcctcca ggtcatgcac gacggccgct ggctcaccat cgaccccatc        900
ccgggatcgt tcgtcgtcaa cgtcggcgac cacctagaga tctacagcaa cgggcggtac        960
aagagcgcgc tgcaccgggt gcacgtgaac tccacgcggc cgcgcatctc ggtggcgtcg       1020
ttccacagcc tgccggcgga gcgagtgatc gggccggcgc cggagctggt ggacgacgag       1080
gccggcaacc cgcggcggta catggacacc gacttcgcta ccttcctcgc ctacctcgca       1140
tccgcggacg gcaagaacaa gaccttcctc cagtcaagga agctgcctgc tgctgctcct       1200
ccatgcctct ag                                                           1212
```

<210> SEQ ID NO 27
<211> LENGTH: 403
<212> TYPE: PRT
<213> ORGANISM: Zea mays

<400> SEQUENCE: 27

```
Met Ser Leu Val Ala Ala Pro Met Ala Ile Val Asp Val Ala Asn Ala
1               5                   10                  15

Gln Leu Gln Gln Ala Ala Ala Ala Ala Ala Lys Lys Asp Glu Asp Gly
            20                  25                  30

His Glu Gln Gln Glu Ser Ser Tyr Asp Tyr Gly Ala Leu Met Lys Gly
        35                  40                  45

Val Arg His Leu Ser Asp Ser Gly Ile Thr Arg Leu Pro Asp Arg Tyr
    50                  55                  60

Val Leu Pro Ala Ser Asp Arg Pro Gly Val Leu Ala Val Ser Ser Ser
65                  70                  75                  80

Val Ala Gly Ser Gly Arg Val Lys Leu Pro Val Val Asn Leu Ala Gly
                85                  90                  95

Leu Arg Asp Pro Cys Gln Arg Ala Ala Val Leu Ala Thr Leu Asp Ala
            100                 105                 110

Ala Cys Arg Glu Tyr Gly Phe Phe Gln Val Val Asn His Gly Phe Gly
        115                 120                 125

Ser Asp Val Ser Gly Gly Met Leu Asp Val Ala Gln Arg Phe Phe Glu
        130                 135                 140

Leu Pro Leu Ala Glu Arg Ala Arg His Met Ser Ala Asp Val Arg Ala
145                 150                 155                 160
```

```
Pro Val Arg Tyr Gly Thr Ser Phe Asn Gln Ala Lys Asp Asp Val Leu
            165                 170                 175

Cys Trp Arg Asp Phe Leu Lys Leu Val Cys Gln Pro Leu Gln Ala Val
            180                 185                 190

Leu Pro Tyr Trp Pro Gln Gln Pro Ala Asp Leu Arg Asp Val Ala Thr
            195                 200                 205

Arg Tyr Ala Thr Ala Ser His Arg Leu Phe Met Glu Val Met Glu Ala
        210                 215                 220

Ala Leu Glu Ala Leu Gly Ile Pro Thr Ala Gly Gly Val Leu Gly Glu
225                 230                 235                 240

Leu Ala Ala Ser Ser Ser His Met Met Thr Val Asn Cys Tyr Pro Ala
                245                 250                 255

Cys Pro Gln Pro Glu Leu Thr Leu Gly Met Pro Ser His Ser Asp Tyr
            260                 265                 270

Gly Leu Phe Thr Phe Val Leu Gln Asp His Val Glu Gly Leu Gln Val
            275                 280                 285

Met His Asp Gly Arg Trp Leu Thr Ile Asp Pro Ile Pro Gly Ser Phe
        290                 295                 300

Val Val Asn Val Gly Asp His Leu Glu Ile Tyr Ser Asn Gly Arg Tyr
305                 310                 315                 320

Lys Ser Ala Leu His Arg Val His Val Asn Ser Thr Arg Pro Arg Ile
                325                 330                 335

Ser Val Ala Ser Phe His Ser Leu Pro Ala Glu Arg Val Ile Gly Pro
            340                 345                 350

Ala Pro Glu Leu Val Asp Asp Glu Ala Gly Asn Pro Arg Arg Tyr Met
            355                 360                 365

Asp Thr Asp Phe Ala Thr Phe Leu Ala Tyr Leu Ala Ser Ala Asp Gly
        370                 375                 380

Lys Asn Lys Thr Phe Leu Gln Ser Arg Lys Leu Pro Ala Ala Ala Pro
385                 390                 395                 400

Pro Cys Leu
```

```
<210> SEQ ID NO 28
<211> LENGTH: 1863
<212> TYPE: DNA
<213> ORGANISM: Zea mays

<400> SEQUENCE: 28
tgccaccata ccactagtgc aaggtcctag atttacactt ggtgctacac cttgcttcgc        60
ccccttcctt ccttccttcc ttccttccct ccttccttgg tctctaggca gctagcagtg       120
tggtgctgct gccggccgcc tattggccgc ctgggactgg gatccattaa ttactgcgcg       180
cgcgcggcta accaaccaat cccagcgtgc gtaatctatt gcccacatgc cgacgccgtc       240
gcacctcaac aagaacccgc gctacctgga cttccgggcg gcgcggcggg tgccggagtc       300
gcacgcctgg ccgggcctgc acgaccaccc cgtcgtggac ggcggcgcgc cgggccccga       360
cgccgtgccg gtggtggacc tgggcgccgc ggacccggcg ccggcgccgg cggcggcggt       420
ggcccgcgcc gccgagcaat ggggcgcgtt cctgctcacg gccacggcg tccccgcgga        480 cctgctggcg cgcgtggagg accggatcgc caccatgttc gcgctgccgg ccgacgacaa       540
gatgcgcgcc gtgcgcgggc ccggcgacgc ctgcggctac ggctccccgc ccatctcctc       600
cttcttctcc aagtgcatgt ggtccgaggg ctacaccttc tcgccggcct ccctccgcgc       660
cgacctccgc aagctctggc ccaaggccgg cgacgactac accagcttct gtgatgtgat       720
```

-continued

```
ggaggagttc cacaagcaca tgcgcgccct cgcggacaag ctgctggagc tgttcctcat      780
ggcgctgggg ctcaccgacg agcaggccag cgccgtcgag gccgagcgga ggatcgccga      840
gacgatgacc gccaccatgc atctcaactg gtacccgagg tgcccggacc cgcggcgcgc      900
gctggggctg atcgcgcaca ccgactcggg cttcttcacc ttcgtgatgc agagcctcgt      960
gcccgggctg cagctcttcc gccacgcccc ggaccggtgg gtggcggtgc cggccgtgcc     1020
gggcgccttc gtcgtcaacg tgggcgacct cttccacatc ctcaccaacg gccggttcca     1080
cagcgtgtac caccgcgccg tcgtgaaccg ggacctcgac aggatctcgc tcggctactt     1140
cctcggcccg ccgccgcacg ccaaggtggc cgcgctgcgc gaggccgtgc cgcccggccg     1200
ggcccccgcg taccgcgccg tcacgtggcc cgagtacatg ggcgtccgca agaaggcctt     1260
caccaccggc gcctccgcgc tcaagatggt cgccctcgcc gccgccgcg acctcgacga     1320 cgacggcgac gccgccgtcg tccatcagca gcagcagcta gtcgtctcgt cgtagccgag     1380
accgatcgcc ggagactgat gctgatgatg atgcatatat acatgagaga aatcgtcgag     1440
tagactagcc gattgcaaaa gcaacccag ctgccgaaac ctggcatatc gatcccattc     1500
tctgctgcgc acatgtatgc atgcatgcgc ttcgtccgtt cgactcgtgt gtgcttgctt     1560
gcttgcgcgt gcagcagaac taattccgtt ccgcagctag ctgctctgct ctgctctgct     1620
ggaatgtaat taagtagtag tatatggtag tagagaaaag attagctagg cgatcgatat     1680
agatgacggg ccggggaaga agacgaatta attaagatcg atcgacgacg acgagctgtg     1740
cgtggctggc tgtgttcttc tctagcctag ttacagaggc cggctgctgc tgcttccaat     1800
cgggctgctt gtcgctactg acgatcgtta gtggatccat taactaatct ggaattctgg     1860
att                                                                 1863

<210> SEQ ID NO 29
<211> LENGTH: 1149
<212> TYPE: DNA
<213> ORGANISM: Zea mays

<400> SEQUENCE: 29
atgccgacgc cgtcgcacct caacaagaac ccgcgctacc tggacttccg ggcggcgcgg       60
cgggtgccgg agtcgcacgc ctggccgggc ctgcacgacc accccgtcgt ggacggcggc      120
gcgccgggcc ccgacgccgt gccggtggtg gacctgggcg ccgcggaccc ggcgccggcg      180
ccggcggcgg cggtggcccg cgccgccgag caatggggcg cgttcctgct cacgggccac      240
ggcgtccccg cggacctgct ggcgcgcgtg gaggaccgga tcgccaccat gttcgcgctg      300
ccggccgacg acaagatgcg cgccgtgcgc gggcccggcg acgcctgcgg ctacggctcc      360
ccgcccatct cctccttctt ctccaagtgc atgtggtccg agggctacac cttctcgccg      420
gcctccctcc gcgccgacct ccgcaagctc tggcccaagg ccggcgacga ctacaccagc      480
ttctgtgatg tgatggagga gttccacaag cacatgcgcg ccctcgcgga caagctgctg      540
gagctgttcc tcatggcgct ggggctcacc gacgagcagg ccagcgccgt cgaggccgag      600
cggaggatcg ccgagacgat gaccgccacc atgcatctca actggtaccc gaggtgcccg      660
gacccgcggc gcgctgggc gctgatcgcg cacaccgact cgggcttctt caccttcgtg      720
atgcagagcc tcgtgcccgg gctgcagctc ttccgccacg ccccggaccg gtgggtggcg      780
gtgccggccg tgccgggcgc cttcgtcgtc aacgtgggcg acctcttcca catcctcacc      840 aacgccggt ccacagcgt gtaccaccgc gccgtcgtga accgggacct cgacaggatc      900
tcgctcggct acttcctcgg cccgccgccg cacgccaagg tggcgccgct gcgcgaggcc      960
```

```
gtgccgcccg gccgggcccc cgcgtaccgc gccgtcacgt ggcccgagta catgggcgtc    1020
cgcaagaagg ccttcaccac cggcgcctcc gcgctcaaga tggtcgccct cgccgccgcc    1080
gccgacctcg acgacgacgg cgacgccgcc gtcgtccatc agcagcagca gctagtcgtc    1140
tcgtcgtag                                                            1149
```

```
<210> SEQ ID NO 30
<211> LENGTH: 382
<212> TYPE: PRT
<213> ORGANISM: Zea mays

<400> SEQUENCE: 30

Met Pro Thr Pro Ser His Leu Asn Lys Asn Pro Arg Tyr Leu Asp Phe
1               5                   10                  15

Arg Ala Ala Arg Arg Val Pro Glu Ser His Ala Trp Pro Gly Leu His
                20                  25                  30

Asp His Pro Val Val Asp Gly Gly Ala Pro Gly Pro Asp Ala Val Pro
            35                  40                  45

Val Val Asp Leu Gly Ala Ala Asp Pro Ala Pro Ala Pro Ala Ala Ala
        50                  55                  60

Val Ala Arg Ala Ala Glu Gln Trp Gly Ala Phe Leu Leu Thr Gly His
65                  70                  75                  80

Gly Val Pro Ala Asp Leu Leu Ala Arg Val Glu Asp Arg Ile Ala Thr
                85                  90                  95

Met Phe Ala Leu Pro Ala Asp Asp Lys Met Arg Ala Val Arg Gly Pro
                100                 105                 110

Gly Asp Ala Cys Gly Tyr Gly Ser Pro Pro Ile Ser Ser Phe Phe Ser
            115                 120                 125

Lys Cys Met Trp Ser Glu Gly Tyr Thr Phe Ser Pro Ala Ser Leu Arg
            130                 135                 140

Ala Asp Leu Arg Lys Leu Trp Pro Lys Ala Gly Asp Asp Tyr Thr Ser
145                 150                 155                 160

Phe Cys Asp Val Met Glu Glu Phe His Lys His Met Arg Ala Leu Ala
                165                 170                 175

Asp Lys Leu Leu Glu Leu Phe Leu Met Ala Leu Gly Leu Thr Asp Glu
            180                 185                 190

Gln Ala Ser Ala Val Glu Ala Glu Arg Arg Ile Ala Glu Thr Met Thr
            195                 200                 205

Ala Thr Met His Leu Asn Trp Tyr Pro Arg Cys Pro Asp Pro Arg Arg
        210                 215                 220

Ala Leu Gly Leu Ile Ala His Thr Asp Ser Gly Phe Phe Thr Phe Val
225                 230                 235                 240

Met Gln Ser Leu Val Pro Gly Leu Gln Leu Phe Arg His Ala Pro Asp
                245                 250                 255

Arg Trp Val Ala Val Pro Ala Val Pro Gly Ala Phe Val Val Asn Val
                260                 265                 270

Gly Asp Leu Phe His Ile Leu Thr Asn Gly Arg Phe His Ser Val Tyr
            275                 280                 285

His Arg Ala Val Val Asn Arg Asp Leu Asp Arg Ile Ser Leu Gly Tyr
        290                 295                 300

Phe Leu Gly Pro Pro His Ala Lys Val Ala Pro Leu Arg Glu Ala
305                 310                 315                 320

Val Pro Pro Gly Arg Ala Pro Ala Tyr Arg Ala Val Thr Trp Pro Glu
                325                 330                 335
```

```
Tyr Met Gly Val Arg Lys Lys Ala Phe Thr Thr Gly Ala Ser Ala Leu
        340                 345                 350

Lys Met Val Ala Leu Ala Ala Ala Ala Asp Leu Asp Asp Asp Gly Asp
        355                 360                 365

Ala Ala Val Val His Gln Gln Gln Gln Leu Val Val Ser Ser
    370                 375                 380

<210> SEQ ID NO 31
<211> LENGTH: 1439
<212> TYPE: DNA
<213> ORGANISM: Zea mays

<400> SEQUENCE: 31
gacctccatt ttgattatct ctatcctgta cgtgccgaga gtccttcaaa gccgacgacg      60
agacgacgat gcagtcgtcg tcgtcatcag cctcgacgcc ggctgccgct tccggcctcg     120
tcttcgatct cgggtctgcg gcgggcgtgc cggagacaca cgcgtggccg ggggtgaacg     180
agtacccgtc ggtggagtcc gctggccgcg acgtggtccc ggtggtggac atggggggtgg    240 cctgcccgga cgcgacgcgg gcgttggcgc gcgccgcaga cgagtggggc gtgtttctgc     300
tcgtcggcca cggcgtgccc cgggaagtgg cggcgcgtgc cgaggagcag gtcgcgcgcc     360
tgttcgtgct cccggctcct gacaaggccc gcgcggggcg ccgccccggg gagcccacgg     420
ccaccggcta cggcaggccg cccctggcac tccgcttctc caagctcatg tggtccgagg     480
ggtacacgtt ccgcgccgcc accgtccgcg aagagttccg ccgcgtctgg cccgacggcg     540
gcgacgacta cctccgcttc tgcgacgtga tggaggagta cgacagagag atgagggctc     600
tcggtggcag gctgctcgac ctcttcttca tggcgctcgg cctcaccgac gtccagttcg     660
ccaccggcga gacggagcgg aggatccgcg agacctggac ggcgacgatg cacccaatcc     720
tgtgtccgga accggagcgc gccatcgggc tgacggcgca cacggactcg ggcttcatca     780
cgctcatcat gcagagcccc gtgcccgggc tgcagctgct ccgccgcggg ccggaccggt     840
gggtgacggt gccggcgccg ccgggcgcgc tcatcgtcat gctcggcgac ctgttccagg     900
tgctcacgaa cggccgcttc cggagcccta tccaccgcgc cgtcgtaagc cgagagcgcg     960
agcggatctc cgtgccctac ttcctctgcc cgccggagga catgacggtg gcgccgctcg    1020
cgtccgctct gctgccgggg aggaaggccg tgttccgggc cgtgacgtgg ccagagtaca    1080
tggaggtcaa gcacaaggtg ttcggcacgg atgcgccggc cctggagatg ctgcagctgc    1140
aggtggatga ggaagaacaa ggtgaaaggg ccgccaccac ctaagcccta aggaactact    1200
agctgaatcc ataaactaat aaagaattcg tgaataaggg cgttggaaga ctggacacaa    1260
cacaagagag ttgctatata tcgtatttct gaaatttaag gcaaatatct tagttaaaaa    1320
actggtatat ttaaatagac aatatatatc taaaataaag atagttcacc atttttacgg    1380
tcgaacaatg ataaagttat atattgtctg aatagtaaca aattaaagat ttccaggag     1439

<210> SEQ ID NO 32
<211> LENGTH: 1116
<212> TYPE: DNA
<213> ORGANISM: Zea mays

<400> SEQUENCE: 32
atgcagtcgt cgtcgtcatc agcctcgacg ccggctgccg cttccggcct cgtcttcgat      60
ctcgggtctg cggcgggcgt gccggagaca cacgcgtggc cggggggtgaa cgagtacccg    120 tcggtggagt ccgctggccg cgacgtggtc ccggtggtgg acatggggggt ggcctgcccg    180
```

```
gacgcgacgc gggcgttggc gcgcgccgca gacgagtggg gcgtgtttct gctcgtcggc      240
cacggcgtgc cccgggaagt ggcggcgcgt gccgaggagc aggtcgcgcg cctgttcgtg      300
ctcccggctc ctgacaaggc ccgcgcgggg cgccgccccg gggagcccac ggccaccggc      360
tacggcaggc cgcccctggc actccgcttc tccaagctca tgtggtccga ggggtacacg      420
ttccgcgccg ccaccgtccg cgaagagttc cgccgcgtct ggcccgacgg cggcgacgac      480
tacctccgct tctgcgacgt gatggaggag tacgacagag agatgagggc tctcggtggc      540
aggctgctcg acctcttctt catggcgctc ggcctcaccg acgtccagtt cgccaccggc      600
gagacggagc ggaggatccg cgagacctgg acggcgacga tgcacccaat cctgtgtccg      660
gaaccggagc gcgccatcgg gctgacggcg cacacggact cgggcttcat cacgctcatc      720
atgcagagcc ccgtgcccgg gctgcagctg ctccgccgcg ggccggaccg gtgggtgacg      780
gtgccggcgc cgccgggcgc gctcatcgtc atgctcggcg acctgttcca ggtgctcacg      840
aacggccgct ccggagcccc tatccaccgc gccgtcgtaa gccgagagcg cgagcggatc      900
tccgtgccct acttcctctg cccgccggag gacatgacgg tggcgccgct cgcgtccgct      960
ctgctgccgg ggaggaaggc cgtgttccgg gccgtgacgt ggccagagta catggaggtc     1020
aagcacaagg tgttcggcac ggatgcgccg gccctggaga tgctgcagct gcaggtggat     1080
gaggaagaac aaggtgaaag ggccgccacc acctaa                               1116
```

<210> SEQ ID NO 33
<211> LENGTH: 371
<212> TYPE: PRT
<213> ORGANISM: Zea mays

<400> SEQUENCE: 33

```
Met Gln Ser Ser Ser Ser Ser Ala Ser Thr Pro Ala Ala Ala Ser Gly
1               5                   10                  15

Leu Val Phe Asp Leu Gly Ser Ala Ala Gly Val Pro Glu Thr His Ala
            20                  25                  30

Trp Pro Gly Val Asn Glu Tyr Pro Ser Val Glu Ser Ala Gly Arg Asp
        35                  40                  45

Val Val Pro Val Val Asp Met Gly Val Ala Cys Pro Asp Ala Thr Arg
    50                  55                  60

Ala Leu Ala Arg Ala Ala Asp Glu Trp Gly Val Phe Leu Leu Val Gly
65                  70                  75                  80

His Gly Val Pro Arg Glu Val Ala Ala Arg Ala Glu Glu Gln Val Ala
                85                  90                  95

Arg Leu Phe Val Leu Pro Ala Pro Asp Lys Ala Arg Ala Gly Arg Arg
            100                 105                 110

Pro Gly Glu Pro Thr Ala Thr Gly Tyr Gly Arg Pro Pro Leu Ala Leu
        115                 120                 125

Arg Phe Ser Lys Leu Met Trp Ser Glu Gly Tyr Thr Phe Arg Ala Ala
    130                 135                 140

Thr Val Arg Glu Glu Phe Arg Arg Val Trp Pro Asp Gly Gly Asp Asp
145                 150                 155                 160

Tyr Leu Arg Phe Cys Asp Val Met Glu Glu Tyr Asp Arg Glu Met Arg
                165                 170                 175

Ala Leu Gly Gly Arg Leu Leu Asp Leu Phe Phe Met Ala Leu Gly Leu
            180                 185                 190

Thr Asp Val Gln Phe Ala Thr Gly Glu Thr Glu Arg Arg Ile Arg Glu
        195                 200                 205
```

```
Thr Trp Thr Ala Thr Met His Pro Ile Leu Cys Pro Glu Pro Glu Arg
    210                 215                 220
```

```
Ala Ile Gly Leu Thr Ala His Thr Asp Ser Gly Phe Ile Thr Leu Ile
225                 230                 235                 240
```

```
Met Gln Ser Pro Val Pro Gly Leu Gln Leu Leu Arg Arg Gly Pro Asp
                245                 250                 255
```

```
Arg Trp Val Thr Val Pro Ala Pro Pro Gly Ala Leu Ile Val Met Leu
                260                 265                 270
```

```
Gly Asp Leu Phe Gln Val Leu Thr Asn Gly Arg Phe Arg Ser Pro Ile
                275                 280                 285
```

```
His Arg Ala Val Val Ser Arg Glu Arg Glu Arg Ile Ser Val Pro Tyr
    290                 295                 300
```

```
Phe Leu Cys Pro Pro Glu Asp Met Thr Val Ala Pro Leu Ala Ser Ala
305                 310                 315                 320
```

```
Leu Leu Pro Gly Arg Lys Ala Val Phe Arg Ala Val Thr Trp Pro Glu
                325                 330                 335
```

```
Tyr Met Glu Val Lys His Lys Val Phe Gly Thr Asp Ala Pro Ala Leu
                340                 345                 350
```

```
Glu Met Leu Gln Leu Gln Val Asp Glu Glu Glu Gln Gly Glu Arg Ala
    355                 360                 365
```

```
Ala Thr Thr
    370
```

```
<210> SEQ ID NO 34
<211> LENGTH: 8800
<212> TYPE: DNA
<213> ORGANISM: Zea mays

<400> SEQUENCE: 34
taaatttgtg atccttgtga agttgttata tcatgaattg tgaacttgtt gcatttgtga         60
tcttttgtca actttgttgt attgtgaagt ttgatatgtt taccgatcgt attttagatt        120
tcgatcgtta ccggtgtatt ttccgcacca aacttttgtt tccgatgttt tcgaaatacc        180
gatatcgttt ccgtttctat agttaccctt ttcaatttta tttccgatta aaaatatgaa        240
aacggtaatg gttttagtgt ttatcgaccg ttttcatctc taatcatccc tgccggtgaa        300
gtttaatttt tcccttggct aaagagatgc aagctgctgt aaaatacgtt aaaacaggca        360
aggcagcccc agcagccagc atcgcgtgcc cgtctatgta catcagtgga tacgtagcat        420
ctctagtgag taatataacg attgcatttg gctggaggac gtatgttata taagtatgtc        480
atttaccagt tgcattagta tcttccctaa ctcctataat aactctcttc gtggaatgga        540
cgtagacgta tgctatataa gtattaaaaa atagtttttt aagctggtgt cctcaatttt        600
gctattgttc tcgtttttat ctttagttgt gtcacaaatt taatccgtac aacaaatcaa        660
aaataccata cccttcttat attaattttc taacataaca tttgtttaga tattttcagt        720
cgtgaaaata caattctaat tctaacgtcg tagtatcaaa tcaaaccatc cagaatttga        780
ccaagcttaa ttataaaaaa tataaaattt atgatactga atagatagca ttagatttgt        840
tatataatat atttttataa aataccattt ttatggtata aatattggta ctcctttact        900
ttaaactata gatagttttg actaaggatg caactagaat tgcatcctct tttcactgca        960
ccttcattag ttttaatatt tatttagatg ggcccttgca aactgtagat atcatctctt       1020
gcaacattct ttctatagca ccacgaaaat gtattgcggc tttgaaatta taattgaatt       1080
agttgtatca tttctttcac cgatgcgtta aattcaaaat taagtgttat atttcttcat       1140
```

```
aatttgttaa atatatagac cctataatcc accattattt actataatag catacattaa    1200
cattggtttt agcctacact acgacactcg aggcattgaa ttttcctcta tcaaagaatt    1260
atatgtgtag tagtattgtt cttgacaaaa agggggatta aaattaaact accaatattg    1320
atacttatct tatcacatcc atgaatacaa tcaacactct tacaaaagat aagatacaag    1380
attaaaaagt accatgataa tacattaaga ttattagcaa tgcattaaat taaataaatg    1440
tgcaagtgaa tcatgatttt agttttatct attttacttt taaaatatga tattctctga    1500
ctacttctaa gcataaatgt gattctaagt catgaccgat cgtgcttatt cagaaaaatg    1560
aaggagacac agatttctat aaaaaaaggt tgtcatggga ctattgggtc aaccatctta    1620
ttcatttggg aaaataagtt tagaacacat caacccattt tagatgttga gtttggccct    1680
aatggtccat tgaccttact tttgtggggt gacatagacc atctatccca agttattgtt    1740
gtgtcacatt ccctgatatc atgaatctat attttagctt tccgttttca tattttttagt    1800 cgttacatat tttttatccg cgtactagat taaaactcta gttgttgcaa tacattttgt    1860
tcattttttt ctatttcttc tttactaaca acatattcta gttcctagct acattcttaa    1920
gtaccatagt gctataaaca tttttttatcc tacattattc cacttaagaa attgaatttt    1980
ctgcataaaa aaattatatg tccagtagtg ttgtcttata aaagcataaa gtgattaaaa    2040
ttaaaaccat tattgatatc ttatttttca aaaaaaaata taagcttata gaaagtgaat    2100
taatttcatg gtaaattaat atagtttaaa ttgaattatt agtgttatta ctatgtttat    2160
tatcaatgaa acattttca tggttgatat aacttagtgt tacttatttt agtatttttt    2220
atataattct agttaacttt tagttttttga tttaaaaaaa cgagaattgt gtcctttgt    2280 ggagtgagta taaagaaagt aatatctgtt catcataatt tggtttttta aggtacgtga    2340
aacttgcttt atatttggac tcaagctatg tctaaataca tagtaaaaaa gcaatatttc    2400
tagaaaagac aaaacatctt ataatttaga atcaaggaaa tatatagatt ttatgtgcag    2460
tgagaagcca tttacaatgg aacgttcaac gttgggccaa tagatatttt gcgatatgat    2520
gatgggcata tttttgcatg gttgtccctc cactagctat agtttgatga tacgatacgc    2580
tgcacacacc attgggttgt accatgttag tgtagcaaca gtagaaaccc aattgtggcc    2640
gtgaaccatg ataatactag gtagagtgct agctagaggt ttcaggctat tgatgcgtga    2700
attaaacttt ctgttgtgtt gcgaggaaac gagtattgtg aaatatttga aacggttttt    2760
tttgtgaaag atttgaaacg gtatttttgt tgtgaaataa agatcaaggc taaataaatt    2820
caaactaata aaacatatta attgacggcc tgaagccccc gcccccatgg ccccatgcca    2880
tagcatcagg tcccacatga catgaggccg cgcctccctc tatgttggct ccctgccttc    2940
gccgttgtcg tcgctcccga actccctctc ctccctgtt acaaataccc ccacccgccc    3000
ggacagcttc cctgcacact cgcagctcgc acatctcatg gtgtcctaag aacggcaaga    3060
gccagctctg cctagcagca gcgcacagcc acatccatgg acgccagccc gaccccaccg    3120
ctccccctcc gcgccccaac tcccagcatt gacctcccccg ctggcaagga cagggccgac    3180
gcggcggcta acaaggccgc ggctgtgttc gacctgcgcc gggagcccaa gatcccggag    3240
ccattcctgt ggccgcacga agaggcgcgg ccgacctcgg ccgcggagct ggaggtgccg    3300
gtggtggacg tgggcgtgct gcgcaatggc gacggcgcgg ggctccgccg cgccgcggcg    3360
caagtggcgg cggcgtgcgc gacgcacggg ttcttccagg tgtgcgggca cggcgtggac    3420
gcggcgctgg ggcgcgccgc gctggacggc gccagcgact tcttccggct gccgctggct    3480
```

-continued

```
gagaagcagc gggcccggcg cgtccccggc accgtgtccg ggtacacgag cgcgcacgcc    3540
gaccggttcg cgtccaagct cccctggaag gagaccctgt ccttcggctt ccacgacggc    3600
gccgcggcgc ccgtcgtcgt ggactacttc accggcaccc tcggccaaga tttcgagcca    3660
gtggggtgag taaagaagaa gatggcgccg aatttacatt tataagtagg accagcagaa    3720
gcccctgccc ctgggggcct tagcattgca ttcgactgat gaatacgcat ggcaggcggg    3780
tgtaccagag gtactgcgag gagatgaagg agctgtcgct gacgatcatg gagctgctgg    3840
agctgagcct gggcgtggag cgcggctact accgggagtt cttcgaggac agccgctcca    3900
tcatgcggtg caactactac ccgccgtgcc cggtgccgga gcgcacgctg ggcacgggcc    3960
cgcactgcga ccccacggcg ctgaccatcc tcctgcagga cgacgtcggc gggctggagg    4020
tcctggtgga cggcgagtgg cgccccgtcc ggccgtccc aggcgccatg gtcatcaaca    4080
tcggcgacac cttcatggta acgaacgaaa gcgccggctc ctctgctttt cttggcctct    4140
ttgtccctgc cctgtgctgc tgtgcatatt cattcattca gttctctgtg gggttttttt    4200
tttgtttaat ttttttttgg gatcgtatcc agtgcacaag ggccacgccg tgcacaaatg    4260
cacaaaacga aatctggccg tccattttcc atccaacgac atgacggcgc ggggggtttt    4320
tcacaaaaca gactcggcaa gctacggagg ttgcgggagg gttcatctgc atatttacga    4380
cggccgttgg atggaaaatg gacggccaga tttcgttttg tgtatttgtg cacggcgtgg    4440
cccttgtgca ctggatacga tcccattttt ttttttgccc cgaatcctag tggacctaac    4500
tggacagatt acagcacgca cacgtaggca tgtcatgtag cagcactgca gtcgggtgca    4560
gtccagtcca gtcctgtcca gccgcgacac tgtagtacat agcgatgcaa cggagacacg    4620
cgttggagtt ggttccatct cttctcggcg gccgtgccga ggcttccgcg gggaagctgc    4680
gacaacagaa cggaccgccg ggggtgggca ggcagcaagc tccctgttgg cttgtgccgt    4740
tgcgcagcgg cgggtaccgg acaacgcttt cggcggcgcg cggcctcgtc ggcttcccct    4800 gttttttgatg ccgcctctcg gtgtccgggg accgggagga tcgatggggc ccgtgccgtc    4860
tgatccgcca cgcgagcggt cctatgcgat cgcccgcacg agcgcggggg ggccgtggaa    4920
cagtacacag ctgggtcact cactcactca tcccgctggt tgtggctgct tggttgcaac    4980
ttggctcggc tgtctgtctg ttgccccgc cgcgtttttct agccgtttcc gctttgctcg    5040
cggtttcgct ggcgatccgg cacgcggcgc ccacacccgg ggctggcccc ttggccgagt    5100
gggtggcagg cacttgcatg catccggccg gtttcccgcg accaagctgg cccgccgcaa    5160
caatgagagt gagacgagac tttgtgtcag tgtgtgtatg tacatgtatg tctgcgcgac    5220
agccctaccg tccgacacga tgattcttgt gcactgtact gtactgtact aactcccccc    5280
accccctccg gtatgtaacg catgccatat gcaggcgctg tccaacgggc ggtacaagag    5340
ctgcctgcac cgcgcggtgg tgaaccggcg gcaggagcgg caatcgctgg ccttcttcct    5400
gtgcccgcgc gaggaccggg tggtgcgccc gccggccagc gccgcgccgc ggcagtaccc    5460
ggacttcacc tgggccgacc tcatgcgctt cacgcagcgc cactaccgcg ccgacacccg    5520
cacgctggac gccttcaccc gctggctctc ccacggcccg cggcggcgg ctccctgcac    5580 ctaacgagcc ggccgtctct ttcgccgggg cccgcgcggg gttcgcccac gtggtgatca    5640
ggtggcagac atgtggccca cgggccccgc gccgccttcc ccattttttgg acgaccctac    5700 tgctactact actagtgtac atatgcaaaa aaatacatat atatataggt actttctcta    5760 atattttttat atataagcaa ggcggcctgg tgttcttttc tttgttttgt cgacaactgt    5820
ttgatcccat cctatggacg atggatagtt caatgtttgt acgtacgtaa ctactctcta    5880
```

-continued

```
tagactagaa tgggctcatg aaactggacc gatcgacacg gacgtcacgt gcgtctggta    5940
ccggtagtgc aacgggtgcc gaatgtttgc tgggcccgga cgagaatcgc ttctcctcgt    6000
cctcggtcct caccctgaac gaacgaataa ggaaaatgct gcaccgaaag ctccagacgt    6060
ttccgaattc caaattccaa aaccccaaat cttcttgctt cacatcagtc ttacccggtt    6120
catctgtgac aaaaaaaaaa tagtgctagt ttaggaactc aggtcgagat tgaaggcaat    6180
tgtggaggaa tttaccctat aatccttatg agaatttgag ttcccaaact aactgagttg    6240
gagcattcaa catttcccta aattttgtgc acatgtttct ttgctattta tctttggaca    6300
tgggacgatg ggagacgcag atttagggga cccttcaatt cagaacttca ggtgcacaaa    6360
ccgaggttgg cttgcctgca ttcttgtttc ggacatgccc aactaggcca ctactcacta    6420
ccttcatctg agataccaat tgctgaccta aatgacaagt atacacttac atttcagtga    6480
tagctgcaac aaaaaaaaaa atcttaccgc attttatctc tgcattctgc atgccgcatc    6540
ctgaacatta cgtatctttc ccggtgctct gttgcgttct cacgcagttg atggcatgca    6600
gtcttgcgcc accgaatcca gtgtactggt cgtggtgact tgtcgcacag acagcagccc    6660
ggcagcacca agcgtgtcac tgtaaactgt tgggcgttaa acaacaactt gcacaacagc    6720
tcaaatatgg catatgctat ccgacaaact gaacaaggtg cccaattgat ctgaatgtac    6780
ctgtgatttc cagcactatc gtacagcaac gttgtcaaaa caagtggggt ggggttgggg    6840
acagattttt tcgataaaga agcttttata aaaaataaca atgatacaaa tcctgggtta    6900
tagatgtaca gaaagcacga agcacgaaag tccagtccaa agcacgtttt tttgcctggt    6960
actagcccga tccggccggc acgaataagc gggtcgagct cggacgggaa gctaagcacg    7020
acggactagc ccgacacgac ccgtttacct ctaatcccgt taaacccgct tttttgcact    7080
aaaccgtgct taccgaaccg tttagcccgt tttttggcct gatttttcgt gcttaacggg    7140
ccaggctcgg acaaggaaac aagcccgcgg gcttagacga tccggcctgg tttttttaacc   7200 gtgcctagcg ggtcgagccc aaaataggtc gggcttcact gggcccgagc cgggcgaccc    7260
gtttggccat ctctaacctg agtacaactt ccgacttctg caaaatacat acagccaaat    7320
aaaagaaaag taaaaagatc taaaaaatct cagctagaaa caatcaatcc gaagactaga    7380
tcgcctccca taagtctgga aaaaagagac catggccact tgcaccaaga tgtgtgcatt    7440
attctacggt tacaccaaag attttttgttc tttaagggct agtttgggaa ccataatttt    7500
caaagggatt tctattttcc taaggaaaat tagttcattt ttccataaga aattagaaat    7560
ccattggaaa attgtggttc tcaaactagc cctaagcgtc gaaaagaacc atatgcatat    7620
ctagagacaa aattcctcta atttctattc aggcttcagc acatatactt cacgtgcttg    7680
cgtcaagttc cttgggccgc cacatggact tatggacttc tcgacgcagc gaaagccgtc    7740
gttgcccttg gtgtagctag gtcatccgca cctcccactg gccagtggcc actgcaggga    7800 cttgccatg ggcttgtttg gttcagcttt tttctgacca gcttttctga aaatctggct     7860
gtgtgaagaa tctggctgtg agagaatctg agtatcatta cgattacgtg tggatgaaga    7920
taaagttgtt cataggctc aggatctaga aagtgacgga ttcctactat tacaatgact      7980
caaccgatta tgtgtttatg ttgattttgg atgatttttg ccccaacaaa ttttatagaa    8040
gctggctgaa aagctgagcg tttggcagtc cacaacagtt tttggtggcc agaagctgcc    8100
agaagccgat acaaacaggg tccatgcttt ccatttcgtt taccgtgtac gcggtgtccc    8160
tcacaatcaa tcagtttacc ttgtggctcc aacacacatc aacctcggca caacaacact    8220
```

```
gtgaatcatt ttcggcggtc catattattt tcgacggttc atccctggcc gccgaaaatt    8280
gtctgttatt ttcggcggct tgacctagcc gtcgaaaata ggctgctatt ttcggcggcc    8340
aaatccgagc cgccgaaaat aaggctttta aaaaccgtcg gctccttctt cttctctgtt    8400
ctttctctcc tctcccaaag cccgccgccg ctcacccgcc gctcgctcgc cgggctgccc    8460
gccactccgc cgtcgtcgtc gagccaccgc atcgagaggt aaattttttt tgcgtgtttt    8520
attccttatt ttcggcggtt gatatttagg cgccgccaaa attagtgtat atttgtaatt    8580
gtgtttgttt aattactatt tgtaattagt attattgttt aattcgattt cattaatgta    8640
ttagtggtat atgtgattta gggattaggg gcatattgta tttaggcatt aatttcatat    8700
taatatgtgg tattattata ttattggttt taatagtaca ttatattggt acgtagaata    8760
gttgcattat tagtgtttgt ggtacttagt ttgacttgat                          8800
```

<210> SEQ ID NO 35
<211> LENGTH: 8859
<212> TYPE: DNA
<213> ORGANISM: Zea mays

<400> SEQUENCE: 35

```
cctattttgt gtctaatact cttcttatat taattgtttg gtcaaacttt agataaattt      60
gactaatgat gcaattaaaa ctgcatcacc tttactaagg tactgcttta tatgtttcga     120
caaaattttc aattattctc tatgtgtttt aatctttgcg ctacacctcc attgattaa      180 atactcattt attttaaacc ataacttaaa ttatatcgga tctttgcatc ctttctatgg     240
caccatacat gaatcgatat tttggctgca aatttttaat catgttagtt ttagcatttt     300
ttcatatcca tgtgttaagt ttgaatcatg tgttgttttt atataattta ttgaaaatat     360
agatcctaaa cttcactaat acttacaaca atagcatcat catgtgtttt aatccacgcc     420
acaacactca aggcattgaa ttttcttcta ccaaagagtt gtatgtgtgt attgttckttt     480 aaaaaataga gtgattataa ttaaactacc agtattcata tgtaaaatgt atagacatct     540
aaaataaaat ttgcaaaaaa cattgttgca gactttcaat ataattaaga atgggtttta     600
gggtcatgat atatggtttg ttaaagaaac ttgttttttt ttgcaattga taaactataa     660
aatacatttt cactattgtg tgcatatgta cttggtatac atagtggcat atatcatttt     720
tgtttacttt gaggtttgaa ttatctatgt taaaattgga taacatagat acattggtgt     780
gcgtcctttg gcccatttac ttgactgagg agcaatacta taaagtaaaa catatttgga     840
tattttatct taaactccta gcataatatt gatttaatta tgaacaaata tatgtttagg     900
tgatagtttc atgggtggta aactatataa gaaggcttac catgatcttt gcaaactcta     960
ggctatgaaa gagttccatg atttgtctta gaagcataga caaaacagtg ataatgatct    1020
aaatcacact tatggcactg atgaccatat atgcaaagct aaatgcatgt taagttgtat    1080
tatatcatat gttacaatg actatcgcat ataacgagga atacattgtc tatatagata    1140
gctattactg tagtagtgcc aaatgttgga caacatgaat cataatcttc aaacctagag    1200
aaattgtagt cagtcgtaca catatcgtct agtaagttgt ctatactttt tatttattgt    1260
atcaaatttt attgttatct tgcttgcttg tttgtttgta ccatagacac aatatggtca    1320
aaaagtggtc aatcgattcg aagaagattg caattgacga gtgctaacag ttgatccttt    1380
tgttgtgcac gctagcggag tagcatgaaa agagtaaaat atgaaattag cgttctaaac    1440
tgtttgtgct ataggtactt cgtatttaat ggagtgacta actataggaa ggtgagagct    1500
cagaagtcag caccctcaca cagagttcta gagttagtgg tcatcgaacc acgacaaact    1560
```

-continued

```
acatgatgag cagaagaggc aacatcaaga ctatgatcaa tagtttcggg tcaatgaatg    1620
acatcgtgat gagtatttat ctaactatat agaacaacaa cacatgatgt tttaagtaag    1680
ttcaactgat cttctattgc tatctttaag tatttaacgt agcgaataat gttttatcta    1740
tttcattcat aaataatgtt gtgacaaaag gggataacca tcacttttac catgttctag    1800
ataccacaac catctccacc atcataatgg gttcttcatt ggtgcttgga cctcaaataa    1860
tcatatctat agccaactta gctcaattct aataaaatta ggcaacttgg cttcattgta    1920
gcaaaaatag ccaacttagc tcaatttat ctaaacttag ctaatctagc acaacttaga     1980
tcaatattag gaaaaactaa tcaatctaat ctagctcaac tatagcgaaa gatagatatt    2040
gtagcataac ttagtagatc tatctcaaat tttagcaaaa actaatcaat ttagataaac    2100
tctataaaat tttaatcatt atgacttatt tccaactaat tgtaacttgc atgatttta      2160 tgttccttct ttataattag caacacctaa agacacgaat gatgagggggt ctaacgcatt    2220 cattaaccag ttgttaaata atactctagg tagatgataa gaactctaat tattctatga    2280
atctaagcta aaagatgttt aatatttaag tattggtgtt tattatgtta tttagaacga    2340
ttcatgttac ttaaagattt gttatgattt ttaaatatga ttatgataat ttatgtggtg    2400
tggattaact tgtgaacata tgtgatgtag atgaatatgt atgttgtgga tggaaccata    2460
tgaatatata tacacactca tatactattc gttggtgtag gtaaagcttc atccatcggt     2520
aattactaaa tggtcttcag tcattaccac taggtgaagc ttcacacgac cgataattat     2580
tgaagaacgc tcattaattt ccggtaatgg cttattggcc ttcactagtc ggtgaaaatt     2640 agctatttt ataccaataa aaattagcta atatatgtaa accaggtcta attttttatgg      2700 gcctcttacc gaccaaaatt gattagatta ttgttacaat agtttagtc aaaagctagc      2760 tatgctataa aaattttgaa ttaaagtgag tttcgtaata aaaattgcat acttttaaaa     2820
taaaataatt aaaaaacagt ttttagaaat acaatcaaac accttatgct ataaaaaaat     2880
tgtaatgtac ctacaaatat ataatacttt actttaaaat aggcctgtgc cttctcggct     2940
ctatatgggc tgcctccaac gaagcgccat ggccatgggc tccactgtgt cgggtcccac     3000
atgaggccgc gcctccctcc aaatgttccc tccctgcctt cgtctttgtc gttgctcgca     3060
aactccctgt cctcccctgt tacaaatacc cccacccgcc cggacagctt ccctgcatac     3120
ttgcagctcg cacatctcat ggtgtcgcag gaacgacaag agccagctgt gcctagcagc     3180
agcagcagca gcgccaagcg cgcagccacg tccatggacg ccagcccggc cccgccgctc     3240
ctcctccgcg cccccactcc cagccccagc attgacctcc ccgctggcaa ggacaaggcc     3300
gacgcggcgg ccagcaaggc cggcgcggcc gtgttcgacc tgcgccggga gcccaagatc     3360
cccgcgccat tcctgtggcc gcaggaagag gcgcggccgt cctcggccgc ggagctggag     3420
gtgccgatgg tggacgtggg cgtgctgcgc aatggcgacc gcgcggggct gcggcgcgcc     3480
gcggcgcagt ggccgcgggc gtgcgcgacg cacgggttct tccaggtgtg cgggcacggc     3540
gtggacgcgg cgctgggggcg cgccgcgctg gacgcgccca gcgacttctt ccggctgccg     3600
ctcgccgaga agcagcgcgc ccggcgcgtc cccggcaccg tgtccgggta cacgagcgcg     3660
cacgccgacc ggttcgcggc caagctcccc tggaaggaga ccctgtcgtt cggctaccac     3720
gacggcgccg cgtcgcctgt cgtcgtggac tacttcgtcg gcaccctcgg ccaggatttc     3780
gagccaatgg ggtaagtaag gtagtaagaa ggagcgccgg tttacattta ccgcacgtcg     3840
gcgtgcggtc gagtcgggac tcgggagacg tatgaacccc cgtcccgtcc catgcatgtg     3900
```

-continued

```
tggcaggtgg gtgtaccaga ggtactgcga ggagatgaag gagctgtcgc tgacgatcat    3960
ggagctgctg gagctgagcc tgggcgtgga gctgcgcggc tactaccggg agttcttcga    4020
ggacagccgg tccatcatgc ggtgcaacta ctacccgccg tgcccggagc cggagcgcac    4080
gctgggcacg ggcccgcact gcgaccccac ggcgctcacc atcctcctgc aggacgacgt    4140
gggcgggctg gaggtgctgg tggacggtga gtggcgcccc gtccggcccg tcccgggcgc    4200
catggtcatc aacatcggcg acaccttcat ggtaacgaaa cgaaagcgct cgctcctctg    4260 tttttccttgg ccgctcttgt cctgtgtgta tattcagttg agctctctct gtgctgttat    4320
ttcccgaatc ctagtggacc taaacgggca ggttattaca gcacgcacac gtaggcatgt    4380
catgtagcta gtacatacat agcgatgccg atgcaaatgc aatagagaca tgcgttcgag    4440
ttggttccta tctcggcggg ctacggcagg tacacgcggc cgcggcgcgc tctctctagt    4500
ctatccgcgg ccgcgcccag gccgatcgag gcttccgggg gagagttgcg acaagagaac    4560
ggaccgaggg ggtcggctag cggtagcaag ttccctgttg gtttgtggcg ttggagcgtt    4620
gcggagaggc ttgcgcggcg gcggggacgt cgacggggac gtggcgggga gacgatacga    4680
tgggtgccgg gcagggcaac gctttcggcg ggtggccgtg tccaggtgcg cgcggccttg    4740
tcggtttccc cctctcggtg tccatggccg agaaatgggt cgacgaccga gaccgacgct    4800
cggtgcggcg cccatcccgt ctgatccgcc gcgccacgcg agcggcccta tgcgatgccg    4860
cacgggcgcg gagggccgtc gcgcggagta taatgtatag tatatagtac aaggttggtt    4920
ggagtcgggt tgggttggat cgggtcaccg gtacgtggtg gctgctgttg cccccgccgt    4980
ttccgcttgc acttttgtcg cggtttcgct ggcgatccgg cacgcggcgc ccacaccacg    5040
ccggggctcc aaacagctcg ggcccttggc cgtgtgggtg gcaggcactt gcacgcgtcc    5100
ggttgtcgcg gcctggcccg ccgcgcggcg caccgcaaca atgagacagc ccgacacgat    5160
gattcttgtg cactgtgcta acccgcatgc catgcaggcg ctgtcgaacg ggaggtacaa    5220
gagctgcctg caccgcgcgg tggtgaacca gcggcgcggcg cggcggtcgc tggccttctt    5280
cctgtgcccg cgcgaggacc gggtggtgcg cccgccggcc agtgctgcgc cgcggcgcta    5340
cccggacttc acctgggccg acctcatgcg cttcacgcag cgccactacc gcgccgacac    5400
ccgcacgctg gacgccttca cccgctggct ctcccacggc ccggcccagg cggcggcgcc    5460
tccctgcacc tagcgagccg ggccaaggcc gtctctttcg ccccacgtgc gcgcccagct    5520
gggcaggtgg ccagacacgc ggcccgcggg ccccgcgccg ccttgccatt ttttgacgct    5580
ggccctactg ctgtgctact agtgtacata tgcaagagta catatatata tatatata    5640 cgtattttct atatattata tataaaagca aggcggcccg gtgcccttct cttgtttgt    5700 ccacaactgt ttgatcccat tattctatgg accatggata cttcaatgtt tgtactaaga    5760
ccgtgaacgt gggattcttt tccttcctct gtgttttttc tgagaaaaat taaactgatt    5820
tctgtgaaat ttctttgttt taacaagaaa acagaaaaat tacatgagga aaacgctcca    5880
tttatttcaa caagaaaaaa atacatgaaa cagaaggaga aaaaacgtgt tcgttctatc    5940
attttcacac gagaaaaaaa aacatagaaa acagaaaaac tccccgcgtt cagatgagct    6000
caagaaaatg gaacgacacg gacgtcaccc gcgtcttgta gcagtgggcg cacgggtgcc    6060
gaatgtttgc tgggcccca agagaatcgc ttctcctcac gctgaatgaa tgaatcaacg    6120
agggaaacgc tgcaccctga gttccagacg tttccgaatt ccaaacgttt ttgtggcgtg    6180
cgtccatggg gcgcccccaa acttcggacg tttccggcgc tccaacaaat cttctcgctt    6240
cacacgtcac cgtcgtcccg gattcatttg cctcgtcgct ccaccattcg ctgctctcct    6300
```

-continued

```
ctccacgtac tcttaccctg acctttggga aagaactgaa cattcgagat gcacaacagt    6360
tcaaatataa catatgcagc acaagatcgt tcgactgcta tccgacaagc caacaacgtg    6420
cccagtagaa ctgaatgtac ctgtgatttc cagcactaac ttacagcaac gttgtgaaaa    6480
aacaaaaacg aaaacaaacg gcagaaaaaa cagatgtatt gttctacagt tacaccaaat    6540
attttctggt cctttcagca ccaacaagag ccatacgcat atctagaaga caaaattcct    6600
ctaatttcac ccctacgtgg tagcagttcc tcctcaacac agttcacgtg ctagcgtcga    6660
gttctttggg ccgccacatc gacttctcga cgcagagcag gccctcgctg cccttggtgt    6720
aggtcatccg cacctcccac tgcacggact tggccatgct ctccagctca tttatcgtgt    6780
ccgcggtgtc cctcacgatc agcttgccct gtggcctcag tacacggtcg acctcggcga    6840
aaactgcagc cagtttgcat ctgtaaacag gcaacacaga tttttagtat ctaaaacact    6900
gcaggcaaac gccacaggtt ttagtcgcaa gaagcaataa aagcatgcaa acaatgctac    6960
gtgtacgtat caaaggaaca tgtcaaaact cgttgcatga acgatcattg atgtttcctt    7020
gctgaactag tcacatcagt ctgcttcaac ttctgggttt cactagtaga tataccagaa    7080
gggtagaata atgtgaagag caagaaatac agacctcttt ctgagctttg agaacagatg    7140
gtccgcgtgc agaaggtcat acgttcttgg gtaagtgctg aaagactcgc accagtcatg    7200
gtacatgcca aacaaaccgc gctcgtagat gatgggcagc gtgtctggtg aatcgatcgg    7260
cacgatattc atgacccaga cctttggtc cctcagagct gcagcaaaac tgccatgcaa    7320
caatgtaaag cattagtcaa gaagaaggtg tacagtgcat ttctccttgt caacagtctt    7380
cagtaacaaa aaaaaagtgt tatgcttgac tgaatctttc aaagaaatat gcttgatgac    7440
ttatggtgga caagttgcct gttatagtgt tatgttttaa ttaactatgt gccagcttgg    7500
gtaactagta gttatgtagt gtgatctgaa ttaccaaaat ataaataaat aaataaacat    7560
gcccaagaaa ctacgaaaac catttactta ccctccatag acagctctca tgtccatgac    7620
atttctcact ttggaccagt caattcccat gccattcaca tacgatttac ttacaacccg    7680
tttccagtgg gcattatctg cctcaaaatc ttcatttgca ggctttccat agacaccaac    7740
cttggaacca tcaatccaga aaggggtctt ctcaagcctt tgcggccata actctggcca    7800
ttttgatcct cggactttg agccaccagg cagtttgtgc atgcatgctt ccaacggtac    7860
attcctgcaa atcaaaaggc tgtgtaagca aagcagagaa gcacttttct ccattgaaaa    7920
tatactcttc tcaaagaacc gaaaccatac caagcagcat ctgcatcatc agattccttg    7980
cacaatggcg ggctgttttc agatctttc tcatagcaaa tattgtccat tggtttctga    8040
tatatgacca taccaacttg gtttaactta tccttagtct tgttgaccat cttccagcac    8100
atggactttg tcaaagtaga catggctgaa aagggtatgt ggccacatgt tatgttagaa    8160
ataaaattca attttgaaca gttggtccat agcatgtatt ttgaacaaat gcaatccttc    8220
tccatccatg aaagaagttg acccttcata cttaggatta ttcagtactt tcactcatgt    8280
ctgctgaatt tgttctcttg gtagttgcta tacaagaaag ggggaagtac agagtagcta    8340
aacttataca agctatagtc tgatatttgt atgaaacata aattttggta tggatgtctt    8400
attaaaatgg gaggttgtat aatatttttc tagcctacct caacttgctt gagactaaaa    8460
ggctttgttg ttgttgttga ggctgtatgg tgctttgact ttacaaatca agttatcagc    8520
taccctactt atggatatac acctctcata aaatgatggt aagaagtttc gatatgtcac    8580
attaacataa gaacttcatt cagttagggt acaacgaagt taagtagtta cggaaatacc    8640
```
attccaaatc tcaacatcct ctgggagctt ttggtaaaca ggagtggcag accagacaaa          8700
gtaaccacca gggcgtaaca agcggttcaa ttccagcaaa agcatgccac ctaaaagtag          8760
cgagccagca ataagattca gttctatagc aaatcaataa atgaaaggag gacatgtcaa          8820
tatgtaacca gcaggacaaa ccttcgatgt gccaaggga                                8859

<210> SEQ ID NO 36
<211> LENGTH: 1788
<212> TYPE: DNA
<213> ORGANISM: Zea mays

<400> SEQUENCE: 36
aatcccagcg tgcgtaatct attgcccaca tgccgacgcc gtcgcacctc aacaagaacc           60
cgcgctacct ggacttccgg gcggcgcggc gggtgccgga gtcgcacgcc tggccgggcc          120
tgcacgacca ccccgtcgtg gacggcgcg cgccgggccc cgacgccgtg ccggtggtgg          180
acctgggcgc cgcggacccg gcgccggcgc cggcggcggc ggtggcccgc gccgccgagc          240
aatggggcgc gttcctgctc acgggccacg gcgtccccgc ggacctgctg gcgcgcgtgg          300
aggaccggat cgccaccatg ttcgcgctgc cggccgacga caagatgcgc gccgtgcgcg          360
ggcccggcga cgcctgcggc tacggctccc cgcccatctc ctccttcttc tccaagtgca          420
tgtggtccga gggctacacc ttctcgccgg cctccctccg cgccgacctc cgcaagctct          480
ggcccaaggc cggcgacgac tacaccagct ctggtacgt tgcgttgcgt gcttgtgtgc          540
gcgcacacct gccgaccgcg gccacaccgt acgcaaccca cgcgtacgta cgtgcgctag          600
ctacctgctt cgctcgcttc gctcctctcg cctcgccatg catatgcacg tacggccgta          660
caggtacagc agcaggtcac acgcacgaac gcacgcacgc accagcaccg atatgataca          720
tcatcgacgt gtcgtccccc cgtctaaggc catgcatgca tgcaagcacg cctagctagc          780
ccttttggct tgctagctga cgaggggagc taggacgagc atacttactg tgcgcgtcat          840
gctcaattgc tcacactata ctactacttg ttactacagt gatgtgatgg aggagttcca          900
caagcacatg cgcgccctcg cggacaagct gctggagctg ttcctcatgg cgctgggggct          960 caccgacgag caggccagcg ccgtcgaggc cgagcggagg atcgccgaga cgatgaccgc         1020
caccatgcat ctcaactggt gggtatatat tattgtctgt catgttgtcg tcgtcgtacg         1080
cgttgcggtt gggtgtacat gtatataaca caaacaacaa aaaactaacg ccgtgccgac         1140
gacgacgacg atcatcaggt acccgaggtg cccggacccg cggcgcgcgc tggggctgat         1200
cgcgcacacc gactcgggct tcttcacctt cgtgatgcag agcctcgtgc ccgggctgca         1260
gctcttccgc cacgccccgg accggtgggt ggcggtgccg gccgtgccgg cgccttcgt         1320 cgtcaacgtg ggcgacctct tccacatcct caccaacggc cggttccaca gcgtgtacca         1380
ccgcgccgtc gtgaaccggg acctcgacag gatctcgctc ggctacttcc tcggcccgcc         1440
gccgcacgcc aaggtggcgc cgctgcgcga ggccgtgccg cccggccggg cccccgcgta         1500
ccgcgccgtc acgtggcccg agtacatggg cgtccgcaag aaggccttca ccaccggcgc         1560
ctccgcgctc aagatggtcg ccctcgccgc cgccgccgac ctcgacgacg acggcgacgc         1620
cgccgtcgtc catcagcagc agcagctagt cgtctcgtcg tagccgagac cgatcgccgg         1680
agactgatgc tgatgatgat gcatatatac atgagagaaa tcgtcgagta gactagccga         1740
ttgcaaaagc aaccccagct gccgaaacct ggcatatcga tcccattc                     1788

<210> SEQ ID NO 37
<211> LENGTH: 1698

```
<212> TYPE: DNA
<213> ORGANISM: Zea mays

<400> SEQUENCE: 37
cgtgccgaga gtccttcaaa gccgacgacg agacgacgat gcagtcgtcg tcgtcatcag      60
cctcgacgcc ggctgccgct tccggcctcg tcttcgatct cgggtctgcg gcgggcgtgc     120
cggagacaca cgcgtggccg ggggtgaacg agtacccgtc ggtggagtcc gctggccgcg     180
acgtggtccc ggtggtggac atggggggtgg cctgcccgga cgcgacgcgg gcgttggcgc     240
gcgccgcaga cgagtggggc gtgtttctgc tcgtcggcca cggcgtgccc cgggaagtgg     300
cggcgcgtgc cgaggagcag gtcgcgcgcc tgttcgtgct cccggctcct gacaaggccc     360
gcgcggggcg ccgccccggg gagcccacgg ccaccggcta cggcaggccg cccctggcac     420
tccgcttctc caagctcatg tggtccgagg ggtacacgtt ccgcgccgcc accgtccgcg     480
aagagttccg ccgcgtctgg cccgacggcg gcgacgacta cctccgcttc tggtacgtac     540
gagcgccatg tcacgtgctt gtgctttcat gcctcgtacc gtcgtcgtgc tgtacgtgtt     600
atgtttatcg gccggtacgt cacgcgtgct acactggtta acgacgtgag cgtgcccacg     660
ttgactgcat gcatgtgcat gcgcgcgccc agcgacgtga tggaggagta cgacagagag     720
atgagggctc tcggtggcag gctgctcgac ctcttcttca tggcgctcgg cctcaccgac     780
gtccagttcg ccaccggcga cacggagcgg aggatccgcg agacctggac ggcgacgatg     840
cacccaatcc tgtacgtacg tcaaaaacga atatctgacc aatgcaaacg tttttctgca     900
atgccagtca tccactcatc ctgtacgtac ctctggactc tgcttgtcca tctactgatg     960
acacgtatgg taggtacccc aggtgtccgg aaccggagcg cgccatcggg ctgacggcgc    1020
acacggactc gggcttcatc acgctcatca tgcagagccc cgtgcccggg ctgcagctgc    1080
tccgccgcgg gccggaccgg tgggtgacgg tgccggcgcc gccgggcgcg ctcatcgtca    1140
tgctcggcga cctgttccag gtgctcacga acggccgctt ccggagccct atccaccgcg    1200
ccgtcgtaag ccgagagcgc gagcggatct ccgtgcccta cttcctctgc ccgccggagg    1260
acatgacggt ggcgccgctc gcgtccgctc tgctgccggg gaggaaggcc gtgttccggg    1320
ccgtgacgtg gccagagtac atggaggtca agcacaaggt gttcggcacg gatgcgccgg    1380
ccctggagat gctgcagctg caggtggatg aggaagaaca aggtgaaagg gccgccacca    1440 cctaagcccct aaggaactac tagctgaatc cataaactaa taaagaattc gtgaataagg    1500
gcgttggaag actggacaca acacaagaga gttgctatat atcgtatttc tgaaatttaa    1560
ggcaaatatc ttagttaaaa aactggtata tttaaataga caatatatat ctaaaataaa    1620
gatagttcac catttttacg gtcgaacaat gataaagtta tatattgtct gaatagtaac    1680
aaattaaaga tttccagg                                                  1698

<210> SEQ ID NO 38
<211> LENGTH: 4095
<212> TYPE: DNA
<213> ORGANISM: Zea mays

<400> SEQUENCE: 38
cggtctaagt gaccgtttga gagaggaaaa gggttgaaag agacccggtc tttgtgacca      60
cctcaacggg gagtaggttt ataagaaccg aacctcggta aaacgaatca ccgtgtcatc     120
cgccttattt gcttgtgatt tgttttcgcc ctctctttcg gactcgttta tatttctaac     180 gctaacccccg acttgtagtt gtgcttaaag tttgtaaatt tcagattcgc cctattcacc     240
```

```
ccctctaggc gactttcata taaatattgg gagaaatatg aaaaacaaat gaaggtcgaa      300
cgagtcagag acaccataaa aaagaggtcg tcttaactag ggtgctaaac ctcaacattg      360
tagtagatct tagtactgag tttgacatct ttgacaccaa caagatggtg atacgttact      420
ttctacgtta acttgggtag gtatatcgac tatagtggcc tataacacta ggctatgtaa      480
tatgatattg tgttgagtct ttataaacat gattttttt aaaaaaaaga gctaaaataa      540
aaaatagaaa tcgacggtac gatgcaagtt cttctcaaga caaccaaacg cacccttgcc      600 ccttttattga aattgaagta tgtgctttat caaatgttta aatactaatt ataagtatta      660
aatataattt aattataata ctaattatat agataaagac taaataacaa gacaaattta      720
ttaaatataa ttaattcatt attaacaaat acttaatgta gcacgatcga atcatggact      780
aattagtctt gatagactcg tcttaccatt taatcataat tagttttgta tactgttat       840 aatatttcta actagctagt attaaacttt tgatgtaacc taactaaagt ttagtcacgc      900
caatacataa ggactcggat cgttcgatca cccatgacat cacgtatact aagagcatct      960
ccaaaagctc tccagaagtc tcccctaaat ctattttttt gggaaaaaca caaaaacatg     1020
tctccaacag ttcccttaaa gcgcccccaa ctttttcata gcccttaaaa ctccctcatt     1080
tgtagctaca aatgaggggt tttttgggct ccccagaaac aaactgttga tttaagggat     1140
ctgttggaga aaggattaaa atttaccctc acttattatt tagatgtccc ttaaaactga     1200
ttttgaggag tcgtttatg tagagctctt ggagatgctc taacacaccg agcacaaccg     1260
catcatcaat caaaacaacc caaagtttgt tcggtacaag tcatcagcct gtgtacacac     1320
atcagcctcg gcccgggag aagcgctagc aaacaaggtt cacctaaaaa tccatccaga     1380
ttcattgaat ccaaccagca caaacgtccc atttattaat cacctcatca caggtccccc     1440
cagcctcact ctcgcgccgg ctcaaggtac attgcgtgtc ctagccaaga cacgcagctc     1500
atctcagcct cacacgcaca gcaagagcga ggcgtgattc gccatgggcg gcctcactat     1560
ggaccaggcc ttcgtgcagg cccccgagca ccgccccaag cccatcgtca ccgaggccac     1620
cggcatccct ctcatcgacc tctcgcctct ggccgccagc ggcggcgccg tggacgcgct     1680
ggccgccgag gtgggcgcgg cgagccggga ctggggcttc ttcgtggtcg tgggccacgg     1740
cgtgcccgca gagaccgtgg cgcgcgcgac ggaggcgcag cgagcgttct tcgcgctgcc     1800
ggcagagcgg aaggccgccg tgcggaggaa cgaggcggag ccgctcgggt actacgagtc     1860
ggagcacacc aagaacgtga gggactggaa ggaggtgtac gacctcgtgc cgcgcgagcc     1920
gccgccgccg gcagccgtgg ccgacggcga gcttgtgttc gataacaagt ggccccagga     1980
tctaccgggc ttcaggtgac gaaattaact atatatccct ttcgatcata gttgcgttaa     2040
taaattaagg gaatcgtgag cgtacgtacg taagtttccg cagagaggcg ctggaggagt     2100
acgcgaaagc gatggaagag ctggcgttca agctgctgga gctgatcgcc cggagcctga     2160
agctgaggcc cgaccggctg cacggcttct tcaaggacca gacgaccttc atccggctga     2220
accactaccc tccttgcccg agccccgacc tggccctcgg cgtggggcgg cacaaggacg     2280
ccggcgccct gaccatcctg taccaggacg acgtcggggg gctcgacgtc cggcggcgct     2340
ccgacgcgcg gtgggtccgc gtcaggcccg tgcccgactc gttcatcatc aacgtcggcg     2400
acctcatcca ggtacgtgcc cacctgatga actgagctga acgtaggttg catgcactgc     2460
atgtgtatag gcttctcaga tcgcttcgtg tggcgtaagg tgtggagcaa cgacaggtac     2520 gagagcgcg agcaccgggt gtcggtgaac tcggcgagga gaggttctc catgccctac     2580 ttcttcaacc cggcgaccta caccatggtg gagccggtgg aggagctggt gagcaaggac     2640
```

```
gatccgccca ggtacgacgc ctacaactgg ggcgacttct tcagcaccag gaagaacagc      2700
aacttcaaga agctcaacgt ggagaacatt cagatcgcgc atttcaagaa gagcctcgtc      2760
ctcgcctaac tactgctact gctaggatcc atgccattgc catgtcgtct tcagattcag      2820
agcacgccat gtcgtcgcta gcttcgtggt agaacaaata atgatgtgcg tgctgtgtgt      2880
aagcatggat atggatgtga atatgtaata tgatgagcac tcctactttg gtatgtttgg      2940
gaataacaga cttgtgttgg tctggttcat tatttgtaag aaaatcaaaa agagttagta      3000
gggcaggagg ctaaccacag tcatgctgca ccacatccct ggtggaaagc tggccgggtt      3060
acgctacgct cgtgcagcca gattactgca gggccgggat atgcttccgg tggaaggaag      3120
gggacggtgg ctgaggacca tggggctgga gcctgggaga gaggtcgagc tagaagaaag      3180
ggggagagag aagacgcaca acgaagatgg gtcagccagg gatttcgacc caaggggggag      3240 ctagtggatt ttgggagaaa acagaaaaga gaaaagagaa aagaagaaaa atttgttggt      3300
gtgaacacaa ggttgatttg tcttttctta tttggattga tgatgagtcg tggactaacc      3360
gacccgtgag ctattgtgtc gtataatcat gtctctcggt ttctggtgtg caggtttgaa      3420
gcacagagac ggtggtcgac gcaaaggtga acgtcatgca ggttcgtgcc gatggaccgg      3480
gagcagtgaa agacgagcgt tgggacttga acaagggacc agagtcgccg gatgactagc      3540
cgcagtggct gacgcctgga acacgcatag acgtgaggac gtggtagagc aggtgaaaat      3600
cgcctagagg gggggggggt gaatagacaa aacctaaaaa ttataaactt tgaacacaaa      3660
ctttacctga ggttaccgtt agaacgagta ttaatgaaat cggagtgcgg aaggcaagtt      3720
cttcttgcta cgagttgctt aatcaatatt gataactttg ggagtcaact caaaatgatc      3780
acaagcaaaa gaactagaga gagaggagag gaagaatcaa ctcgcaaagt aatgatcaac      3840
acaaatgaac acaatgattt atttctcgag gtttggttcc gaagaaccta ctccccgttc      3900
aggagtccac ataggacatg tctctttcaa ccctttctct ctctcaaatg gtcacataga      3960
ctggttcagt tgagagcacc tagaggggggg tgaataggtg atcttgtaaa atcaaacact      4020
aatagccaca aaacttagtt taaagtgtta gtacggctaa gtagctttga agcgagttat      4080
tgtgaacaca acaat                                                        4095

<210> SEQ ID NO 39
<211> LENGTH: 21
<212> TYPE: DNA
<213> ORGANISM: Artificial Sequence
<220> FEATURE:
<223> OTHER INFORMATION: suppression oligo

<400> SEQUENCE: 39
ctccatcatg cggtgcaact a                                                      21

<210> SEQ ID NO 40
<211> LENGTH: 21
<212> TYPE: RNA
<213> ORGANISM: Artificial Sequence
<220> FEATURE:
<223> OTHER INFORMATION: suppression oligo

<400> SEQUENCE: 40
uaguugcacc gcaugaugga g                                                      21

<210> SEQ ID NO 41
<211> LENGTH: 19
<212> TYPE: DNA
```

-continued

```
<213> ORGANISM: Artificial Sequence
<220> FEATURE:
<223> OTHER INFORMATION: suppression oligo

<400> SEQUENCE: 41
ggtactgcga ggagatgaa                                             19

<210> SEQ ID NO 42
<211> LENGTH: 21
<212> TYPE: RNA
<213> ORGANISM: Artificial Sequence
<220> FEATURE:
<223> OTHER INFORMATION: suppression oligo

<400> SEQUENCE: 42
uucaucuccu cgcaguaccu a                                          21

<210> SEQ ID NO 43
<211> LENGTH: 19
<212> TYPE: DNA
<213> ORGANISM: Artificial Sequence
<220> FEATURE:
<223> OTHER INFORMATION: suppression oligo

<400> SEQUENCE: 43
caggcgccat ggtcatcaa                                             19

<210> SEQ ID NO 44
<211> LENGTH: 21
<212> TYPE: RNA
<213> ORGANISM: Artificial Sequence
<220> FEATURE:
<223> OTHER INFORMATION: suppression oligo

<400> SEQUENCE: 44
uugaugacca uggcgccugg a                                          21

<210> SEQ ID NO 45
<211> LENGTH: 19
<212> TYPE: DNA
<213> ORGANISM: Artificial Sequence
<220> FEATURE:
<223> OTHER INFORMATION: suppression oligo

<400> SEQUENCE: 45
tcatgcggtg caactacta                                             19

<210> SEQ ID NO 46
<211> LENGTH: 21
<212> TYPE: RNA
<213> ORGANISM: Artificial Sequence
<220> FEATURE:
<223> OTHER INFORMATION: suppression oligo

<400> SEQUENCE: 46
uaguaguugc accgcaugau a                                          21

<210> SEQ ID NO 47
<211> LENGTH: 19
<212> TYPE: DNA
<213> ORGANISM: Artificial Sequence
<220> FEATURE:
<223> OTHER INFORMATION: suppression oligo

<400> SEQUENCE: 47
tcgctcgcct tcttcctca                                             19
```

-continued

```
<210> SEQ ID NO 48
<211> LENGTH: 21
<212> TYPE: RNA
<213> ORGANISM: Artificial Sequence
<220> FEATURE:
<223> OTHER INFORMATION: suppression oligo

<400> SEQUENCE: 48
ugaggaagaa ggcgagcgac a                                          21

<210> SEQ ID NO 49
<211> LENGTH: 19
<212> TYPE: DNA
<213> ORGANISM: Artificial Sequence
<220> FEATURE:
<223> OTHER INFORMATION: suppression oligo

<400> SEQUENCE: 49
tccaacgggc ggtacaaga                                             19

<210> SEQ ID NO 50
<211> LENGTH: 21
<212> TYPE: RNA
<213> ORGANISM: Artificial Sequence
<220> FEATURE:
<223> OTHER INFORMATION: suppression oligo

<400> SEQUENCE: 50
ucuuguaccg cccguuggac c                                          21

<210> SEQ ID NO 51
<211> LENGTH: 19
<212> TYPE: DNA
<213> ORGANISM: Artificial Sequence
<220> FEATURE:
<223> OTHER INFORMATION: suppression oligo

<400> SEQUENCE: 51
gcatcaacag gtacaacta                                             19

<210> SEQ ID NO 52
<211> LENGTH: 21
<212> TYPE: RNA
<213> ORGANISM: Artificial Sequence
<220> FEATURE:
<223> OTHER INFORMATION: suppression oligo

<400> SEQUENCE: 52
uaguuguacc uguugaugcg a                                          21

<210> SEQ ID NO 53
<211> LENGTH: 19
<212> TYPE: DNA
<213> ORGANISM: Artificial Sequence
<220> FEATURE:
<223> OTHER INFORMATION: suppression oligo

<400> SEQUENCE: 53
tggacgatgg atagttcaa                                             19

<210> SEQ ID NO 54
<211> LENGTH: 21
<212> TYPE: RNA
<213> ORGANISM: Artificial Sequence
<220> FEATURE:
```

-continued

<223> OTHER INFORMATION: suppression oligo

<400> SEQUENCE: 54
uugaacuauc caucguccau c                                                                 21

<210> SEQ ID NO 55
<211> LENGTH: 19
<212> TYPE: DNA
<213> ORGANISM: Artificial Sequence
<220> FEATURE:
<223> OTHER INFORMATION: suppression oligo

<400> SEQUENCE: 55
tggaccatgg atacttcaa                                                                    19

<210> SEQ ID NO 56
<211> LENGTH: 21
<212> TYPE: RNA
<213> ORGANISM: Artificial Sequence
<220> FEATURE:
<223> OTHER INFORMATION: suppression oligo

<400> SEQUENCE: 56
uugaaguauc caugguccau c                                                                 21

<210> SEQ ID NO 57
<211> LENGTH: 19
<212> TYPE: DNA
<213> ORGANISM: Artificial Sequence
<220> FEATURE:
<223> OTHER INFORMATION: suppression oligo

<400> SEQUENCE: 57
gcaaggtcct agatttaca                                                                    19

<210> SEQ ID NO 58
<211> LENGTH: 21
<212> TYPE: RNA
<213> ORGANISM: Artificial Sequence
<220> FEATURE:
<223> OTHER INFORMATION: suppression oligo

<400> SEQUENCE: 58
uguaaaucua ggaccuugca a                                                                 21

<210> SEQ ID NO 59
<211> LENGTH: 19
<212> TYPE: DNA
<213> ORGANISM: Artificial Sequence
<220> FEATURE:
<223> OTHER INFORMATION: suppression oligo

<400> SEQUENCE: 59
cagagtacat ggaggtcaa                                                                    19

<210> SEQ ID NO 60
<211> LENGTH: 21
<212> TYPE: RNA
<213> ORGANISM: Artificial Sequence
<220> FEATURE:
<223> OTHER INFORMATION: suppression oligo

<400> SEQUENCE: 60
uugaccucca uguacucugg a                                                                 21

-continued

```
<210> SEQ ID NO 61
<211> LENGTH: 19
<212> TYPE: DNA
<213> ORGANISM: Artificial Sequence
<220> FEATURE:
<223> OTHER INFORMATION: suppression oligo

<400> SEQUENCE: 61
ccatgcccta cttcttcaa                                                           19

<210> SEQ ID NO 62
<211> LENGTH: 21
<212> TYPE: RNA
<213> ORGANISM: Artificial Sequence
<220> FEATURE:
<223> OTHER INFORMATION: suppression oligo

<400> SEQUENCE: 62
uugaagaagu agggcaugga a                                                        21

<210> SEQ ID NO 63
<211> LENGTH: 19
<212> TYPE: DNA
<213> ORGANISM: Artificial Sequence
<220> FEATURE:
<223> OTHER INFORMATION: suppression oligo

<400> SEQUENCE: 63
acatggcggt caacttcta                                                           19

<210> SEQ ID NO 64
<211> LENGTH: 21
<212> TYPE: RNA
<213> ORGANISM: Artificial Sequence
<220> FEATURE:
<223> OTHER INFORMATION: suppression oligo

<400> SEQUENCE: 64
uagaaguuga ccgccaugug a                                                        21

<210> SEQ ID NO 65
<211> LENGTH: 726
<212> TYPE: DNA
<213> ORGANISM: Rice tungro bacilliform virus

<400> SEQUENCE: 65
tcctacaaaa gggagtagta atatttaatg agcttgaagg aggatatcaa ctctctccaa         60
ggtttattgg agacctttat gctcatggtt ttattaaaca aataaacttc acaaccaagg        120
ttcctgaagg gctaccgcca atcatagcgg aaaaacttca agactataag ttccctggat        180
caaataccgt cttaatagaa cgagagattc ctcgctggaa cttcaatgaa atgaaaagag        240
aaacacagat gaggaccaac ttatatatct tcaagaatta tcgctgtttc tatggctatt        300
caccattaag gccatacgaa cctataactc ctgaagaatt tgggtttgat tactacagtt        360
gggaaaatat ggttgatgaa gacgaaggag aagttgtata catctccaag tatactaaga        420
ttatcaaagt cactaaagag catgcatggg cttggccaga acatgatgga gacacaatgt        480
cctgcaccac atcaatagaa gatgaatgga tccatcgtat ggacaatgct aaagaagct        540 ttatcaaaag caactttaag tacgaatcaa taaagaagga ccagaagata taaagcggga        600
acatcttcac atgctaccac atggctagca tctttacttt agcatctcta ttattgtaag        660
agtgtataat gaccagtgtg cccctggact ccagtatata aggagcacca gagtagtgta        720
```

```
atagat                                                              726

<210> SEQ ID NO 66
<211> LENGTH: 165
<212> TYPE: DNA
<213> ORGANISM: Rice tungro bacilliform virus

<400> SEQUENCE: 66
acgaatcaat aaagaaggac cagaagatat aaagctggaa catcttcaca tgctaccaca      60
tggctagcat ctttacttta gcatctctat tattgtaaga gtgtataatg accagtgtgc     120
ccctggactc cagtatataa ggagcaccag agtagtgtaa tagat                     165

<210> SEQ ID NO 67
<211> LENGTH: 2000
<212> TYPE: DNA
<213> ORGANISM: Zea mays

<400> SEQUENCE: 67
ctgcaatata tacaccaaaa gtattataaa ctgtcatata tatgaccaaa acctttttat      60
tttagaaaag tatattaatc atggtatatt aatcaaagtt gttgttgggg ctgcaaaaat     120
catacccttc ttccacaagc tgttccttga actgcaggta ctcaggaact ctcagctcct     180
caacagcgag ctcactgacg ttgaccctca catactccca gacaccaggc ctagggcgga     240
tggcaagtgc aacccatggg gggatgacaa tcgcctcctg taagataata gagctagaat     300
gattaaagaa ggtgcacact acaaaaggaa cagtgctgtc cagcgagatc tgaatctgat     360
gcaaacctga gctgccctca ggacatcctc aaaagcacca tccttgagct tctcgcgctc     420
agcctcaggg atcgcattgt tgtactcggc aatgatctgg tggggctgca gcataccctt     480
tccaaggttt ttcagcctgc gcaaaacgat gtgccaaata acatcagact atgccagatc     540
tataaactca tcaaacatat acaatttcaa gaaatagttt agacgtatga tcagcagtca     600
gtagcgtggg aacatatgca acatagcgaa gaggcacaac agcaaattca ttcgaaaaaa     660
tgaaaacaaa gattcctctc ttttaactga acttctcgaa accccttttca tgcctacaca     720 tccgatctag tcagatgcct atgcgttcat gctgaacaga acgtgtcaga actaagcata     780
aactggttag caagcattat cgtattcgat agacccttta gtaacaagct atacattggg     840
taagttcaga ctccaatcat tctgttcaga aacatcgtat tgaatataaa actaaagaac     900
acacatgcag gtgcagccag atctaacagc agtttacagt cggtactaaa aaaagcatgg     960
tgtatgtatg tatcatcagt atccagtact aggtttcgac aaaatcctgg atgctaatta    1020
aatactcatc ttattaggga acacaggaac attatgtcta cagcattgaa tgatggccac    1080
atcatgctag atctaacaat acataatatg atggaactgg tcttaaaaag tcgcattcgc    1140
tcaaataata cccgtagcaa aataaatgta aacttgcaga cgaagcgggg gaaatgaggg    1200
cagacctggt gaagacggcg acaagctcat tggggtgggc agagagtgag tcgccaatgc    1260
gctccctgac gctgtggagg cggctcagga cacggtcacc tgcaccttcc cccattgctg    1320
tcctcttcct ggatcctcag gcctgcacag cgaaaccgaa acggaagcgg aagcttcagt    1380
cagcagagaa aactgaaacc gaaaaacggt tcagatccgt tgacataaaa gctgcgatga    1440
catcctaaaa ctaaaacccc tccagcaaga cataaaccca actgccaaca accagtcttt    1500
taagtctcga cacacccttg acgctgcgcc acgaaactat attgcaggca agaaaccaac    1560
agaacctaac tctggaaggg gggaaagaaa cggcagacag gagcaagacc caaaaaaaaa    1620
cgactcagat cctggtacta tagtcctagt acctagacca gaaagaagaa acaaccaata    1680
```

-continued

```
caacaagagg catacaagaa ctgaatcgat gaactgaaac gcttcagagg accgaggaat    1740
ggcggagaag ggaggcgcct atttatacag atctgacgag agaaccgaac aaaaacacat    1800
cgatgggaac catggagaag aaaagggctg gccgcatggc accaatggcc tcggcctcca    1860
aaaagccgtt gaatccaaag caggcgagga cgaagcgtga cgcggcaggg tacttctcta    1920
gaaaagcacg gcatcagcaa ggtggggggg ctggggttcc ttattgcagg caatcacgag    1980
gtgattagca caaacggaag                                                2000

<210> SEQ ID NO 68
<211> LENGTH: 2000
<212> TYPE: DNA
<213> ORGANISM: Oryza sativa

<400> SEQUENCE: 68
ctgaaatata catcagagat attacaatga catatatatc gataaaagaa aaataataaa      60
attaagtttt aaattttaag aatatatgtt tttagtatcc caattatgca gatttcatac     120
ccttcttcca caagctgttc cttgaactgc aagtactcgg ggactgtcag caactcaaca     180
gcgagctcgc tcacattgac cctcacatac tcccagacac cgggcctcgg gcggatggca     240
agggcaaccc atggggagat aacaatcccc tcctgcatga taaaaaacaa ttacaagtta     300
agttagagca agcggtagag taaagatgga tctctgtgat gcaatgaaat ctgaatctga     360
ttcaaacctg tgcactcctc aggacatcct caaaagcacc gtccttcagc ttctcacgat     420
cagcctcaga gattgcgttg ttgtactcag caatgatctg gtgggcctga agcattccct     480
ttccgaggtt aaccagcctg cgcaaataac agtgtcaaca aaaatatcag gccagatcta     540
tcaactcagc ctataaatat ctcaataaga taattttagc acttgagcat ttgcgcataa     600
taagaaaatt tgctattagc cacttaaaaa gaccatatat gatctgtttg cattgagatg     660
aattaaaaat ttcattgtag atatgaaatg attagttttg accatttaat tggacttaat     720
gaaatatgcg cgataatcag atctacgcgc tcgcgccaat agatctagta agatgtaggt     780
ttttattttt ttttgtgaaa ctttgctacc acaacaagca tctgtaccag tgcagaattc     840
attacttgta ttcagtttgt aaaccgtata tataatataa ataacatgca catgcagtca     900
gatctagcac taccagtcca cagtaatcca aaactacatt tgtatatttc atcattattc     960
agtagtacta ggtttgtaca aaatcttggc tgcagaaggc cgcacttaaa tattcattct    1020
aatcagaaac ttaaaaaaaa agtgactaca aaatgattgc atccaattca gtaaatatga    1080
gccattcctg gccagatcta acaatctcaa caacaaagat cctatatgaa catctccttc    1140
taaaagaaaa tacagtaaca tctgaaggca gtagactaga aaccaacaaa atctaatgct    1200
gggaaatcac taaatcagca cgaacctggt gaagacggcg acgagctcat tggggtgggc    1260
ggagagggag tcgccgatgc gctccctgac gctgtggagg cggctcagga cgcggtcgcc    1320
ggcagcttcc cccattgctc tcctcttcct cttggctcct caagcctgcg tgcacaacca    1380
accaccatca tcagatacat ccagacccag tcaacacaat cactccagga aaaaaaaaag    1440
tcaagccata aaccccaacc aaaaaccacg cctttgacaa acactggaag aaaaagaaaa    1500
tcgcagcttt ttcacaagca atctagaaga aaagaaaaag aaaagactac atagcagcta    1560
taattgactg agaagcatac aggaatcaaa caatggagaa ggggagggag gaagaacaat    1620
gatgctccag gctgaggacc gaggaactgg gtgaagcggg gtaggcgcgt atttatgcag    1680
atctgaggag agaaaccacc aaaacaatcc gatggtttca acgaaaaaga tcgtcgcttc    1740
```

-continued

```
ttgctgcacc agctcaccca tagccgttga gatcgaagct aagctagcag cagcaaagct    1800
ggaacgaaga gtgacgcatt caagctcctc tcctctcctc tcctctcctc cggagcacga    1860
ggccagcatg ggatggattg gggtttcttg ttggccatgg caaaggagga ggtcattaac    1920
gttgacacgg cgtaatttaa ttaaatctta tcttaaaata tgatttaagt ggtagtaaca    1980
aggaagatta atactatgaa                                                2000

<210> SEQ ID NO 69
<211> LENGTH: 2000
<212> TYPE: DNA
<213> ORGANISM: Oryza sativa

<400> SEQUENCE: 69
gctgtttaag aaaaacagaa gtaaaattca gtcactgtta tttttgcttca gttataatct      60 gcaaatcgtc gttctggtac ttactgtcca tcaacaagct gttccttgaa tgccaagtac     120
tcagaaacac tcagctcttc cactgccaac tcacttacat tcacccgaat gtagtcccag     180
acaccaggcc ttggcctgat ggccagtgca acccagggcg gcagcacaat ggcttcctac     240
atacagtcaa ggaagtaagt tagaaagact ggtatttgac tttgagttga ctatcataac     300
catcctggct cattgccaaa tttacctgag cagcccggga aatgtcttca aagggagcat     360
atttctcttt gtcagcttcg atcaaggcat cgaactccgc aagcagctgg tgacgctgga     420
gcattccctt tccctggtta acatacctgc atagagtgat atttaagaaa tagaaccaat     480
gcttagatct cacatccttt ctgcggctga actatgttaa tggcactacc acataaacct     540
gatttttact tcttattttt aagaccacat gatctgtact taatctagct atgaacaaac     600
aatatttcaa catcatctaa gattcatgac tcaagacaaa aatgttagag ctcatcacag     660
attattatag ataccatcat taaaactaaa gagatgcata accttgtcag ctaagaattt     720
gtaacatact aacatgttat cgtttcacat ctgggttgac taagaactaa ccaactgtat     780
ggataaaatc attgaaaact caaaacaatt agtagcaggt tccaagaaga cacaagatat     840
tatattgaga tcttcaccta gagaagagtg caatcaactc attgggatga gacgagaagg     900
tggcaccgag gcgttcgcgg agactgtgga ggcgagctag cttggcagcc atgactcaat     960
ttcaggaact gcaaagaaag gttacactta gcaacacgta ccaaaaccac tcacttgcac    1020
aagaataatt agtcaacagc catcactaag cattgcaaga ctatctctga acaggaaagc    1080
catgctaaat caacactaat aacatcacac aaaagcattg gaagatcaaa acataactaa    1140
aaacagctgt ttcatctaca caactgaaag catctatggt ttacgaagca gagtgcgagt    1200
actgattcaa aataaatcaa cctgaaccaa tatactctga caatgttttc aaagggataa    1260
aagaaccagc tttatcaaat ggatttgttg ggttttagta agtatcattg agataccgat    1320
ggcatatctc aaactttgca aaattataat ggcatggttc caaattaccc tttagtatta    1380
gcaccagtta gatcctaatt cctaaatccg ataggacaga gcgaaagatc cctggagata    1440
tgaagatttg gctacagatt aagcagagcc aacatgaagt tccgaatatt atgaatccgc    1500
aagcggggag atcaaagaga agaatacgga aggtcgcgac tccatgaaag aatccaacca    1560
aaaacccaaa gattttctc agttcaaaaa aaaaaaaccc ttcatttttg gttcgccatc    1620
caccgacagg caccaagaca ttcctcagga agcaaaaaag attaagcaga acaagtgata    1680
agcaagacac agtatcaacg gactacgagt cgagaaaatc actgaggcgc gattcttact    1740
gcaccaagta aaaaaaaatt tggggcaaaa aagaactctg caatgggcg gagcaacgtg    1800 gcagcaaaac taaaggtcga ggatttgagg ttttttgccg gttttcctcg aaaccccgaa    1860
```

-continued

| tccgctcata gtaaacccac taaactgcag cagaaacccc cctcttggtt cagatttacc | 1920 |
|---|---|
| gaaagcagta aacccaagaa catgtcagca aaaactcctg caagattcag ctgacgaccc | 1980 |
| accaaagaat cgcaagaaat | 2000 |

```
<210> SEQ ID NO 70
<211> LENGTH: 2000
<212> TYPE: DNA
<213> ORGANISM: Oryza sativa

<400> SEQUENCE: 70
```

| tggcggacgc gccacgcaca aacacaaacc tgcacacccc tgtgtcagag gaggagaggc | 60 |
|---|---|
| caagaaagga aatcgagtgg aggaagtgag gagcggcgga gacgtaggag gaggagggggg | 120 |
| agatggaaat ggaaagccgc gcgagagagg aggcgcgtgc tggatgggag gaggaggagg | 180 |
| aggtggtggg tttgtgtttg gagagacgag cgagagaggc gaagcattta aagggaggaa | 240 |
| gaggggggaga gagagagaga gagagagaga gagagagaga gagagaaaa ggaggaatat | 300 |
| aataaagggt ggtgcacctg ccaactgcta tgctcaccaa cactttgtac acacccagtt | 360 |
| acacccccct gcctttatta tttccagtgc agtaataact tcaacaatta ttgaaatgaa | 420 |
| aatggaatta atggagttag tatcggatta gcgacacgct tgccgagctt ctagacggtg | 480 |
| cgattatttc agcgggaacg actttctgta ggtgaattta atagaggagt gttttaaatc | 540 |
| cactcgacgt tgtaatagct ggtttaattc gtttgtactg tcgagtagtt atccaaaatc | 600 |
| aattttggat atttaaaaga aaaaaaaaca gatccgaagt attggaccta ctggcaaata | 660 |
| ggaattttgc tatatatagg tgtgcgttca tttataatgg agtagcatgg agtttttatta | 720 |
| atccagtaaa tgttttcatt gatttaatta atataacgaa tttcgcttga ggccatattt | 780 |
| gttaaacgct tttatctcta tcatcattca tcctaccagt aaagagcacc ggagatcgca | 840 |
| cttcatttaa atatatgtcc atgttggata aaccatagtt tattatagtg ttctttttata | 900 |
| tgttttgtgg ggaatttaga ttgtttaata tggcatacat atccatccat cattattata | 960 |
| ttctaacaca actggataag tgttctaaac tattgtagaa taactttgta gtatgatcga | 1020 |
| tcttgtggaa taaaaaaagt ctgacaataa cctttcataa aggaatatga ataccgtaa | 1080 |
| tcaacgcatc aaatcattca cggtgtacgc ctagcgaatt cgttggcgag tgctcgtgcg | 1140 |
| gccgtgggct cgctgtgatg catgcatggc tctctggcta cgtcgagata gcgattagta | 1200 |
| gcaaaattaa gcaagccact tattaattaa tctttggaga tatcatatga ttaaggcatt | 1260 |
| aattcgtacg tactcgtcgt cagcgttttc tgcaaagtcc actacagttt tttctttctt | 1320 |
| tgctgaaaat gctgatgtgt tggagatgga gtgacgtgca caacctgccg ccacgtggat | 1380 |
| ggttgctgga gcctacgtgt catcttaatt tgaacaaaaa aaaaagagga ataatacatc | 1440 |
| aatacatttt cgaatttcag ttctgccatt gaccagtaat acacatgtcg gcctcacatt | 1500 |
| ttaccctgat cttagtaacg ggtggtcgcc tggtcggtca ctgaaaaaag ttcaggaaat | 1560 |
| tatagtcaaa ctgaaacgaa catattcact ccttaaaaaa actaaatctt tttatatatt | 1620 |
| tgtgatattg taaaatagct acgggataat gatatagata tatatagtga taagggatag | 1680 |
| atggatcgag atatggagtt gtgctttctt taatttccac tacttgggct accatattat | 1740 |
| ggtagttggt atgaaaagat acacagcagt atagtgatgt gatcaatgac atgtatatct | 1800 |
| cacatgctcc catgttggag tcaaattttg ctagactaaa atccaattcc aagcagtccc | 1860 |
| tagccaagaa caaacaaaat tcagtgaggt cactgctgca ccaaggactg catgcatgca | 1920 |

-continued ggagaagggc attttctctt ttttcttttg gagactcgat tcaattcggt cggtcggtcg     1980
caatggtcag cttaattaaa                                                2000

<210> SEQ ID NO 71
<211> LENGTH: 2000
<212> TYPE: DNA
<213> ORGANISM: Oryza sativa

<400> SEQUENCE: 71
tgtgaaaggt ggcggcacca gcttagccgc agcttctctc gtcgtctccc tgaaacgaga       60
gggaggaagt tggtagcgtg atatatttag gcatgtcatc tcttgtataa gaagtcttat      120
ctgtgctaat tcacacggtt ctctaatctc tctccattct gttttgtaa attggttcag      180 tagatagcgt agggttatgc ttatatatac tccgtgaagt atatatttaa aaattagtca      240
cacgtaaagt actatacatg ttttatcgtc taataacaat aaaaacacta atcataaaat      300 tttttaaat aatacgaatg gttaaacgtt gaatatgaac cgtgcaaaac tatatttatt      360
ttgtaacaga gaaaatattt cacattaatt agattgttgt tttatggaag gttggagagc      420
tgcgccgccg ttgcgcagac ctaggaggct gcttataagt tataatcaat caattcacgg      480
atgccggctg ggacgcggcc catcgtccgg aagacgaca actcaacgca aaaagccgat       540
atgcctccaa attgccattg ccacctctac ggctgtttat actgctccaa atcaaaagcg      600
tccatggaag aatctagtat ttcccgcaaa gacgatgatg atatgcagga ttggatatat      660
agggggttgt tgcatgattg ctagaactcc cgtttccgaa gttgttcgtc cattttttaaa      720 gctgccaaat aggaatttat tttgtttca agtgtaatag agttctgtcc agatgagtga      780
attataattt ggttcacatt ttatttgcta agtttcagtt tgaacattct caaataactt      840
ttttcttcac tttttaaccg agtaacttag ttatttttc cgtttggacc acccaacaat      900
ttgttgctaa gtgcatctca cccgtcaaat aattcctttg aatccaaatt caattatatc      960
ccaaaaataa aaaacttctg aattccacat caattcaaac cccaaccatt ttaatttctc     1020
tccatatttt ccatttctct attttttacct ttctctttt tccatctatt tatttttttc     1080
cttttctatt tctttctttc tccttccttt ctctgtttcc ttcttcttct cctcggctag     1140
gcccgagcca gcccgtgccg cctcgcgcca accctgtgcc gccttacgcc gcgcttgcgt     1200
gcgctcgcgc ccacctcgtg cccaacccgc gcacgccaca cgcacacacg aggacgatcg     1260
acggacgaat gcaatcatat cccccttcctt actcagctag aaggctcaag aaccgcaact     1320
ttgatctctt ccaccctctc aaatccgccc caacccctgc tgactcaatc gccattaccg     1380
gaggaaaaat ccccgaaacc ctattaccgg cgccactaac agagctccaa aattcgtcgc     1440
ataattcgaa aatattctga aattgaaggt aaaaatggaa tctacatgcg aagtactccc     1500
tttcccctcc aatccgtcac tggaacgccg ccggcgccgc ctcccgctgc cactgccctg     1560
tttggccgcc gacagccgca cggcgcgccg ctgctccagg ccgccctagc ttcaaccacc     1620
gccacctttg gctccgcctc cctcctctta tgctcaccaa gcccgcctcc ctcgccggag     1680
atcgccggaa ccaccgccgc catggccgcc accgcctcct gcttctggcc gccgccgcca     1740
gcctcgccac cggcgcctat gccaccgccg accacggaaa cggagtccct acaccttggg     1800
gaccacaaaa ccggcggcat ccctcccaaa accggcctcc tccaccgccg gcgttcgtgg     1860
gattccggcc agttctgtgc agagcgagag aagaagagga aaaatagatt ttcctattga     1920
aagataaatc agaaaattcc tttttctttt cctatcaagt tgaccatccg tttgacctca     1980
aaatcaaaat ctgagaccta                                                2000

-continued

```
<210> SEQ ID NO 72
<211> LENGTH: 786
<212> TYPE: DNA
<213> ORGANISM: Zea mays

<400> SEQUENCE: 72
gacatggagg tggaaggcct gacgtagata gagaagatgc tcttagcttt cattgtcttt      60
cttttgtagt catctgattt acctctctcg tttatacaac tggttttta aacactcctt      120 aacttttcaa attgtctctt tctttaccct agactagata attttaatgg tgattttgct      180
aatgtggcgc catgttagat agaggtaaaa tgaactagtt aaaagctcag agtgataaat      240
caggctctca aaaattcata aactgttttt taaatatcca aatattttta catggaaaat      300
aataaaattt agtttagtat taaaaaattc agttgaatat agttttgtct tcaaaaatta      360
tgaaactgat cttaattatt tttccttaaa accgtgctct atctttgatg tctagtttga      420
gacgattata taattttttt tgtgcttaac tacgacgagc tgaagtacgt agaaatacta      480
gtggagtcgt gccgcgtgtg cctgtagcca ctcgtacgct acagcccaag cgctagagcc      540
caagaggccg gaggtggaag gcgtcgcggc actatagcca ctcgccgcaa gagcccaaga      600
gaccggagct ggaaggatga gggtctgggt gttcacgaat tgcctggagg caggaggctc      660
gtcgtccgga gccacaggcg tggagacgtc cgggataagg tgagcagccg ctgcgatagg      720
ggcgcgtgtg aaccccgtcg cgccccacgg atggtataag aataaaggca ttccgcgtgc      780
aggatt                                                                  786

<210> SEQ ID NO 73
<211> LENGTH: 1160
<212> TYPE: DNA
<213> ORGANISM: Zea mays

<400> SEQUENCE: 73
atgtgctggt gccccataag gtaggcacct aggtctgtgt ttgaagcatc gacagatttg      60
taaacatgtt cctatgaacc tatttctgat tgataatttg tcaaaactca tcatttgtct      120
tcatccttgc ctgcttgcgt tcacgtgaca aagtacgtgt atgtcttcgg cctttgctgt      180
gtatgtttcg cattgcttag atgtggtgaa agaacatcag aagatgcatt gatggcgtgc      240
ttaaaccagt gatgtgctcc aggtgttcct gcagctgca gagatattta ctcttgtagt      300
cttgttgaca gcacagttgt atgtgatttc ttggatgtaa tgtaaaccaa atgaaagata      360
ggaacagttc gtcctcttcc gtatacgaag gtcactgtat catttgtcgt ggcacaagat      420
gatctgcagg caggactgca acatggtttc ttggactgtc ctgaatgccc gttcttgttc      480
tttagttgag ccagagcagc agcctggtgt cggtgcctga gacctgacga agcacacggc      540
aaacaaacaa gtcgcagcag ctagcagggg cgttgccatc gccacaagcc cccaagagac      600
ccgccgagga aaagaaaaaa aaactacggc cgccgttgcc aagccgagcg tgcgaaccga      660
tccacggatg ggagatcaga gatcacccac cgcaggcggg cggcagtggc tggcgaggtg      720
cgtccacaga acctgctgca ggtccctgtc cgtcccggcg accccttttc taggcgagca      780
actccccatg gcagagctgc acgcagcagg gcccgtcgtt ggttgcagct ttaacccttt      840 ttgtttaac catacaatgc agagtcgcag aggtgaaaca ggacggaaat tacagaaaag      900
atggtggtgt gccagcagcc ccagcatgaa gaagatcagg acaaaagaaa agcttgtgat      960
tggtgacagc aacaggattg gattggagcc aagctaggca gtgagaggca ggcagcaaga     1020
```

-continued

```
cgcgtcagcc actgaaatcc agagggcaac ctcggcctca caactcatat cccccttgtgc   1080 tgttgcgcgc cgtggttagc caggtgtgct gcaggcctcc tccttgttta tatatgggag   1140
atgctctcac cctctaaggt                                                1160

<210> SEQ ID NO 74
<211> LENGTH: 1532
<212> TYPE: DNA
<213> ORGANISM: Oryza sativa

<400> SEQUENCE: 74
tagtcctcta atatatgaaa ttttgatata ggtaaagaag ggtattgcaa ggataagaat     60
gtaaaaagaa ataagagtaa tccttaccga taatagtatt ccttctctac cgttaaaagt    120
taaacctgtg cgtgtagcat tttaatccag gatctatcga atccgtccct cgttggcgtg    180
ggcgacgaac acgtgcagaa gaagctttcc ccagaaagca cctcaccgcc tcgccgtctg    240
gcagactggc acgcggggcc ctaccctcgc tgcgcctggg cccgtccgcc ttctgcacac    300
tgtcacgccc ccacccgctc gccgcctcgc gcctctctct ccgcctccgc cgcggccgcc    360
cgacgtgata gcgacacgta ggactcgcca aacacaaaaa atccatcgcg attttttggaa   420 ttttgttaca aaccaaatcc cgcattagag atttaatttg atttaattta attacgtagg    480
agtaccagat aaggagatcg agttaaaaaa gctaacggcg cggcgtggtt atctccgaat    540
cggctgtggc tccccgcgtc ggcgtcggcg cggcggcggc gcgccggccg aaccctggcc    600
gtcggatcgg gcgtcgtcct gggccccacg cgccacgggc ggctgtcgtt tgctcctcgg    660
agcggggtgg gcccaccatg gccaccacca caggtcgcgg tcgcggctga cctggcggtg    720
gtcccgtgct cgcggtgttt tttttttttc actctctttc tctcggtgga cagtagcggg    780
ggccgcggcc cgcgggggca gagattgcaa aaacagcgga aacggaagat tgcaaaattg    840
caactgcttt cctgtttta attcgggatc aaaaagattc tttcgtcggg gtccccgtgc     900
cattgttgta ttgcgcgtag gtccttgctt gtaaaagata atctccttaa ttttttctttt   960 gtactactag tgtatatgca gtaagaatat accatgagta aaatgaacca caaaactaat   1020
tacgatatac cattctcatg tagacgttct ctttttctttt gctagtcata cgtgcatata  1080
taaccaaaca aaaaaatgtt tgaagtactc ctatccaatt tattactcca gtagacaaca   1140
aaagaaaatg tttgaagtaa taactgatcc atggtacagt agggttgtcg tcaatcttgt   1200
gtttctttca ttccattgta cttacaatcg tactccagct agcacagcac aatgggctta   1260
agctttggac cccaaattct gatcttgtcg gggacccgta cgaaaatact cccgtagaga   1320
tgcagatacc gtcacaacct acaaccaacg aatgttaaga aaacaaaggg aaaaaaaaag   1380
aggcgaattc ggaggagaaa aaacggtggc taaaatatag tgcgggtgtg gggacgcgac   1440
gcgagcgacg aaagaggaga gaggatgggt tggcctgccc cccctccccc tgtctataaa   1500
tgcagaggcg ccgagtgccc tagtcgccgc tc                                 1532

<210> SEQ ID NO 75
<211> LENGTH: 841
<212> TYPE: DNA
<213> ORGANISM: Oryza sativa

<400> SEQUENCE: 75
tcgaggtcat tcatatgctt gagaagagag tcgggatagt ccaaaataaa acaaaggtaa     60
gattacctgg tcaaaagtga aaacatcagt taaaaggtgg tataaagtaa aatatccggta   120 ataaaaggtg gcccaaagtg aaatttactc ttttctacta ttataaaaat tgaggatgtt    180
```

```
tttgtcggta ctttgatacg tcattttttgt atgaattggt ttttaagtttt attcgctttt      240 ggaaatgcat atctgtatttt gagtcgggtt ttaagttcgt ttgctttttgt aaatacagag      300 ggatttgtat aagaaatatc tttagaaaaa cccatatgct aatttgacat aattttttgag      360 aaaaatatat attcaggcga attctcacaa tgaacaataa taagattaaa atagctttcc      420
cccgttgcag cgcatgggta ttttttctag taaaaataaa agataaactt agactcaaaa      480
catttacaaa aacaacccct aaagttccta aagcccaaag tgctatccac gatccatagc      540
aagcccagcc caacccaacc caacccaacc caccccagtc cagccaactg gacaatagtc      600
tccacacccc cccactatca ccgtgagttg tccgcacgca ccgcacgtct cgcagccaaa      660
aaaaaaaaga aagaaaaaaa agaaaaagaa aaaacagcag gtgggtccgg gtcgtgggggg      720 ccggaaacgc gaggaggatc gcgagccagc gacgaggccg gccctccctc cgcttccaaa      780
gaaacgcccc ccatcgccac tatatacata ccccccccctc tcctcccatc cccccaaccc      840
t                                                                         841

<210> SEQ ID NO 76
<211> LENGTH: 1392
<212> TYPE: DNA
<213> ORGANISM: Oryza sativa

<400> SEQUENCE: 76
ctcgaggtca ttcatatgct tgagaagaga gtcgggatag tccaaaataa aacaaaggta       60
agattacctg gtcaaaagtg aaaacatcag ttaaaaggtg gtataagtaa aatatcggta      120
ataaaaggtg gcccaaagtg aaatttactc ttttctacta ttataaaaat tgaggatgtt      180
ttgtcggtac tttgatacgt cattttttgta tgaattggtt tttaagttta ttcgcgattt      240
tggaaatgca tatctgtatt tgagtcgggt tttaagttcg tttgctttttg taaatacaga      300 gggatttgta taagaaatat ctttaaaaaa acccatatgc taatttgaca taattttttga      360 gaaaaatata tattcaggcg aattctcaca atgaacaata ataagattaa aatagcttgc      420
ccccgttgca gcgatgggta ttttttctag taaaataaaa gataaactta gactcaaaac      480
atttacaaaa acaacccta aagtcctaaa gcccaaagtg ctatgcacga tccatagcaa      540
gcccagccca acccaaccca acccaaccca ccccagtgca gccaactggc aaatagtctc      600
cacaccccgg cactatcacc gtgagttgtc cgcaccaccg cacgtctcgc agccaaaaaa      660
aaaaaaagaa agaaaaaaaa gaaaaagaaa aaacagcagg tgggtccggg tcgtgggggc      720 cggaaagcg aggaggatcg cgagcagcga cgaggccggc cctccctccg cttccaaaga      780
aacgcccccc atcgccacta tacataccc cccctctc tcccatccc cccaacccta      840 ccaccaccac caccaccacc tcctcccccc tcgctgccgg acgacgagct cctcccccct      900 cccctccgc cgccgccggt aaccaccccg cgtccctctc ctctttctttt ctccgttttttt      960 ttttccgtc tcgtctcgat ctttggcctt ggtagtttgg gggcgagagg cggcttcgtc     1020
gcccagatcg gtgcgcggga ggggcgggat ctcgcggctg ggtctcggcg tgcggccgga     1080
tcctcgcggg gaatgggct ctcggatgta gatctgatcc gccgttgttg ggggagatga     1140
tggggcgttt aaaatttcgc catgctaaac aagatcagga agaggggaa agggcactat     1200 ggttttatat tttttatatat tctgctgctg ctcgtcaggc ttagatgtgc tagatctttc     1260 tttcttctttt ttgtgggtag aatttgaatc cctcagcatt gttcatcggt agttttttctt     1320 ttcatgattt gtgacaaatg cagcctcgtg cggagctttt ttgtaggtag aagatggctg     1380
```

-continued acgccgagga ta                                                          1392

<210> SEQ ID NO 77
<211> LENGTH: 743
<212> TYPE: DNA
<213> ORGANISM: Oryza sativa

<400> SEQUENCE: 77
gaattcccgg acctccatgc ctacatcaac taatttgatt ccttgagttt acgtttagtg      60
atatgtctat ttttagagct tgttgggget tcggcctcag ctctagccag ccaaacatgt     120
tctaccaagt accctatgtt ggcatgatat agtgatgcat tataacaata aatgagcgag     180
ggattgctgg ctgaaaaagc tatactagct gcatttggtt atagttaacc gaactattaa     240
ttgcgtgtac aacaaaataa aaaaaatgca tgttgcacat tctttcatta acattatgtt     300
ttggtagtgt gaattagaaa tttgattgac agtagatcga caaacatagt ttcaatatgc     360
ttaagttagt tatgacttta acatatcagt ctccttgata ttttcgtttt agattcgtct     420
ctctactagt gtgtatgtcc accttccata gcagtgaagg gttccattcc atccctggta     480
aaaaaaaatc aaccactact atttatttcc taaaaagcaa aatgataaaa tatcattttt     540
ttaataaaaa taaaaaaatt ttggggtaca taattgatgt tgccccttgg gattaacctt     600
aaaaaagggc gaattttcta gggtttggcc aagttttgca atgcaccaaa ttattcccct     660
tgggccggcc gccaccccaa aaaaaacccc aaccccaac tttccattga aggccgggcc       720
cccttaaatc ctcatccccc caa                                             743

<210> SEQ ID NO 78
<211> LENGTH: 144
<212> TYPE: DNA
<213> ORGANISM: Oryza sativa

<400> SEQUENCE: 78
taaaaaaggg cgaattttct agggtttggc caagttttgc aatgcaccaa attattcccc      60
ttgggccggc cgccacccca aaaaaaaccc caaccccaa ctttccattg aaggccgggc      120
cccctaaaat cctcatcccc ccaa                                            144

<210> SEQ ID NO 79
<211> LENGTH: 612
<212> TYPE: DNA
<213> ORGANISM: Cauliflower mosaic virus

<400> SEQUENCE: 79
ggtccgattg agacttttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa     180
gatggacccc cacccacgag gagcatcgtg aaaaagaag acgttccaac cacgtcttca      240
aagcaagtgg attgatgtga tggtccgatt gagacttttc aacaaagggt aatatccgga     300
aacctcctcg gattccattg cccagctatc tgtcacttta ttgtgaagat agtggaaaag     360
gaaggtggct cctacaaatg ccatcattgc gataaaggaa aggccatcgt tgaagatgcc     420
tctgccgaca gtggtcccaa agatggaccc ccacccacga ggagcatcgt ggaaaaagaa     480
gacgttccaa ccacgtcttc aaagcaagtg gattgatgtg atatctccac tgacgtaagg     540
gatgacgcac aatcccacta tccttcgcaa gacccttcct ctataaagg aagttcattt      600 catttggaga gg                                                         612

-continued

```
<210> SEQ ID NO 80
<211> LENGTH: 837
<212> TYPE: DNA
<213> ORGANISM: Coix lacryma-jobi

<400> SEQUENCE: 80
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180 tagggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactcttttc ttcttaataa caatcatacg caaatttttt gcgtattcga     360
gaaaaaaaga agattctatc tgtttttttt ttgaaatggc tccaatttat aggaggagcc     420
cgtttaacgg cgtcgacaaa tctaacggac accaaccagc gaatgagcga acccaccagc     480
gccaagctag ccaagcgaag cagacggccg agacgctgac acccttgcct tggcgcggca     540
tctccgtcgc tggctcgctg gctctggccc cttcgcgaga gttccggtcc acctccacct     600
gtgtcggttt ccaactccgt tccgccttcg cgtgggactt gttccgttca tccgttggcg     660
gcatccggaa attgcgtggc gtagagcacg gggccctcct ctcacacggc acggaaccgt     720
cacgagctca cggcaccggc agcacggcgg ggattccttc cccaccaccg ctccttccct     780
ttcccttcct cgcccgccat cataaatagc caccccctccc agcttccttc gccacat      837

<210> SEQ ID NO 81
<211> LENGTH: 947
<212> TYPE: DNA
<213> ORGANISM: Oryza sativa

<400> SEQUENCE: 81
aatccgaaaa gtttctgcac cgttttcacg tcctaactaa caatataggg aacgtgtgct      60
aaatataaaa tgagacctta tatatgtagc gctgataact agaactatgt aagaaaaact     120
catccaccta ctttagtggc aatcgggcta aataaaaaag agtcgctaca ctagtttcgt     180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagat attttttttt aaaaaaaaat     360
agaatgaaga tattctgaac gtatcggcaa agatttaaac atataattat ataattttat     420
agtttgtgca ttcgttatat cgcacgtcat taaggacatg tcttactcca tctcaatttt     480
tatttagtaa ttaaagacaa ttgacttatt tttattattt atcttttttc gattagatgc     540
aaggtactta cgcacacact ttgtgctcat gtgcatgtgt gagtgcacct cctcaataca     600
cgttcaacta gcgacacatc tccaatatca ctcgcctatt taatacattt aggtagcaat     660
atctgaattc aagcactcca ccatcaccag accacttta ataatatcta aaatacaaaa     720
aataatttta cagaatagca tgaaaagtat gaaacgaact atttaggttt ttcacataca     780
aaaaaaaaaa gaattttgct cgtgcgcgag cgccaatctc ccatattggg cacacaggca     840
acaacagagt ggctgcccac agaacaaccc acaaaaaacg atgatctaac ggaggacagc     900
aagtccgcaa caacctttta acagcaggct ttgcggccag gagagag             947

<210> SEQ ID NO 82
```

```
<211> LENGTH: 721
<212> TYPE: DNA
<213> ORGANISM: Mirabilis mosaic caulimovirus

<400> SEQUENCE: 82
tggagattca gaaaaatctc catcaacaaa taatccaagt aaggattaat ggattgatca      60
acatccttac cgctatgggt aagattgatg aaaagtcaaa aacaaaaatc aattatgcac     120
accagcatgt gttgatcacc agctattgtg ggacaccaat ttcgtccaca gacatcaaca     180
tcttatcgtc ctttgaagat aagataataa tgttgaagat aagagtggga gccaccacta     240
aaacattgct ttgtcaaaag ctaaaaaaga tgatgcccga cagccacttg tgtgaagcat     300
gtgaagccgg tccctccact aagaaaatta gtgaagcatc ttccagtggt ccctccactc     360
acagctcaat cagtgagcaa caggacgaag gaaatgacgt aagccatgac gtctaatccc     420
acaagaattt ccttatataa ggaacacaaa tcagaaggaa gagatcaatc gaaatcaaaa     480
tcggaatcga aatcaaaatc ggaatcgaaa tctctcatct ctctctacct tctctctaaa     540
aaacacttag atgtgtgagt aatcacccac ttggggttgt aatatgtagt agtaaataag     600
ggaaccttag ggtataccat tgttgtaata ttattttcag tatcaataaa ataatctttc     660
agtttatctt atattcattt gtgtgacacc gtattcccat aaaaccgatc ctaatctctc     720
c                                                                     721

<210> SEQ ID NO 83
<211> LENGTH: 352
<212> TYPE: DNA
<213> ORGANISM: Peanut chlorotic streak caulimovirus

<400> SEQUENCE: 83
acagagggat ttctctgaag atcatgtttg ccagctatgc gaacaatcat cgggagatct      60
tgagccaatc aaagaggagt gatgtagacc taaagcaata atggagccat gacgtaaggg     120
cttacgccat tacgaaataa ttaaaggctg atgtgacctg tcggtctctc agaaccttta     180 cttttttatat ttggcgtgta tttttaaatt tccacggcaa tgacgatgtg acctgtgcat    240
ccgctttgcc tataaataag ttttagtttg tattgatcga cacgatcgag aagacacggc     300
catttggacg atcatttgag agtctaaaag aacgagtctt gtaatatgtt tt             352

<210> SEQ ID NO 84
<211> LENGTH: 1648
<212> TYPE: DNA
<213> ORGANISM: Sorghum bicolor

<400> SEQUENCE: 84
cactcgcaca tctcatggtg tcccaagaac ggcaagagcc agcactgcct ctgcctagca      60
acagcagcag cgccaagcga gcagccgcgt ccatggacgc cagcagcccg gccccgccgc     120
tcctcctccg cgcccccact cccagtccca gcattgacct ccccgctgcc gctggcaagg     180
ccgcggccgt gttcgacctg cggcgggagc ccaagatccc ggcgccattc ctgtggccgc     240
acgaggaggc gcgcccgacc tcggccgcgg agctggaggt tccggtggtg gacgtgggcg     300
tgctgcgcaa tggcgaccgc gcggggctgc ggcgcgccgc ggcgcaggtg gcctcggcgt     360
gcgcgacgca cgggttcttc caggtgtgcg ggcacggcgt ggacgcggcc ctggggcgcg     420
ccgcgctgga cggcgccagc gacttcttcc ggctgccgct ggccgacaag cagcgcgccc     480
ggcgcgtccc cggcaccgtg tccgggtaca cgagcgcgca cgccgaccgg ttcgcgtcca     540
agctcccctg gaaggagacc ctgtccttcg gcttccacga cggcgccgcg tcgcccgtcg     600
```

```
tcgtggacta cttcaccggc accctcggcc aagatttcga gccaatgggg cgggtgtacc      660
agaggtactg cgagaagatg aaggagctgt cgctgacgat catggagctg ctggagctga      720
gcctgggcgt ggagcgcggc tactaccggg agttcttcga ggacagccgc tccatcatgc      780
ggtgcaacta ctacccgccg tgcccggagc cggagcgcac gctgggcacg ggcccgcact      840
gcgaccctac ggcgctgacc atcctcctgc aggacgacgt cggcgggctg gaggtgctgg      900
tggacggcga gtggcgcccc gtccggcccg tcccaggcgc catggtcatc aacatcggcg      960
acaccttcat ggcgctgtcg aacgggcggt acaagagctg cctgcaccgc gcggtggtga     1020
accagcggca ggagcggcgg tcgctggcct tcttcctgtg cccgcgcgag gaccgggtgg     1080
tgcggccgcc ggccagcagc gccacgccgc ggcagtaccc ggacttcacc tgggccgacc     1140
tcatgcgctt cacgcagcgc cactaccgcg ccgacacccg cacgctggac gccttcaccc     1200
gctggctctc ccacggccca gtcccagccc aggaggcggc ggctccctgc acctagcgag     1260
cgagcgagcc gggccaaaca aacaaggggc aaaggccatc tctttcgccg gggcccgcgc     1320
gcggggttcg cccacgtgcg cgcccaggtg ggcgctggcc gcgggcaggt ggcggacatg     1380
tggcctgcgg gccccgcgcc gccttcccat ttttggacgc tgccgcgcat gccgcatgcg     1440
tgcgtcgacg gccctactac ttctactact gctactgcga ctactagtgt acatacgcaa     1500
aaatacatat atacgtattt tctatatata tatatataag caaggcggcc ccccggtgac     1560 ctttttctttg tttttgtcga caactgtgtt ttgatcccat tctagctgtt ctatggacca     1620
tggatggttc gttcaatgtt tgtacgta                                        1648
```

```
<210> SEQ ID NO 85
<211> LENGTH: 1242
<212> TYPE: DNA
<213> ORGANISM: Sorghum bicolor

<400> SEQUENCE: 85
```

```
atggtgtccc aagaacggca agagccagca ctgcctctgc ctagcaacag cagcagcgcc       60
aagcgagcag ccgcgtccat ggacgccagc agcccggccc cgccgctcct cctccgcgcc      120
cccactccca gtcccagcat tgacctcccc gctgccgctg caaggccgc ggccgtgttc      180 gacctgcggc gggagcccaa gatcccggcg ccattcctgt ggccgcacga ggaggcgcgc      240
ccgacctcgg ccgcggagct ggaggttccg gtggtggacg tgggcgtgct gcgcaatggc      300
gaccgcgcgg ggctgcggcg cgccgcggcg caggtggcct cggcgtgcgc gacgcacggg      360
ttcttccagg tgtgcgggca cggcgtggac gcggccctgg ggcgcgccgc gctggacggc      420
gccagcgact tcttccggct gccgctggcc gacaagcagc gcgcccggcg cgtccccggc      480
accgtgtccg ggtacacgag cgcgcacgcc gaccggttcg cgtccaagct cccctggaag      540
gagaccctgt ccttcggctt ccacgacggc gccgcgtcgc ccgtcgtcgt ggactacttc      600
accggcaccc tcggccaaga tttcgagcca atggggcggg tgtaccagag gtactgcgag      660
aagatgaagg agctgtcgct gacgatcatg gagctgctgg agctgagcct gggcgtggag      720
cgcggctact accgggagtt cttcgaggac agccgctcca tcatgcggtg caactactac      780
ccgccgtgcc ggagccgga gcgcacgctg gcacgggcc gcactgcga ccctacggcg      840 ctgaccatcc tcctgcagga cgacgtcggc gggctggagg tgctggtgga cggcgagtgg      900
cgccccgtcc ggcccgtccc aggcgccatg gtcatcaaca tcggcgacac cttcatggcg      960
ctgtcgaacg gcggtacaa gagctgcctg caccgcgcgg tggtgaacca gcggcaggag     1020
```

```
cggcggtcgc tggccttctt cctgtgcccg cgcgaggacc gggtggtgcg gccgccggcc      1080
agcagcgcca cgccgcggca gtacccggac ttcacctggg ccgacctcat gcgcttcacg      1140
cagcgccact accgcgccga caccgcacg ctggacgcct tcaccgctg gctctcccac         1200 ggcccagtcc cagcccagga ggcggcggct ccctgcacct ag                        1242
```

<210> SEQ ID NO 86
<211> LENGTH: 413
<212> TYPE: PRT
<213> ORGANISM: Sorghum bicolor

<400> SEQUENCE: 86

```
Met Val Ser Gln Glu Arg Gln Glu Pro Ala Leu Pro Leu Pro Ser Asn
1               5                   10                  15

Ser Ser Ser Ala Lys Arg Ala Ala Ala Ser Met Asp Ala Ser Ser Pro
            20                  25                  30

Ala Pro Pro Leu Leu Leu Arg Ala Pro Thr Pro Ser Pro Ser Ile Asp
        35                  40                  45

Leu Pro Ala Ala Ala Gly Lys Ala Ala Ala Val Phe Asp Leu Arg Arg
    50                  55                  60

Glu Pro Lys Ile Pro Ala Pro Phe Leu Trp Pro His Glu Glu Ala Arg
65                  70                  75                  80

Pro Thr Ser Ala Ala Glu Leu Glu Val Pro Val Val Asp Val Gly Val
                85                  90                  95

Leu Arg Asn Gly Asp Arg Ala Gly Leu Arg Arg Ala Ala Ala Gln Val
            100                 105                 110

Ala Ser Ala Cys Ala Thr His Gly Phe Phe Gln Val Cys Gly His Gly
            115                 120                 125

Val Asp Ala Ala Leu Gly Arg Ala Ala Leu Asp Gly Ala Ser Asp Phe
    130                 135                 140

Phe Arg Leu Pro Leu Ala Asp Lys Gln Arg Ala Arg Arg Val Pro Gly
145                 150                 155                 160

Thr Val Ser Gly Tyr Thr Ser Ala His Ala Asp Arg Phe Ala Ser Lys
                165                 170                 175

Leu Pro Trp Lys Glu Thr Leu Ser Phe Gly Phe His Asp Gly Ala Ala
            180                 185                 190

Ser Pro Val Val Val Asp Tyr Phe Thr Gly Thr Leu Gly Gln Asp Phe
            195                 200                 205

Glu Pro Met Gly Arg Val Tyr Gln Arg Tyr Cys Glu Lys Met Lys Glu
    210                 215                 220

Leu Ser Leu Thr Ile Met Glu Leu Leu Glu Leu Ser Leu Gly Val Glu
225                 230                 235                 240

Arg Gly Tyr Tyr Arg Glu Phe Phe Glu Asp Ser Arg Ser Ile Met Arg
                245                 250                 255

Cys Asn Tyr Tyr Pro Pro Cys Pro Glu Pro Glu Arg Thr Leu Gly Thr
            260                 265                 270

Gly Pro His Cys Asp Pro Thr Ala Leu Thr Ile Leu Leu Gln Asp Asp
            275                 280                 285

Val Gly Gly Leu Glu Val Leu Val Asp Gly Glu Trp Arg Pro Val Arg
    290                 295                 300

Pro Val Pro Gly Ala Met Val Ile Asn Ile Gly Asp Thr Phe Met Ala
305                 310                 315                 320

Leu Ser Asn Gly Arg Tyr Lys Ser Cys Leu His Arg Ala Val Val Asn
                325                 330                 335
```

```
Gln Arg Gln Glu Arg Arg Ser Leu Ala Phe Phe Leu Cys Pro Arg Glu
            340                 345                 350

Asp Arg Val Val Arg Pro Pro Ala Ser Ser Ala Thr Pro Arg Gln Tyr
        355                 360                 365

Pro Asp Phe Thr Trp Ala Asp Leu Met Arg Phe Thr Gln Arg His Tyr
    370                 375                 380

Arg Ala Asp Thr Arg Thr Leu Asp Ala Phe Thr Arg Trp Leu Ser His
385                 390                 395                 400

Gly Pro Val Pro Ala Gln Glu Ala Ala Ala Pro Cys Thr
                405                 410

<210> SEQ ID NO 87
<211> LENGTH: 12906
<212> TYPE: DNA
<213> ORGANISM: Sorghum bicolor

<400> SEQUENCE: 87
cactcgcaca tctcatggtg tcccaagaac ggcaagagcc agcactgcct ctgcctagca      60
acagcagcag cgccaagcga gcagccgcgt ccatggacgc cagcagcccg gccccgccgc     120
tcctcctccg cgcccccact cccagtccca gcattgacct ccccgctgcc gctggcaagg     180
ccgcggccgt gttcgacctg cggcgggagc ccaagatccc ggcgccattc ctgtggccgc     240
acgaggaggc gcgcccgacc tcggccgcgg agctggaggt tccggtggtg acgtgggcg      300 tgctgcgcaa tggcgaccgc gcggggctgc ggcgcgccgc ggcgcaggtg gcctcggcgt     360
gcgcgacgca cgggttcttc caggtgtgcg ggcacggcgt ggacgcggcc ctggggcgcg     420
ccgcgctgga cggcgccagc gacttcttcc ggctgccgct ggccgacaag cagcgcgccc     480
ggcgcgtccc cggcaccgtg tccgggtaca cgagcgcgca cgccgaccgg ttcgcgtcca     540
agctcccctg gaaggagacc ctgtccttcg gcttccacga cggcgccgcg tcgcccgtcg     600
tcgtggacta cttcaccggc accctcggcc aagatttcga gccaatgggg taagcgaagc     660
accgatttac atttaccgcg cgtcggcccc tgaggcctgg gtcttagtct tagcactgca     720
tatacggtcg gtagctctgg atatgatacg tatatatgaa accccgttcc aatcccatgc     780
acggtgtaca caggcgggtg taccagaggt actgcgagaa gatgaaggag ctgtcgctga     840
cgatcatgga gctgctggag ctgagcctgg gcgtggagcg cggctactac cgggagttct     900
tcgaggacag ccgctccatc atgcggtgca actactaccc gccgtgcccg gagccggagc     960
gcacgctggg cacgggcccg cactgcgacc ctacggcgct gaccatcctc ctgcaggacg    1020
acgtcggcgg gctggaggtg ctggtggacg gcgagtggcg ccccgtccgg cccgtcccag    1080
gcgccatggt catcaacatc ggcgacacct tcatggtaac ccctgctctg tttttcttg     1140 tcctcctctt gtcctgtgtg tgtgtatatt cacttctctc tgtttttttg ccccgaatcc    1200
tagtggacct aactggacgg attacagcac gcacacgtag gcatgtcatg tagcagcagt    1260
ctgcagcact gtagtactta gcgatgcaat agagacatgc gttccagtcg gttccatctc    1320
ggtgggctac agctacagtc ctacacggac gcggctcgta gtcgtaggga cgggcgcgtt    1380
ctctgtatcc acacacggct gcgcccaggc cgaggcttcc gccgcgggaa agttgcgaca    1440
acagaacggg gtttgtgccg ttggagcgtt gcggagaggc agaggcttgg ggggacgggg    1500
gcgcgatacg ctgcgatggg tgggtgaccg aggcgacgct ttcggcgggg gcccgggcct    1560
gcccaggtgc gcgcggcctc gtcgccttcc cctgtttttt tgatgccgcc gctcggtcct    1620
cggtgttctg gctccgcccg cccgctcgct gggtgcccat cccatctgat ccgatccgct    1680
```

-continued

```
ccgctccgcg gtggcggtcc tatgcgatgc cgccgcacga gcgcgggggg ccgcccgtgg    1740
aggagtagaa agtggtacaa ggttggttgg aacttggaat tgtgggggt tactgctgct     1800 ggtggctgct gctttgcaac ttgccaggct gctgcctgtt gccccccgcg ttttctagcc    1860
gtttccgctc gcgatccggc acgcggcgcc cacaccgggg ctccagctcg gccccttggc    1920
cgtgtaggta gcaggcactt gcatctgtcc gttcgacacg atgattcttg tgcactgtgt    1980
acgtatgtac taaccctttc tggtatgatg tacgcatggc atgcaggcgc tgtcgaacgg    2040
gcggtacaag agctgcctgc accgcgcggt ggtgaaccag cggcaggagc ggcggtcgct    2100
ggccttcttc ctgtgcccgc gcgaggaccg ggtggtgcgg ccgccggcca gcagcgccac    2160
gccgcggcag tacccggact tcacctgggc cgacctcatg cgcttcacgc agcgccacta    2220
ccgcgccgac acccgcacgc tggacgcctt cacccgctgg ctctcccacg gcccagtccc    2280
agcccaggag gcggcggctc cctgcaccta gcgagcgagc gagccgggcc aaacaaacaa    2340
ggggcaaagg ccatctcttt cgccggggcc cgcgcgcggg gttcgcccac gtgcgcgccc    2400
aggtgggcgc tggccgcggg caggtggcgg acatgtggcc tgcgggcccc gcgccgcctt    2460
cccatttttg gacgctgccg cgcatgccgc atgcgtgcgt cgacggccct actacttcta    2520
ctactgctac tgcgactact agtgtacata cgcaaaaata catatatacg tattttctat    2580
atatatatat ataagcaagg cggcccccccg gtgacctttt ctttgttttt gtcgacaact   2640
gtgttttgat cccattctag ctgttctatg gaccatggat ggttcgttca atgtttgtac    2700
gtactccacg taaccaaact actctagtgg actagtagat cgggctcatg tgatgaaact    2760
ggaccgacgc ggacgtcacg tgcgtcaccc gcgtctggta gcggtagcgc acgagcgccg    2820
aatgtttcct gggcccgcaa gagaatcgct tctcatctcc tctcaccatg aatggggaaa    2880
aatgctgcgt cgaaagttcc agacgtttcc aaattccaaa cggttttgtg gcgtccgatc    2940
catggggcgc cccaaacttc caagacgttt tcaggttcca aatcttcgtg ctccacatca    3000
ccttcttccc agattcattt gcctcgtcgc ttgctctcct gtgttattca cgggtcccac    3060
tgttgccccg tctgcgagaa agaaatttat tagagttgaa gcattcgaca tttcgactga    3120
ctgattgtta gtatcactaa attttgtgca catgtttctt tggtcattca tctctggata    3180 tttttttttag ataatggata taaatatcgg gcctctacat ctgaggaagt acacagccaa   3240
ttattttcat ctctggacat gggacgatgg aagaggcaga tagatttagg agaccccttca   3300 attcagaatt tcaggtgcac aaggcctgcc tggcttgccc ggattcttgt ttcggacatg    3360
accaactagg ccgcactact tgcactgata gctggagaaa aaacaaaact ttgcaaacag    3420
caggattatc tacaagggaa actccatcca cgtgaaccag catttcaggg agagatgcga    3480
caaaaaaaaa gaggcggcaa caaaaaaatc ttactgcaat tttatctctg cattgaacct    3540
cttccaacca tgccgcatcc tgtactgttt tgtatctttc ccggtggtcc gttgcgttct    3600
cacgcagttg ataacatgca gtcacgcacc accgaatcca gtgtactagg ggtagtgact    3660
tgtcacgcgg aacaacaggt cggtagcacc aagcaagtcg ctgtagactt gggcgtttaa    3720
caacgacttg cacaacagtt caaatatagc atatgcaatt atgcacaaga ttgttcgact    3780
gctatccgac aaactgaaga agctgcccaa ttgaacagaa tgtaccagtg atttccagca    3840
cactatctta cagcagcgtt gagaatgaaa caacaaatgg gggaaaacag atgtgtatta    3900
ttctacagtt acaccaaaga gtttgtcctt tcagcatcaa caagaatcat atgcatatct    3960
agtgacaaaa attcctctaa tttttacccta cttggtaaca gttctcttca acacatatat   4020
ttcacgtgct tgcatcgagt tccttgggcc gccacatcga cttctcgacg caaagcaagc    4080
```

-continued

```
cctcgttgcc cttggtgtag gtcattcgca cctcccactg cagggacttg gccatgcttt   4140
ccagttcgtt tattgtgtcc gcagtgtccc tcacaatcag tttgccttgg ggcctcagta   4200
cacgatcaac ctcggcaaaa actgccatca atttgcatct gtaaacaagc aacacagatt   4260
tagcatctgt aaacaccaca ggtttcattg caagaagcat aaagcatgca aacatgctac   4320
ttgtacatgt caaagaaaca tgtcaaactc aaacacatga aaatcattat tattgttttc   4380
ttgctgaact gatcacatta gttggtttca atttctgagt tccactagta atctatacca   4440
gaaggataga ataatgtcaa gaacaagaga tacaaacctc tttgtgagct ttgagaatag   4500
atggtccgcg tgcagaaggt cataagttct tgggtaagtg ctcaaagact cgcaccagtc   4560
atggtacata ccaaacaaac cacgctcgta aatgatgggc agtgtgtctg gtgaatcaat   4620
cggcacaata ttcatgaccc agacctttg gtccctcaga gctgcagcaa aactgccatg   4680
caacgatgta aagcattagt aaaaatattg ggttttttaa accaaaacca agaaagataa   4740
ttcctccagc ttaactgaaa gaaagaaaga aaaaaactgc ttaatgactt atggtggaca   4800
agttgcctgt tatgttttat gatagctatg tgccagcttg gctaactggt agttatgtag   4860
tgtgatctga attaccaaaa aagagaagaa aaaaaaatca tgcccaagaa actgagaaag   4920
acacccattt acttaccctc catacacagc tctcatgtcc attacatttc tcactttgga   4980
ccagtcaatt cccatgccat tcacatacga tttacttaca acccttttcc agtgagcatt   5040
atctgcctcg aaatcttcat ttgcaggctt tccatagacc ccaaccttgg aaccatcaat   5100
ccagaaagga gtcttctcaa gccttgtgg ccaaaactct ggccattttg accctcgaac   5160
tttcgagcca acaggcagtt tgtgcatgca tgcttccaaa ggtacattcc tgcaaatcaa   5220
aagattgtgt aagcaaagca gaggaagcac ttcgccgcat tgaaaatacg ttcttctcaa   5280
agaaacaaaa ccataccaag ctgcatctgc atcatcagat tccttgcaca atggtgggtt   5340
gttttcggat cttttctcat agcaaatgtt gtccattggt ttctgaaata tgaccatacc   5400
aacttgattt aacttatcct tagtcttgtt gaccatcttc cagcacatgg actttgtcaa   5460
agtggacatc gctgaaaaga ttaaggggtc atatgttatg atagaaataa aattcaattt   5520
tgcactgttg gtacatagca tctgtttga acaaatgcaa tccttcctta tccatgaaag   5580
aagttaaccc ctgatactta ggattattca gtactttcac tcatgaactg ctgaatttgt   5640
tctgccagta gttgctatac tagaaatgtt cagtgtacca aacataaatt tggtacgggt   5700
tccttattaa agatgggagg ctgtatggta tttcgacgta acaaatcaag ttagcagcta   5760
ccctacttat ggatatacac ttctcaaaat gaatatacat agttttgata ggtgacatta   5820
attaatataa gaacttcatg cagttagggt gaaactaaac taagcagtta cggaaatacc   5880
attccaaatc tcaacatcct ctgggagctt ttggtaaaca ggagtggcag accagacaaa   5940
gtaaccacca gggcgtaaca agcggttcaa ttccagcaaa agcatgccac ctaaaaggag   6000
tcagtaataa gattcagttc tatagcaaat caataaatga aaggaagaca tgtcaccaac   6060
aagacaaacc ttcaatgtgc caagggaccc tgcagcgagc gcaatgaatg acatcaaaga   6120
ctctgctggg gtatggaagt ctcttggtgc ccatcacagc tgatattgct ggaattcccc   6180
tttctaatgc aaattgtact tgagcttcat gctcatcttt cggagcaaaa gacatggtaa   6240
gcacatctct atcaaacatg tagcctccaa agctggcaac tccacaaccg acatctagaa   6300
tgacgcggct tcgtttgccc catgcaatat caggcagtgc ctgtgaatga cagtttaatc   6360
agcatatgat gaaagcaagt gtgataatat caagttcaaa gatgcaacat gaaactttca   6420
```

-continued

```
taatcatgga cagtactaag cttgcttgat agattaatgt atggatgaga ctaaaaaaaa      6480
ggaaagttgt atccatcaga acgagaggct gaaaacacat ggctggctgt gaaagcctga      6540
tgtcgtttag tctagcataa acaaactgtc ctcagcatgt agatttccat agggtggcat      6600
ttgacaaatt atgattgtgg actagcgaat caatcactga ttctcaaaag tgtgagacag      6660
atgagttcaa gtctaagggg tgactaatat gggatgctgg gatgatgatg atgatatata      6720
cctgctgaat agtatcaata tagtggaggg caccattctt gaactgagtc ccacccccag      6780
ggaacaggag gtagtcacct gatactttaa cccaattttg atgtcccttg tactctgcga      6840
gcctagtgtg aggaacattg ctgtaccata cctgcaaaaa gcagcacaag atggtaataa      6900
gtaaacagag atcttggtca gctaaagatg attcagtgtc gtacaattta gaatagacag      6960
aatcaccttg tccctgctcc ttggccactc aattgggcgt ttatatcctt ctgggagtgg      7020
aacaaggcag gtaggaggct cctcagggca atgcctctca cgatgttcat aatgtttagt      7080
agttcgaagc ttcttgatag ccttctcgtt gtcaaggcaa ggtatgtaat ctgtcgaggc      7140
actgctatta catagtttcc aggaatagct agtcgcatca cctgaagact ttgatgacgc      7200
ttggacttcc tttcattct tggactctgc agcctgtgtg gggaatgaac cattctgggt      7260
atttgactcc ttcagaagct ctgattgggc cccatcagga aatacctcgt tggagtttga      7320
gctctgatcc ttctctccat tttcttccac cttctcttct atctgaggtt gctcctcctg      7380
agtggcatca ccttcaggct tctcttcttg atcatccttg ctctctccat caggttttc      7440 atcaccactc tcatttgtga tttcatcatc tttcttctcc ccactcttct ccccgtcacc      7500
atcgttcttc atgtcatctg accgcccttc tgattttcca tttgcatcat caaacatatc      7560
cttggtctca gctttctctg tcggcacttc cggctccttc tcttcaggct tctcctctgg      7620
cttctcagtg aacttctctt ccatcgtggc atccttgtta ttcggctcct ccggcatcgt      7680
ggcatcattg ttgtcggtgt cctcaaattt ctcagaacct tcaccagcat tgtcctgtga      7740
ggccccaaaa ttgacaggcg caggctgctg cttcaccacc ggcttcttat tcgaggagat      7800
ctccagcggg aagacagtgg acgaggtcat catccacgcg ccgaccaggc agagcgccac      7860
aaagacgacg accgtggtgg tcgtgcagaa cgacgacgac gtcgaggacg gccggcggcc      7920
gtccatcttc ccacctcggc caaatgccat tagtgcctgg cgaacatgta ccagagcacc      7980
gaccttcacg cgatttatct ccaccaacta ctgctggacc aagaacccec aaaaaaatcg      8040 cacctttgtc tgctttgtgc tgctacagcc gcgcggcacc tgaagcaaac cacaaaaaaa      8100
acttaaatcg ccgcggacat aaatcaaggt gctggatcta aagaacaaac gctggatcta      8160
ctcaagcaac aacggaagga agatccgcta ttggtgctag tattagcttc ttgtttccta      8220
gtactacagc ggctctttcc cagtataaga acacgggaaa acgcggagaa atcccccttc      8280
gtggccaaac atggaaagaa aattagtaaa gcgtgtgctt taaaacccec tcgttctgtt      8340 ccttccgcgg agagctaccg catcttccaa ttgagctggt tctcagctgg gcgcaaaacg      8400
cgcactaatc aatgtccgat tccatccaca aagaaaaaaa agacgggaac agctaatcca      8460
gcagctcgct cgctagctag ctagctcatc ggcggaagga cggaaccagc tttgctggat      8520
ccaggacagc aagagtgtgc aaggagaaag aacggagcag caatgcggat tgcggaggcg      8580
gtggattggt acctcgccgg aaccgaccgg agtggtcgcg gtggccctcc gcgcggatct      8640
cgaagaggag cgaggaaggg gaaggcggat gcgcgtcctt gggttctctg ccaccgcact      8700
gggcctcgcc gcgttataaa ggcggcgggg cgggcgggca gcgcagtgtg agtggagtgc      8760
aatctgttgt gtagtgtgtg aagaggcgga agcggaagcg gaggagatgg gttcgcatta      8820
```

-continued

```
gacgaccgta cgtaattata cgctatacta gtacttgggt tagattactc gggagatctt    8880
ggccaaaatg tccggtctga gtgtttggta gttttatgga tttgcccttt taagatgttg    8940
gtatttctcc gggagcttag aaagaagaaa tggcgatgct ttaggccttg tttagatgcg    9000
aaaaaaattt ggatttcgct actgtggcat ttttatttgt ttgtagcaaa tattgtccaa    9060
acacggacta actaagattc atctcgcgat ttacagttaa actgtacaat tagtttttat    9120
tttcatttat atttaatgtt tcatggatgt gtcgaaagat acgatatgat agaaaatttt    9180
gaaaactttt tagttattga ggttaactaa acaatgcctt aattgagaat ttactcgagc    9240
aaaaagagtt aggtcagtct cagtggagag tttcatggtg ttgtttccaa gactgccata    9300
tcatgtgaaa tgaaatgaaa cttggttgaa acactcactc tcaatggaga gtttcatttt    9360
atagtttcat gggcatttaa tttcaatact catagagagt tgatatcgtg ccaactcatt    9420
tcttctctct cttcttaaat acacagtcat atcatcaaaa aaaatcctat gtagcaacat    9480
atttaatgca aataaaactc atatggtgga ctgtaggagt agcattaggc caagggcaca    9540
cacacggtca cggtgtgagt gcgacggtgc gagtgggccc gcggcggtag taagtgcgtg    9600
cgcgcccggc gccccctcc gcggcgacga cgcagcggca gcgcgtcgtc cagtgcaccg    9660
tctgctgttc ggcgctgcgg gtcctccgcg ccacggcgca gtgaaccggg cgcgtgcatc    9720
ccgggagcgg cggcttggca ctcccctgct tgtcggtggc ggccgtcggc atcgctcggc    9780
cccggagcgt cacgaggctg ctgattggga gcgagagcga gtagtggggc tggttgggga    9840
caatcccatt cccaccggc ccaccaggct gggactggcc cactagtcac tagtgggtgg    9900
ctcatgggtg tgggtgggct ggctaatgcc gcctgcccaa caaccaaccc aaccctgtg    9960 gacgctggta ccggtagttg ccgcgccatg gtggactgct gccgcctgat gcctttgcct    10020
gccacgctcc acgagttgag gcgcaccaaa ctgtgctgtg ctcctgattt gtgctaatcg    10080
gccgacgcgt accattcttt ctttctttcg tctacgcgca gagaggccgg ttgactgttt    10140
cttcgttgga gggccatgtt gactcgtact aataataaaa ataataatac taggttgact    10200
ttttcaattc caacgcagca gtgcaaagct gcccacctat gagcacaggt ccttttttaa    10260
ctccgttttt gtacgtacac acgtactgtc cagcctgtgt ctaataatct taccaaaaac    10320
ctgtcatctc actatcaacc aatcaggctc tccgcctgtt cgtcgaggaa cagcagttgt    10380
tttccctact ccaacataga gtacactatg gacgcacatt accatgccag cttgagctta    10440
gcattgccca ccgttggata actgccatgc cattctcagg ccctgtttag ttcccatcta    10500
aaaatttttc atccattcca tcgaatcttt ggacacatgc atggaacatt aaatgtagat    10560
aaaaaaataa actaattaca cagtttagtt gagaatcgcg agacgaatct tttaagtcta    10620
gttactccat aattagcctt aagtgctaca gtaatccaca tatactaatg acagattaat    10680
tatgcttaat aaatttgtct tacagtttcc tgacgagcta tgtaatttgt ttttttatta    10740
gtttctaaaa accctcccg acatccttcc gacatatccg atgtgacaac caaaaaattt    10800
tcatcttcaa tctaaacagg ccctcactct catcatctca tgccggggca gcaggtccgt    10860
cgtcaggtct gtcgtcccgt cccgtgccgt ctgaagcaac aggcgagaga aacgccgttc    10920
catcggtttg ccgagcgtgc agaggataga gctatactcg atccgagag gattgtgaaa    10980 cgaagcacgg ttaagcagtg ccgcgcacgt gctgctctgc tcctggatcc gatccagatc    11040
gactcggggc gtctcggcct cagcggcgat ggcaatcatc gcgcgcgctg ctggagctgg    11100
acgttttcgt cttgcattgc aggaggcgga acagaacgga gaaagccacg gcgcgctttg    11160
```

```
ccgacgccac gcgctgacac gagggacccg ttcagcggcc agcacgcagc ctaatcatgc   11220
ctgtcggggg gagctcatcc gttcctgaat ttgggtcatg ctccagtatc aggtattcag   11280
gtactagtac tcctgagcca tgtgctgcga caaaaaagcg aggctcctgt agtagagcct   11340
tgtttactta caaaattttt tacattctca gttatattaa atcttgtgac acatgcataa   11400
agcattaaat atacataaaa gaaataatta tttacacagt tacttataat ttgcgaaacg   11460 aatctttttaa gactggttag tttatgatta gataatattt attaaataca aatgaaagta   11520
atattattta tattttgcaa aaagtaaata agacctaggt agctaggcca acgtgagcat   11580
gtcggacccg gaccggttcg ttctacggcg cgtcccgcaa acctgcagcc aggtagtagt   11640
agtacaccgt gcacgggaga ggtgcgccat gcatgctcgg gcaaaagatc atagagaaag   11700
gtgcagcgtt tcagttgcac acctgaccga gtgacgcctc gccttgtttg gctttgttcc   11760
caaaattttt taaaattcct catcacatta aatctttgaa cgaatatatg gagcattaaa   11820
tataaataaa agaaataatt aatcatacaa tttgtctgta atttgcgaga cgaatctttt   11880
gagcctagtt agtttataat taaataatat ttgttaaata caaacgaaaa tgctacgtta   11940
gccaaaacta aaatttttct ccaaacgtga cccagcacct tccgatcaat catcactcag   12000
cgggtcacgt cagaagatca gatggacctt gccgtccggg cctgtctctc ggcctcctcc   12060
ccatctggaa cgaacagagg tccagtcctg tttcgagtcg agctgagtcg atcagatggg   12120
cctaaatagg ccgaagacgt aggcaaaggg cccgctgatt tatctgattc ttctaggacc   12180
gtgcatgcgc ggatgggcct aggtggaaac ccaacagatg tgaggcttca aagaggaaga   12240
agtccgttac acatggagag ttagtctata atgggataat atttaccaca aacaaataaa   12300
aatactacag tagcgaaatc caaaattttt cacatctaaa caaggcccta gatgttttgt   12360
cagtgccaga ccagagaaaa tctcgtcttc tgctgtcaat agctttgatg attcctggcg   12420
gcagaggtaa agcttgcctg ggccttgttt agttccgaaa agtgaaaagt tttcggtact   12480
gtagcacttt tgtttgttcg tgacaaatat catccaatta tggactaact agaattaaaa   12540
gattcgtctc gtgatctaca gctaaactgt gtaattagtt tttgtttttcg tctatattta   12600 atgtttcatg catgtgccac aagattcgat gtgacggaga attttgaaaa ttttttggtt   12660
ttcagagtga actaaacaag gcccagatgt aattgaccat gccatcgagc gcgagttgac   12720
tagagtgagt cggccctgat ggttaagtag tgcagactgc caagtggaca accgtctatc   12780
aactttgcag agtggggcga atgcactgag gatgttggag aggggcaagc caaggtaaac   12840
ttgaggaaag atgcttgttg acactgtagt atgtgaacaa tcctgtttaa ttttgtgtcc   12900
tcgacg                                                            12906
```

<210> SEQ ID NO 88
<211> LENGTH: 1790
<212> TYPE: DNA
<213> ORGANISM: Setaria italica

<400> SEQUENCE: 88

```
tctcatggtg tcccaagcac agcaagagcc agctctgcct cacagcagca gcaccgccaa    60
gcgcgcagcc gcgtcactca tggacgcccg cccggcccag cctctcctcc tccgcgcccc   120
gactcccagc attgacctcc ccgcgtccaa gccggacagg gccgccgcgg cggccggcaa   180
ggccgccgcc gcctccgtgt tcgacctgcg gcgggagccc aagatcccgg cgccattcgt   240
gtggccgcac gacgacgcgc ggccggccgtc ggcggcggag ctggacgtgc cgttggtgga   300
cgtgggcgtg ctgcgcaatg cgaccgcgc ggggctgcgg cgcgctgcgg cgcaggtggc   360
```

```
cgcggcgtgc gcgacgcacg ggttcttcca ggtgtgcggg cacgcgcgtgg gcgcggacct    420 ggcgcgcgcg gcgctggacg gcgccagtga cttcttccgg ctgccgctgg cggagaagca    480
gcgcgcccgg cgcgtcccgg ggaccgtgtc cgggtacacg agcgcgcacg ccgaccggtt    540
cgcgtccaag ctccctgga aggagaccct ctccttcggg ttccacgacg gcgccgcgtc    600
gcccgtcgtc gtcgactact tcgccggcac cctcgggcag gacttcgagg cagtggggcg    660
ggtgtaccag aggtactgcg aggagatgaa ggctctgtcg ctgacgatca tggagctcct    720
ggagctgagc ctgggcgtgg agcgcggcta ctaccgcgac ttcttcgagg acagccgctc    780
catcatgcgg tgcaactact acccgccgtg cccggagccg gagcgcacgc tgggcacggg    840
cccgcactgc gacccccaccg cgctgaccat cctcctccag gacgacgtcg gcgggctcga    900
ggtcctcgtc gacggcgact ggcgcccccgt ccgccccgtc cccggcgcca tggtcatcaa    960
catcggcgac accttcatgg ctctgtccaa cgggcggtac aagagctgcc tgcaccgggc   1020
ggtggtgaac cagcggcagg agcggcggtc gctggccttc ttcctgtgcc cgcgcgagga   1080
ccgggtggtg cgcccgccgg ccagcggcgc cgtcggcgag gcgccccgcc gctaccgga   1140 cttcacctgg gccgacctca tgcgcttcac gcagcgccac taccgcgccg acacccgcac   1200
gctggacgcc ttcacacgct ggctctccca cggcccggcc caggacgcgc cagtggcggc   1260
ggcggcttcc acctagctag cggcgcggat ccgaccgagc ccattgacga cgccgtccct   1320
ttccgccgcc gccgggggcccc gcgcgggggt tcaccccacg tgcgcgccca ggtgggcgag   1380
gtggcggcct cgtggcccgc gggccccgcg ccgccttccc atttttgggc gctgccgccc   1440
cgcgcgcatg ccggatgcgt gcgtccacgg cctactgctg ctactagtgt acatatacaa   1500
acatacatat atacgtagta taaatatata agcaagcggc ccggtgcccc ttttcgtttt   1560
cttgttttgt cgatcacaat ctctggattc gatggatgga taaatgtttg tacgcatgca   1620
tgtagatggg ctcatgaaat ttcagaatct ggaacggacg aggagctcac gtgcctcttc   1680
cgtgtctggt agcggtagct gcgtgccaaa tgtctggtgg gcccaaagaa attctagtgc   1740
cacccgtccg gatccggcat ccgaaagttc ccgacggttc gacacccgaa   1790
```

<210> SEQ ID NO 89
<211> LENGTH: 1272
<212> TYPE: DNA
<213> ORGANISM: Setaria italica
<400> SEQUENCE: 89

```
atggtgtccc aagcacagca agagccagct ctgcctcaca gcagcagcac cgccaagcgc     60
gcagccgcgt cactcatgga cgcccgcccg gcccagcctc tcctcctccg cgccccgact    120
cccagcattg acctccccgc gtccaagccg gacaggccg ccgcggcggc cggcaaggcc    180
gccgccgcct ccgtgttcga cctgcggcgg gagcccaaga tcccggcgcc attcgtgtgg    240
ccgcacgacg acgcgcggcc ggcgtcggcg cggagctgg acgtgccgtt ggtggacgtg    300
ggcgtgctgc gcaatggcga ccgcgcgggg ctgcggcgcg ctgcggcgca ggtggccgcg    360
gcgtgcgcga cgcacgggtt cttccaggtg tgcgggcacg gcgtgggcgc ggacctggcg    420
cgcgcggcgc tggacggcgc cagtgacttc ttccggctgc cgctggcgga gaagcagcgc    480
gcccggcgcg tcccggggac cgtgtccggg tacacgagcg cgcacgccga ccggttcgcg    540
tccaagctcc cctggaagga gaccctctcc ttcgggttcc acgacggcgc cgcgtcgccc    600
gtcgtcgtcg actacttcgc cggcaccctc gggcaggact cgaggcagt ggggcggggtg    660
```

```
taccagaggt actgcgagga gatgaaggct ctgtcgctga cgatcatgga gctcctggag       720
ctgagcctgg gcgtggagcg cggctactac cgcgacttct tcgaggacag ccgctccatc       780
atgcggtgca actactaccc gccgtgcccg gagccggagc gcacgctggg cacgggcccg       840
cactgcgacc ccaccgcgct gaccatcctc ctccaggacg acgtcggcgg gctcgaggtc       900
ctcgtcgacg gcgactggcg ccccgtccgc cccgtccccg gcgccatggt catcaacatc       960
ggcgacacct tcatggctct gtccaacggg cggtacaaga gctgcctgca ccgggcggtg      1020
gtgaaccagc ggcaggagcg gcggtcgctg gccttcttcc tgtgcccgcg cgaggaccgg      1080
gtggtgcgcc cgccggccag cggcgccgtc ggcgaggcgc cccgccgcta cccggacttc      1140
acctgggccg acctcatgcg cttcacgcag cgccactacc gcgccgacac ccgcacgctg      1200
gacgccttca cacgctggct ctcccacggc ccggcccagg acgcgccagt ggcggcggcg      1260
gcttccacct ag                                                          1272

<210> SEQ ID NO 90
<211> LENGTH: 423
<212> TYPE: PRT
<213> ORGANISM: Setaria italica

<400> SEQUENCE: 90

Met Val Ser Gln Ala Gln Gln Glu Pro Ala Leu Pro His Ser Ser Ser
1               5                   10                  15

Thr Ala Lys Arg Ala Ala Ala Ser Leu Met Asp Ala Arg Pro Ala Gln
            20                  25                  30

Pro Leu Leu Leu Arg Ala Pro Thr Pro Ser Ile Asp Leu Pro Ala Ser
        35                  40                  45

Lys Pro Asp Arg Ala Ala Ala Ala Ala Gly Lys Ala Ala Ala Ala Ser
    50                  55                  60

Val Phe Asp Leu Arg Arg Glu Pro Lys Ile Pro Ala Pro Phe Val Trp
65                  70                  75                  80

Pro His Asp Asp Ala Arg Pro Ala Ser Ala Ala Glu Leu Asp Val Pro
                85                  90                  95

Leu Val Asp Val Gly Val Leu Arg Asn Gly Asp Arg Ala Gly Leu Arg
            100                 105                 110

Arg Ala Ala Ala Gln Val Ala Ala Ala Cys Ala Thr His Gly Phe Phe
        115                 120                 125

Gln Val Cys Gly His Gly Val Gly Ala Asp Leu Ala Arg Ala Ala Leu
    130                 135                 140

Asp Gly Ala Ser Asp Phe Phe Arg Leu Pro Leu Ala Glu Lys Gln Arg
145                 150                 155                 160

Ala Arg Arg Val Pro Gly Thr Val Ser Gly Tyr Thr Ser Ala His Ala
                165                 170                 175

Asp Arg Phe Ala Ser Lys Leu Pro Trp Lys Glu Thr Leu Ser Phe Gly
            180                 185                 190

Phe His Asp Gly Ala Ala Ser Pro Val Val Val Asp Tyr Phe Ala Gly
        195                 200                 205

Thr Leu Gly Gln Asp Phe Glu Ala Val Gly Arg Val Tyr Gln Arg Tyr
    210                 215                 220

Cys Glu Glu Met Lys Ala Leu Ser Leu Thr Ile Met Glu Leu Leu Glu
225                 230                 235                 240

Leu Ser Leu Gly Val Glu Arg Gly Tyr Tyr Arg Asp Phe Phe Glu Asp
                245                 250                 255

Ser Arg Ser Ile Met Arg Cys Asn Tyr Tyr Pro Pro Cys Pro Glu Pro
```

```
                 260              265              270
Glu Arg Thr Leu Gly Thr Gly Pro His Cys Asp Pro Thr Ala Leu Thr
        275              280              285

Ile Leu Leu Gln Asp Asp Val Gly Gly Leu Glu Val Leu Val Asp Gly
        290              295              300

Asp Trp Arg Pro Val Arg Pro Val Pro Gly Ala Met Val Ile Asn Ile
305              310              315              320

Gly Asp Thr Phe Met Ala Leu Ser Asn Gly Arg Tyr Lys Ser Cys Leu
                325              330              335

His Arg Ala Val Val Asn Gln Arg Gln Glu Arg Arg Ser Leu Ala Phe
                340              345              350

Phe Leu Cys Pro Arg Glu Asp Arg Val Val Arg Pro Pro Ala Ser Gly
                355              360              365

Ala Val Gly Glu Ala Pro Arg Arg Tyr Pro Asp Phe Thr Trp Ala Asp
        370              375              380

Leu Met Arg Phe Thr Gln Arg His Tyr Arg Ala Asp Thr Arg Thr Leu
385              390              395              400

Asp Ala Phe Thr Arg Trp Leu Ser His Gly Pro Ala Gln Asp Ala Pro
                405              410              415

Val Ala Ala Ala Ala Ser Thr
                420
```

<210> SEQ ID NO 91
<211> LENGTH: 2888
<212> TYPE: DNA
<213> ORGANISM: Setaria italica

<400> SEQUENCE: 91

```
tctcatggtg tcccaagcac agcaagagcc agctctgcct cacagcagca gcaccgccaa      60
gcgcgcagcc gcgtcactca tggacgcccg cccggcccag cctctcctcc tccgcgcccc     120
gactcccagc attgacctcc ccgcgtccaa gccggacagg gccgccgcgg cggccggcaa     180
ggccgccgcc gcctccgtgt cgacctgcg gcgggagccc aagatcccgg cgccattcgt     240
gtggccgcac gacgacgcgc ggccggcgtc ggcggcggag ctggacgtgc cgttggtgga     300
cgtgggcgtg ctgcgcaatg cgaccgcgc ggggctgcgg cgcgctgcgg cgcaggtggc     360
cgcggcgtgc gcgacgcacg ggttcttcca ggtgtgcggg cacggcgtgg cgcggaccct     420
ggcgcgcgcg gcgctggacg cgccagtga cttcttccgg ctgccgctgg cggagaagca     480
gcgcgcccgg cgcgtcccgg ggaccgtgtc cgggtacacg agcgcgcacg ccgaccggtt     540
cgcgtccaag ctccctgga aggagaccct ctccttcggg ttccacgacg cgccgcgtc     600 gcccgtcgtc gtcgactact cgccggcac cctcgggcag gacttcgagg cagtggggta     660
agtatgtagg aatgaacttg gcacgcattg catccacatg gcgtgctgat cgaacgagct     720
gagccaaccg gcatgcacac atggcgtggc aggcgggtgt accagaggta ctgcgaggag     780
atgaaggctc tgtcgctgac gatcatggag ctcctggagc tgagcctggg cgtggagcgc     840
ggctactacc gcgacttctt cgaggacagc cgctccatca tgcggtgcaa ctactacccg     900
ccgtgcccgg agccggagcg cacgctgggc acgggcccgc actgcgaccc caccgcgctg     960
accatcctcc tccaggacga cgtcggcggg ctcgaggtcc tcgtcgacgg cgactggcgc    1020
cccgtccgcc ccgtccccgg cgccatggtc atcaacatcg gcgacacctt catggtacgg    1080
ccgccgctaa tccatccttt tgttgctctt atctcctctg gcgagtgcga gtaacgaaag    1140
cgctagctcc cctgctcctt gtcctgctct gtttcccaag tcctaatgga gctaaccggg    1200
```

```
cagactgcaa cacgcacgcg taggcatgtc acgtagccac cacttgcact gtgctgcgca      1260
gcgacgacgc aacgcggacg tgcgttcgag tcggttccat ctcggcgccg ctacacgcgg      1320
ccgcggctcc tagcctccta gggctccctg atccctatcc ccgagcccctt ccgcgggaaa     1380 agttcgttgg cgacggcaga ggagagccga cgggtccgtg ccgttggagc gtggcggcag      1440
gagaggccgg gagggtgttt tgttgcgttg cgcggcggcg cggaggatgc gatggcgcgg      1500
gcgggcggcg ctttcggcgg tggcccccgc gacccacgtg cgcgcgcggt ctcgtcgcct      1560
tccctgtttt ggtgccacct ctctgtgtcc gggaatgggt tggcttagcg gcgaccgaga      1620
ccgggcggtg gtctggcctg ctcccggcgc ccatcccgcc tggtctctca tcctgctcct      1680
cctatgcgcg aggggggcctg tagcggctgg agtacaagca gattggttgg gttgggttgc      1740
tgctgcttgg ctgttgcccg cccgctttct agccgtttcc gctcgccatc cggcacgcgg      1800
cgcccacgcc ggggctccag ctcggcccct ttggccgtgt gggtggcagg cacccctgca      1860
tcgtctcgtg cgtccggttt ccgcgcctgg cccccgcct tgaggtttcc ctgtgctttt       1920
gacaagactt tcgtagatat atgtgtgtgt atgtgtgtgt gtgcgtgcgc gcgtgtgtgt      1980
atatatatat ataaataaat aacatctgtg aatgatggat tacacgtgta gctgaccggc      2040
tgattgtgtt cgcgtgtgtg tcttcgatgc attgcaggct ctgtccaacg ggcggtacaa      2100
gagctgcctg caccgggcgg tggtgaacca gcggcaggag cggcggtcgc tggccttctt      2160
cctgtgcccg cgcgaggacc gggtggtgcg cccgccggcc agcggcgccg tcggcgaggc      2220
gccccgccgc tacccggact tcacctgggc cgacctcatg cgcttcacgc agcgccacta      2280
ccgcgccgac acccgcacgc tggacgcctt cacacgctgg ctctcccacg gcccggccca      2340
ggacgcgcca gtggcggcgg cggcttccac ctagctagcg gcgcggatcc gaccgagccc      2400
attgacgacg ccgtcccttt ccgccgccgc cggggcccgc gcgggggttc accccacgtg      2460
cgcgcccagg tgggcgaggt ggcggcctcg tggcccgcgg gccccgcgcc gccttcccat      2520
ttttgggcgc tgccgccccg cgcgcatgcc ggatgcgtgc gtccacggcc tactgctgct      2580
actagtgtac atatacaaac atacatatat acgtagtata aatatataag caagcggccc      2640
ggtgcccctt ttcgttttct tgttttgtcg atcacaatct ctggattcga tggatggata      2700
aatgtttgta cgcatgcatg tagatgggct catgaaattt cagaatctgg aacggacgag      2760
gagctcacgt gcctcttccg tgtctggtag cggtagctgc gtgccaaatg tctggtgggc      2820
ccaaagaaat tctagtgcca cccgtccgga tccggcatcc gaaagttccc gacggttcga      2880
cacccgaa                                                               2888
```

```
<210> SEQ ID NO 92
<211> LENGTH: 1567
<212> TYPE: DNA
<213> ORGANISM: Oryza sativa

<400> SEQUENCE: 92
tgcccagaca gctcgccctg cacacacaca cacactcaca ctcacacacg ctctcaactc        60
actcccgctc aacacagcgc tcacttctca tctccaatct catggtggcc gagcacccca       120
cgccaccaca gccgcaccaa ccaccgccca tggactccac cgccggctct ggcattgccg       180
ccccggcggc ggcggcggtg tgcgacctga ggatggagcc caagatcccg gagccattcg       240 tgtgccgaa cggcgacgcg aggccggcgt cggcggcgga gctggacatg cccgtggtcg       300
acgtgggcgt gctccgcgac ggcgacgccg aggggctgcg ccgcgccgcg gcgcaggtgg       360
```

```
ccgccgcgtg cgccacgcac gggttcttcc aggtgtccga gcacggcgtc gacgccgctc      420
tggcgcgcgc cgcgctcgac ggcgccagcg acttcttccg cctcccgctc gccgagaagc      480
gccgcgcgcg ccgcgtcccg ggcaccgtgt ccggctacac cagcgcccac gccgaccgct      540
tcgcctccaa gctcccatgg aaggagaccc tctccttcgg cttccacgac cgcgccgccg      600
cccccgtcgt cgccgactac ttctccagca ccctcggccc cgacttcgcg ccaatgggga      660
gggtgtacca gaagtactgc gaggagatga aggagctgtc gctgacgatc atggaactcc      720
tggagctgag cctgggcgtg gagcgaggct actacaggga gttcttcgcg gacagcagct      780
caatcatgcg gtgcaactac tacccgccat gcccggagcc ggagcggacg ctcggcacgg      840
gcccgcactg cgaccccacc gccctcacca tcctcctcca ggacgacgtc ggcggcctcg      900
aggtcctcgt cgacggcgaa tggcgccccg tcagccccgt ccccggcgcc atggtcatca      960
acatcggcga caccttcatg gcgctgtcga acgggaggta taagagctgc ctgcacaggg     1020
cggtggtgaa ccagcggcgg gagcggcggt cgctggcgtt cttcctgtgc ccgcgggagg     1080
acagggtggt gcggccgccg ccgagcgccg ccacgccgca gcactacccg gacttcacct     1140
gggccgacct catgcgcttc acgcagcgcc actaccgcgc cgacacccgc acgctcgacg     1200
ccttcacgcg ctggctcgcg ccgccggccg ccgacgccgc cgcgacggcg caggtcgagg     1260
cggccagctg atcgccgaac ggaacgaaac ggaacgaaca gaagccgatt tttggcgggg     1320
cccacgccca cgtgaggccc cacgtggaca gtgggcccgg gcggaggtgg cacccacgtg     1380
gaccgcgggc cccgcgccgc cttccaattt tggaccctac cgctgtacat attcatatat     1440
tgcaagaaga agcaaaacgt acgtgtgggt tgggttgggc ttctctctat tactaaaaaa     1500
aatataatgg aacgacggat gaatggatgc ttatttattt atctaaattg aattcgaatt     1560
cggctca                                                                 1567
```

<210> SEQ ID NO 93
<211> LENGTH: 1170
<212> TYPE: DNA
<213> ORGANISM: Oryza sativa

<400> SEQUENCE: 93

```
atggtggccg agcaccccac gccaccacag ccgcaccaac caccgcccat ggactccacc       60
gccggctctg gcattgccgc cccggcggcg gcggcggtgt cgacctgag gatggagccc      120 aagatcccgg agccattcgt gtggccgaac ggcgacgcga ggccggcgtc ggcggcggag      180
ctggacatgc ccgtggtcga cgtgggcgtg ctccgcgacg gcgacgccga ggggctgcgc      240
cgcgccgcgg cgcaggtggc cgccgcgtgc gccacgcacg ggttcttcca ggtgtccgag      300
cacggcgtcg acgccgctct ggcgcgcgcc gcgctcgacg gcgccagcga cttcttccgc      360
ctcccgctcg ccgagaagcg ccgcgcgcgc gcgtcccgg gcaccgtgtc cggctacacc      420
agcgcccacg ccgaccgctt cgcctccaag ctcccatgga aggagaccct ctccttcggc      480
ttccacgacc gcgccgccgc ccccgtcgtc gccgactact tctccagcac cctcggcccc      540
gacttcgcgc caatggggag ggtgtaccag aagtactgcg aggagatgaa ggagctgtcg      600
ctgacgatca tggaactcct ggagctgagc ctgggcgtgg agcgaggcta ctacagggag      660
ttcttcgcgg acagcagctc aatcatgcgg tgcaactact acccgccatg cccggagccg      720
gagcggacgt cggcacgggg cccgcactgc gaccccaccg ccctcaccat cctcctccag      780
gacgacgtcg gcggcctcga ggtcctcgtc gacggcgaat ggcgccccgt cagccccgtc      840
cccggcgcca tggtcatcaa catcggcgac accttcatgg cgctgtcgaa cgggaggtat      900
```

```
aagagctgcc tgcacagggc ggtggtgaac cagcggcggg agcggcggtc gctggcgttc      960
ttcctgtgcc cgcgggagga cagggtggtg cggccgccgc cgagcgccgc cacgccgcag     1020
cactacccgg acttcacctg ggccgacctc atgcgcttca cgcagcgcca ctaccgcgcc     1080
gacacccgca cgctcgacgc cttcacgcgc tggctcgcgc cgccggccgc cgacgccgcc     1140
gcgacggcgc aggtcgaggc ggccagctga                                       1170
```

```
<210> SEQ ID NO 94
<211> LENGTH: 389
<212> TYPE: PRT
<213> ORGANISM: Oryza sativa

<400> SEQUENCE: 94

Met Val Ala Glu His Pro Thr Pro Pro Gln Pro His Gln Pro Pro Pro
1               5                   10                  15

Met Asp Ser Thr Ala Gly Ser Gly Ile Ala Ala Pro Ala Ala Ala Ala
            20                  25                  30

Val Cys Asp Leu Arg Met Glu Pro Lys Ile Pro Glu Pro Phe Val Trp
        35                  40                  45

Pro Asn Gly Asp Ala Arg Pro Ala Ser Ala Ala Glu Leu Asp Met Pro
    50                  55                  60

Val Val Asp Val Gly Val Leu Arg Asp Gly Asp Ala Glu Gly Leu Arg
65                  70                  75                  80

Arg Ala Ala Ala Gln Val Ala Ala Ala Cys Ala Thr His Gly Phe Phe
                85                  90                  95

Gln Val Ser Glu His Gly Val Asp Ala Ala Leu Ala Arg Ala Ala Leu
            100                 105                 110

Asp Gly Ala Ser Asp Phe Phe Arg Leu Pro Leu Ala Glu Lys Arg Arg
            115                 120                 125

Ala Arg Arg Val Pro Gly Thr Val Ser Gly Tyr Thr Ser Ala His Ala
        130                 135                 140

Asp Arg Phe Ala Ser Lys Leu Pro Trp Lys Glu Thr Leu Ser Phe Gly
145                 150                 155                 160

Phe His Asp Arg Ala Ala Ala Pro Val Val Ala Asp Tyr Phe Ser Ser
                165                 170                 175

Thr Leu Gly Pro Asp Phe Ala Pro Met Gly Arg Val Tyr Gln Lys Tyr
            180                 185                 190

Cys Glu Glu Met Lys Glu Leu Ser Leu Thr Ile Met Glu Leu Leu Glu
            195                 200                 205

Leu Ser Leu Gly Val Glu Arg Gly Tyr Tyr Arg Glu Phe Phe Ala Asp
        210                 215                 220

Ser Ser Ser Ile Met Arg Cys Asn Tyr Tyr Pro Pro Cys Pro Glu Pro
225                 230                 235                 240

Glu Arg Thr Leu Gly Thr Gly Pro His Cys Asp Pro Thr Ala Leu Thr
                245                 250                 255

Ile Leu Leu Gln Asp Asp Val Gly Gly Leu Glu Val Leu Val Asp Gly
            260                 265                 270

Glu Trp Arg Pro Val Ser Pro Val Pro Gly Ala Met Val Ile Asn Ile
        275                 280                 285

Gly Asp Thr Phe Met Ala Leu Ser Asn Gly Arg Tyr Lys Ser Cys Leu
    290                 295                 300

His Arg Ala Val Val Asn Gln Arg Arg Glu Arg Arg Ser Leu Ala Phe
305                 310                 315                 320
```

```
Phe Leu Cys Pro Arg Glu Asp Arg Val Val Arg Pro Pro Pro Ser Ala
            325                 330                 335

Ala Thr Pro Gln His Tyr Pro Asp Phe Thr Trp Ala Asp Leu Met Arg
            340                 345                 350

Phe Thr Gln Arg His Tyr Arg Ala Asp Thr Arg Thr Leu Asp Ala Phe
            355                 360                 365

Thr Arg Trp Leu Ala Pro Pro Ala Ala Asp Ala Ala Ala Thr Ala Gln
    370                 375                 380

Val Glu Ala Ala Ser
385
```

<210> SEQ ID NO 95
<211> LENGTH: 3140
<212> TYPE: DNA
<213> ORGANISM: Oryza sativa

<400> SEQUENCE: 95

```
tgcccagaca gctcgccctg cacacacaca cacactcaca ctcacacacg ctctcaactc     60
actcccgctc aacacagcgc tcacttctca tctccaatct catggtggcc gagcacccca    120
cgccaccaca gccgcaccaa ccaccgccca tggactccac cgccggctct ggcattgccg    180
ccccggcggc ggcggcggtg tgcgacctga ggatggagcc caagatcccg gagccattcg    240
tgtggccgaa cggcgacgcg aggccggcgt cggcggcgga gctggacatg cccgtggtcg    300
acgtgggcgt gctccgcgac ggcgacgccg aggggctgcg ccgcgccgcg cgcaggtgg     360 ccgccgcgtg cgccacgcac gggttcttcc aggtgtccga gcacggcgtc gacgccgctc    420
tggcgcgcgc cgcgctcgac ggcgccagcg acttcttccg cctcccgctc gccgagaagc    480
gccgcgcgcg ccgcgtcccg ggcaccgtgt ccggctacac cagcgcccac gccgaccgct    540
tcgcctccaa gctcccatgg aaggagaccc tctccttcgg cttccacgac cgcgccgccg    600
cccccgtcgt cgccgactac ttctccagca ccctcggccc cgacttcgcg ccaatggggt    660
aattaaaacg atggtggacg acattgcatt tcaaattcaa aacaaattca aaacacaccg    720
accgagatta tgctgaattc aaacgcgttt gtgcgcgcag gagggtgtac cagaagtact    780
gcgaggagat gaaggagctg tcgctgacga tcatggaact cctggagctg agcctgggcg    840
tggagcgagg ctactacagg gagttcttcg cggacagcag ctcaatcatg cggtgcaact    900
actacccgcc atgcccggag ccggagcgga cgctcggcac gggcccgcac tgcgacccca    960
ccgccctcac catcctcctc caggacgacg tcggcggcct cgaggtcctc gtcgacggcg   1020
aatggcgccc cgtcagcccc gtccccggcg ccatggtcat caacatcggc gacaccttca   1080
tggtaaacca tctcctattc tcctctcctc tgttctcctc tgcttcgaag caacagaaca   1140
agtaattcaa gctttttttt ctctctcgcg cgaaattgac gagaaaaata agatcgtggt   1200
aggggcgggg ctttcagctg aaagcgggaa gaaaccgacc tgacgtgatt tctctgttcc   1260
aatcacaaac aatggaatgc cccactcctc catgtgttat gatttatctc acatcttata   1320
gttaatagga gtaagtaaca agctactttt ttcatattat agttcgtttg attttttttt   1380
tttaaagttt ttttagtttt atccaaattt attgaaaaac ttagcaacgt ttataatacc   1440
aaattagtct catttagttt aatattgtat atattttgat aatatattta tgttatatta   1500
aaaatattac tatatttttc tataaacatt attaaaagcc atttataata taaaatggaa   1560
ggagtaatta atatggatct ccccccgacat gagaatattt ccgatggtg tgacgacgcc    1620 atgtaagctt cggtgggcct ggacggccag aggtgccaac agccacgtcc aacaacccct   1680
```

-continued

```
gggtcccccc ctaacactcc aaacagtagt gagtagtgtc tcgtcgcgtt ttagtatttg   1740
atgacaaaca aagtgtgagt tgagttagcc accaccaact tgcacacgag cacatacatt   1800
tgtgtccatt ctcgccagtc acttccatct ctagtcctaa ctcctatcta gcgatgtaag   1860
cggataattt catcatccgt atataaacct gtttgttata gttaatttcc tatataatac   1920
tataacagta tacattttaa aagaaaacaa aattaggata aacaggccct gctcctatcc   1980
atccatggca cttggaagga ccagactcgg tcatgccatg ccaagccaag atatgggtta   2040
tggaagagta gagaagagga gagatgagag ataagcatgc gttctcctcc tcgttggatg   2100
tgtattttgg agggatttgt gtagtagtag cagcggcgcc gcggggacgg atgcggatgg   2160
tggcgctttc ggtggcgttt tcccgggggg gttttggttt ggcgcttggg ggggatggca   2220
tggcgcggcg tgcggctgca cgccacacac acgcgcgcgc acgcacgtac gtcgtcgtcg   2280
ccgcgggcgg acggtagctt agggtggtgt gttccgcgcg cgggcgcgga ttgttccatg   2340
ccgatcgatt tggcgccacc ctcgccgcgg ctcttgtcgc gtcgtgcgcc tctctcgcgc   2400
ggtttgtcct tgtcgcgttg ctcagccggc gacggggggca cggacattgg cgatgtagcc   2460
ctgcacgtgt cggcctctcc gttgatgaat gatgatgtat gtatgtattt tttttttgtct   2520 gaaggaattt gtggggaatt gttgtgtgtg caggcgctgt cgaacgggag gtataagagc   2580
tgcctgcaca gggcggtggt gaaccagcgg cgggagcggc ggtcgctggc gttcttcctg   2640
tgcccgcggg aggacagggt ggtgcggccg ccgccgagcg ccgccacgcc gcagcactac   2700
ccggacttca cctgggccga cctcatgcgc ttcacgcagc gccactaccg cgccgacacc   2760
cgcacgctcg acgccttcac gcgctggctc gcgccgccgg ccgccgacgc cgccgcgacg   2820
gcgcaggtcg aggcggccag ctgatcgccg aacggaacga aacggaacga acagaagccg   2880 attttttggcg gggcccacgc ccacgtgagg ccccacgtgg acagtgggcc cgggcggagg   2940
tggcacccac gtggaccgcg ggccccgcgc cgccttccaa ttttggaccc taccgctgta   3000
catattcata tattgcaaga agaagcaaaa cgtacgtgtg ggttgggttg ggcttctctc   3060
tattactaaa aaaaatataa tggaacgacg gatgaatgga tgcttatttta tttatctaaa   3120 ttgaattcga attcggctca                                              3140
```

```
<210> SEQ ID NO 96
<211> LENGTH: 1170
<212> TYPE: DNA
<213> ORGANISM: Triticum aestivum

<400> SEQUENCE: 96
```

```
atggacacca gccctgcaac tcccctgctc ctccagcctc ctgctcccag cattgacccg     60
ttcgccgcca aggcggccgt caacaagggc ggcggcgcgg caaccgcggt gtacgacctc    120
cggagggagc cgaagatccc cgccccgttc gtgtggccgc acgccgaggt cgccccacc     180 acggcccagg agctggccgt gccggtggtg gacgtgggcg tgctgcgcaa tggcgacgcc    240
gcggggctcc gccgcgccgt ggcgcaggtg gccgcgcgcgt gcgccacgca cgggttcttc    300
caggtgtccg ggcacggcgt ggacgaggcc ctggcgcgcg cggcgctgga cggcgcgagc    360
ggcttcttcc ggctgccgct ggccgagaag cagcgcgcgc ggcgcgtccc ggggaccgtg    420
tccgggtaca cgagcgcgca cgccgaccgg ttcgcctcca agctcccctg gaaggagacc    480
ctctccttcg gcttccacga ccgcgccggc gccgcgcccg tcgtggtgga ctacttcacc    540
agcaccctcg ggccggacta cgagccaatg gggagggtgt accaggagta ctgcgcgggaag   600 atgaaggagc tgtcgctgag gatcatggag ctgctggagc tgagccaggg cgtggagaag    660
```

```
cgcgggtact accgggagtt cttcgcggac agcagctcca tcatgcggtg caactactac    720
ccgccgtgcc cggagccgga gcgcacgctg ggcacgggcc cgcactgcga ccccacggcg    780
ctcaccatcc tactgcagga cgacgtgggc gggctggagg tcctcgtcga cggcgactgg    840
cgccccgtcc gccccgtccc cggcgccatg gtcatcaaca tcggcgacac cttcatggcg    900
ctgtcgaacg ggcggtacaa gagctgcctg caccgcgcgg tggtgaaccg gcggcaggag    960
cggcggtcgc tggccttctt cctgtgcccg cgcgaggacc gcgtggtgcg ccgccgccg   1020 ggcctgagga gcccgcggcg gtacccggac ttcacctggg ctgacctcat gcgcttcacg   1080
cagcgccact accgcgccga cacgcgcacc ctcgacgcct tcacccagtg gttctcctcc   1140
tcctcctcct cggcccagga ggcggcctga                                    1170
```

<210> SEQ ID NO 97
<211> LENGTH: 389
<212> TYPE: PRT
<213> ORGANISM: Triticum aestivum

<400> SEQUENCE: 97

```
Met Asp Thr Ser Pro Ala Thr Pro Leu Leu Leu Gln Pro Pro Ala Pro
1               5                   10                  15

Ser Ile Asp Pro Phe Ala Ala Lys Ala Ala Val Asn Lys Gly Gly Gly
                20                  25                  30

Ala Ala Thr Ala Val Tyr Asp Leu Arg Arg Glu Pro Lys Ile Pro Ala
            35                  40                  45

Pro Phe Val Trp Pro His Ala Glu Val Arg Pro Thr Thr Ala Gln Glu
        50                  55                  60

Leu Ala Val Pro Val Val Asp Val Gly Val Leu Arg Asn Gly Asp Ala
65                  70                  75                  80

Ala Gly Leu Arg Arg Ala Val Ala Gln Val Ala Ala Ala Cys Ala Thr
                85                  90                  95

His Gly Phe Phe Gln Val Ser Gly His Gly Val Asp Glu Ala Leu Ala
                100                 105                 110

Arg Ala Ala Leu Asp Gly Ala Ser Gly Phe Phe Arg Leu Pro Leu Ala
            115                 120                 125

Glu Lys Gln Arg Ala Arg Arg Val Pro Gly Thr Val Ser Gly Tyr Thr
        130                 135                 140

Ser Ala His Ala Asp Arg Phe Ala Ser Lys Leu Pro Trp Lys Glu Thr
145                 150                 155                 160

Leu Ser Phe Gly Phe His Asp Arg Ala Gly Ala Ala Pro Val Val Val
                165                 170                 175

Asp Tyr Phe Thr Ser Thr Leu Gly Pro Asp Tyr Glu Pro Met Gly Arg
                180                 185                 190

Val Tyr Gln Glu Tyr Cys Gly Lys Met Lys Glu Leu Ser Leu Arg Ile
            195                 200                 205

Met Glu Leu Leu Glu Leu Ser Gln Gly Val Glu Lys Arg Gly Tyr Tyr
        210                 215                 220

Arg Glu Phe Phe Ala Asp Ser Ser Ser Ile Met Arg Cys Asn Tyr Tyr
225                 230                 235                 240

Pro Pro Cys Pro Glu Pro Glu Arg Thr Leu Gly Thr Gly Pro His Cys
                245                 250                 255

Asp Pro Thr Ala Leu Thr Ile Leu Leu Gln Asp Asp Val Gly Gly Leu
            260                 265                 270

Glu Val Leu Val Asp Gly Asp Trp Arg Pro Val Arg Pro Val Pro Gly
```

-continued

```
          275               280               285
Ala Met Val Ile Asn Ile Gly Asp Thr Phe Met Ala Leu Ser Asn Gly
      290               295               300

Arg Tyr Lys Ser Cys Leu His Arg Ala Val Val Asn Arg Arg Gln Glu
305               310               315               320

Arg Arg Ser Leu Ala Phe Phe Leu Cys Pro Arg Glu Asp Arg Val Val
                  325               330               335

Arg Pro Pro Pro Gly Leu Arg Ser Pro Arg Arg Tyr Pro Asp Phe Thr
                  340               345               350

Trp Ala Asp Leu Met Arg Phe Thr Gln Arg His Tyr Arg Ala Asp Thr
              355               360               365

Arg Thr Leu Asp Ala Phe Thr Gln Trp Phe Ser Ser Ser Ser Ser Ser
      370               375               380

Ala Gln Glu Ala Ala
385
```

<210> SEQ ID NO 98
<211> LENGTH: 3050
<212> TYPE: DNA
<213> ORGANISM: Triticum aestivum

<400> SEQUENCE: 98

```
ctcatggtgc tccagaccgc tcagcaagaa ccatccctga cgcgtccgcc tcactgcagc      60
gtcgccagcg cgcgctcgcc ggcggccatg gacaccagcc ctgcaactcc cctgctcctc     120
cagcctcctg ctcccagcat tgacccgttc gccgccaagg cggccgtcaa caagggcggc     180
ggcgcggcaa ccgcggtgta cgacctccgg agggagccga agatccccgc cccgttcgtg     240
tggccgcacg ccgaggtgcg ccccaccacg gcccaggagc tggccgtgcc ggtggtggac     300
gtgggcgtgc tgcgcaatgg cgacgccgcg gggctccgcc gcgccgtggc gcaggtggcc     360
gcggcgtgcg ccacgcacgg gttcttccag gtgtccgggc acggcgtgga cgaggccctg     420
gcgcgcgcgg cgctggacgg cgcgagcggc ttcttccggc tgccgctggc cgagaagcag     480
cgcgcgcggc gcgtcccggg gaccgtgtcc gggtacacga gcgcgcacgc cgaccggttc     540
gcctccaagc tcccctggaa ggagaccctc tccttcggct ccacgaccg cgccggcgcc     600 gcgcccgtcg tggtggacta cttcaccagc acctctgggc cggactacga gccaatgggg     660
taatatatcc acccgcccac acccctatcc ggccagcacg aatccatccc cgccactgca     720
tttttttcct tttgtttccg cgcgaccgta cgttcgatcg gcgcccacgt acgtacgtgc     780
gtacgcagta gcagtacttg aagccgccgt actacgtgct gagtagtgac aactgaacac     840
gtgcaggagg gtgtaccagg agtactgcgg gaagatgaag gagctgtcgc tgaggatcat     900
ggagctgctg gagctgagcc agggcgtgga gaagcgcggg tactaccggg agttcttcgc     960
ggacagcagc tccatcatgc ggtgcaacta ctacccgccg tgcccggagc cggagcgcac    1020
gctgggcacg ggcccgcact cgacccccac ggcgctcacc atcctactgc aggacgacgt    1080
gggcgggctg gaggtcctcg tcgacggcga ctggcgcccc gtccgccccg tccccggcgc    1140
catggtcatc aacatcggcg acaccttcat ggtaattact cctctctcag cgttgctttc    1200
gctgattaat tgcagaaaca gtagtcaact acccatgctc tgttccgctg tgctctgctt    1260
cccaacgagc gaaccggccc ataaaaactg ccttgctgtc ttggaaccaa gaggaaaggg    1320
accgtgggag cctaccgaca cgacgtgatt gcactctgct tcctaacaag cgagccgccg    1380
gtagggctat caccgtaagg gctcctttga ttcaaaggaa tttcttagga tttctgaagg    1440
```

-continued

```
attgaaatcc ttaggatttt ttcctatgtt ggtacttcga ttcataggat tgaatcccat      1500
aggatttttt tcctatgaaa tcttctgtac tacatttcat aggaaatcta acatccactc      1560
caaccttttt ttatatttcc tttgttttc atgtgccatc aaacactcct tgttaatcct      1620
ataggattca agtgggcatg ccactccaat cctatacttt tcccattcct acgttttcaa      1680
aatcctacga atcaaagagg ccctaaagct gctgacatga cgtgattttt ttttctttt      1740 ctttctttct ttctcagctc caatcaacgc tggttattag atcattagag tggacaggtt      1800
gaattaacat gcagtagtta gtagttagca gccacaaacg ggtcccgttc tctgaagtct      1860
gaactgacat aagtcctgat catcgaccat tctttgcttc ctaggacgat gcctgttgga      1920
acttgcgtcc aatgcccgtt agggagtggt aattgtcatc acttttagac tcgtcgattc      1980
cactgatgaa gacgtagcac atggatgagc caacgtatcc gtttctagtg gtctcgaaaa      2040
gtagggtttc attcattcta tctatctatc cgtccgtcca aaagggctgc gatgcgagca      2100
cttgagtcgg agccaatcag agcgcgagaa aagatagggg gggtagcaag ccatgtcgga      2160
ggggcgtttg cttccggcag gtttggattc ttgtggtagg cgggcggctc tgtacagtag      2220
cggcggtgac ggtgaggtgg cggcgctttc ggtggcgggc caacccaggt gcatgcacgc      2280
gcgctcgtcg ttttcccgcc tgaatctgcc gctgcgccca tggcaagggg gtgggtgctg      2340
ccgccgggcg atggagtaga tcacggtcgc cgtcgggctc ggccagttga tcacggttcg      2400
ttcgtgcggt actaggttcc cccacggcac tgtgactgca tcgttccggc cctcgccatt      2460
ggcgatcggg caatctcctg ttcatccgtc gctgttgatt cctcggccac gatagaccat      2520
gcgcgtgccg gtcgtcgccc cgtcgcgctc gcttcacgtg ctcgtcgcgt ggctcccgtc      2580
ccacacgagg ccgccgcttt ctgacccagt ggagcgcgtg atttacagtt tatatatgtc      2640
gctgcatttt tcttttgtg tgctgctcat tttgcttgga cggagaccgg gaacgattag      2700
ccacggatct aacgcgttgt tgcttgtttt caatgcatgc atgcaggcgc tgtcgaacgg      2760
gcggtacaag agctgcctgc accgcgcggt ggtgaaccgg cggcaggagc ggcggtcgct      2820
ggccttcttc ctgtgcccgc gcgaggaccg cgtggtgcgg ccgccgccgg gcctgaggag      2880
cccgcggcgg tacccggact tcacctgggc tgacctcatg cgcttcacgc agcgccacta      2940
ccgcgccgac acgcgcaccc tcgacgcctt cacccagtgg ttctcctcct cctcctcctc      3000
ggcccaggag gcggcctgat tctgctctgc cacgaaacga tcggtccaca      3050
```

```
<210> SEQ ID NO 99
<211> LENGTH: 1486
<212> TYPE: DNA
<213> ORGANISM: Hordeum vulgare

<400> SEQUENCE: 99
```

```
gaccagtagc atatagtttt tcttgtgttt gccatggtgg acgtgtcgaa ctttgtagaa        60
gccaatggca atgcagcagt atcgattcct gccatggaag ttgctgggag tcctcacgtc       120
ccgttcgttc ctcgggacgc gaacgcgaca gacagcaaga atgccaagga cgtcctcgac       180
ctctggcggc agcagaaaca aatcccggct cccttcatct ggccccacgc cgacgcgcgg       240
ccgtcgtcga tcttggagct ggacgtgccc gtggtcgaca tcggcgcggc cctgcacagc       300
gccgccggga tggcccgcgc cgcggcgcag gtggccgagg catgcgcgag ccacggcttc       360
ttccaggtga ccgggcacgg cgtcgacccc gcgctggccc aagcagcgct cgacggcgca       420
gcggacttct tccgcctgcc gctcgccacc aagcagcgcg cccgccgatc cccgggggacc       480 gtcaaagggt acgcctccgc ccacgccgac cgcttcgccg ccaagcttcc ctggaaggag       540
```

-continued

```
actctctcct tcatccacaa ccacgtccac gaggacgtcg gcgcccgcgc aagcagtcac      600
gtcgtcgact acttcacctc cgcccttggc gacgacttca tgcacctagg ggaggtgtac      660
caggagtact gtgaggcgat ggaggacgcg tcgctggcga taatggaggt gctgggggtg      720
agcctggggc tggggagagg gtactacagg gacttcttcg ccgacggcag ctccatcatg      780
aggtgcaact actacccgcg gtgcccggag ccggaccgga cgctggggac ggggccgcac      840
tgcgacccgt cggcgctgac catcctgctg caggacggcg aggtggacgg gctccaggtg      900
ctcgtcgacg gcgcatggcg ctccgtgcgg cccaagcccg gcgagctcgt cgtaaacatc      960
ggcgacacct catggcgct gtcgaacggc cggtacaaga gctgcctcca ccgcgcggtg      1020
gtgcaccggg agaaggagcg ccggtcgctg gcctacttcc tcgccccgcg ggaggaccgg      1080
gtggttcgcc cgccgccttc gccggcgccg gcgccgcggc tctacccgga cttcacctgg      1140
gcggagctca tgcgattcac gcagcgccac taccgcgccg acgcccgcac gctcgacgcc      1200
ttcgcgtgct ggctcgacct gcccagctgc cccaccacgc cccaggccca agggactgtc      1260
tagtgtctgt gatgtatcat ctgtctcagc tgttgtatac gaccacttgt gtctgctagc      1320
tctgcgcttg tgtttcttat gtgagctaac taactaaata gtgtgtatat ttcttgccgc      1380
gccttatgca agccctagtc tagaacatgt aataattaac ttaagcatat acgttgatct      1440
ttggtgtatt tttcatattt ccttcataat gaataatcta ttatgc                    1486
```

<210> SEQ ID NO 100
<211> LENGTH: 1230
<212> TYPE: DNA
<213> ORGANISM: Hordeum vulgare

<400> SEQUENCE: 100

```
atggtggacg tgtcgaactt tgtagaagcc aatggcaatg cagcagtatc gattcctgcc       60
atggaagttg ctgggagtcc tcacgtcccg ttcgttcctc gggacgcgaa cgcgacagac      120
agcaagaatg ccaaggacgt cctcgacctc tggcggcagc agaaacaaat cccggctccc      180
ttcatctggc cccacgccga cgcgcggccg tcgtcgatct tggagctgga cgtgcccgtg      240
gtcgacatcg gcgcggccct gcacagcgcc gccgggatgg cccgcgccgc ggcgcaggtg      300
gccgaggcat gcgcgagcca cggcttcttc caggtgaccg gcacggcgt cgaccccgcg      360 ctggcccaag cagcgctcga cggcgcagcg gacttcttcc gcctgccgct cgccaccaag      420
cagcgcgccc gccgatcccc ggggaccgtc aaagggtacg cctccgccca cgccgaccgc      480
ttcgccgcca agcttccctg gaaggagact ctctccttca tccacaacca cgtccacgag      540
gacgtcggcg cccgcgcaag cagtcacgtc gtcgactact tcacctccgc ccttggcgac      600
gacttcatgc acctagggga ggtgtaccag gagtactgtg aggcgatgga ggacgcgtcg      660
ctggcgataa tggaggtgct ggggtgagc ctggggctgg gagagggta ctacagggac      720 ttcttcgccg acggcagctc catcatgagg tgcaactact acccgcgtg cccggagccg      780 gaccggacgc tggggacggg gccgcactgc gacccgtcgg cgctgaccat cctgctgcag      840
gacggcgagg tggacgggct ccaggtgctc gtcgacggcg catggcgctc cgtgcggccc      900
aagcccggcg agctcgtcgt aaacatcggc gacaccttca tggcgctgtc gaacggccgg      960
tacaagagct gcctccaccg cgcggtggtg caccgggaga aggagcgccg gtcgctggcc     1020
tacttcctcg ccccgcggga ggaccgggtg ttcgcccgc cgccttcgcc ggcgccggcg     1080
ccgcggctct acccggactt cacctgggcg gagctcatgc gattcacgca gcgccactac     1140
```

-continued cgcgccgacg cccgcacgct cgacgccttc gcgtgctggc tcgacctgcc cagctgcccc     1200
accacgcccc aggcccaagg gactgtctag                                       1230

<210> SEQ ID NO 101
<211> LENGTH: 409
<212> TYPE: PRT
<213> ORGANISM: Hordeum vulgare

<400> SEQUENCE: 101

Met Val Asp Val Ser Asn Phe Val Glu Ala Asn Gly Asn Ala Ala Val
1               5                   10                  15

Ser Ile Pro Ala Met Glu Val Ala Gly Ser Pro His Val Pro Phe Val
            20                  25                  30

Pro Arg Asp Ala Asn Ala Thr Asp Ser Lys Asn Ala Lys Asp Val Leu
        35                  40                  45

Asp Leu Trp Arg Gln Gln Lys Gln Ile Pro Ala Pro Phe Ile Trp Pro
    50                  55                  60

His Ala Asp Ala Arg Pro Ser Ser Ile Leu Glu Leu Asp Val Pro Val
65                  70                  75                  80

Val Asp Ile Gly Ala Ala Leu His Ser Ala Ala Gly Met Ala Arg Ala
                85                  90                  95

Ala Ala Gln Val Ala Glu Ala Cys Ala Ser His Gly Phe Phe Gln Val
            100                 105                 110

Thr Gly His Gly Val Asp Pro Ala Leu Ala Gln Ala Ala Leu Asp Gly
        115                 120                 125

Ala Ala Asp Phe Phe Arg Leu Pro Leu Ala Thr Lys Gln Arg Ala Arg
    130                 135                 140

Arg Ser Pro Gly Thr Val Lys Gly Tyr Ala Ser Ala His Ala Asp Arg
145                 150                 155                 160

Phe Ala Ala Lys Leu Pro Trp Lys Glu Thr Leu Ser Phe Ile His Asn
                165                 170                 175

His Val His Glu Asp Val Gly Ala Arg Ala Ser Ser His Val Val Asp
            180                 185                 190

Tyr Phe Thr Ser Ala Leu Gly Asp Asp Phe Met His Leu Gly Glu Val
        195                 200                 205

Tyr Gln Glu Tyr Cys Glu Ala Met Glu Asp Ala Ser Leu Ala Ile Met
    210                 215                 220

Glu Val Leu Gly Val Ser Leu Gly Leu Gly Arg Gly Tyr Tyr Arg Asp
225                 230                 235                 240

Phe Phe Ala Asp Gly Ser Ser Ile Met Arg Cys Asn Tyr Tyr Pro Arg
                245                 250                 255

Cys Pro Glu Pro Asp Arg Thr Leu Gly Thr Gly Pro His Cys Asp Pro
            260                 265                 270

Ser Ala Leu Thr Ile Leu Leu Gln Asp Gly Glu Val Asp Gly Leu Gln
        275                 280                 285

Val Leu Val Asp Gly Ala Trp Arg Ser Val Arg Pro Lys Pro Gly Glu
    290                 295                 300

Leu Val Val Asn Ile Gly Asp Thr Phe Met Ala Leu Ser Asn Gly Arg
305                 310                 315                 320

Tyr Lys Ser Cys Leu His Arg Ala Val Val His Arg Glu Lys Glu Arg
                325                 330                 335

Arg Ser Leu Ala Tyr Phe Leu Ala Pro Arg Glu Asp Arg Val Val Arg
            340                 345                 350

Pro Pro Pro Ser Pro Ala Pro Ala Pro Arg Leu Tyr Pro Asp Phe Thr

```
          355                 360                 365

Trp Ala Glu Leu Met Arg Phe Thr Gln Arg His Tyr Arg Ala Asp Ala
    370                 375                 380

Arg Thr Leu Asp Ala Phe Ala Cys Trp Leu Asp Leu Pro Ser Cys Pro
385                 390                 395                 400

Thr Thr Pro Gln Ala Gln Gly Thr Val
                405

<210> SEQ ID NO 102
<211> LENGTH: 1423
<212> TYPE: DNA
<213> ORGANISM: Sorghum bicolor

<400> SEQUENCE: 102
cctctcatca caggccccag cctcactctt ctcacagcaa gacatcgcag cctcacaacc     60
acacagcaac gtgatcgcca tgggcgggct caccatggag caggccttcg tgcaggcccc    120
cgagcaccgc cccaagccca ccgtcaccga ggccaccggc atcctggtca tcgacctctc    180
gcctctcacc gccagcgaca ccgacgcggc cgcggtggac gcgctggccg ccgaggtggg    240
cgcggcgagc cgggactggg gcttcttcgt ggtggttggc cacggcgtgc cgcggagac     300 cgtggcgcgc gcgacggcgg cgcagcgcgc gttcttcgcg ctgccggcgg agcggaaggc    360
cgccgtgcgg aggagcgagg cggagccgct cgggtactac gagtcggagc acaccaagaa    420
cgtcagggac tggaaggagg tgttcgacct cgtcccgcgc gatccgccgc cgccagcagc    480
cgtggccgac ggcgagctcg tcttcaagaa caagtggccc caggatctgc cgggcttcag    540
agaggcgctg gaggagtacg cggcagcgat ggaggagctg tcgttcaagc tgctggagct    600
gatcgcccgg agcttgaagc tgaggcccga ccggctgcac ggcttcttca aggaccagac    660
gacgttcatc cggctgaacc actaccctcc atgcccgagc ccggacctgg cgctgggagt    720
ggggcggcac aaggacgcgg gggcgctgac catcctgtac caggacgaag tgggcgggct    780
ggacgtccgg cggcgctcct ccgacggcgg cggcggcgag tgggtgcggg tgaggcccgt    840
gccggagtcg ttcgtcatca cgtcggcga cctcgtccag gtgtggagca acgacaggta    900
cgagagcgcg gagcaccggg tgtcggtgaa ctcggcgagg gagaggttct ccatgcccta    960
cttcttcaac ccggcgagct acaccatggt ggagccggtg gaggagctgg tgagcgacga   1020
cgacccgccc aggtacgacg cctacagctg gggcgagttc ttcagcacca ggaagaacag   1080
caacttcaag aagctcagcg tggagaacat tcagatcgcg catttcaaga agaccctcgt   1140
cctcgcctag ataagcagca ggatactaca ggtctacagg actaggacaa gccgatcgag   1200
gtgaccggcc gtcgtcttca gattcagtat atgcgtgtcg ccgttcgtgt tagaacaaat   1260
taataatgtg cgcgctgtgt gctgtgtgtg tggagtaaaa aaaaactaaa catggatgtg   1320
catgttcaaa aaaaaaaaca tggatgcgag tatgtttggg aataataaca ggcttgtgac   1380
ggtctggttt atttgcaaat tcaaaccgaa ttggttgatc ttc                     1423

<210> SEQ ID NO 103
<211> LENGTH: 1071
<212> TYPE: DNA
<213> ORGANISM: Sorghum bicolor

<400> SEQUENCE: 103
atgggcgggc tcaccatgga gcaggccttc gtgcaggccc ccgagcaccg ccccaagccc     60
accgtcaccg aggccaccgg catcctggtc atcgacctct cgcctctcac cgccagcgac    120
```

```
accgacgcgg ccgcggtgga cgcgctggcc gccgaggtgg gcgcggcgag ccgggactgg      180
ggcttcttcg tggtggttgg ccacggccgtg cccgcggaga ccgtggcgcg cgcgacggcg      240
gcgcagcgcg cgttcttcgc gctgccggcg gagcggaagg ccgccgtgcg gaggagcgag      300
gcggagccgc tcgggtacta cgagtcggag cacaccaaga acgtcaggga ctggaaggag      360
gtgttcgacc tcgtcccgcg cgatccgccg ccgccagcag ccgtggccga cggcgagctc      420
gtcttcaaga acaagtggcc ccaggatctg ccgggcttca gagaggcgct ggaggagtac      480
gcggcagcga tggaggagct gtcgttcaag ctgctggagc tgatcgcccg gagcttgaag      540
ctgaggcccg accggctgca cggcttcttc aaggaccaga cgacgttcat ccggctgaac      600
cactaccctc catgcccgag cccggacctg cgctggag tggggcggca caaggacgcg      660
ggggcgctga ccatcctgta ccaggacgaa gtgggcgggc tggacgtccg gcggcgctcc      720
tccgacggcg gcggcggcga gtgggtgcgg gtgaggcccg tgccggagtc gttcgtcatc      780
aacgtcggcg acctcgtcca ggtgtggagc aacgacaggt acgagagcgc ggagcaccgg      840
gtgtcggtga actcggcgag ggagaggttc tccatgccct acttcttcaa cccgcgcgagc      900 tacaccatgg tggagccggt ggaggagctg gtgagcgacg acgacccgcc caggtacgac      960
gcctacagct ggggcgagtt cttcagcacc aggaagaaca gcaacttcaa gaagctcagc     1020
gtggagaaca ttcagatcgc gcatttcaag aagaccctcg tcctcgccta g             1071
```

<210> SEQ ID NO 104
<211> LENGTH: 356
<212> TYPE: PRT
<213> ORGANISM: Sorghum bicolor

<400> SEQUENCE: 104

```
Met Gly Gly Leu Thr Met Glu Gln Ala Phe Val Gln Ala Pro Glu His
1               5                   10                  15

Arg Pro Lys Pro Thr Val Thr Glu Ala Thr Gly Ile Leu Val Ile Asp
            20                  25                  30

Leu Ser Pro Leu Thr Ala Ser Asp Thr Asp Ala Ala Ala Val Asp Ala
        35                  40                  45

Leu Ala Ala Glu Val Gly Ala Ala Ser Arg Asp Trp Gly Phe Phe Val
    50                  55                  60

Val Val Gly His Gly Val Pro Ala Glu Thr Val Ala Arg Ala Thr Ala
65                  70                  75                  80

Ala Gln Arg Ala Phe Phe Ala Leu Pro Ala Glu Arg Lys Ala Ala Val
                85                  90                  95

Arg Arg Ser Glu Ala Glu Pro Leu Gly Tyr Tyr Glu Ser Glu His Thr
            100                 105                 110

Lys Asn Val Arg Asp Trp Lys Glu Val Phe Asp Leu Val Pro Arg Asp
        115                 120                 125

Pro Pro Pro Pro Ala Ala Val Ala Asp Gly Glu Leu Val Phe Lys Asn
        130                 135                 140

Lys Trp Pro Gln Asp Leu Pro Gly Phe Arg Glu Ala Leu Glu Glu Tyr
145                 150                 155                 160

Ala Ala Ala Met Glu Glu Leu Ser Phe Lys Leu Leu Glu Leu Ile Ala
                165                 170                 175

Arg Ser Leu Lys Leu Arg Pro Asp Arg Leu His Gly Phe Phe Lys Asp
            180                 185                 190

Gln Thr Thr Phe Ile Arg Leu Asn His Tyr Pro Pro Cys Pro Ser Pro
            195                 200                 205
```

Asp Leu Ala Leu Gly Val Gly Arg His Lys Asp Ala Gly Ala Leu Thr
    210                 215                 220

Ile Leu Tyr Gln Asp Glu Val Gly Gly Leu Asp Val Arg Arg Arg Ser
225                 230                 235                 240

Ser Asp Gly Gly Gly Gly Glu Trp Val Arg Val Arg Pro Val Pro Glu
                245                 250                 255

Ser Phe Val Ile Asn Val Gly Asp Leu Val Gln Val Trp Ser Asn Asp
                260                 265                 270

Arg Tyr Glu Ser Ala Glu His Arg Val Ser Val Asn Ser Ala Arg Glu
                275                 280                 285

Arg Phe Ser Met Pro Tyr Phe Phe Asn Pro Ala Ser Tyr Thr Met Val
    290                 295                 300

Glu Pro Val Glu Glu Leu Val Ser Asp Asp Asp Pro Pro Arg Tyr Asp
305                 310                 315                 320

Ala Tyr Ser Trp Gly Glu Phe Phe Ser Thr Arg Lys Asn Ser Asn Phe
                325                 330                 335

Lys Lys Leu Ser Val Glu Asn Ile Gln Ile Ala His Phe Lys Lys Thr
                340                 345                 350

Leu Val Leu Ala
        355

<210> SEQ ID NO 105
<211> LENGTH: 1499
<212> TYPE: DNA
<213> ORGANISM: Sorghum bicolor

<400> SEQUENCE: 105
cctctcatca caggccccag cctcactctt ctcacagcaa gacatcgcag cctcacaacc      60
acacagcaac gtgatcgcca tgggcgggct caccatggag caggccttcg tgcaggcccc     120
cgagcaccgc cccaagccca ccgtcaccga ggccaccggc atcctggtca tcgacctctc     180
gcctctcacc gccagcgaca ccgacgcggc cgcggtggac gcgctggccg ccgaggtggg     240
cgcggcgagc cgggactggg gcttcttcgt ggtggttggc cacggcgtgc ccgcggagac     300
cgtggcgcgc gcgacggcgg cgcagcgcgc gttcttcgcg ctgccggcgg agcggaaggc     360
cgccgtgcgg aggagcgagg cggagccgct cgggtactac gagtcggagc acaccaagaa     420
cgtcagggac tggaaggagg tgttcgacct cgtcccgcgc gatccgccgc cgccagcagc     480
cgtggccgac ggcgagctcg tcttcaagaa caagtggccc caggatctgc cgggcttcag     540
gtgacgaaat caacttatct tttcgatcat attttaccat ttaatagttt aacaataatt     600
gaactttttt ttgcagagag cgcctggagg agtacgcggc agcgatggag gagctgtcgt     660
tcaagctgct ggagctgatc gcccggagct tgaagctgag gcccgaccgg ctgcacggct     720
tcttcaagga ccagacgacg ttcatccggc tgaaccacta ccctccatgc ccgagcccgg     780
acctggcgct gggagtgggg cggcacaagg acgcggggc gctgaccatc ctgtaccagg     840
acgaagtggg cgggctggac gtccggcggc gctcctccga cggcggcggc ggcgagtggg     900
tgcgggtgag gcccgtgccg gagtcgttcg tcatcaacgt cggcgacctc gtccaggtgt     960
ggagcaacga caggtacgag agcgcggagc accgggtgtc ggtgaactcg gcgagggaga    1020
ggttctccat gccctacttc ttcaacccgg cgagctacac catggtggag ccggtggagg    1080
agctggtgag cgacgacgac ccgcccaggt acgacgccta cagctggggc gagttcttca    1140
gcaccaggaa gaacagcaac ttcaagaagc tcagcgtgga gaacattcag atcgcgcatt    1200
tcaagaagac cctcgtcctc gcctagataa gcagcaggat actacaggtc tacaggacta    1260

```
ggacaagccg atcgaggtga ccggccgtcg tcttcagatt cagtatatgc gtgtcgccgt      1320
tcgtgttaga acaaattaat aatgtgcgcg ctgtgtgctg tgtgtgtgga gtaaaaaaaa      1380
actaaacatg gatgtgcatg ttcaaaaaaa aaaacatgga tgcgagtatg tttgggaata      1440
ataacaggct tgtgacggtc tggtttattt gcaaattcaa accgaattgg ttgatcttc       1499
```

```
<210> SEQ ID NO 106
<211> LENGTH: 1490
<212> TYPE: DNA
<213> ORGANISM: Setaria italica

<400> SEQUENCE: 106
accccacaca cacacccgca ctgcatgcgg cgtcctagct aatcagtcgc tgctggcagc        60
ctcacaagtc acacaactcc gacgcaggaa agctcgatcc atcgccatgg gcggcttctc       120
catggatcag tccttcgtgc aggcccccga gcaccgcccc aagcccaccg tcaccgaggc       180
cacgggcatc ccgctcatcg acctctcgcc actcaccggc ggtggcggcg gcgacgcggc       240
cgccgtggac gcgctggccg ccgaggtggg cgcggcgagc cgggactggg gcttcttcgt       300
ggtggtgggg cacggtgtgc cggcggagac cgtggcgcgc gccacggagg cgcagcgcgc       360
gttcttcgcc ctgccggcgg agcggaaagc cgccgtgcgg aggagcgagg cggagccgct       420
cgggtactac gagtcggagc acaccaagaa cgtcagggac tggaaggagg tgtacgacct       480
cgtcccgggc gggcttcagc cgccgatagc cgtggccgac ggcgaggtcg tgttcgaaaa       540
caagtggccc gaagacctgc cgggattcag agaggcgttg gaggagtaca tgcaagcgat       600
ggaagagctg gcattcaaga tactggagct gatcgcccgg agcctgaacc tgaggcctga       660
cagactgcac ggcttcttca aggaccagac caccttcatc cggctcaacc actaccctcc       720
ctgcccgagc cccgacctcg ccctcggcgt cggccggcac aaggacgccg gagcactgac       780
catcctctac caggacgacg tcggcgggct cgacgtccgg cgccgttccg acggcgattg       840
ggtccgcgtc aagcctgtcc ccgactcctt catcatcaac gtcggcgacc tcatccaggt       900
ttggagcaac gacaggtacg agagcgcgga gcaccgggtt acggtgaact cggccaagga       960
gaggttctcc aggccctact tcttcaaccc ggcgggctac accatggtgg agccggtgga      1020
ggagctggtg agcgaggagg acccgccccg gtacgacgcc tacaactggg gcaacttctt      1080
cagcaccagg aagaacagca acttcaagaa gctgagcgtg gagaacatcc agatcgcgca      1140
tttcaagagg agcgtcgccg cctaggatac gcacagaaag atcccatatg ctgacttgct      1200
gatgaggcga caggcggccg tgtcgtcttc agattcagag actgggagta aacatttgtg      1260
cggtgttctg taatcgtgat gtgacgagaa ctttagatat atgtttggaa ataacagcct      1320
tgtgttggtc tggcttatcc gcaaagtcaa gattttcttc tacattttgg gattattgtt      1380
ggtaagcatt aagcaacgtc cagttcttac ttcttagctc gatcagtgga cgtaggaccg      1440
gcctctgatg acaagggtga tttatgagaa atgtcatgta tatatgttcc                 1490
```

```
<210> SEQ ID NO 107
<211> LENGTH: 1059
<212> TYPE: DNA
<213> ORGANISM: Setaria italica

<400> SEQUENCE: 107
atgggcggct ctccatgga tcagtccttc gtgcaggccc ccgagcaccg ccccaagccc        60
accgtcaccg aggccacggg catcccgctc atcgacctct cgccactcac cggcggtggc       120
```

```
ggcggcgacg cggccgccgt ggacgcgctg gccgccgagg tgggcgcggc gagccgggac    180
tggggcttct tcgtggtggt ggggcacggt gtgccggcgg agaccgtggc gcgcgccacg    240
gaggcgcagc gcgcgttctt cgccctgccg gcggagcgga agccgccgt gcggaggagc     300 gaggcggagc cgctcgggta ctacgagtcg gagcacacca agaacgtcag ggactggaag    360
gaggtgtacg acctcgtccc gggcgggctt cagccgccga tagccgtggc cgacggcgag    420
gtcgtgttcg aaaacaagtg gcccgaagac ctgccgggat tcagagaggc gttggaggag    480
tacatgcaag cgatggaaga gctggcattc aagatactgg agctgatcgc ccggagcctg    540
aacctgaggc ctgacagact gcacggcttc ttcaaggacc agaccacctt catccggctc    600
aaccactacc ctccctgccc gagccccgac ctcgccctcg gcgtcggccg gcacaaggac    660
gccggagcac tgaccatcct ctaccaggac gacgtcggcg ggctcgacgt ccggcgccgt    720
tccgacggcg attgggtccg cgtcaagcct gtccccgact ccttcatcat caacgtcggc    780
gacctcatcc aggtttggag caacgacagg tacgagagcg cggagcaccg ggttacggtg    840
aactcggcca aggagaggtt ctccaggccc tacttcttca acccggcggg ctacaccatg    900
gtggagccgg tggaggagct ggtgagcgag gaggacccgc cccggtacga cgcctacaac    960
tggggcaact tcttcagcac caggaagaac agcaacttca agaagctgag cgtggagaac   1020
atccagatcg cgcatttcaa gaggagcgtc gccgcctag                          1059
```

<210> SEQ ID NO 108
<211> LENGTH: 352
<212> TYPE: PRT
<213> ORGANISM: Setaria italica

<400> SEQUENCE: 108

```
Met Gly Gly Phe Ser Met Asp Gln Ser Phe Val Gln Ala Pro Glu His
1               5                   10                  15

Arg Pro Lys Pro Thr Val Thr Glu Ala Thr Gly Ile Pro Leu Ile Asp
            20                  25                  30

Leu Ser Pro Leu Thr Gly Gly Gly Gly Asp Ala Ala Ala Val Asp
            35                  40                  45

Ala Leu Ala Ala Glu Val Gly Ala Ala Ser Arg Asp Trp Gly Phe Phe
        50                  55                  60

Val Val Val Gly His Gly Val Pro Ala Glu Thr Val Ala Arg Ala Thr
65                  70                  75                  80

Glu Ala Gln Arg Ala Phe Phe Ala Leu Pro Ala Glu Arg Lys Ala Ala
                85                  90                  95

Val Arg Arg Ser Glu Ala Glu Pro Leu Gly Tyr Tyr Glu Ser Glu His
            100                 105                 110

Thr Lys Asn Val Arg Asp Trp Lys Glu Val Tyr Asp Leu Val Pro Gly
            115                 120                 125

Gly Leu Gln Pro Pro Ile Ala Val Ala Asp Gly Glu Val Val Phe Glu
            130                 135                 140

Asn Lys Trp Pro Glu Asp Leu Pro Gly Phe Arg Glu Ala Leu Glu Glu
145                 150                 155                 160

Tyr Met Gln Ala Met Glu Glu Leu Ala Phe Lys Ile Leu Glu Leu Ile
                165                 170                 175

Ala Arg Ser Leu Asn Leu Arg Pro Asp Arg Leu His Gly Phe Phe Lys
            180                 185                 190

Asp Gln Thr Thr Phe Ile Arg Leu Asn His Tyr Pro Pro Cys Pro Ser
            195                 200                 205
```

```
Pro Asp Leu Ala Leu Gly Val Gly Arg His Lys Asp Ala Gly Ala Leu
    210                 215                 220

Thr Ile Leu Tyr Gln Asp Asp Val Gly Gly Leu Asp Val Arg Arg Arg
225                 230                 235                 240

Ser Asp Gly Asp Trp Val Arg Val Lys Pro Val Pro Asp Ser Phe Ile
                245                 250                 255

Ile Asn Val Gly Asp Leu Ile Gln Val Trp Ser Asn Asp Arg Tyr Glu
                260                 265                 270

Ser Ala Glu His Arg Val Thr Val Asn Ser Ala Lys Glu Arg Phe Ser
            275                 280                 285

Arg Pro Tyr Phe Phe Asn Pro Ala Gly Tyr Thr Met Val Glu Pro Val
    290                 295                 300

Glu Glu Leu Val Ser Glu Glu Asp Pro Pro Arg Tyr Asp Ala Tyr Asn
305                 310                 315                 320

Trp Gly Asn Phe Phe Ser Thr Arg Lys Asn Ser Asn Phe Lys Lys Leu
                325                 330                 335

Ser Val Glu Asn Ile Gln Ile Ala His Phe Lys Arg Ser Val Ala Ala
                340                 345                 350
```

<210> SEQ ID NO 109
<211> LENGTH: 1886
<212> TYPE: DNA
<213> ORGANISM: Setaria italica

<400> SEQUENCE: 109

```
accccacaca cacacccgca ctgcatgcgg cgtcctagct aatcagtcgc tgctggcagc      60
ctcacaagtc acacaactcc gacgcaggaa agctcgatcc atcgccatgg gcggcttctc     120
catggatcag tccttcgtgc aggcccccga gcaccgcccc aagcccaccg tcaccgaggc     180
cacgggcatc ccgctcatcg acctctcgcc actcaccggc ggtggcggcg cgacgcggc      240 cgccgtggac gcgctggccg ccgaggtggg cgcggcgagc cgggactggg gcttcttcgt     300
ggtggtgggg cacggtgtgc cggcggagac cgtggcgcgc gccacggagg cgcagcgcgc     360
gttcttcgcc ctgccggcgg agcggaaagc cgccgtgcgg aggagcgagg cggagccgct     420
cgggtactac gagtcggagc acaccaagaa cgtcagggac tggaaggagg tgtacgacct     480
cgtcccgggc gggcttcagc cgccgatagc cgtggccgac ggcgaggtcg tgttcgaaaa     540
caagtggccc gaagacctgc cgggattcag gtgaatcaac ttgcgcatat tgttgtttct     600
ggcattgcat atgatcgtcg tgccagtatg ttttgacaat atttttgttt tcatatttt      660 ggtgaagatg ggaaaatctt tgttgaaata atcagggaat tttcacatct ttttttaatc     720
aaagatagaa taggttcggt tactgaattt tgatgatgga cagaaaaagc tgtgttttca     780
ctttccatct cagcgatgtt ttttgtgga tgaattctcc taaatttttg tcttttcatg     840
ttaaaacttg aacgggaatt ctcgcagaga ggcgttggag gagtacatgc aagcgatgga     900
agagctggca ttcaagatac tggagctgat cgccggagc ctgaacctga ggcctgacag     960
actgcacggc ttcttcaagg accagaccac cttcatccgg ctcaaccact accctccctg    1020
cccgagcccc gacctcgccc tcggcgtcgg ccggcacaag gacgccggag cactgaccat    1080
cctctaccag gacgacgtcg gcgggctcga cgtccggcgc cgttccgacg gcgattgggt    1140
ccgcgtcaag cctgtccccg actccttcat catcaacgtc ggcgacctca tccaggtaca    1200
acaaacaaaa acacacgtca ttctcaaatc ttttcgtgct gttaatgctc attcacgaat    1260
tgatatctta catgaacgac tgagactttt tcaggtttgg agcaacgaca ggtacgagag    1320
```

```
cgcggagcac cggggttacgg tgaactcggc caaggagagg ttctccaggc cctacttctt    1380
caacccggcg ggctacacca tggtggagcc ggtggaggag ctggtgagcg aggaggaccc    1440
gccccggtac gacgcctaca actggggcaa cttcttcagc accaggaaga acagcaactt    1500
caagaagctg agcgtggaga acatccagat cgcgcatttc aagaggagcg tcgccgccta    1560
ggatacgcac agaaagatcc catatgctga cttgctgatg aggcgacagg cggccgtgtc    1620
gtcttcagat tcagagactg ggagtaaaca tttgtgcggt gttctgtaat cgtgatgtga    1680
cgagaacttt agatatatgt ttggaaataa cagccttgtg ttggtctggc ttatccgcaa    1740
agtcaagatt ttcttctaca ttttgggatt attgttggta agcattaagc aacgtccagt    1800
tcttacttct tagctcgatc agtggacgta ggaccggcct ctgatgacaa gggtgatttta    1860 tgagaaatgt catgtatata tgttcc                                          1886
```

<210> SEQ ID NO 110
<211> LENGTH: 1379
<212> TYPE: DNA
<213> ORGANISM: Oryza sativa

<400> SEQUENCE: 110

```
aagccacacg cacacacaca cacacgctga cacacgagac gaacacttgt gctacagctt      60
ctcgccacca gctactgatc gaccatgggc ggcctctcca tggaccaggc gttcgtgcag     120
gcccccgagc accgccccaa ggcgtccgtc gccgaggccg acggcatccc ggtcatcgac     180
ctctcccctc tcctcgccgc cggcgatggc gacgccgacg gggtggacgc gctcgcggcg     240
gaggtcggga gggcgagccg ggactggggc ttcttcgtgg tggtgcgcca cggtgtgccc     300
gcggaggcgg tggcgcgcgc ggcggaggcg cagaggacgt tcttcgcgct gccgccggag     360
cggagggcgg ccgtggcgcg gagcgaggcg gcgccgatgg ggtactacgc gtccgagcac     420
accaagaacg tcagggactg gaaggaggtg ttcgacctcg tcccgcgcca gacgccgccg     480
ccgccgacga ccgccgtggc cgacggcgac ctggtgttcg acaacaagtg gcccgacgac     540
ctgccgggat tcagggaggc aatggaggag tacggcgaag cggtggagga gctggcgttc     600
aagctgctgg agctgatcgc caggagcctc ggcctgagac ccgaccgcct ccatggcttc     660
ttcaaggacg accagaccac cttcatccgg ctcaaccact accctccctg cccgagcccc     720
gacctcgccc tcggcgtcgg ccgccacaag gacgccggcg cgctcaccgt gctctaccag     780
gacgatgtcg gcggcctcga cgtccgccgc cgatccgacg gcgagtgggt gcgcgtcagg     840
cccgtccctc actccttcat catcaacgtc ggcgacatca tccaggtgtg gagcaatgac     900
aggtacgaga gcgcggagca ccgggtggcg gtgaacgtgg agaaggagag gttctccatc     960
cctttcttct tcaacccggc gggccacacc atggtggagc cactggagga ggtcgtgagc    1020
gacgagagcc cggccaggta caaccctac aactggggcg aattcttcag caccaggaag    1080
aacagcaact tcaagaagct ggacgtggag aacgtccaga tcacgcattt caggaagaat    1140
taacgcgccg gctagatcat gttcagtaaa ttttcagatg atgatgcgtg gacaaccata    1200
tagcctttgc gtcataagtt aataatgtct gtgacagtat atcatgtaaa caatcgtatg    1260
atgtggcttc tctatctgcc ggtgatggta atgtgacatt gtagaagagg gtttgtgaga    1320
tacttccttc acttaacttt tacgaatgaa tatagacaac cacaacatcc ttgtcgtga     1379
```

<210> SEQ ID NO 111
<211> LENGTH: 1059
<212> TYPE: DNA
<213> ORGANISM: Oryza sativa

<400> SEQUENCE: 111

```
atgggcggcc tctccatgga ccaggcgttc gtgcaggccc ccgagcaccg cccccaaggcg      60 tccgtcgccg aggccgacgg catcccggtc atcgacctct ccctctcct cgccgccggc     120 gatggcgacg ccgacggggt ggacgcgctc gcggcggagg tcgggagggc gagccgggac     180
tggggcttct tcgtggtggt cgcccacggt gtgcccgcgg aggcggtggc gcgcgcggcg     240
gaggcgcaga ggacgttctt cgcgctgccg ccggagcgga gggcggccgt ggcgcggagc     300
gaggcggcgc cgatggggta ctacgcgtcc gagcacacca agaacgtcag ggactggaag     360
gaggtgttcg acctcgtccc gcgccagacg ccgccgccgc cgacgaccgc cgtggccgac     420
ggcgacctgg tgttcgacaa caagtggccc gacgacctgc cgggattcag ggaggcaatg     480
gaggagtacg gcgaagcggt ggaggagctg gcgttcaagc tgctggagct gatcgccagg     540
agcctcggcc tgagacccga ccgcctccat ggcttcttca aggacgacca gaccaccttc     600
atccggctca accactaccc tccctgcccg agccccgacc tcgccctcgg cgtcggccgc     660
cacaaggacg ccggcgcgct caccgtgctc taccaggacg atgtcggcgg cctcgacgtc     720
cgccgccgat ccgacggcga gtgggtgcgc gtcaggcccg tccctcactc cttcatcatc     780
aacgtcggcg acatcatcca ggtgtggagc aatgacaggt acgagagcgc ggagcaccgg     840
gtggcggtga cgtggagaa ggagaggttc tccatcccct tcttcttcaa cccgcgcggc     900
cacaccatgg tggagccact ggaggaggtc gtgagcgacg agagcccggc caggtacaac     960
ccctacaact ggggcgaatt cttcagcacc aggaagaaca gcaacttcaa gaagctggac    1020
gtggagaacg tccagatcac gcatttcagg aagaattaa                          1059
```

<210> SEQ ID NO 112
<211> LENGTH: 352
<212> TYPE: PRT
<213> ORGANISM: Oryza sativa

<400> SEQUENCE: 112

```
Met Gly Gly Leu Ser Met Asp Gln Ala Phe Val Gln Ala Pro Glu His
1               5                   10                  15

Arg Pro Lys Ala Ser Val Ala Glu Ala Asp Gly Ile Pro Val Ile Asp
            20                  25                  30

Leu Ser Pro Leu Leu Ala Ala Gly Asp Gly Asp Ala Asp Gly Val Asp
        35                  40                  45

Ala Leu Ala Ala Glu Val Gly Arg Ala Ser Arg Asp Trp Gly Phe Phe
    50                  55                  60

Val Val Val Arg His Gly Val Pro Ala Glu Ala Val Ala Arg Ala Ala
65                  70                  75                  80

Glu Ala Gln Arg Thr Phe Phe Ala Leu Pro Pro Glu Arg Arg Ala Ala
                85                  90                  95

Val Ala Arg Ser Glu Ala Ala Pro Met Gly Tyr Tyr Ala Ser Glu His
            100                 105                 110

Thr Lys Asn Val Arg Asp Trp Lys Glu Val Phe Asp Leu Val Pro Arg
        115                 120                 125

Gln Thr Pro Pro Pro Pro Thr Thr Ala Val Ala Asp Gly Asp Leu Val
        130                 135                 140

Phe Asp Asn Lys Trp Pro Asp Asp Leu Pro Gly Phe Arg Glu Ala Met
145                 150                 155                 160

Glu Glu Tyr Gly Glu Ala Val Glu Glu Leu Ala Phe Lys Leu Leu Glu
                165                 170                 175
```

```
Leu Ile Ala Arg Ser Leu Gly Leu Arg Pro Asp Arg Leu His Gly Phe
        180                 185                 190

Phe Lys Asp Asp Gln Thr Thr Phe Ile Arg Leu Asn His Tyr Pro Pro
        195                 200                 205

Cys Pro Ser Pro Asp Leu Ala Leu Gly Val Gly Arg His Lys Asp Ala
        210                 215                 220

Gly Ala Leu Thr Val Leu Tyr Gln Asp Asp Val Gly Gly Leu Asp Val
225                 230                 235                 240

Arg Arg Arg Ser Asp Gly Glu Trp Val Arg Val Arg Pro Val Pro His
                245                 250                 255

Ser Phe Ile Ile Asn Val Gly Asp Ile Ile Gln Val Trp Ser Asn Asp
                260                 265                 270

Arg Tyr Glu Ser Ala Glu His Arg Val Ala Val Asn Val Glu Lys Glu
        275                 280                 285

Arg Phe Ser Ile Pro Phe Phe Phe Asn Pro Ala Gly His Thr Met Val
        290                 295                 300

Glu Pro Leu Glu Glu Val Val Ser Asp Glu Ser Pro Ala Arg Tyr Asn
305                 310                 315                 320

Pro Tyr Asn Trp Gly Glu Phe Phe Ser Thr Arg Lys Asn Ser Asn Phe
                325                 330                 335

Lys Lys Leu Asp Val Glu Asn Val Gln Ile Thr His Phe Arg Lys Asn
                340                 345                 350

<210> SEQ ID NO 113
<211> LENGTH: 2027
<212> TYPE: DNA
<213> ORGANISM: Oryza sativa

<400> SEQUENCE: 113
aagccacacg cacacacaca cacacgctga cacacgagac gaacacttgt gctacagctt        60
ctcgccacca gctactgatc gaccatgggc ggcctctcca tggaccaggc gttcgtgcag       120
gcccccgagc accgccccaa ggcgtccgtc gccgaggccg acggcatccc ggtcatcgac       180
ctctcccctc tcctcgccgc cggcgatggc gacgccgacg gggtggacgc gctcgcggcg       240
gaggtcggga gggcgagccg ggactggggc ttcttcgtgg tggtgcgcca cggtgtgccc       300
gcggaggcgg tggcgcgcgc ggcggaggcg cagaggacgt tcttcgcgct gccgccggag       360
cggagggcgg ccgtggcgcg gagcgaggcg gcgccgatgg ggtactacgc gtccgagcac       420
accaagaacg tcagggactg gaaggaggtg ttcgacctcg tcccgcgcca gacgccgccg       480
ccgccgacga ccgccgtggc cgacggcgac ctggtgttcg acaacaagtg gcccgacgac       540
ctgccgggat tcaggtcagg tcaccacatc gatcgatcgt cttcttcatc ctcgcatcaa       600
ttcagttcaa cctcatcgaa ttcttgagca gggaggcaat ggaggagtac ggcgaagcgg       660
tggaggagct ggcgttcaag ctgctggagc tgatcgccag gagcctcggc ctgagacccg       720
accgcctcca tggcttcttc aaggacgacc agaccacctt catccggctc aaccactacc       780
ctccctgccc gagccccgac ctcgccctcg gcgtcggccg ccacaaggac gccggcgcgc       840
tcaccgtgct ctaccaggac gatgtcggcg gcctcgacgt ccgccgccga tccgacggcg       900
agtgggtgcg cgtcaggccc gtccctcact ccttcatcat caacgtcggc gacatcatcc       960
aggtactttt tttttgagc agctacatat ttatcaacaa attttcttct aacaatttat      1020
cggacataaa tatattacaa tgaaagaata attgtatcat aacttgtgtg tccttatatg      1080
taagttttag aaatcctata gtaacatggt attttcgcga aagcggagat tgtgagaccg      1140
```

```
tatctttttca cccatgcgcg tcatatgatt tttttttctt gccaacttaa ataaatttca     1200
aagtaaatct aatagattaa aattatgtga aacttacata taagtttttct acggtaacac     1260 gctattttca cgaaacggag gtcgttccaa gttgaatgaa tcttgaagta aatctaacga     1320
tttaaaatta tgtgcataca cgttatatta cagttatata caagttataa tataattaca     1380
ctacaattat aacggtattc atagttgaca aacttttaaa agagaattag ttaataaata     1440
tataacaaca ttgtagttta attgttacta tttgacatca tttttatttg cattttgaat     1500
ttgactgaaa aaattgagag tgcgcttgtc caggtgtgga gcaatgacag gtacgagagc     1560
gcggagcacc gggtggcggt gaacgtggag aaggagaggt tctccatccc tttcttcttc     1620
aacccggcgg gccacaccat ggtggagcca ctggaggagg tcgtgagcga cgagagcccg     1680
gccaggtaca acccctacaa ctggggcgaa ttcttcagca ccaggaagaa cagcaacttc     1740
aagaagctgg acgtggagaa cgtccagatc acgcatttca ggaagaatta acgcgccggc     1800
tagatcatgt tcagtaaatt ttcagatgat gatgcgtgga caaccatata gcctttgcgt     1860
cataagttaa taatgtctgt gacagtatat catgtaaaca atcgtatgat gtggcttctc     1920
tatctgccgg tgatggtaat gtgacattgt agaagagggt ttgtgagata cttccttcac     1980 ttaacttta cgaatgaata tagacaacca caacatcctt gtcgtga                    2027
```

<210> SEQ ID NO 114
<211> LENGTH: 1747
<212> TYPE: DNA
<213> ORGANISM: Triticum aestivum

<400> SEQUENCE: 114

```
tcactcaagg ccacaacaca ctcgccagtc catcgccacc atacgtgaca acttgagtta      60
cttgatctgt tgctcatcga tctcgacatc gccatgggcg gcctctccat ggaccaggcc     120
ttcgtgcagg cccccgagca tcgcaccaag gcgaacctcg ccgacgcggc cggcatcccg     180
gtcatcgacc tctcccctct cgccgccggc gacaaggccg gcctggacgc cctcgcggcc     240
gaggtgggca gggcgagccg tgactggggg ttcttcgtgg tggtgcgcca cggcgtgccg     300
gcggagacgg tggcgcgggc gctggaggcg cagagggcct tcttcgcgct gcccgcggac     360
cggaaggcgg ccgtgcggag ggacgaggcg gcgccgctgg ggtactacga gtcggagcac     420
accaagaacg tcagggactg gaaggaggtg ttcgacctcg tcccccgcga gccgccgccg     480
cctgccgcgg ttgccgacgg cgagctcatg ttcgagaaca agtggcccga ggacctgccg     540
gggttcagag aggctctcga agagtacgag aaagcgatgg aggagctggc gttcaagctg     600
ctggagctga tcgcccggag cctgggactg agaccggacc ggctgcacgg cttcttcaag     660
gaccagacca ccttcatccg gctgaaccac tacccgccct gccccagccc cgacctcgcc     720
ctcggcgtcg gtcgccacaa ggacgccggc gcgctcacca tcctctacca ggacgacgtc     780
ggcgggctcg acgtccggcg ccgctccgac ggcgagtggg tgcgcgtcag gcctgtcccg     840
gactcctacg tcatcaacgt cggcgacatc atccaggtgt ggagcaacga caggtacgag     900
agcgcggagc acagggtgtc ggtgaactcg cacaaggaga ggttctccat gccctacttc     960 ttcgacccecg ggagcgacgc catgatcgag ccgttggagg agatggtgag cgacgaaagg    1020
ccggccaggt acgacgccta caactggggc aacttcttca gcaccaggaa gaacagcaac    1080
ttcaggaagc tcgccgtcga aaacgtccag atcgcacact tcagaaagga ccgaccttaa    1140
atgaaggatc cctcatgaat tcatgatcct tccgctctcc tcagtgatcc tagtgctaca    1200
```

```
actacaagca tctccccgtt tgtagtaatc atatataaat aagtattccc tccgtaaact      1260
aatataagag catttaaaac actactctag tgatctaaat gctcttatat tagtttacag      1320
agagagtatt gtgtattaat aatgactttc tctgtttcaa aataagtgat gacgtggttt      1380
tagttcaatt tttttagag aggaggcatc tgacgggcct taaactgagg accttagagt        1440
acaaacaagg ttcgacgaaa gtaagtttaa gggatacaag gccgtagcca acaaaacgcg        1500
acgcagcgcg caatctaaaa tcagcgtgct gtcaaggtag ctggagacgt ccatgccgtt       1560
aatctctctc aagaagctcg ccgaagctca gtgcaccttg cgtgcactct tgtgaagagc       1620
accttcacgt gtcctttgtc ctgagatttt gtcaacagtt tccatgactg caagaaaaac       1680
actagtttgt ataatagctc agcgggatgt cgaatgaatt gcccctcaat caaagcttta      1740
tttctag                                                                1747
```

```
<210> SEQ ID NO 115
<211> LENGTH: 1047
<212> TYPE: DNA
<213> ORGANISM: Triticum aestivum

<400> SEQUENCE: 115
atgggcggcc tctccatgga ccaggccttc gtgcaggccc ccgagcatcg caccaaggcg       60
aacctcgccg acgcggccgg catcccggtc atcgacctct ccctctcgc cgccggcgac        120 aaggccggct ggacgccct cgcggccgag gtgggcaggg cgagccgtga ctgggggttc        180
ttcgtggtgg tgcgccacgg cgtgccggcg gagacggtgg cgcgggcgct ggaggcgcag        240
agggccttct tcgcgctgcc cgcggaccgg aaggcggccg tgcggaggga cgaggcggcg        300
ccgctggggt actacgagtc ggagcacacc aagaacgtca gggactggaa ggaggtgttc        360
gacctcgtcc ccgcgagcc gccgccgcct gccgcgttg ccgacggcga gctcatgttc         420
gagaacaagt ggcccgagga cctgccgggg ttcagagagg ctctcgaaga gtacgagaaa       480 gcgatggag agctggcgtt caagctgctg gagctgatcg cccggagcct gggactgaga        540
ccggaccggc tgcacggctt cttcaaggac cagaccacct tcatccggct gaaccactac       600
ccgccctgcc ccagccccga cctcgccctc ggcgtcggtc gccacaagga cgccggcgcg       660
ctcaccatcc tctaccagga cgacgtcggc gggctcgacg tccggcgccg ctccgacggc       720
gagtgggtgc gcgtcaggcc tgtcccggac tcctacgtca tcaacgtcgg cgacatcatc       780
caggtgtgga gcaacgacag gtacgagagc gcggagcaca gggtgtcggt gaactcgcac       840
aaggagaggt tctccatgcc ctacttcttc gaccccggga gcgacgccat gatcgagccg       900
ttggaggaga tggtgagcga cgaaaggccg gccaggtacg acgcctacaa ctggggcaac       960
ttcttcagca ccaggaagaa cagcaacttc aggaagctcg ccgtcgaaaa cgtccagatc      1020
gcacacttca gaaaggaccg accttaa                                          1047
```

```
<210> SEQ ID NO 116
<211> LENGTH: 348
<212> TYPE: PRT
<213> ORGANISM: Triticum aestivum

<400> SEQUENCE: 116

Met Gly Gly Leu Ser Met Asp Gln Ala Phe Val Gln Ala Pro Glu His
1               5                   10                  15

Arg Thr Lys Ala Asn Leu Ala Asp Ala Ala Gly Ile Pro Val Ile Asp
            20                  25                  30

Leu Ser Pro Leu Ala Ala Gly Asp Lys Ala Gly Leu Asp Ala Leu Ala
```

-continued

```
            35                  40                  45
Ala Glu Val Gly Arg Ala Ser Arg Asp Trp Gly Phe Phe Val Val Val
            50                  55                  60
Arg His Gly Val Pro Ala Glu Thr Val Ala Arg Ala Leu Glu Ala Gln
65                  70                  75                  80
Arg Ala Phe Phe Ala Leu Pro Ala Asp Arg Lys Ala Ala Val Arg Arg
                    85                  90                  95
Asp Glu Ala Ala Pro Leu Gly Tyr Tyr Glu Ser Glu His Thr Lys Asn
                    100                 105                 110
Val Arg Asp Trp Lys Glu Val Phe Asp Leu Val Pro Arg Glu Pro Pro
                    115                 120                 125
Pro Pro Ala Ala Val Ala Asp Gly Glu Leu Met Phe Glu Asn Lys Trp
            130                 135                 140
Pro Glu Asp Leu Pro Gly Phe Arg Glu Ala Leu Glu Glu Tyr Glu Lys
145                 150                 155                 160
Ala Met Glu Glu Leu Ala Phe Lys Leu Leu Glu Leu Ile Ala Arg Ser
                    165                 170                 175
Leu Gly Leu Arg Pro Asp Arg Leu His Gly Phe Phe Lys Asp Gln Thr
                    180                 185                 190
Thr Phe Ile Arg Leu Asn His Tyr Pro Pro Cys Pro Ser Pro Asp Leu
            195                 200                 205
Ala Leu Gly Val Gly Arg His Lys Asp Ala Gly Ala Leu Thr Ile Leu
            210                 215                 220
Tyr Gln Asp Asp Val Gly Gly Leu Asp Val Arg Arg Arg Ser Asp Gly
225                 230                 235                 240
Glu Trp Val Arg Val Arg Pro Val Pro Asp Ser Tyr Val Ile Asn Val
                    245                 250                 255
Gly Asp Ile Ile Gln Val Trp Ser Asn Asp Arg Tyr Glu Ser Ala Glu
                    260                 265                 270
His Arg Val Ser Val Asn Ser His Lys Glu Arg Phe Ser Met Pro Tyr
            275                 280                 285
Phe Phe Asp Pro Gly Ser Asp Ala Met Ile Glu Pro Leu Glu Glu Met
            290                 295                 300
Val Ser Asp Glu Arg Pro Ala Arg Tyr Asp Ala Tyr Asn Trp Gly Asn
305                 310                 315                 320
Phe Phe Ser Thr Arg Lys Asn Ser Asn Phe Arg Lys Leu Ala Val Glu
                    325                 330                 335
Asn Val Gln Ile Ala His Phe Arg Lys Asp Arg Pro
            340                 345
```

```
<210> SEQ ID NO 117
<211> LENGTH: 1863
<212> TYPE: DNA
<213> ORGANISM: Triticum aestivum

<400> SEQUENCE: 117
tcactcaagg ccacaacaca ctcgccagtc catcgccacc atacgtgaca acttgagtta        60
cttgatctgt tgctcatcga tctcgacatc gccatgggcg gcctctccat ggaccaggcc       120
ttcgtgcagg cccccgagca tcgcaccaag gcgaacctcg ccgacgcggc cggcatcccg       180
gtcatcgacc tctcccctct cgccgccggc gacaaggccg gcctggacgc cctcgcggcc       240
gaggtgggca gggcgagccg tgactggggg ttcttcgtgg tggtgcgcca cggcgtgccg       300
gcggagacgg tggcgcgggc gctggaggcg cagagggcct tcttcgcgct gcccgcggac       360
```

```
cggaaggcgg ccgtgcggag ggacgaggcg gcgccgctgg ggtactacga gtcggagcac      420
accaagaacg tcagggactg gaaggaggtg ttcgacctcg tcccccgcga gccgccgccg      480
cctgccgcgg ttgccgacgg cgagctcatg ttcgagaaca agtggcccga ggacctgccg      540
gggttcaggt acggtcatca actcaatcaa ttctgcgacc ccgagagaaa tggttcacta      600
ttattcgtgg ttcatacgta tgattcagac gttaatctcg atgcaaattg atttgtgcat      660
gcagagaggc tctcgaagag tacgagaaag cgatggagga gctggcgttc aagctgctgg      720
agctgatcgc ccggagcctg ggactgagac cggaccggct gcacggcttc ttcaaggacc      780
agaccacctt catccggctg aaccactacc cgccctgccc cagccccgac ctcgccctcg      840
gcgtcggtcg ccacaaggac gccggcgcgc tcaccatcct ctaccaggac gacgtcggcg      900
ggctcgacgt ccggcgccgc tccgacggcg agtgggtgcg cgtcaggcct gtcccggact     960
cctacgtcat caacgtcggc gacatcatcc aggtgtggag caacgacagg tacgagagcg    1020
cggagcacag ggtgtcggtg aactcgcaca aggagaggtt ctccatgccc tacttcttcg    1080
accccgggag cgacgccatg atcgagccgt tggaggagat ggtgagcgac gaaaggccgg    1140
ccaggtacga cgcctacaac tggggcaact tcttcagcac caggaagaac agcaacttca    1200
ggaagctcgc cgtcgaaaac gtccagatcg cacacttcag aaaggaccga ccttaaatga    1260
aggatccctc atgaattcat gatccttccg ctctcctcag tgatcctagt gctacaacta    1320
caagcatctc cccgtttgta gtaatcatat ataaataagt attccctccg taaactaata    1380
taagagcatt taaaacacta ctctagtgat ctaaatgctc ttatattagt ttacagagag    1440
agtattgtgt attaataatg actttctctg tttcaaaata agtgatgacg tggtttttagt    1500 tcaattttttt ttagagagga ggcatctgac gggccttaaa ctgaggacct tagagtacaa    1560
acaaggttcg acgaaagtaa gtttaaggga tacaaggccg tagccaacaa aacgcgacgc    1620
agcgcgcaat ctaaaatcag cgtgctgtca aggtagctgg agacgtccat gccgttaatc    1680
tctctcaaga agctcgccga agctcagtgc accttgcgtg cactcttgtg aagagcacct    1740
tcacgtgtcc tttgtcctga gattttgtca acagtttcca tgactgcaag aaaaacacta    1800
gtttgtataa tagctcagcg ggatgtcgaa tgaattgccc ctcaatcaaa gctttatttc    1860
tag                                                                  1863
```

```
<210> SEQ ID NO 118
<211> LENGTH: 349
<212> TYPE: PRT
<213> ORGANISM: Hordeum vulgare

<400> SEQUENCE: 118

Met Gly Gly Leu Ser Met Gly Gln Ala Phe Val Gln Ala Pro Glu His
1               5                   10                  15

Arg Thr Lys Pro Thr Leu Ala Asp Ala Asp Gly Ile Pro Val Ile Asp
            20                  25                  30

Leu Ser Pro Leu Ala Ala Gly Asp Glu Ala Gly Val Asp Ala Leu Ala
        35                  40                  45

Ala Glu Val Gly Arg Ala Ser Arg Asp Trp Gly Phe Phe Val Val Val
    50                  55                  60

Arg His Gly Val Pro Ala Glu Thr Val Ala Arg Ala Leu Glu Ala Gln
65                  70                  75                  80

Arg Ala Phe Phe Ala Leu Pro Ala Glu Arg Lys Ala Ala Val Arg Arg
                85                  90                  95

Asp Glu Ala Ala Pro Leu Gly Tyr Tyr Glu Ser Glu His Thr Lys Asn
```

-continued

```
            100            105            110
Val Arg Asp Trp Lys Glu Val Phe Asp Phe Val Pro Arg Glu Pro Pro
        115            120            125

Pro Pro Ala Ala Val Ala Asp Gly Glu Leu Val Phe Glu Asn Lys Trp
    130            135            140

Pro Glu Asp Leu Pro Gly Phe Arg Val Ala Phe Glu Glu Tyr Ala Lys
145            150            155            160

Ala Met Glu Glu Leu Ala Phe Lys Leu Leu Glu Leu Ile Ala Arg Ser
            165            170            175

Leu Gly Leu Thr Pro Asp Arg Leu Asn Gly Phe Phe Lys Asp His Gln
            180            185            190

Thr Thr Phe Ile Arg Leu Asn His Tyr Pro Pro Cys Pro Ser Pro Asp
            195            200            205

Leu Ala Leu Gly Val Gly Arg His Lys Asp Ala Gly Ala Leu Thr Val
    210            215            220

Leu Tyr Gln Asp Asp Val Gly Gly Leu Asp Val Arg His Arg Ser Asp
225            230            235            240

Gly Glu Trp Val Arg Val Arg Pro Val Pro Asp Ser Tyr Val Ile Asn
            245            250            255

Val Gly Asp Ile Ile Gln Val Trp Ser Asn Asp Arg Tyr Glu Ser Ala
            260            265            270

Glu His Arg Val Ser Val Asn Ser Asp Lys Glu Arg Phe Ser Met Pro
            275            280            285

Tyr Phe Phe Asn Pro Gly Ser Asp Ala Met Val Glu Pro Leu Glu Glu
    290            295            300

Met Val Ser Asp Glu Arg Pro Ala Arg Tyr Asp Ala Tyr Asn Trp Gly
305            310            315            320

His Phe Phe Ser Thr Arg Lys Asn Ser Asn Phe Lys Lys Leu Asp Val
            325            330            335

Glu Asn Val Gln Ile Ala His Phe Arg Lys Leu His Leu
    340            345
```

<210> SEQ ID NO 119
<211> LENGTH: 1963
<212> TYPE: DNA
<213> ORGANISM: Sorghum bicolor

<400> SEQUENCE: 119

```
tataaatacc acgccatgta cttctctgct tctacacttc tccagcttct ctcatgccat      60
accactagtg caaggtccta gatttacact tggtgctaca gcttcttcct ccctccctcc     120
cctctctagg cagctagcac gcagcgcagc acacgaaaca tctattgacc ggccgcctcc     180 gccgggatc cataattact atactaccaa tcggccagcg tcatgccgac gccgtcgcac     240
ctcgcgaacc cgcgctactt cgacttccgt gcggcgcggc gggtgccgga gacgcacgcc     300
tggccggggc tgcacgacca ccccgtcgtg gacggcggcg cgccggggcc agacgccgtc     360
cccgtggtgg acctcgcggg ggcggcggac gagccgagag ccgcggtggt ggcccaagtg     420
gcgcgcgccg ccgagcaatg gggcgcgttc ctgctcacgg ggcacggcgt ccccgcggag     480
ctgctggcgc gcgtcgagga ccggatcgcc accatgttcg cgctgccagc ggacgacaag     540
atgcgcgccg tgcgcgggcc tggcgacgcc tgcggctacg gctccccgcc catctcctcc     600
ttcttctcca agtgcatgtg gtcggaggga tacaccttct cgccggccaa cctccgcgcc     660
gacctccgca agctctggcc taaggccggc gacgactaca ccagcttctg tgatgtgatg     720
```

```
gaggagttcc acaagcacat gcgtgccctc gcggacaagc tgctggagct gttcctcatg      780
gcgctggggc tcaccgacga gcaggtcggc ggcgtggagg cggagcggag gatcgccgag      840
acgatgaccg ccaccatgca cctcaactgg taccctcggt gcccggaccc gcgccgcgcg      900
ctggggctga tcgcgcacac cgactcgggc ttcttcacct tcgtgctgca gagcctcgtc      960
ccggggctgc agctcttccg ccacgccccg gaccggtggg tggcggtgcc ggcggtaccg     1020
ggcgccttcg tcgtcaacgt gggcgacctc ttccacatcc tcaccaacgg ccggttccac     1080
agcgtgtacc accgcgccgt cgtgaaccgg gacctcgaca ggatatctct cggctacttc     1140
ctcggcccgc cgccgcacgc caaggtggcg ccgctaaggg aggccgtgcc gcccggccgc     1200
acccccgcgt accgcgccgt cacgtggccc gagtacatgg gcgtccgcaa gaaggccttc     1260
accaccggcg catccgcgct caagatggtc gccctcgccg ccgccgccgc cgccgccgac     1320
ctcgacgatg acgccggtgc tggcgccgcc gccgaacctg tcgtccatca gcagctactc     1380
gtctcgtcgt agccgatcga tcgccggatc ggtcgagact gatgatgatg atgcatatat     1440
actcgtcgat ggagtagaca gactaatcaa gcaaccctga aactatgaat gcatgcgtgc     1500
gcttcgtgct tgcttgcgca tgcagctagc aggcttcatt ccgttccgca gctgctctgc     1560
tccaacctgc tctgctggat tgatgtatat ggtagaagaa ttaagagatc gatggatgac     1620
ggaggaagaa gaagacgaag acgacgatga ggaaaaggac acgctgtacg tagctggttc     1680
ttctagtcta gtttacagca ggccgggcgg ccggctgctg cttccaatcg agtttgtcgt     1740
tactgacgat tgttagtgga tcgattaact aatctggaat tctggattat taatataatg     1800
catgtggttt ggcatctggc gtaaagcagg taatggtacc tagccagtag ccagtagcca     1860
ggctggtcaa tgataggtct ataccctgat cctgtactgt tgtttctttc ggtctttctg     1920
agagagaaaa aaaacgaata tatggcgtac tcaattcatc aaa                       1963
```

```
<210> SEQ ID NO 120
<211> LENGTH: 1170
<212> TYPE: DNA
<213> ORGANISM: Sorghum bicolor

<400> SEQUENCE: 120
atgccgacgc cgtcgcacct cgcgaacccg cgctacttcg acttccgtgc ggcgcggcgg       60
gtgccggaga cgcacgcctg gccggggctg cacgaccacc ccgtcgtgga cggcggcgcg      120
ccggggccag acgccgtccc cgtggtggac ctcgcggggg cggcggacga gccgagagcc      180
gcggtggtgg cccaagtggc gcgcgccgcc gagcaatggg gcgcgttcct gctcacgggg      240
cacggcgtcc ccgcggagct gctggcgcgc gtcgaggacc ggatcgccac catgttcgcg      300
ctgccagcgg acgacaagat gcgcgccgtg cgcgggcctg gcgacgcctg cggctacggc      360
tccccgccca tctcctcctt cttctccaag tgcatgtggt cggagggata caccttctcg      420
ccggccaacc tccgcgccga cctccgcaag ctctggccta aggccggcga cgactacacc      480
agcttctgtg atgtgatgga ggagttccac aagcacatgc gtgccctcgc ggacaagctg      540
ctggagctgt tcctcatggc gctggggctc accgacgagc aggtcggcgg cgtggaggcg      600
gagcggagga tcgccgagac gatgaccgcc accatgcacc tcaactggta ccctcggtgc      660
ccggacccgc gccgcgcgct ggggctgatc gcgcacaccg actcgggctt cttcaccttc      720
gtgctgcaga gcctcgtccc ggggctgcag ctcttccgcc acgccccgga ccggtgggtg      780
gcggtgccgg cggtaccggg cgccttcgtc gtcaacgtgg cgacctctt ccacatcctc       840 accaacggcc ggttccacag cgtgtaccac cgcgccgtcg tgaaccggga cctcgacagg      900
```

-continued

```
atatctctcg gctacttcct cggcccgccg ccgcacgcca aggtggcgcc gctaagggag    960
gccgtgccgc ccggccgcac ccccgcgtac cgcgccgtca cgtggcccga gtacatgggc   1020
gtccgcaaga aggccttcac caccggcgca tccgcgctca agatggtcgc cctcgccgcc   1080
gccgccgccg ccgccgacct cgacgatgac gccggtgctg gcgccgccgc cgaacctgtc   1140
gtccatcagc agctactcgt ctcgtcgtag                                    1170
```

<210> SEQ ID NO 121
<211> LENGTH: 389
<212> TYPE: PRT
<213> ORGANISM: Sorghum bicolor

<400> SEQUENCE: 121

```
Met Pro Thr Pro Ser His Leu Ala Asn Pro Arg Tyr Phe Asp Phe Arg
1               5                   10                  15

Ala Ala Arg Arg Val Pro Glu Thr His Ala Trp Pro Gly Leu His Asp
                20                  25                  30

His Pro Val Val Asp Gly Gly Ala Pro Gly Pro Asp Ala Val Pro Val
            35                  40                  45

Val Asp Leu Ala Gly Ala Ala Asp Glu Pro Arg Ala Ala Val Val Ala
        50                  55                  60

Gln Val Ala Arg Ala Ala Glu Gln Trp Gly Ala Phe Leu Leu Thr Gly
65                  70                  75                  80

His Gly Val Pro Ala Glu Leu Leu Ala Arg Val Glu Asp Arg Ile Ala
                85                  90                  95

Thr Met Phe Ala Leu Pro Ala Asp Asp Lys Met Arg Ala Val Arg Gly
            100                 105                 110

Pro Gly Asp Ala Cys Gly Tyr Gly Ser Pro Pro Ile Ser Ser Phe Phe
        115                 120                 125

Ser Lys Cys Met Trp Ser Glu Gly Tyr Thr Phe Ser Pro Ala Asn Leu
    130                 135                 140

Arg Ala Asp Leu Arg Lys Leu Trp Pro Lys Ala Gly Asp Asp Tyr Thr
145                 150                 155                 160

Ser Phe Cys Asp Val Met Glu Glu Phe His Lys His Met Arg Ala Leu
                165                 170                 175

Ala Asp Lys Leu Leu Glu Leu Phe Leu Met Ala Leu Gly Leu Thr Asp
            180                 185                 190

Glu Gln Val Gly Gly Val Glu Ala Glu Arg Arg Ile Ala Glu Thr Met
        195                 200                 205

Thr Ala Thr Met His Leu Asn Trp Tyr Pro Arg Cys Pro Asp Pro Arg
    210                 215                 220

Arg Ala Leu Gly Leu Ile Ala His Thr Asp Ser Gly Phe Phe Thr Phe
225                 230                 235                 240

Val Leu Gln Ser Leu Val Pro Gly Leu Gln Leu Phe Arg His Ala Pro
                245                 250                 255

Asp Arg Trp Val Ala Val Pro Ala Val Pro Gly Ala Phe Val Val Asn
            260                 265                 270

Val Gly Asp Leu Phe His Ile Leu Thr Asn Gly Arg Phe His Ser Val
        275                 280                 285

Tyr His Arg Ala Val Val Asn Arg Asp Leu Asp Arg Ile Ser Leu Gly
    290                 295                 300

Tyr Phe Leu Gly Pro Pro Pro His Ala Lys Val Ala Pro Leu Arg Glu
305                 310                 315                 320
```

```
Ala Val Pro Pro Gly Arg Thr Pro Ala Tyr Arg Ala Val Thr Trp Pro
                325                 330                 335

Glu Tyr Met Gly Val Arg Lys Lys Ala Phe Thr Thr Gly Ala Ser Ala
            340                 345                 350

Leu Lys Met Val Ala Leu Ala Ala Ala Ala Ala Ala Asp Leu Asp
        355                 360                 365

Asp Asp Ala Gly Ala Gly Ala Ala Ala Glu Pro Val Val His Gln Gln
    370                 375                 380

Leu Leu Val Ser Ser
385
```

```
<210> SEQ ID NO 122
<211> LENGTH: 2321
<212> TYPE: DNA
<213> ORGANISM: Sorghum bicolor

<400> SEQUENCE: 122
tataaatacc acgccatgta cttctctgct tctacacttc tccagcttct ctcatgccat      60
accactagtg caaggtccta gatttacact tggtgctaca gcttcttcct ccctccctcc     120
cctctctagg cagctagcac gcagcgcagc acacgaaaca tctattgacc ggccgcctcc     180
gccggggatc cataattact atactaccaa tcggccagcg tcatgccgac gccgtcgcac     240
ctcgcgaacc cgcgctactt cgacttccgt gcggcgcggc gggtgccgga gacgcacgcc     300
tggccggggc tgcacgacca ccccgtcgtg gacggcggcg cgccggggcc agacgccgtc     360
cccgtggtgg acctcgcggg ggcggcggac gagccgagag ccgcggtggt ggcccaagtg     420
gcgcgcgccg ccgagcaatg gggcgcgttc ctgctcacgg ggcacggcgt ccccgcggag     480
ctgctggcgc gcgtcgagga ccggatcgcc accatgttcg cgctgccagc ggacgacaag     540
atgcgcgccg tgcgcgggcc tggcgacgcc tgcggctacg gctccccgcc catctcctcc     600
ttcttctcca agtgcatgtg gtcggaggga tacaccttct cgccggccaa cctccgcgcc     660
gacctccgca agctctggcc taaggccggc gacgactaca ccagcttctg gtacgtgcac     720
ccgccggccg cgcgccgcca cacaccgtac ccacacacgt gcgcgctcgc gcctagctac     780
tagtagctgc tttgctttgc ttacctttga ttctcgcctt tgccatgcat atgcatgatg     840
cacgtacagg tactgcaggt acaacatgtc acacgcacgc acgcacgcac aacccatagt     900
ccgatacgat acatcatcga tcgacgtgtc gtcaccgtct aaggccatgc atgcatgcaa     960
gcacacgcct agaccttttt agcatgctgg ctgacgagga gtatactagc taataagcta    1020
cttgtcactg cgcgtcttgc ttaattacac tagtgcatat ttctacagtg atgtgatgga    1080
ggagttccac aagcacatgc gtgccctcgc ggacaagctg ctggagctgt tcctcatggc    1140 gctgggctc accgacgagc aggtcggcgg cgtggaggcg gagcggagga tcgccgagac    1200
gatgaccgcc accatgcacc tcaactggta ccctcggtgc ccggacccgc gccgcgcgct    1260
ggggctgatc gcgcacaccg actcgggctt cttcaccttc gtgctgcaga gcctcgtccc    1320
ggggctgcag ctcttccgcc acgccccgga ccggtgggtg gcggtgccgg cggtaccggg    1380
cgccttcgtc gtcaacgtgg gcgacctctt ccacatcctc accaacggcc ggttccacag    1440
cgtgtaccac cgcgccgtcg tgaaccggga cctcgacagg atatctctcg gctacttcct    1500
cggcccgccg ccgcacgcca aggtggcgcc gctaagggag gccgtgccgc ccggccgcac    1560
ccccgcgtac cgcgccgtca cgtggcccga gtacatgggc gtccgcaaga aggccttcac    1620
caccggcgca tccgcgctca agatggtcgc cctcgccgcc gccgccgccg ccgccgacct    1680
```

-continued

```
cgacgatgac gccggtgctg gcgccgccgc cgaacctgtc gtccatcagc agctactcgt      1740
ctcgtcgtag ccgatcgatc gccggatcgg tcgagactga tgatgatgat gcatatatac      1800
tcgtcgatgg agtagacaga ctaatcaagc aaccctgaaa ctatgaatgc atgcgtgcgc      1860
ttcgtgcttg cttgcgcatg cagctagcag gcttcattcc gttccgcagc tgctctgctc      1920
caacctgctc tgctggattg atgtatatgg tagaagaatt aagagatcga tggatgacgg      1980
aggaagaaga agacgaagac gacgatgagg aaaaggacac gctgtacgta gctggttctt      2040
ctagtctagt ttacagcagg ccgggcggcc ggctgctgct tccaatcgag tttgtcgtta      2100
ctgacgattg ttagtggatc gattaactaa tctggaattc tggattatta atataatgca      2160
tgtggtttgg catctggcgt aaagcaggta atggtaccta gccagtagcc agtagccagg      2220
ctggtcaatg ataggtctat accctgatcc tgtactgttg tttctttcgg tctttctgag      2280
agagaaaaaa aacgaatata tggcgtactc aattcatcaa a      2321
```

```
<210> SEQ ID NO 123
<211> LENGTH: 1796
<212> TYPE: DNA
<213> ORGANISM: Setaria italica

<400> SEQUENCE: 123
```

```
actagtgcaa ggtcctagat ttacacttgg tgcttgcttg tttcttccta gttgctactg       60
gtagcacgca gtggctggct ggccgtaatc tattgtctgg gctcgatcgg tgattaggaa      120
gtagccaaag caagctaagg ccgccgccgc cgccgccatg ccgacgccgt cgcacctcaa      180
gaacccgctc tacttcgact tccgcgccgc gcggcgggtg ccggagtccc acgcctggcc      240
ggggctcgac gaccaccccg tggtggacgg cggcggcgcg ccggggtccc cggacgccgt      300
gccggtggtg gacctgcgcg agccgggcgc gcgcggcggtg gcccgcgtgg cgcgcgccgc      360
cgagcagtgg ggcgcgttcc tgctcaccgg ccacggcgtc cccgcggagc tcctggcgcg      420
cgtcgaggac cgcgtcgcgt gcatgttcgc gctgccggcc gccgacaaga tgcgcgcgt       480 gcgcgggccg ggggacgcct gcggctacgg ctcgccgccc atctcctcct tcttctccaa      540
gtgcatgtgg tccgagggct acaccttctc gccggcctcc ctccgccgcg acctccgcaa      600
gctctggccc aaggccggcg acgactacga cagcttctgt gacgtgatgg aggagttcca      660
caaggagatg cgcgccctcg ccgacaggct cctggagctg ttcctcaggg cgctcgggct      720
caccggcgag caggtcggcg ccgtcgaggc ggagcggagg atcggcgaga cgatgaccgc      780
caccatgcac ctcaactggt atccgaggtg cccggacccg cggcgcgcgc tggggctgat      840
cgcgcacacg gactcgggct tcttcacctt cgtgctgcag agcctcgtgc cggggctgca      900
gctgttccgg cacggcccca accggtgggg ggcggtgccg gccgtgccgg cgcgccttcgt     960 cgtcaacgtc ggcgacctct tccacatcct cacgaacggc cgcttccaca gcgtgtacca     1020
ccgcgccgtc gtcaaccggg acctcgaccg gatatcgctc ggctacttcc tcggcccgcc     1080
gccccacgcc aaggtggcgc cgctccggga ggtcgtgccg ccgggccggg cccccgccta     1140
ccgcgccgtc acgtggcccg agtacatggg cgtccgcaag aaggccttca ccaccggcgc     1200
ctccgcgctc aagatggtcg ccgcgccgcg cgccgccacc gaatccgacg acaccgacgc     1260
agccgccgcc gccgttcacc agccgccggt cgtcgtctca tcgtagccga tcgatcgccg     1320
gaaacacaga cgatgcatac cgtaccccga gcaatctaat caaaacaagg catccattct     1380
cgcgcgcatg cagcggccag ccgggcttcc gcagctgctc ggcctcctct gctggctgtg     1440
gaaatggaaa attttaatct gagatgaaga cgaagacgaa gacgaaacgg agaggaaaag     1500
```

-continued

```
gacatgctgt agctgtttct tctagttgcg caggccgctc ccagtcgagt ttgtcgttac    1560
tgacgattat tactctgatg aaaactaatc tgaattaatg catgtagttt ggcaatttgg    1620
tactaaaggt aggcacctag ccaggctggt caatgatagg tctataacct gatcctgttc    1680
tctgttgttt tcctttgtct gagaaaaaat ggaaataatt gatccggccg gacgggtgta    1740
ctgataggtg atgctgaatt gctgatgcaa gaggttgcga gctgcagtga gcagca        1796
```

<210> SEQ ID NO 124
<211> LENGTH: 1149
<212> TYPE: DNA
<213> ORGANISM: Setaria italica

<400> SEQUENCE: 124

```
atgccgacgc cgtcgcacct caagaacccg ctctacttcg acttccgcgc cgcgcggcgg      60
gtgccggagt cccacgcctg gccgggggctc gacgaccacc ccgtggtgga cggcggcggc     120
gcgccggggt ccccggacgc cgtgccggtg gtggacctgc gcgagccggg cgccgcggcg     180
gtggcccgcg tggcgcgcgc cgccgagcag tggggcgcgt tcctgctcac cggccacggc     240
gtccccgcgg agtcctggc gcgcgtcgag gaccgcgtcg cgtgcatgtt cgcgctgccg       300
gccgccgaca agatgcgcgc cgtgcgcggg ccgggggacg cctgcggcta cggctcgccg      360
cccatctcct ccttcttctc caagtgcatg tggtccgagg ctacaccttc tcgccggcc       420 tccctccgcc gcgacctccg caagctctgg cccaaggccg gcgacgacta cgacagcttc      480
tgtgacgtga tggaggagtt ccacaaggag atgcgcgccc tcgccgacag gctcctggag      540
ctgttcctca gggcgctcgg gctcaccggc gagcaggtcg gcgccgtcga ggcggagcgg      600
aggatcggcg agacgatgac cgccaccatg cacctcaact ggtatccgag gtgcccggac      660
ccgcggcgcg cgctggggct gatcgcgcac acggactcgg gcttcttcac cttcgtgctg      720
cagagcctcg tgccggggct gcagctgttc cggcacggcc ccaaccggtg ggtggcggtg      780
ccggccgtgc cgggcgcctt cgtcgtcaac gtcggcgacc tcttccacat cctcacgaac      840
ggccgcttcc acagcgtgta ccaccgcgcc gtcgtcaacc gggacctcga ccggatatcg      900
ctcggctact cctcggcccc gccgccccac gccaaggtgg cgccgctccg ggaggtcgtg      960
ccgccgggcc gggccccccgc ctaccgcgcc gtcacgtggc ccgagtacat gggcgtccgc    1020
aagaaggcct tcaccaccgg cgcctccgcg ctcaagatgt cgccgccgcc cgccgccgcc    1080
accgaatccg acgacaccga cgcagccgcc gccgccgttc accagccgcc ggtcgtcgtc    1140
tcatcgtag                                                           1149
```

<210> SEQ ID NO 125
<211> LENGTH: 382
<212> TYPE: PRT
<213> ORGANISM: Setaria italica

<400> SEQUENCE: 125

```
Met Pro Thr Pro Ser His Leu Lys Asn Pro Leu Tyr Phe Asp Phe Arg
1               5                   10                  15

Ala Ala Arg Arg Val Pro Glu Ser His Ala Trp Pro Gly Leu Asp Asp
            20                  25                  30

His Pro Val Val Asp Gly Gly Gly Ala Pro Gly Ser Pro Asp Ala Val
        35                  40                  45

Pro Val Val Asp Leu Arg Glu Pro Gly Ala Ala Ala Val Ala Arg Val
    50                  55                  60
```

-continued

```
Ala Arg Ala Ala Glu Gln Trp Gly Ala Phe Leu Leu Thr Gly His Gly
65              70              75              80

Val Pro Ala Glu Leu Leu Ala Arg Val Glu Asp Arg Val Ala Cys Met
            85              90              95

Phe Ala Leu Pro Ala Ala Asp Lys Met Arg Ala Val Arg Gly Pro Gly
            100             105             110

Asp Ala Cys Gly Tyr Gly Ser Pro Pro Ile Ser Ser Phe Phe Ser Lys
            115             120             125

Cys Met Trp Ser Glu Gly Tyr Thr Phe Ser Pro Ala Ser Leu Arg Arg
    130             135             140

Asp Leu Arg Lys Leu Trp Pro Lys Ala Gly Asp Asp Tyr Asp Ser Phe
145             150             155             160

Cys Asp Val Met Glu Glu Phe His Lys Glu Met Arg Ala Leu Ala Asp
            165             170             175

Arg Leu Leu Glu Leu Phe Leu Arg Ala Leu Gly Leu Thr Gly Glu Gln
            180             185             190

Val Gly Ala Val Glu Ala Glu Arg Arg Ile Gly Glu Thr Met Thr Ala
            195             200             205

Thr Met His Leu Asn Trp Tyr Pro Arg Cys Pro Asp Pro Arg Arg Ala
    210             215             220

Leu Gly Leu Ile Ala His Thr Asp Ser Gly Phe Phe Thr Phe Val Leu
225             230             235             240

Gln Ser Leu Val Pro Gly Leu Gln Leu Phe Arg His Gly Pro Asn Arg
            245             250             255

Trp Val Ala Val Pro Ala Val Pro Gly Ala Phe Val Val Asn Val Gly
            260             265             270

Asp Leu Phe His Ile Leu Thr Asn Gly Arg Phe His Ser Val Tyr His
            275             280             285

Arg Ala Val Val Asn Arg Asp Leu Asp Arg Ile Ser Leu Gly Tyr Phe
            290             295             300

Leu Gly Pro Pro Pro His Ala Lys Val Ala Pro Leu Arg Glu Val Val
305             310             315             320

Pro Pro Gly Arg Ala Pro Ala Tyr Arg Ala Val Thr Trp Pro Glu Tyr
            325             330             335

Met Gly Val Arg Lys Lys Ala Phe Thr Thr Gly Ala Ser Ala Leu Lys
            340             345             350

Met Val Ala Ala Ala Ala Ala Thr Glu Ser Asp Asp Thr Asp Ala
            355             360             365

Ala Ala Ala Ala Val His Gln Pro Pro Val Val Val Ser Ser
    370             375             380
```

```
<210> SEQ ID NO 126
<211> LENGTH: 2146
<212> TYPE: DNA
<213> ORGANISM: Setaria italica

<400> SEQUENCE: 126
actagtgcaa ggtcctagat ttacacttgg tgcttgcttg tttcttccta gttgctactg     60
gtagcacgca gtggctggct ggccgtaatc tattgtctgg gctcgatcgg tgattaggaa    120
gtagccaaag caagctaagg ccgccgccgc cgccgccatg ccgacgccgt cgcacctcaa    180
gaacccgctc tacttcgact tccgcgccgc gcggcgggtg ccggagtccc acgcctggcc    240
ggggctcgac gaccaccccg tggtggacgg cggcggcgcg ccggggtccc cggacgccgt    300
gccggtggtg gacctgcgcg agccgggcgc cgcggcggtg gcccgcgtgg cgcgcgccgc    360
```

-continued

```
cgagcagtgg ggcgcgttcc tgctcaccgg ccacggcgtc cccgcggagc tcctggcgcg      420
cgtcgaggac cgcgtcgcgt gcatgttcgc gctgccggcc gccgacaaga tgcgcgccgt      480
gcgcgggccg ggggacgcct gcggctacgg ctcgccgccc atctcctcct tcttctccaa      540
gtgcatgtgg tccgagggct acaccttctc gccggcctcc ctccgccgcg acctccgcaa      600
gctctggccc aaggccggcg acgactacga cagcttctgg tacgtcgtcg tctatagcta      660
gtagctagcc gccggcacac gtgcgcctga cctgctccgc catgcatggt gcacgtatgc      720
agatcgatca cacgcaccga tcgatcgacg tgtcccggtc aaggccatgc atgcatgcaa      780
gcaaccaaca gcacgcctcc tgatactgct tgttgcttac accgttggta tgtgcctgtt      840
gcctacagtg acgtgatgga ggagttccac aaggagatgc gcgccctcgc cgacaggctc      900
ctggagctgt tcctcagggc gctcgggctc accggcgagc aggtcggcgc cgtcgaggcg      960
gagcggagga tcggcgagac gatgaccgcc accatgcacc tcaactggta tgtgccatgc     1020
catgaccacc tgcgtctatg aactaacgga agcttccatc gcgtgtccat gacgatttag     1080
aagctgtagt ccagagcttg agacaaacga aacgaagctt acatggtggc gtgacgtgtc     1140
gcgtgcaggt atccgaggtg cccggacccg cggcgcgcgc tggggctgat cgcgcacacg     1200
gactcgggct tcttcacctt cgtgctgcag agcctcgtgc cggggctgca gctgttccgg     1260
cacggcccca accggtgggt ggcggtgccg gccgtgccgg gcgccttcgt cgtcaacgtc     1320
ggcgacctct tccacatcct cacgaacggc cgcttccaca gcgtgtacca ccgcgccgtc     1380
gtcaaccggg acctcgaccg gatatcgctc ggctacttcc tcggcccgcc gccccacgcc     1440
aaggtggcgc cgctccggga ggtcgtgccg ccgggccggg cccccgccta ccgcgccgtc     1500
acgtggcccg agtacatggg cgtccgcaag aaggccttca ccaccggcgc ctccgcgctc     1560
aagatggtcg ccgccgccgc cgccgccacc gaatccgacg acaccgacgc agccgccgcc     1620
gccgttcacc agccgccggt cgtcgtctca tcgtagccga tcgatcgccg gaaacacaga     1680
cgatgcatac cgtaccccga gcaatctaat caaaacaagg catccattct cgcgcgcatg     1740
cagcggccag ccgggcttcc gcagctgctc ggcctcctct gctggctgtg gaaatggaaa     1800
attttaatct gagatgaaga cgaagacgaa gacgaaacgg agaggaaaag gacatgctgt     1860
agctgtttct tctagttgcg caggccgctc ccagtcgagt ttgtcgttac tgacgattat     1920
tactctgatg aaaactaatc tgaattaatg catgtagttt ggcaatttgg tactaaaggt     1980
aggcacctag ccaggctggt caatgatagg tctataacct gatcctgttc tctgttgttt     2040
tcctttgtct gagaaaaaat ggaaataatt gatccggccg gacgggtgta ctgataggtg     2100
atgctgaatt gctgatgcaa gaggttgcga gctgcagtga gcagca                    2146
```

<210> SEQ ID NO 127
<211> LENGTH: 1933
<212> TYPE: DNA
<213> ORGANISM: Oryza sativa

<400> SEQUENCE: 127

```
actactcatt ccactattgt aaagtcatag aaaaaattta tatagagaga aaaaattagt       60
gttgttattg ttactggctt tctgccagac gagacgagcg agcgcgcgag tgtgttgctc      120
tctggtcatc gtcgtcgtcg tcgcgatgcc gacgccgtcg cacttgaaga acccgctctg      180
cttcgacttc cggcggcgga ggcgggtgcc ggagacgcac gcgtggccgg ggctggacga      240
ccacccggtg gtggacggcg gcggcggcgg cggcgaggac gcggtgccgg tggtggacgt      300
```

-continued

```
cggggcgggc gacgcggcgg cgcgggtggc gcgggcggcg gagcagtggg gcgcgttcct      360
tctggtcggg cacggcgtgc cggcggcgct gctgtcgcgc gtcgaggagc gcgtcgcccg      420
cgtgttctcc ctgccggcgt cggagaagat gcgcgccgtc cgcggccccg cgcagccctg      480
cggctacggc tcgccgccca tctcctcctt cttctccaag ctcatgtggt ccgagggcta      540
caccttctcc ccttcctccc tccgctccga gctccgccgc ctctggccca agtccggcga      600
cgactacctc ctcttctgtg acgtgatgga ggagtttcac aaggagatgc ggcggctagc      660
cgacgagttg ctgaggttgt tcttgagggc gctggggctc accggcgagg aggtcgccgg      720
agtcgaggcg gagaggagga tcggcgagag gatgacggcg acggtgcacc tcaactggta      780
cccgaggtgc ccggagccgc ggcgagcgct ggggctcatc gcgcacacgg actcgggctt      840
cttcaccttc gtgctccaga gcctcgtccc ggggctgcag ctgttccgtc gagggcccga      900
ccggtgggtg gcggtgccgg cggtggcggg ggccttcgtc gtcaacgtcg gcgacctctt      960
ccacatcctc accaacggcc gcttccacag cgtctaccac cgcgccgtcg tgaaccgcga     1020
ccgcgaccgg gtctcgctcg gctacttcct cggcccgccg ccggacgccg aggtggcgcc     1080
gctgccggag gccgtgccgg ccggccggag ccccgcctac cgcgctgtca cgtggccgga     1140
gtacatggcc gtccgcaaga aggccttcgc caccggcggc tccgccctca agatggtctc     1200
caccgacgcc gccgccgccg ccgacgaaca cgacgacgtc gccgccgccg ccgacgtcca     1260
cgcataagct atagctacta gctacctcga tctcacgcaa aaaaaaaag aaacaattaa     1320 tagagcaaaa aaaaaagaa gagaaaatgg tggtacttgt gtttaaggtt tcctccatgc     1380
aaaatggttt gcatgcatgc atgcaaagct agcatctgca gctgcaagaa ttacaagagc     1440
agagaagcag acagctagat ggagataatt aattaattaa ttaatctaat taagcatgca     1500
ataattaaga ttattattct gatttcagaa ctgaaaaaaa aagtgtggtt aattaattat     1560
tggttaggct taattttatc tagatgtaga aaaagaatca agatcttcaa gcaagagaga     1620
agaggatcga agaagaagga aaagaaaacg aaaaggacat gctgtgttgt ctcttctagt     1680
tgtaccctgg ctgctgatta agtgctttgt tttgttgctg caagcttgtc gttactgatt     1740
attagttagt tatgcatcta attgattaaa ctaatctgtt tggcattttg gctcgagcta     1800
agctatagcc aggctggtca atgataggaa cttgtacaat ttaagcaatt gaacctgatc     1860
ctgtactggc atgtatgtat atatgcaagt gatgagaacc actagctagt atagctagac     1920
atgtatttgt ata                                                        1933
```

<210> SEQ ID NO 128
<211> LENGTH: 1122
<212> TYPE: DNA
<213> ORGANISM: Oryza sativa

<400> SEQUENCE: 128

```
atgccgacgc cgtcgcactt gaagaacccg ctctgcttcg acttccgggc ggcgaggcgg       60
gtgccggaga cgcacgcgtg gccggggctg acgaccacc cggtggtgga cggcggcggc      120
ggcggcggcg aggacgcggt gccggtggtg gacgtcgggg cggcgacgc ggcggcgcgg      180 gtggcgcggg cggcggagca gtggggcgcg ttccttctgg tcgggcacgg cgtgccggcg      240
gcgctgctgt cgcgcgtcga ggagcgcgtc gcccgcgtgt ctccctgcc ggcgtcggag      300 aagatgcgcg ccgtccgcgg ccccggcgag ccctgcggct acggctcgcc gcccatctcc      360
tccttcttct ccaagctcat gtggtccgag ggctacacct ctcccccttc ctccctccgc      420
tccgagctcc gccgcctctg gcccaagtcc ggcgacgact acctcctctt ctgtgacgtg      480
```

```
atggaggagt ttcacaagga gatgcggcgg ctagccgacg agttgctgag gttgttcttg      540
agggcgctgg ggctcaccgg cgaggaggtc gccggagtcg aggcggagag gaggatcggc      600
gagaggatga cggcgacggt gcacctcaac tggtacccga ggtgcccgga ccgcggcga       660 gcgctggggc tcatcgcgca cacggactcg ggcttcttca ccttcgtgct ccagagcctc      720
gtcccggggc tgcagctgtt ccgtcgaggg cccgaccggt gggtggcggt gccggcggtg      780
gcgggggcct tcgtcgtcaa cgtcggcgac ctcttccaca tcctcaccaa cggccgcttc      840
cacagcgtct accaccgcgc cgtcgtgaac cgcgaccgcg accgggtctc gctcggctac      900
ttcctcggcc cgccgccgga cgccgaggtg gcgccgctgc cggaggccgt gccggccggc      960
cggagccccg cctaccgcgc tgtcacgtgg ccggagtaca tggccgtccg caagaaggcc     1020
ttcgccaccg cgggctccgc cctcaagatg gtctccaccg acgccgccgc cgccgccgac     1080
gaacacgacg acgtcgccgc cgccgccgac gtccacgcat aa                        1122
```

<210> SEQ ID NO 129
<211> LENGTH: 373
<212> TYPE: PRT
<213> ORGANISM: Oryza sativa

<400> SEQUENCE: 129

```
Met Pro Thr Pro Ser His Leu Lys Asn Pro Leu Cys Phe Asp Phe Arg
1               5                   10                  15

Ala Ala Arg Arg Val Pro Glu Thr His Ala Trp Pro Gly Leu Asp Asp
                20                  25                  30

His Pro Val Val Asp Gly Gly Gly Gly Gly Glu Asp Ala Val Pro
                35                  40                  45

Val Val Asp Val Gly Ala Gly Asp Ala Ala Ala Arg Val Ala Arg Ala
        50                  55                  60

Ala Glu Gln Trp Gly Ala Phe Leu Leu Val Gly His Gly Val Pro Ala
65                  70                  75                  80

Ala Leu Leu Ser Arg Val Glu Glu Arg Val Ala Arg Val Phe Ser Leu
                85                  90                  95

Pro Ala Ser Glu Lys Met Arg Ala Val Arg Gly Pro Gly Glu Pro Cys
                100                 105                 110

Gly Tyr Gly Ser Pro Pro Ile Ser Ser Phe Phe Ser Lys Leu Met Trp
                115                 120                 125

Ser Glu Gly Tyr Thr Phe Ser Pro Ser Ser Leu Arg Ser Glu Leu Arg
        130                 135                 140

Arg Leu Trp Pro Lys Ser Gly Asp Asp Tyr Leu Leu Phe Cys Asp Val
145                 150                 155                 160

Met Glu Glu Phe His Lys Glu Met Arg Arg Leu Ala Asp Glu Leu Leu
                165                 170                 175

Arg Leu Phe Leu Arg Ala Leu Gly Leu Thr Gly Glu Glu Val Ala Gly
                180                 185                 190

Val Glu Ala Glu Arg Arg Ile Gly Glu Arg Met Thr Ala Thr Val His
        195                 200                 205

Leu Asn Trp Tyr Pro Arg Cys Pro Glu Pro Arg Arg Ala Leu Gly Leu
        210                 215                 220

Ile Ala His Thr Asp Ser Gly Phe Phe Thr Phe Val Leu Gln Ser Leu
225                 230                 235                 240

Val Pro Gly Leu Gln Leu Phe Arg Arg Gly Pro Asp Arg Trp Val Ala
                245                 250                 255
```

-continued

```
Val Pro Ala Val Ala Gly Ala Phe Val Val Asn Val Gly Asp Leu Phe
        260                 265                 270

His Ile Leu Thr Asn Gly Arg Phe His Ser Val Tyr His Arg Ala Val
        275                 280                 285

Val Asn Arg Asp Arg Asp Arg Val Ser Leu Gly Tyr Phe Leu Gly Pro
        290                 295                 300

Pro Pro Asp Ala Glu Val Ala Pro Leu Pro Glu Ala Val Pro Ala Gly
305                 310                 315                 320

Arg Ser Pro Ala Tyr Arg Ala Val Thr Trp Pro Glu Tyr Met Ala Val
                325                 330                 335

Arg Lys Lys Ala Phe Ala Thr Gly Gly Ser Ala Leu Lys Met Val Ser
        340                 345                 350

Thr Asp Ala Ala Ala Ala Ala Asp Glu His Asp Asp Val Ala Ala Ala
        355                 360                 365

Ala Asp Val His Ala
        370
```

<210> SEQ ID NO 130
<211> LENGTH: 2040
<212> TYPE: DNA
<213> ORGANISM: Oryza sativa

<400> SEQUENCE: 130

```
actactcatt ccactattgt aaagtcatag aaaaaattta tatagagaga aaaaattagt      60
gttgttattg ttactggctt tctgccagac gagacgagcg agcgcgcgag tgtgttgctc     120
tctggtcatc gtcgtcgtcg tcgcgatgcc gacgccgtcg cacttgaaga acccgctctg     180
cttcgacttc cgggcggcga ggcgggtgcc ggagacgcac gcgtggccgg ggctggacga     240
ccacccggtg gtggacggcg gcggcggcgg cggcgaggac gcggtgccgg tggtggacgt     300
cggggcgggc gacgcggcgg cgcgggtggc gcgggcggcg gagcagtggg gcgcgttcct     360
tctggtcggg cacggcgtgc cggcggcgct gctgtcgcgc gtcgaggagc gcgtcgcccg     420
cgtgttctcc ctgccggcgt cggagaagat gcgcgccgtc cgcggccccg gcgagccctg     480
cggctacggc tcgccgccca tctcctcctt cttctccaag ctcatgtggt ccgagggcta     540
caccttctcc ccttcctccc tccgctccga gctccgccgc ctctggccca agtccggcga     600
cgactacctc ctcttctggt atatatacat atatactctc ccatgcattc catgcacata     660
cactctacgt atatatctac ctctacgtat atatctacgt attgatctac gtataatata     720
cgcagtgacg tgatggagga gtttcacaag gagatgcggc ggctagccga cgagttgctg     780
aggttgttct tgagggcgct ggggctcacc ggcgaggagg tcgccggagt cgaggcggag     840
aggaggatcg gcgagaggat gacggcgacg gtgcacctca actggtaccc gaggtgcccg     900
gagccgcggc gagcgctggg gctcatcgcg cacacggact cgggcttctt caccttcgtg     960
ctccagagcc tcgtcccggg gctgcagctg ttcgtcgag ggcccgaccg gtgggtggcg    1020
gtgccggcgg tggcgggggc cttcgtcgtc aacgtcggcg acctcttcca catcctcacc    1080
aacggccgct ccacagcgt ctaccaccgc gccgtcgtga accgcgaccg cgaccgggtc    1140
tcgctcggct acttcctcgg cccgccgccg gacgccgagg tggcgccgct gccggaggcc    1200
gtgccggccg gccggagccc cgcctaccgc gctgtcacgt ggccggagta catggccgtc    1260
cgcaagaagg ccttcgccac cggcggctcc gccctcaaga tggtctccac cgacgccgcc    1320
gccgccgccg acgaacacga cgacgtcgcc gccgccgccg acgtccacgc ataagctata    1380
gctactagct acctcgatct cacgcaaaaa aaaaagaaaa caattaatag agcaaaaaaa    1440
```

```
aaaagaagag aaaatggtgg tacttgtgtt taaggtttcc tccatgcaaa atggtttgca        1500
tgcatgcatg caaagctagc atctgcagct gcaagaatta caagagcaga gaagcagaca        1560
gctagatgga gataattaat taattaatta atctaattaa gcatgcaata attaagatta        1620
ttattctgat ttcagaactg aaaaaaaaag tgtggttaat taattattgg ttaggcttaa        1680
ttttatctag atgtagaaaa agaatcaaga tcttcaagca agagagaaga ggatcgaaga        1740
agaaggaaaa gaaaacgaaa aggacatgct gtgttgtctc ttctagttgt accctggctg        1800
ctgattaagt gctttgtttt gttgctgcaa gcttgtcgtt actgattatt agttagttat        1860
gcatctaatt gattaaacta atctgtttgg cattttggct cgagctaagc tatagccagg        1920
ctggtcaatg ataggaactt gtacaattta agcaattgaa cctgatcctg tactggcatg        1980
tatgtatata tgcaagtgat gagaaccact agctagtata gctagacatg tatttgtata        2040

<210> SEQ ID NO 131
<211> LENGTH: 1332
<212> TYPE: DNA
<213> ORGANISM: Hordeum vulgare

<400> SEQUENCE: 131
acactcactc ctcaatccat ccgtctccac cattgctcgc tagctcgagc tctactagct          60
agcactgcaa agtcagccgg gccggagttg atttggtcct tgttagcttg accgatcgta         120
tacgtatcgc caggatgccg acgccgtcgc acctgagcaa ggacccgcac tacttcgact         180
tccgggcggc gcggcgggtg ccggagacac acgcgtggcc ggggctgcac gaccacccgg         240
tggtggacgg cggcggcgcg ggcggagggc cggacgcggt gccggtggtg gacatgcgcg         300
acccgtgcgc cgcggaggcg gtggcgctgg ccgcgcagga ctggggcgcc ttcctcttgc         360
agggccacgg cgtcccgttg gagctgctgg cccgcgtgga ggccgcgata gcgggcatgt         420
tcgcgctgcc ggcgtcggag aagatgcgcg ccgtgcggcg gcccggcgac tcgtgcggct         480
acgggtcgcc gcccatctcc tccttcttct ccaagtgcat gtggtccgag ggctacacct         540
tctccccggc caacctccgc tccgacctcc gcaagctctg gcccaaggcc ggccacgact         600
accgccactt ctgtgccgtg atggaggagt tccacaggga gatgcgcgtt ctggccgaca         660
agctgctgga gctgttcctg gtggccctcg ggctcaccgg cgagcaggtc gccgccgtcg         720
agtcggagca caagatcgcc gagaccatga ccgccacaat gcacctcaac tggtaccccca        780 agtgcccgga cccgaagcga gcgctgggcc tgatcgcgca cacggactcg ggcttcttca        840
ccttcgtgct ccagagcctg gtgcccgggc tgcagctgtt ccggcacggc cccgaccgtt        900
gggtgacggt gcccgccgtg ccgggcgcca tggtcgtcaa cgtcggcgac ctcttccaca        960
tcctcaccaa tggccgcttc cacagcgtct accaccgcgc cgtcgtcaac cgcgacagcg       1020
accggatatc gctgggggtac ttcctcggcc cgcccgccca cgttaaggtg gcgccgctca       1080
gggaggccct cgccggcacg cccgctgcct accgcgccgt cacgtggccc gagtacatgg       1140
gcgtgcgcaa gaaggccttc accaccggcg cctccgcgct caagatggtc gccatctcca       1200
ccgacgacgc cgccgacgtc ctccccgacg tcctctcgtc gtagatcggc gccggccatc       1260
acccggccgg ccaagagacc gatctataca aacaattagt gaacaaaaaa aaaaaaaaaa       1320
aaaaaaaaaa aa                                                           1332

<210> SEQ ID NO 132
<211> LENGTH: 1110
<212> TYPE: DNA
```

<213> ORGANISM: Hordeum vulgare

<400> SEQUENCE: 132

```
atgccgacgc cgtcgcacct gagcaaggac ccgcactact tcgacttccg ggcggcgcgg         60
cgggtgccgg agacacacgc gtggccgggg ctgcacgacc acccggtggt ggacggcggc        120
ggcgcgggcg gagggccgga cgcggtgccg gtggtggaca tgcgcgaccc cgtgcgccgcg       180 gaggcggtgg cgctggccgc gcaggactgg ggcgccttcc tcttgcaggg ccacggcgtc        240
ccgttggagc tgctggcccg cgtggaggcc gcgatagcgg gcatgttcgc gctgccggcg        300
tcggagaaga tgcgcgccgt gcggcggccc ggcgactcgt gcggctacgg gtcgccgccc        360
atctcctcct tcttctccaa gtgcatgtgg tccgagggct acaccttctc cccggccaac        420
ctccgctccg acctccgcaa gctctggccc aaggccggcc acgactaccg ccacttctgt        480
gccgtgatgg aggagttcca cagggagatg cgcgttctgg ccgacaagct gctggagctg        540
ttcctggtgg ccctcgggct caccggcgag caggtcgccg ccgtcgagtc ggagcacaag        600
atcgccgaga ccatgaccgc cacaatgcac ctcaactggt accccaagtg cccggacccg        660
aagcgagcgc tgggcctgat cgcgcacacg gactcgggct tcttcacctt cgtgctccag        720
agcctggtgc ccgggctgca gctgttccgg cacggccccg accgttgggt gacggtgccc        780
gccgtgccgg cgccatggt cgtcaacgtc ggcgacctct ccacatcct caccaatggc        840 cgcttccaca cgtctacca ccgcgccgtc gtcaaccgcg cagcgaccg gatatcgctg        900 gggtacttcc tcggcccgcc cgcccacgtt aaggtggcgc cgctcaggga ggccctcgcc        960
ggcacgcccg ctgcctaccg cgccgtcacg tggcccgagt acatgggcgt gcgcaagaag       1020
gccttcacca ccggcgcctc cgcgctcaag atggtcgcca tctccaccga cgacgccgcc       1080
gacgtcctcc ccgacgtcct ctcgtcgtag                                        1110
```

<210> SEQ ID NO 133
<211> LENGTH: 369
<212> TYPE: PRT
<213> ORGANISM: Hordeum vulgare

<400> SEQUENCE: 133

```
Met Pro Thr Pro Ser His Leu Ser Lys Asp Pro His Tyr Phe Asp Phe
1               5                   10                  15

Arg Ala Ala Arg Arg Val Pro Glu Thr His Ala Trp Pro Gly Leu His
            20                  25                  30

Asp His Pro Val Val Asp Gly Gly Ala Gly Gly Gly Pro Asp Ala
        35                  40                  45

Val Pro Val Val Asp Met Arg Asp Pro Cys Ala Ala Glu Ala Val Ala
    50                  55                  60

Leu Ala Ala Gln Asp Trp Gly Ala Phe Leu Leu Gln Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
            100                 105                 110

Ser Cys Gly Tyr Gly Ser Pro Pro Ile Ser Ser Phe Phe Ser Lys Cys
        115                 120                 125

Met Trp Ser Glu Gly Tyr Thr Phe Ser Pro Ala Asn Leu Arg Ser Asp
    130                 135                 140

Leu Arg Lys Leu Trp Pro Lys Ala Gly His Asp Tyr Arg His Phe Cys
145                 150                 155                 160
```

```
Ala Val Met Glu Glu Phe His Arg Glu Met Arg Val Leu Ala Asp Lys
            165                 170                 175

Leu Leu Glu Leu Phe Leu Val Ala Leu Gly Leu Thr Gly Glu Gln Val
            180                 185                 190

Ala Ala Val Glu Ser Glu His Lys Ile Ala Glu Thr Met Thr Ala Thr
            195                 200                 205

Met His Leu Asn Trp Tyr Pro Lys Cys Pro Asp Pro Lys Arg Ala Leu
    210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
            260                 265                 270

Leu Phe His Ile Leu Thr Asn Gly Arg Phe His Ser Val Tyr His Arg
            275                 280                 285

Ala Val Val Asn Arg Asp Ser Asp Arg Ile Ser Leu Gly Tyr Phe Leu
    290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
                340                 345                 350

Ala Ile Ser Thr Asp Asp Ala Ala Asp Val Leu Pro Asp Val Leu Ser
            355                 360                 365

Ser
```

<210> SEQ ID NO 134
<211> LENGTH: 1653
<212> TYPE: DNA
<213> ORGANISM: Triticum aestivum
<220> FEATURE:
<221> NAME/KEY: misc_feature
<222> LOCATION: (1594)..(1600)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t

<400> SEQUENCE: 134

```
cacgagatcc atccgtctcc accattgctc gctagctcga gctcctagct agtactgcaa      60
agtcagccgg ggagttgatt tggtccttct tggcttgacc gatcgtacgt gccgccagga     120
tgccgacgcc ggcgcacctg agcaaggacc cgcgctactt cgacttccgg gcggcgcggc     180
gggtgccgga gacgcacgcg tggcccgggc tgcacgacca cccgtggtg gacggcagcg      240 gcgcgggcgg agggccggac gcggtgccgg tggtggacat gcgcgacccg tgcgcggcgg     300
aggcggtggc gctggcggcg caggactggg gcgccttcct cctggagggc cacggcgtcc     360
cgttggagct gctggcgcgc gtggaggccg cgatcgcggg catgttcgcg ctgccggcgt     420
cggagaagat gcgcgccgtg cggcggcccg cgactcgtg cggctacggg tcgccgccca      480
tctcctcctt cttctccaag tgcatgtggt ccgagggcta caccttctcc ccggccaacc     540
tccgctccga cctccgcaag ctctggccca aggccggcca cgactaccgc cacttctgcg     600
ccgtgatgga ggagttccac agggagatgc gcgcgctggc cgacaagctg ctggagctgt     660
```

-continued

```
tcctggtggc cctcgggctc accggcgagc aggtcgccgc cgtcgagtcc gagcagaaga      720
tcgccgagac catgaccgcc acaatgcacc tcaactggta ccccaagtgc ccggacccga      780
agcgggcgct gggcctgatc gcgcacacgg actcgggctt cttcaccttc gtgctgcaga      840
gccttgtgcc cgggctgcag ctgttccggc acggccccga ccggtgggtg acggtgcccg      900
ccgtgccggg ggccatggtc gtcaacgtcg gcgacctctt ccagatcctc accaacggcc      960
gcttccacag cgtctaccac cgcgccgtcg tcaaccgcga cagcgaccgg atatcgctcg     1020
gctacttcct cggcccgccc gcccacgtca aggtggcgcc gctcagggag gccctggccg     1080
gcacgcccgc cgcctaccgc gccgtcacgt ggcccgagta catgggcgtg cgcaagaagg     1140
ccttcaccac cggcgcctcc gcgctcaaga tggtcgccat ctccactgac aacgacgccg     1200
ccaaccacac ggacgacctg atctcgtcgt agatcggcgc cggccatcac cggccggcca     1260
agggatcgat ctacacacac aattagtgaa caaaaaaatg ccagagatgg tgcatggtgg     1320
gctggtagct tagctgaggt agctaggagg aagagcgcgc gtgcggctgt cgttcgtgcg     1380
gctgttcccg caaaaaaaaa aaaggtttcc tccatatatg tctccatgca gaactgcaga     1440
tgctggtggt ggatgcgtcc atgcagcagg gaacgaacta attgtaagaa aatcaagcaa     1500
acttagttct acatctgtaa ttaagtatgc atgccacttg gtttaattca attcaagtgc     1560
agaaaaaatt atgatgggaa aaaaaagac atgnnnnnnn aaaaaaaaaa aaaaaaaaaa     1620
aaaaaaaaaa aaaaaaaaaa naaaaaaaaa aaa                               1653
```

```
<210> SEQ ID NO 135
<211> LENGTH: 1113
<212> TYPE: DNA
<213> ORGANISM: Triticum aestivum

<400> SEQUENCE: 135
```

```
atgccgacgc cggcgcacct gagcaaggac ccgcgctact tcgacttccg ggcggcgcgg       60
cgggtgccgg agacgcacgc gtggcccggg ctgcacgacc accccgtggt ggacggcagc      120
ggcgcgggcg gagggccgga cgcggtgccg gtggtggaca tgcgcgaccc gtgcgcggcg      180
gaggcggtgg cgctggcggc gcaggactgg ggcgccttcc tcctggaggg ccacggcgtc      240
ccgttggagc tgctggcgcg cgtggaggcc gcgatcgcgg gcatgttcgc gctgccggcg      300
tcggagaaga tgcgcgccgt cgcggcggcc ggcgactcgt cgcggctacgg gtcgccgccc      360 atctcctcct tcttctccaa gtgcatgtgg tccgagggct acaccttctc cccggccaac      420
ctccgctccg acctccgcaa gctctggccc aaggccggcc acgactaccg ccacttctgc      480
gccgtgatgg aggagttcca cagggagatg cgcgcgctgg ccgacaagct gctggagctg      540
ttcctggtgg ccctcgggct caccggcgag caggtcgccg ccgtcgagtc cgagcagaag      600
atcgccgaga ccatgaccgc cacaatgcac ctcaactggt accccaagtg cccggacccg      660
aagcgggcgc tgggcctgat cgcgcacacg gactcgggct tcttcacctt cgtgctgcag      720
agccttgtgc ccgggctgca gctgttccgg cacggccccg accggtgggt gacggtgccc      780
gccgtgccgg gggccatggt cgtcaacgtc ggcgacctct tccagatcct caccaacggc      840
cgcttccaca gcgtctacca ccgcgccgtc gtcaaccgcg acagcgaccg gatatcgctc      900
ggctacttcc tcggcccgcc cgcccacgtc aaggtggcgc cgctcaggga ggccctggcc      960
ggcacgcccg ccgcctaccg cgccgtcacg tggcccgagt acatgggcgt gcgcaagaag     1020
gccttcacca ccggcgcctc cgcgctcaag atggtcgcca tctccactga caacgacgcc     1080
```

-continued gccaaccaca cggacgacct gatctcgtcg tag                                          1113

<210> SEQ ID NO 136
<211> LENGTH: 370
<212> TYPE: PRT
<213> ORGANISM: Triticum aestivum

<400> SEQUENCE: 136

Met Pro Thr Pro Ala His Leu Ser Lys Asp Pro Arg Tyr Phe Asp Phe
1               5                   10                  15

Arg Ala Ala Arg Arg Val Pro Glu Thr His Ala Trp Pro Gly Leu His
                20                  25                  30

Asp His Pro Val Val Asp Gly Ser Gly Ala Gly Gly Gly Pro Asp Ala
            35                  40                  45

Val Pro Val Val Asp Met Arg Asp Pro Cys Ala Ala Glu Ala Val Ala
        50                  55                  60

Leu Ala Ala Gln Asp Trp Gly Ala Phe Leu Leu Glu Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
            100                 105                 110

Ser Cys Gly Tyr Gly Ser Pro Pro Ile Ser Ser Phe Phe Ser Lys Cys
            115                 120                 125

Met Trp Ser Glu Gly Tyr Thr Phe Ser Pro Ala Asn Leu Arg Ser Asp
        130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Ala Leu Ala Asp Lys
                165                 170                 175

Leu Leu Glu Leu Phe Leu Val Ala Leu Gly Leu Thr Gly Glu Gln Val
            180                 185                 190

Ala Ala Val Glu Ser Glu Gln Lys Ile Ala Glu Thr Met Thr Ala Thr
            195                 200                 205

Met His Leu Asn Trp Tyr Pro Lys Cys Pro Asp Pro Lys Arg Ala Leu
        210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
                260                 265                 270

Leu Phe Gln Ile Leu Thr Asn Gly Arg Phe His Ser Val Tyr His Arg
            275                 280                 285

Ala Val Val Asn Arg Asp Ser Asp Arg Ile Ser Leu Gly Tyr Phe Leu
        290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
            340                 345                 350

Ala Ile Ser Thr Asp Asn Asp Ala Ala Asn His Thr Asp Asp Leu Ile
            355                 360                 365

-continued

Ser Ser
    370

<210> SEQ ID NO 137
<211> LENGTH: 1884
<212> TYPE: DNA
<213> ORGANISM: Triticum aestivum

<400> SEQUENCE: 137

```
tatatataca gctccttgta cttctctcgt tcttacactc actcctcaat ccatccgtct     60
ccaccattgc tcgctagctc gagctcctag ctagtactgc aaagtcagcc ggggagttga    120
tttggtcctt cttggcttga ccgatcgtac gtgccgccag gatgccgacg ccggcgcacc    180
tgagcaagga cccgcgctac ttcgacttcc gggcggcgcg gcgggtgccg gagacgcacg    240
cgtggcccgg gctgcacgac cacccgtgg  tggacggcag cggcgcgggc ggagggccgg    300
acgcggtgcc ggtggtggac atgcgcgacc cgtgcgcggc ggaggcggtg gcgctggcgg    360
cgcaggactg gggcgccttc ctcctggagg ccacggcgt  cccgttggag ctgctggcgc    420
gcgtggaggc cgcgatcgcg ggcatgttcg cgctgccggc gtcggagaag atgcgcgccg    480
tgcggcggcc cggcgactcg tgcggctacg ggtcgccgcc catctcctcc ttcttctcca    540
agtgcatgtg gtccgagggc tacaccttct ccccggccaa cctccgctcc gacctccgca    600
agctctggcc caaggccggc cacgactacc gccacttctg gtacgtacgc cggccgccga    660
tgcgcatata cacgtcatag tacggcacct acctaactgg ctctggccaa ccgtccgtac    720
acacgtgaag gggcgacgtg tccgactccg accatgcatg catgcacgcg cgcgaaactt    780
gttactcctg ttctgctatg gcagcagcta gccgcgtgtg tccgttcgta ggagtagtta    840
cttacacagt tacacttacg ccgtccgtcg tgttcctcga cgtgcagcgc cgtgatggag    900
gagttccaca gggagatgcg cgcgctggcc gacaagctgc tggagctgtt cctggtggcc    960
ctcgggctca ccggcgagca ggtcgccgcc gtcgagtccg agcagaagat cgccgagacc   1020
atgaccgcca caatgcacct caactggtac gttccactac tactccagta gtacaagtac   1080
aatatataga atacaaatgg cagcagccac gacgacacgt actccaccat gcagcaaagc   1140
atatattgtc ggtgcggcgg ttgacacgga gttgtgtcgt gtcgttgatt cacaggtacc   1200
ccaagtgccc ggacccgaag cgggcgctgg gcctgatcgc gcacacggac tcgggcttct   1260
tcaccttcgt gctgcagagc cttgtgcccg ggctgcagct gttccggcac ggccccgacc   1320
ggtgggtgac ggtgcccgcc gtgccggggg ccatggtcgt caacgtcggc gacctcttcc   1380
agatcctcac caacggccgc ttccacagcg tctaccaccg cgccgtcgtc aaccgcgaca   1440
gcgaccggat atcgctcggc tacttcctcg gcccgcccgc ccacgtcaag gtggcgccgc   1500
tcagggaggc cctggccggc acgcccgcg  cctaccgcgc cgtcacgtgg cccgagtaca   1560
tgggcgtgcg caagaaggcc ttcaccaccg gcgcctccgc gctcaagatg gtcgccatct   1620
ccactgacaa cgacgccgcc aaccacacgg acgacctgat ctcgtcgtag atcggcgccg   1680
gccatcaccg gccggccaag ggatcgatct acacacacaa ttagtgaaca aaaaaatgcc   1740
agagatggtg catggtgggc tggtagctta gctgaggtag ctaggaggaa gagcgcgcgt   1800
gcggctgtcg ttcgtgcggc tgttcccgca aaaaaaaaa  ggtttcctcc atatakgtcc   1860
ccakscaaaa tsgmaawgct gggg                                          1884
```

<210> SEQ ID NO 138
<211> LENGTH: 20
<212> TYPE: RNA

-continued

```
<213> ORGANISM: Artificial Sequence
<220> FEATURE:
<223> OTHER INFORMATION: suppression oligo

<400> SEQUENCE: 138
acggguucuu ccaggugugc                                              20

<210> SEQ ID NO 139
<211> LENGTH: 20
<212> TYPE: RNA
<213> ORGANISM: Artificial Sequence
<220> FEATURE:
<223> OTHER INFORMATION: suppression oligo

<400> SEQUENCE: 139
cacggguucu uccaggugug                                              20

<210> SEQ ID NO 140
<211> LENGTH: 20
<212> TYPE: RNA
<213> ORGANISM: Artificial Sequence
<220> FEATURE:
<223> OTHER INFORMATION: suppression oligo

<400> SEQUENCE: 140
cauugaccuc cccgcuggca                                              20

<210> SEQ ID NO 141
<211> LENGTH: 20
<212> TYPE: RNA
<213> ORGANISM: Artificial Sequence
<220> FEATURE:
<223> OTHER INFORMATION: suppression oligo

<400> SEQUENCE: 141
ccagcgggga ggucaaugcu                                              20

<210> SEQ ID NO 142
<211> LENGTH: 20
<212> TYPE: RNA
<213> ORGANISM: Artificial Sequence
<220> FEATURE:
<223> OTHER INFORMATION: suppression oligo

<400> SEQUENCE: 142
cccagcauug accuccccgc                                              20

<210> SEQ ID NO 143
<211> LENGTH: 20
<212> TYPE: RNA
<213> ORGANISM: Artificial Sequence
<220> FEATURE:
<223> OTHER INFORMATION: suppression oligo

<400> SEQUENCE: 143
cgcgcucgug uacccggaca                                              20

<210> SEQ ID NO 144
<211> LENGTH: 20
<212> TYPE: RNA
<213> ORGANISM: Artificial Sequence
<220> FEATURE:
<223> OTHER INFORMATION: suppression oligo

<400> SEQUENCE: 144
cucccggcgc aggucgaaca                                              20
```

-continued

```
<210> SEQ ID NO 145
<211> LENGTH: 20
<212> TYPE: RNA
<213> ORGANISM: Artificial Sequence
<220> FEATURE:
<223> OTHER INFORMATION: suppression oligo

<400> SEQUENCE: 145
guguacccgg acacggugcc                                                     20

<210> SEQ ID NO 146
<211> LENGTH: 20
<212> TYPE: RNA
<213> ORGANISM: Artificial Sequence
<220> FEATURE:
<223> OTHER INFORMATION: suppression oligo

<400> SEQUENCE: 146
ugcagggaag cguccgggc                                                      20

<210> SEQ ID NO 147
<211> LENGTH: 20
<212> TYPE: RNA
<213> ORGANISM: Artificial Sequence
<220> FEATURE:
<223> OTHER INFORMATION: suppression oligo

<400> SEQUENCE: 147
uucuuccagg ugugcgggca                                                     20

<210> SEQ ID NO 148
<211> LENGTH: 20
<212> TYPE: RNA
<213> ORGANISM: Artificial Sequence
<220> FEATURE:
<223> OTHER INFORMATION: suppression oligo

<400> SEQUENCE: 148
agauccccgc gccauuccug                                                     20

<210> SEQ ID NO 149
<211> LENGTH: 20
<212> TYPE: RNA
<213> ORGANISM: Artificial Sequence
<220> FEATURE:
<223> OTHER INFORMATION: suppression oligo

<400> SEQUENCE: 149
augcagggaa gcguccggg                                                      20

<210> SEQ ID NO 150
<211> LENGTH: 20
<212> TYPE: RNA
<213> ORGANISM: Artificial Sequence
<220> FEATURE:
<223> OTHER INFORMATION: suppression oligo

<400> SEQUENCE: 150
auuccugugg ccgcaggaag                                                     20

<210> SEQ ID NO 151
<211> LENGTH: 20
<212> TYPE: RNA
<213> ORGANISM: Artificial Sequence
<220> FEATURE:
```

-continued

<223> OTHER INFORMATION: suppression oligo

<400> SEQUENCE: 151
cagcggggag gucaaugcug                                           20

<210> SEQ ID NO 152
<211> LENGTH: 20
<212> TYPE: RNA
<213> ORGANISM: Artificial Sequence
<220> FEATURE:
<223> OTHER INFORMATION: suppression oligo

<400> SEQUENCE: 152
caggaauggc gcggggaucu                                           20

<210> SEQ ID NO 153
<211> LENGTH: 20
<212> TYPE: RNA
<213> ORGANISM: Artificial Sequence
<220> FEATURE:
<223> OTHER INFORMATION: suppression oligo

<400> SEQUENCE: 153
gacuacuucg ucggcacccu                                           20

<210> SEQ ID NO 154
<211> LENGTH: 20
<212> TYPE: RNA
<213> ORGANISM: Artificial Sequence
<220> FEATURE:
<223> OTHER INFORMATION: suppression oligo

<400> SEQUENCE: 154
gccaggauuu cgagccaaug                                           20

<210> SEQ ID NO 155
<211> LENGTH: 20
<212> TYPE: RNA
<213> ORGANISM: Artificial Sequence
<220> FEATURE:
<223> OTHER INFORMATION: suppression oligo

<400> SEQUENCE: 155
ggaacauuug gagggaggcg                                           20

<210> SEQ ID NO 156
<211> LENGTH: 20
<212> TYPE: RNA
<213> ORGANISM: Artificial Sequence
<220> FEATURE:
<223> OTHER INFORMATION: suppression oligo

<400> SEQUENCE: 156
gggaggucaa ugcuggggcu                                           20

<210> SEQ ID NO 157
<211> LENGTH: 20
<212> TYPE: RNA
<213> ORGANISM: Artificial Sequence
<220> FEATURE:
<223> OTHER INFORMATION: suppression oligo

<400> SEQUENCE: 157
uuggcucgaa auccuggccg                                           20

-continued

```
<210> SEQ ID NO 158
<211> LENGTH: 20
<212> TYPE: RNA
<213> ORGANISM: Artificial Sequence
<220> FEATURE:
<223> OTHER INFORMATION: suppression oligo

<400> SEQUENCE: 158
acggguucuu ccaggugugc                                                  20

<210> SEQ ID NO 159
<211> LENGTH: 20
<212> TYPE: RNA
<213> ORGANISM: Artificial Sequence
<220> FEATURE:
<223> OTHER INFORMATION: suppression oligo

<400> SEQUENCE: 159
cacggguucu uccaggugug                                                  20

<210> SEQ ID NO 160
<211> LENGTH: 20
<212> TYPE: RNA
<213> ORGANISM: Artificial Sequence
<220> FEATURE:
<223> OTHER INFORMATION: suppression oligo

<400> SEQUENCE: 160
cauugaccuc cccgcuggca                                                  20

<210> SEQ ID NO 161
<211> LENGTH: 20
<212> TYPE: RNA
<213> ORGANISM: Artificial Sequence
<220> FEATURE:
<223> OTHER INFORMATION: suppression oligo

<400> SEQUENCE: 161
ccagcgggga ggucaaugcu                                                  20

<210> SEQ ID NO 162
<211> LENGTH: 20
<212> TYPE: RNA
<213> ORGANISM: Artificial Sequence
<220> FEATURE:
<223> OTHER INFORMATION: suppression oligo

<400> SEQUENCE: 162
cccagcauug accucccgc                                                   20

<210> SEQ ID NO 163
<211> LENGTH: 20
<212> TYPE: RNA
<213> ORGANISM: Artificial Sequence
<220> FEATURE:
<223> OTHER INFORMATION: suppression oligo

<400> SEQUENCE: 163
cgcgcucgug uacccggaca                                                  20

<210> SEQ ID NO 164
<211> LENGTH: 20
<212> TYPE: RNA
<213> ORGANISM: Artificial Sequence
<220> FEATURE:
<223> OTHER INFORMATION: suppression oligo
```

```
<400> SEQUENCE: 164
cucccggcgc aggucgaaca                                                      20

<210> SEQ ID NO 165
<211> LENGTH: 20
<212> TYPE: RNA
<213> ORGANISM: Artificial Sequence
<220> FEATURE:
<223> OTHER INFORMATION: suppression oligo

<400> SEQUENCE: 165
guguacccgg acacggugcc                                                      20

<210> SEQ ID NO 166
<211> LENGTH: 20
<212> TYPE: RNA
<213> ORGANISM: Artificial Sequence
<220> FEATURE:
<223> OTHER INFORMATION: suppression oligo

<400> SEQUENCE: 166
ugcagggaag cguccgggc                                                       20

<210> SEQ ID NO 167
<211> LENGTH: 20
<212> TYPE: RNA
<213> ORGANISM: Artificial Sequence
<220> FEATURE:
<223> OTHER INFORMATION: suppression oligo

<400> SEQUENCE: 167
uucuuccagg ugugcgggca                                                      20

<210> SEQ ID NO 168
<211> LENGTH: 2488
<212> TYPE: DNA
<213> ORGANISM: Zea Mays

<400> SEQUENCE: 168
atggacgcca gcccgacccc accgctcccc ctccgcgccc caactcccag cattgacctc        60
cccgctggca aggacagggc cgacgcggcg gctaacaagg ccgcggctgt gttcgacctg       120
cgccgggagc ccaagatccc ggagccattc ctgtggccgc acgaagaggc gcggccgacc       180
tcggccgcgg agctggaggt gccggtggtg gacgtgggcg tgctgcgcaa tggcgacggc       240
gcggggctcc gccgcgccgc ggcgcaagtg gcggcggcgt gcgcgacgca cgggttcttc       300
caggtgtgcg ggcacggcgt ggacgcggcg ctggggcgcg ccgcgctgga cggcgccagc       360
gacttcttcc ggctgccgct ggctgagaag cagcgggccc ggcgcgtccc cggcaccgtg       420
tccgggtaca cgagcgcgca cgccgaccgg ttcgcgtcca agctcccctg gaaggagacc       480
ctgtccttcg gcttccacga cggcgccgcg gcgcccgtcg tcgtggacta cttcaccggc       540
accctcggcc aagatttcga gccagtgggg tgagtaaaga agaagatggc gccgaattta       600
catttataag taggaccagc agaagcccct gcccctgggg gccttagcat tgcattcgac       660
tgatgaatac gcatggcagg cgggtgtacc agaggtactg cgaggagatg aaggagctgt       720
cgctgacgat catggagctg ctggagctga gcctgggcgt ggagcgcggc tactaccggg       780
agttcttcga ggacagccgc tccatcatgc ggtgcaacta ctacccgccg tgcccggtgc       840
cggagcgcac gctgggcacg ggcccgcact gcgaccccac ggcgctgacc atcctcctgc       900
aggacgacgt cggcgggctg gaggtcctgg tggacggcga gtggcgcccc gtccggcccg       960
```

```
tcccaggcgc catggtcatc aacatcggcg acaccttcat ggtaacgaac gaaagcgccg    1020
gctcctctgc tttcttggc ctctttgtcc ctgccctgtg ctgctgtgca tattcattca     1080
ttcagttctc tgtggggttt tttttttgtt taattttttt ttgggatcgt atccagtgca    1140
caagggccac gccgtgcaca aatgcacaaa acgaaatctg gccgtccatt ttccatccaa    1200
cgacatgacg gcgcgggggg tttttcacaa aacagactcg gcaagctacg gaggttgcgg    1260
gagggttcat ctgcatattt acgacggccg ttggatggaa aatggacggc cagatttcgt    1320
tttgtgtatt tgtgcacggc gtggcccttg tgcactggat acgatcccat ttttttttt     1380 gccccgaatc ctagtggacc taactggaca gattacagca cgcacacgta ggcatgtcat    1440
gtagcagcac tgcagtcggg tgcagtccag tccagtcctg tccagccgcg acactgtagt    1500
acatagcgat gcaacggaga cacgcgttgg agttggttcc atctcttctc ggcggccgtg    1560
ccgaggcttc cgcgggggaag ctgcgacaac agaacggacc gccggggggtg ggcaggcagc   1620 aagctccctg ttggcttgtg ccgttgcgca gcggcgggta ccggacaacg ctttcggcgg    1680
cgcgcggcct cgtcggcttc ccctgttttt gatgccgcct ctcggtgtcc ggggaccggg    1740
aggatcgatg gggcccgtgc cgtctgatcc gccacgcgag cggtcctatg cgatgcgccg    1800
cacgagcgcg gggggggccgt ggaacagtac acagctgggt cactcactca ctcatcccgc    1860
tggttgtggc tgcttggttg caacttggct cggctgtctg tctgttgccc ccgccgcgtt    1920
ttctagccgt ttccgctttg ctcgcggttt cgctggcgat ccggcacgcg gcgcccacac    1980
ccggggctgg ccccttggcc gagtgggtgg caggcacttg catgcatccg gccggtttcc    2040
cgcgaccaag ctggcccgcc gcaacaatga gagtgagacg agactttgtg tcagtgtgtg    2100
tatgtacatg tatgtctgcg cgacagccct accgtccgac acgatgattc ttgtgcactg    2160
tactgtactg tactaactcc ccccacccccc tccggtatgt aacgcatgcc atatgcaggc   2220
gctgtccaac gggcggtaca agagctgcct gcaccgcgcg gtggtgaacc ggcggcagga    2280
gcggcaatcg ctggccttct tcctgtgccc gcgcgaggac cgggtggtgc gcccgccggc    2340
cagcgccgcg ccgcggcagt acccggactt cacctgggcc gacctcatgc gcttcacgca    2400
gcgccactac cgcgccgaca cccgcacgct ggacgccttc acccgctggc tctcccacgg    2460
cccggcggcg cggctccct gcacctaa                                        2488
```

```
<210> SEQ ID NO 169
<211> LENGTH: 2473
<212> TYPE: DNA
<213> ORGANISM: Zea Mays

<400> SEQUENCE: 169
atgaggccgc gcctccctcc aaatgttccc tccctgcctt cgtctttgtc gttgctcgca      60
aactccctgt cctcccctgt tacaaatacc cccacccgcc cggacagctt ccctgcatac      120
ttgcagctcg cacatctcat ggtgtcgcag gaacgacaag agccagctgt gcctagcagc      180
agcagcagca gcgccaagcg cgcagccacg tccatggacg ccagcccggc cccgccgctc      240
ctcctccgcg cccccactcc cagccccagc attgacctcc ccgctggcaa ggacaaggcc      300
gacgcggcgc cagcaaggc cggcgcggcc gtgttcgacc tgcgccggga gcccaagatc       360
cccgcgccat tcctgtggcc gcaggaagag gcgcggccgt cctcggccgc ggagctggag      420
gtgccgatgg tggacgtggg cgtgctcgcg aatggcgacc gcgcggggct gcggcgcgcc      480
gcggcgcagg tggccgcggc gtgcgcgacg cacgggttct tccaggtgtg cgggcacggc      540
```

-continued

```
gtggacgcgg cgctggggcg cgccgcgctg gacggcgcca gcgacttctt ccggctgccg    600
ctcgccgaga agcagcgcgc ccggcgcgtc cccggcaccg tgtccgggta cacgagcgcg    660
cacgccgacc ggttcgcggc caagctcccc tggaaggaga ccctgtcgtt cggctaccac    720
gacggcgccg cgtcgcctgt cgtcgtggac tacttcgtcg gcaccctcgg ccaggatttc    780
gagccaatgg ggtaagtaag gtagtaagaa ggagcgccgg tttacattta ccgcacgtcg    840
gcgtgcggtc gagtcgggac tcgggagacg tatgaacccc cgtcccgtcc catgcatgtg    900
tggcaggtgg gtgtaccaga ggtactgcga ggagatgaag gagctgtcgc tgacgatcat    960
ggagctgctg gagctgagcc tgggcgtgga gctgcgcggc tactaccggg agttcttcga    1020
ggacagccgg tccatcatgc ggtgcaacta ctacccgccg tgcccggagc cggagcgcac    1080
gctgggcacg ggcccgcact gcgaccccac ggcgctcacc atcctcctgc aggacgacgt    1140
gggcgggctg gaggtgctgg tggacggtga gtggcgcccc gtccggcccg tcccgggcgc    1200
catggtcatc aacatcggcg acaccttcat ggtaacgaaa cgaaagcgct cgctcctctg    1260
ttttccttgg ccgctcttgt cctgtgtgta tattcagttg agctctctct gtgctgttat    1320
ttcccgaatc ctagtggacc taaacgggca ggttattaca gcacgcacac gtaggcatgt    1380
catgtagcta gtacatacat agcgatgccg atgcaaatgc aatagagaca tgcgttcgag    1440
ttggttccta tctcggcggg ctacggcagg tacacgcggc cgcggcgcgc tctctctagt    1500
ctatccgcgg ccgcgcccag gccgatcgag gcttccgggg gagagttgcg acaagagaac    1560
ggaccgaggg ggtcggctag cggtagcaag ttccctgttg gtttgtggcg ttggagcgtt    1620
gcggagaggc ttgcgcggcg gcggggacgt cgacgggggac gtggcgggga gacgatacga    1680
tgggtgccgg gcagggcaac gctttcggcg ggtggccgtg tccaggtgcg cgcggccttg    1740
tcggtttccc cctctcggtg tccatggccg agaaatgggt cgacgaccga gaccgacgct    1800
cggtgcggcg cccatcccgt ctgatccgcc gcgccacgcg agcggcccta tgcgatgccg    1860
cacgggcgcg gagggccgtc gcgcggagta taatgtatag tatatagtac aaggttggtt    1920
ggagtcgggt tgggttggat cgggtcaccg gtacgtggtg gctgctgttg cccccgccgt    1980
ttccgcttgc acttttgtcg cggtttcgct ggcgatccgg cacgcggcgc ccacaccacg    2040
ccggggctcc aaacagctcg ggcccttggc cgtgtgggtg gcaggcactt gcacgcgtcc    2100
ggttgtcgcg gcctggcccg ccgccgggcg caccgcaaca atgagacagc ccgacacgat    2160
gattcttgtg cactgtgcta acccgcatgc catgcaggcg ctgtcgaacg ggaggtacaa    2220
gagctgcctg caccgcgcgg tggtgaacca gcggcgggcg cggcggtcgc tggccttctt    2280
cctgtgcccg cgcgaggacc gggtggtgcg cccgccggcc agtgctgcgc cgcggcgcta    2340
cccggacttc acctgggccg acctcatgcg cttcacgcag cgccactacc gcgccgacac    2400
ccgcacgctg gacgccttca cccgctggct ctcccacggc ccggcccagg cggcggcgcc    2460
tccctgcacc tag    2473
```

<210> SEQ ID NO 170
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 170

```
tcgtggacta cttcaccaag atttcgagcc    30
```

-continued

```
<210> SEQ ID NO 171
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 171
actacttcac cggcacctcg gccaagattt                                          30

<210> SEQ ID NO 172
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 172
actacttcac cggcaccccc tcggccaaga tt                                       32

<210> SEQ ID NO 173
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 173
gactacttca ccggcccctc ggccaagatt                                          30

<210> SEQ ID NO 174
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 174
ggactacttc accggcctcg gccaagattt                                          30

<210> SEQ ID NO 175
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 175
tccccggcac cgtgtgggta cacgagcgcg                                          30

<210> SEQ ID NO 176
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 176
tccccggcac cgtgtaccgg gtacacgagc g                                        31

<210> SEQ ID NO 177
<211> LENGTH: 31
<212> TYPE: DNA
<213> ORGANISM: Artificial Sequence
<220> FEATURE:
<223> OTHER INFORMATION: mutant sequence by gene editing
```

-continued

<400> SEQUENCE: 177
tccccggcac cgtgttccgg gtacacgagc g                                                31

<210> SEQ ID NO 178
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 178
ccaagatttc gagccgtggg gtgagtaaag                                                  30

<210> SEQ ID NO 179
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 179
ccaagatttc gagccaagtg gggtgagtaa ag                                               32

<210> SEQ ID NO 180
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 180
caagatttcg agccacgtgg ggtgagtaaa ga                                               32

<210> SEQ ID NO 181
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 181
cagcattgac ctcccccgct ggcaaggaca gg                                               32

<210> SEQ ID NO 182
<211> LENGTH: 47
<212> TYPE: DNA
<213> ORGANISM: Artificial Sequence
<220> FEATURE:
<223> OTHER INFORMATION: mutant sequence by gene editing

<400> SEQUENCE: 182
ccgcggcgcc cgtcgtcgtg gactacttca ccaagatttc gagccag                              47

<210> SEQ ID NO 183
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 183
ccgcggcgcc cgtcgtcgtg gactacttca ccggcacctc ggccaagatt tcgagccag              59

<210> SEQ ID NO 184
<211> LENGTH: 62

<212> TYPE: DNA
<213> ORGANISM: Artificial Sequence
<220> FEATURE:
<223> OTHER INFORMATION: mutant sequence by gene editing

<400> SEQUENCE: 184
ccgcggcgcc cgtcgtcgtg gactacttca ccggcacccc ctcggccaag atttcgagcc      60
ag                                                                     62

<210> SEQ ID NO 185
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 185
ccgcggcgcc cgtcgtcgtg gactacttca ccggcccctc ggccaagatt tcgagccag      59

<210> SEQ ID NO 186
<211> LENGTH: 57
<212> TYPE: DNA
<213> ORGANISM: Artificial Sequence
<220> FEATURE:
<223> OTHER INFORMATION: mutant sequence by gene editing

<400> SEQUENCE: 186
ccgcggcgcc cgtcgtcgtg gactacttca ccggcctcgg ccaagatttc gagccag      57

<210> SEQ ID NO 187
<211> LENGTH: 58
<212> TYPE: DNA
<213> ORGANISM: Artificial Sequence
<220> FEATURE:
<223> OTHER INFORMATION: mutant sequence by gene editing

<400> SEQUENCE: 187
ccggcgcgtc cccggcaccg tgtgggtaca cgagcgcgca cgccgaccgg ttcgcgtc      58

<210> SEQ ID NO 188
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 188
ccggcgcgtc cccggcaccg tgtaccgggt acacgagcgc gcacgccgac cggttcgcgt      60
c                                                                      61

<210> SEQ ID NO 189
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 189
ccggcgcgtc cccggcaccg tgttccgggt acacgagcgc gcacgccgac cggttcgcgt      60
c                                                                      61

<210> SEQ ID NO 190
<211> LENGTH: 59
<212> TYPE: DNA

<213> ORGANISM: Artificial Sequence
<220> FEATURE:
<223> OTHER INFORMATION: mutant sequence by gene editing

<400> SEQUENCE: 190
ctacttcacc ggcaccctcg gccaagattt cgagccgtgg ggtgagtaaa gaagaagat        59

<210> SEQ ID NO 191
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 191
ctacttcacc ggcaccctcg gccaagattt cgagccaagt ggggtgagta aagaagaaga        60
t                                                                        61

<210> SEQ ID NO 192
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 192
ctacttcacc ggcaccctcg gccaagattt cgagccacgt ggggtgagta aagaagaaga        60
t                                                                        61

<210> SEQ ID NO 193
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 193 tcccctccg cgccccaact cccagcattg acctcccccg ctggcaagga cagggccgac        60
g                                                                        61

<210> SEQ ID NO 194
<211> LENGTH: 60
<212> TYPE: DNA
<213> ORGANISM: Zea mays

<400> SEQUENCE: 194
ccgcggcgcc cgtcgtcgtg gactacttca ccggcaccct cggccaagat ttcgagccag        60

<210> SEQ ID NO 195
<211> LENGTH: 60
<212> TYPE: DNA
<213> ORGANISM: Zea mays

<400> SEQUENCE: 195
ccgcggcgcc cgtcgtcgtg gactacttca ccggcaccct cggccaagat ttcgagccag        60

<210> SEQ ID NO 196
<211> LENGTH: 60
<212> TYPE: DNA
<213> ORGANISM: Zea mays

<400> SEQUENCE: 196
ccgcggcgcc cgtcgtcgtg gactacttca ccggcaccct cggccaagat ttcgagccag        60

<210> SEQ ID NO 197
<211> LENGTH: 60
<212> TYPE: DNA
<213> ORGANISM: Zea mays

<400> SEQUENCE: 197
ccgcggcgcc cgtcgtcgtg gactacttca ccggcaccct cggccaagat ttcgagccag          60

<210> SEQ ID NO 198
<211> LENGTH: 60
<212> TYPE: DNA
<213> ORGANISM: Zea mays

<400> SEQUENCE: 198
ccgcggcgcc cgtcgtcgtg gactacttca ccggcaccct cggccaagat ttcgagccag          60

<210> SEQ ID NO 199
<211> LENGTH: 60
<212> TYPE: DNA
<213> ORGANISM: Zea mays

<400> SEQUENCE: 199
ccggcgcgtc cccggcaccg tgtccgggta cacgagcgcg cacgccgacc ggttcgcgtc          60

<210> SEQ ID NO 200
<211> LENGTH: 60
<212> TYPE: DNA
<213> ORGANISM: Zea mays

<400> SEQUENCE: 200
ccggcgcgtc cccggcaccg tgtccgggta cacgagcgcg cacgccgacc ggttcgcgtc          60

<210> SEQ ID NO 201
<211> LENGTH: 60
<212> TYPE: DNA
<213> ORGANISM: Zea mays

<400> SEQUENCE: 201
ccggcgcgtc cccggcaccg tgtccgggta cacgagcgcg cacgccgacc ggttcgcgtc          60

<210> SEQ ID NO 202
<211> LENGTH: 60
<212> TYPE: DNA
<213> ORGANISM: Zea mays

<400> SEQUENCE: 202
ctacttcacc ggcaccctcg gccaagattt cgagccagtg gggtgagtaa agaagaagat          60

<210> SEQ ID NO 203
<211> LENGTH: 60
<212> TYPE: DNA
<213> ORGANISM: Zea mays

<400> SEQUENCE: 203
ctacttcacc ggcaccctcg gccaagattt cgagccagtg gggtgagtaa agaagaagat          60

<210> SEQ ID NO 204
<211> LENGTH: 60
<212> TYPE: DNA
<213> ORGANISM: Zea mays

<400> SEQUENCE: 204

```
ctacttcacc ggcaccctcg gccaagattt cgagccagtg gggtgagtaa agaagaagat        60

<210> SEQ ID NO 205
<211> LENGTH: 60
<212> TYPE: DNA
<213> ORGANISM: Zea mays

<400> SEQUENCE: 205 tcccctccg cgccccaact cccagcattg acctccccgc tggcaaggac agggccgacg        60

<210> SEQ ID NO 206
<211> LENGTH: 2475
<212> TYPE: DNA
<213> ORGANISM: Artificial Sequence
<220> FEATURE:
<223> OTHER INFORMATION: mutant sequence by gene editing

<400> SEQUENCE: 206
atggacgcca gcccgacccc accgctcccc ctccgcgccc caactcccag cattgacctc        60
cccgctggca aggacagggc cgacgcggcg gctaacaagg ccgcggctgt gttcgacctg       120
cgccgggagc ccaagatccc ggagccattc ctgtggccgc acgaagaggc gcggccgacc       180
tcggccgcgg agctggaggt gccggtggtg gacgtgggcg tgctgcgcaa tggcgacggc       240
gcggggctcc gccgcgccgc ggcgcaagtg gcggcggcgt gcgcgacgca cgggttcttc       300
caggtgtgcg ggcacggcgt ggacgcggcg ctggggcgcg ccgcgctgga cggcgccagc       360
gacttcttcc ggctgccgct ggctgagaag cagcgggccc ggcgcgtccc cggcaccgtg       420
tccgggtaca cgagcgcgca cgccgaccgg ttcgcgtcca agctcccctg gaaggagacc       480
ctgtccttcg gcttccacga cggcgccgcg gcgcccgtcg tcgtggacta cttcaccaag       540
atttcgagcc agtggggtga gtaaagaaga agatggcgcc gaatttacat ttataagtag       600
gaccagcaga gcccctgcc cctgggggcc ttagcattgc attcgactga tgaatacgca       660
tggcaggcgg gtgtaccaga ggtactgcga ggagatgaag gagctgtcgc tgacgatcat       720
ggagctgctg gagctgagcc tgggcgtgga gcgcggctac taccgggagt cttcgagga       780 cagccgctcc atcatgcggt gcaactacta cccgccgtgc ccggtgccgg agcgcacgct       840
gggcacgggc ccgcactgcg accccacggc gctgaccatc ctcctgcagg acgacgtcgg       900
cgggctggag gtcctggtgg acggcgagtg gcgccccgtc cggcccgtcc caggcgccat       960
ggtcatcaac atcggcgaca ccttcatggt aacgaacgaa agcgccggct cctctgcttt      1020
tcttggcctc tttgtccctg ccctgtgctg ctgtgcatat tcattcattc agttctctgt      1080
ggggtttttt ttttgtttaa tttttttttg ggatcgtatc cagtgcacaa gggccacgcc      1140
gtgcacaaat gcacaaaacg aaatctggcc gtccattttc catccaacga catgacggcg      1200 cgggggggttt ttcacaaaac agactcggca agctacggag gttgcgggag ggttcatctg      1260
catatttacg acggccgttg gatggaaaat ggacggccag atttcgtttt gtgtatttgt      1320
gcacggcgtg gcccttgtgc actggatacg atcccatttt ttttttttgcc ccgaatccta      1380 gtggacctaa ctggacagat tacagcacgc acacgtaggc atgtcatgta gcagcactgc      1440
agtcgggtgc agtccagtcc agtcctgtcc agccgcgaca ctgtagtaca tagcgatgca      1500
acggagacac gcgttggagt tggttccatc tcttctcggc ggccgtgccg aggcttccgc      1560
ggggaagctg cgacaacaga acggaccgcc ggggtgggc aggcagcaag ctccctgttg      1620
gcttgtgccg ttgcgcagcg gcgggtaccg gacaacgctt cggcggcgc gcggcctcgt      1680 cggcttcccc tgtttttgat gccgcctctc ggtgtccggg gaccgggagg atcgatgggg      1740
```

```
cccgtgccgt ctgatccgcc acgcgagcgg tcctatgcga tgcgccgcac gagcgcgggg    1800
gggccgtgga acagtacaca gctgggtcac tcactcactc atcccgctgg ttgtggctgc    1860
ttggttgcaa cttggctcgg ctgtctgtct gttgcccccg ccgcgttttc tagccgtttc    1920
cgctttgctc gcggtttcgc tggcgatccg gcacgcggcg cccacacccg gggctggccc    1980
cttggccgag tgggtggcag gcacttgcat gcatccggcc ggtttcccgc gaccaagctg    2040
gcccgccgca acaatgagag tgagacgaga ctttgtgtca gtgtgtgtat gtacatgtat    2100
gtctgcgcga cagccctacc gtccgacacg atgattcttg tgcactgtac tgtactgtac    2160
taactccccc cacccctcc ggtatgtaac gcatgccata tgcaggcgct gtccaacggg     2220
cggtacaaga gctgcctgca ccgcgcggtg gtgaaccggc ggcaggagcg gcaatcgctg    2280
gccttcttcc tgtgcccgcg cgaggaccgg gtggtgcgcc cgccggccag cgccgcgccg    2340
cggcagtacc cggacttcac ctgggccgac ctcatgcgct tcacgcagcg ccactaccgc    2400
gccgacaccc gcacgctgga cgccttcacc cgctggctct cccacggccc ggcggcggcg    2460
gctccctgca cctaa                                                    2475
```

```
<210> SEQ ID NO 207
<211> LENGTH: 2487
<212> TYPE: DNA
<213> ORGANISM: Artificial Sequence
<220> FEATURE:
<223> OTHER INFORMATION: mutant sequence by gene editing

<400> SEQUENCE: 207
atggacgcca gcccgacccc accgctcccc ctccgcgccc caactcccag cattgacctc      60
cccgctggca aggacagggc cgacgcggcg gctaacaagg ccgcggctgt gttcgacctg     120
cgccgggagc ccaagatccc ggagccattc ctgtggccgc acgaagaggc gcggccgacc     180
tcggccgcgg agctggaggt gccggtggtg gacgtgggcg tgctgcgcaa tggcgacggc     240
gcggggctcc gccgcgccgc ggcgcaagtg gcggcggcgt gcgcgacgca cgggttcttc     300
caggtgtgcg ggcacggcgt ggacgcggcg ctggggcgcg ccgcgctgga cggcgccagc     360
gacttcttcc ggctgccgct ggctgagaag cagcgggccc ggcgcgtccc cggcaccgtg     420
tccgggtaca cgagcgcgca cgccgaccgg ttcgcgtcca agctcccctg gaaggagacc     480
ctgtccttcg gcttccacga cggcgccgcg gcgcccgtcg tcgtggacta cttcaccggc     540
acctcggcca agatttcgag ccagtggggt gagtaaagaa gaagatggcg ccgaatttac     600
atttataagt aggaccagca gaagcccctg cccctggggg ccttagcatt gcattcgact     660
gatgaatacg catggcaggc gggtgtacca gaggtactgc gaggagatga aggagctgtc     720
gctgacgatc atggagctgc tggagctgag cctgggcgtg gagcgcggct actaccggga     780
gttcttcgag gacagccgct ccatcatgcg gtgcaactac tacccgccgt gccgggtgcc     840
ggagcgcacg ctgggcacgg gcccgcactg cgacccccacg gcgctgacca tcctcctgca     900
ggacgacgtc ggcgggctgg aggtcctggt ggacggcgag tggcgccccg tccggcccgt     960
cccaggcgcc atggtcatca acatcggcga caccttcatg gtaacgaacg aaagcgccgg    1020
ctcctctgct tttcttggcc tctttgtccc tgccctgtgc tgctgtgcat attcattcat    1080
tcagttctct gtgggttttt tttttgttt aatttttttt tgggatcgta tccagtgcac     1140
aagggccacg ccgtgcacaa atgcacaaaa cgaaatctgg ccgtccattt tccatccaac    1200
gacatgacgg cgcggggggt ttttcacaaa acagactcgg caagctacgg aggttgcggg    1260
```

-continued

```
agggttcatc tgcatattta cgacggccgt tggatggaaa atggacggcc agatttcgtt    1320
ttgtgtattt gtgcacggcg tggcccttgt gcactggata cgatcccatt ttttttttg     1380 ccccgaatcc tagtggacct aactggacag attacagcac gcacacgtag gcatgtcatg    1440
tagcagcact gcagtcgggt gcagtccagt ccagtcctgt ccagccgcga cactgtagta    1500
catagcgatg caacggagac acgcgttgga gttggttcca tctcttctcg gcggccgtgc    1560
cgaggcttcc gcggggaagc tgcgacaaca gaacggaccg ccgggggtgg gcaggcagca    1620
agctccctgt tggcttgtgc cgttgcgcag cggcgggtac cggacaacgc tttcggcggc    1680
gcgcggcctc gtcggcttcc cctgtttttg atgccgcctc tcggtgtccg gggaccggga    1740
ggatcgatgg ggcccgtgcc gtctgatccg ccacgcgagc ggtcctatgc gatgcgccgc    1800
acgagcgcgg gggggccgtg gaacagtaca cagctgggtc actcactcac tcatcccgct    1860
ggttgtggct gcttggttgc aacttggctc ggctgtctgt ctgttgcccc cgccgcgttt    1920
tctagccgtt tccgctttgc tcgcggtttc gctggcgatc cggcacgcgg cgcccacacc    1980
cggggctggc cccttggccg agtgggtggc aggcacttgc atgcatccgg ccggtttccc    2040
gcgaccaagc tggcccgccg caacaatgag agtgagacga ctttgtgt cagtgtgtgt     2100 atgtacatgt atgtctgcgc gacagcccta ccgtccgaca cgatgattct tgtgcactgt    2160
actgtactgt actaactccc cccacccct ccggtatgta acgcatgcca tatgcaggcg     2220
ctgtccaacg ggcggtacaa gagctgcctg caccgcgcgg tggtgaaccg gcggcaggag    2280
cggcaatcgc tggccttctt cctgtgcccg cgcgaggacc gggtggtgcg cccgccggcc    2340
agcgccgcgc cgcggcagta cccggacttc acctgggccg acctcatgcg cttcacgcag    2400
cgccactacc gcgccgacac ccgcacgctg gacgccttca cccgctggct ctcccacggc    2460
ccggcggcgg cggctccctg cacctaa                                        2487
```

<210> SEQ ID NO 208
<211> LENGTH: 2490
<212> TYPE: DNA
<213> ORGANISM: Artificial Sequence
<220> FEATURE:
<223> OTHER INFORMATION: mutant sequence by gene editing

<400> SEQUENCE: 208

```
atggacgcca gcccgacccc accgctcccc ctccgcgccc caactcccag cattgacctc      60
cccgctggca aggacagggc cgacgcggcg gctaacaagg ccgcggctgt gttcgacctg     120
cgccgggagc ccaagatccc ggagccattc ctgtggccgc acgaagaggc gcggccgacc     180
tcggccgcgg agctggaggt gccggtggtg gacgtgggcg tgctgcgcaa tggcgacggc     240
gcggggctcc gccgcgccgc ggcgcaagtg gcggcggcgt gcgcgacgca cgggttcttc     300
caggtgtgcg ggcacggcgt ggacgcggcg ctggggcgcg ccgcgctgga cggcgccagc     360
gacttcttcc ggctgccgct ggctgagaag cagcgggccc ggcgcgtccc cggcaccgtg     420
tccgggtaca cgagcgcgca cgccgaccgg ttcgcgtcca agctcccctg gaaggagacc     480
ctgtccttcg gcttccacga cggcgccgcg cgcgcccgtcg tcgtggacta cttcaccggc     540
accccctcgg ccaagatttc gagccagtgg ggtgagtaaa gaagaagatg gcgccgaatt     600
tacatttata agtaggacca gcagaagccc ctgcccctgg gggccttagc attgcattcg      660
actgatgaat acgcatggca ggcgggtgta ccagaggtac tgcgaggaga tgaaggagct     720
gtcgctgacg atcatggagc tgctggagct gagcctgggc gtggagcgcg gctactaccg     780
ggagttcttc gaggacagcc gctccatcat gcggtgcaac tactacccgc cgtgcccggt     840
```

-continued

```
gccggagcgc acgctgggca cgggcccgca ctgcgacccc acggcgctga ccatcctcct    900
gcaggacgac gtcggcgggc tggaggtcct ggtggacggc gagtggcgcc ccgtccggcc    960
cgtcccaggc gccatggtca tcaacatcgg cgacaccttc atggtaacga acgaaagcgc   1020
cggctcctct gcttttcttg gcctctttgt ccctgccctg tgctgctgtg catattcatt   1080
cattcagttc tctgtggggt ttttttttttg tttaattttt ttttgggatc gtatccagtg   1140
cacaagggcc acgccgtgca caaatgcaca aaacgaaatc tggccgtcca ttttccatcc   1200
aacgacatga cggcgcgggg ggttttttcac aaaacagact cggcaagcta cggaggttgc   1260
gggagggttc atctgcatat ttacgacggc cgttggatgg aaaatggacg gccagatttc   1320
gttttgtgta tttgtgcacg gcgtggccct tgtgcactgg atacgatccc atttttttttt   1380 ttgccccgaa tcctagtgga cctaactgga cagattacag cacgcacacg taggcatgtc   1440
atgtagcagc actgcagtcg ggtgcagtcc agtccagtcc tgtccagccg cgacactgta   1500
gtacatagcg atgcaacgga gacacgcgtt ggagttggtt ccatctcttc tcggcggccg   1560
tgccgaggct tccgcgggga agctgcgaca acagaacgga ccgccggggg tgggcaggca   1620
gcaagctccc tgttggcttg tgccgttgcg cagcggcggg taccggacaa cgctttcggc   1680
ggcgcgcggc ctcgtcggct tcccctgttt ttgatgccgc ctctcggtgt ccggggaccg   1740
ggaggatcga tggggcccgt gccgtctgat ccgccacgcg agcggtccta tgcgatgcgc   1800
cgcacgagcg cgggggggcc gtggaacagt acacagctgg gtcactcact cactcatccc   1860
gctggttgtg gctgcttggt tgcaacttgg ctcggctgtc tgtctgttgc ccccgccgcg   1920
ttttctagcc gtttccgctt tgctcgcggt ttcgctggcg atccggcacg cggcgcccac   1980 acccgggggct ggccccttgg ccgagtgggt ggcaggcact tgcatgcatc cggccggttt   2040
cccgcgacca agctggcccg ccgcaacaat gagagtgaga cgagactttg tgtcagtgtg   2100
tgtatgtaca tgtatgtctg cgcgacagcc ctaccgtccg acacgatgat tcttgtgcac   2160
tgtactgtac tgtactaact ccccccaccc cctccggtat gtaacgcatg ccatatgcag   2220
gcgctgtcca acgggcggta caagagctgc ctgcaccgcg cggtggtgaa ccggcggcag   2280
gagcggcaat cgctggcctt cttcctgtgc ccgcgcgagg accgggtggt gcgcccgccg   2340
gccagcgccg cgccgcggca gtacccggac ttcacctggg ccgacctcat gcgcttcacg   2400
cagcgccact accgcgccga cacccgcacg ctggacgcct tcacccgctg gctctcccac   2460
ggcccggcgg cggcggctcc ctgcacctaa                                     2490
```

```
<210> SEQ ID NO 209
<211> LENGTH: 2487
<212> TYPE: DNA
<213> ORGANISM: Artificial Sequence
<220> FEATURE:
<223> OTHER INFORMATION: mutant sequence by gene editing

<400> SEQUENCE: 209
```

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
```

-continued

```
gacttcttcc ggctgccgct ggctgagaag cagcgggccc ggcgcgtccc cggcaccgtg        420
tccgggtaca cgagcgcgca cgccgaccgg ttcgcgtcca agctcccctg gaaggagacc        480
ctgtccttcg gcttccacga cggcgccgcg gcgcccgtcg tcgtggacta cttcaccggc        540
ccctcggcca agatttcgag ccagtggggt gagtaaagaa gaagatggcg ccgaatttac        600
atttataagt aggaccagca gaagcccctg cccctggggg ccttagcatt gcattcgact        660
gatgaatacg catggcaggc gggtgtacca gaggtactgc gaggagatga aggagctgtc        720
gctgacgatc atggagctgc tggagctgag cctgggcgtg gagcgcggct actaccggga        780
gttcttcgag gacagccgct ccatcatgcg gtgcaactac tacccgccgt gcccggtgcc        840
ggagcgcacg ctgggcacgg gcccgcactg cgaccccacg gcgctgacca tcctcctgca        900
ggacgacgtc ggcgggctgg aggtcctggt ggacggcgag tggcgccccg tccgcccgt         960 cccaggcgcc atggtcatca acatcggcga caccttcatg gtaacgaacg aaagcgccgg        1020
ctcctctgct tttcttggcc tctttgtccc tgccctgtgc tgctgtgcat attcattcat        1080
tcagttctct gtggggtttt ttttttgttt aatttttttt tgggatcgta tccagtgcac        1140
aagggccacg ccgtgcacaa atgcacaaaa cgaaatctgg ccgtccattt tccatccaac        1200
gacatgacgg cgcggggggt ttttcacaaa acagactcgg caagctacgg aggttgcggg        1260
agggttcatc tgcatattta cgacggccgt tggatggaaa atggacggcc agatttcgtt        1320
ttgtgtattt gtgcacggcg tggcccttgt gcactggata cgatcccatt ttttttttg         1380 ccccgaatcc tagtggacct aactggacag attacagcac gcacacgtag gcatgtcatg        1440
tagcagcact gcagtcgggt gcagtccagt ccagtcctgt ccagccgcga cactgtagta        1500
catagcgatg caacggagac acgcgttgga gttggttcca tctcttctcg gcggccgtgc        1560
cgaggcttcc gcggggaagc tgcgacaaca gaacggaccg ccgggggtgg gcaggcagca        1620
agctccctgt tggcttgtgc cgttgcgcag cggcgggtac cggacaacgc tttcggcggc        1680
gcgcggcctc gtcggcttcc cctgtttttg atgccgcctc tcggtgtccg gggaccggga        1740
ggatcgatgg ggcccgtgcc gtctgatccg ccacgcgagc ggtcctatgc gatgcgccgc        1800
acgagcgcgg gggggccgtg gaacagtaca cagctgggtc actcactcac tcatcccgct        1860
ggttgtggct gcttggttgc aacttggctc ggctgtctgt ctgttgcccc cgccgcgttt        1920
tctagccgtt tccgctttgc tcgcggtttc gctggcgatc cggcacgcgg cgcccacacc        1980
cggggctggc cccttggccg agtgggtggc aggcacttgc atgcatccgg ccggtttccc        2040
gcgaccaagc tggcccgccg caacaatgag agtgagacga gactttgtgt cagtgtgtgt        2100
atgtacatgt atgtctgcgc gacagcccta ccgtccgaca cgatgattct tgtgcactgt        2160
actgtactgt actaactccc cccacccccct ccggtatgta acgcatgcca tatgcaggcg       2220
ctgtccaacg ggcggtacaa gagctgcctg caccgcgcgg tggtgaaccg gcggcaggag        2280
cggcaatcgc tggccttctt cctgtgcccg cgcgaggacc gggtggtgcg cccgccggcc        2340
agcgccgcgc gcgcggcagta cccggacttc acctgggccg acctcatgcg cttcacgcag       2400
cgccactacc gcgccgacac ccgcacgctg gacgccttca cccgctggct ctcccacggc        2460
ccggcggcgg cggctccctg cacctaa                                           2487
```

<210> SEQ ID NO 210
<211> LENGTH: 2485
<212> TYPE: DNA
<213> ORGANISM: Artificial Sequence
<220> FEATURE:
<223> OTHER INFORMATION: mutant sequence by gene editing -continued

<400> SEQUENCE: 210

```
atggacgcca gcccgacccc accgctcccc ctccgcgccc caactcccag cattgacctc      60
cccgctggca aggacagggc cgacgcggcg gctaacaagg ccgcggctgt gttcgacctg     120
cgccgggagc ccaagatccc ggagccattc ctgtggccgc acgaagaggc gcggccgacc     180
tcggccgcgg agctggaggt gccggtggtg gacgtgggcg tgctgcgcaa tggcgacggc     240
gcggggctcc gccgcgccgc ggcgcaagtg gcggcggcgt gcgcgacgca cgggttcttc     300
caggtgtgcg ggcacggcgt ggacgcggcg ctggggcgcg ccgcgctgga cggcgccagc     360
gacttcttcc ggctgccgct ggctgagaag cagcgggccc ggcgcgtccc cggcaccgtg     420
tccgggtaca cgagcgcgca cgccgaccgg ttcgcgtcca agctcccctg gaaggagacc     480
ctgtccttcg gcttccacga cggcgccgcg gcgcccgtcg tcgtggacta cttcaccggc     540
ctcggccaag atttcgagcc agtggggtga gtaaagaaga agatggcgcc gaatttacat     600
ttataagtag gaccagcaga agccctgccc cctggggggcc ttagcattgc attcgactga     660
tgaatacgca tggcaggcgg gtgtaccaga ggtactgcga ggagatgaag gagctgtcgc     720
tgacgatcat ggagctgctg gagctgagcc tgggcgtgga gcgcggctac taccgggagt     780
tcttcgagga cagccgctcc atcatgcggt gcaactacta cccgccgtgc ccggtgccgg     840
agcgcacgct gggcacgggc ccgcactgcg accccacggc gctgaccatc ctcctgcagg     900
acgacgtcgg cgggctggag gtcctggtgg acggcgagtg gcgccccgtc cggcccgtcc     960
caggcgccat ggtcatcaac atcggcgaca ccttcatggt aacgaacgaa agcgccggct    1020
cctctgcttt tcttggcctc tttgtccctg ccctgtgctg ctgtgcatat tcattcattc    1080
agttctctgt ggggtttttt ttttgtttaa ttttttttg ggatcgtatc cagtgcacaa    1140
gggccacgcc gtgcacaaat gcacaaaacg aaatctggcc gtccattttc catccaacga    1200
catgacggcg cggggggttt ttcacaaaac agactcggca agctacgag gttgcgggag     1260 ggttcatctg catatttacg acggccgttg gatggaaaat ggacggccag atttcgtttt    1320
gtgtatttgt gcacggcgtg gcccttgtgc actggatacg atcccatttt tttttttgcc    1380
ccgaatccta gtggacctaa ctggacagat tacagcacgc acacgtaggc atgtcatgta    1440
gcagcactgc agtcgggtgc agtccagtcc agtcctgtcc agccgcgaca ctgtagtaca    1500
tagcgatgca acgagacac gcgttggagt tggttccatc tcttctcggc ggccgtgccg      1560
aggcttccgc ggggaagctg cgacaacaga acggaccgcc gggggtgggc aggcagcaag    1620
ctccctgttg gcttgtgccg ttgcgcagcg gcgggtaccg gacaacgctt tcggcggcgc    1680
gcggcctcgt cggcttcccc tgttttttgat gccgcctctc ggtgtccggg gaccgggagg    1740
atcgatgggg cccgtgccgt ctgatccgcc acgcgagcgg tcctatgcga tgcgccgcac    1800
gagcgcgggg gggccgtgga acagtacaca gctgggtcac tcactcactc atcccgctgg    1860
ttgtggctgc ttggttgcaa cttggctcgg ctgtctgtct gttgccccg ccgcgttttc     1920 tagccgtttc cgctttgctc gcggtttcgc tggcgatccg gcacgcggcg cccacacccg    1980
gggctggccc cttggccgag tggtggcag gcacttgcat gcatccggcc ggtttcccgc     2040
gaccaagctg gcccgccgca acaatgagag tgagacgaga ctttgtgtca gtgtgtgtat    2100
gtacatgtat gtctgcgcga cagccctacc gtccgacacg atgattcttg tgcactgtac    2160
tgtactgtac taactccccc caccccctcc ggtatgtaac gcatgccata tgcaggcgct    2220
gtccaacggg cggtacaaga gctgcctgca ccgcgcggtg gtgaaccggc ggcaggagcg    2280
```

-continued

```
gcaatcgctg gccttcttcc tgtgcccgcg cgaggaccgg gtggtgcgcc cgccggccag     2340
cgccgcgccg cggcagtacc cggacttcac ctgggccgac ctcatgcgct tcacgcagcg     2400
ccactaccgc gccgacaccc gcacgctgga cgccttcacc cgctggctct cccacggccc     2460
ggcggcggcg gctccctgca cctaa                                           2485
```

```
<210> SEQ ID NO 211
<211> LENGTH: 2486
<212> TYPE: DNA
<213> ORGANISM: Artificial Sequence
<220> FEATURE:
<223> OTHER INFORMATION: mutant sequence by gene editing

<400> SEQUENCE: 211
```

```
atggacgcca gcccgacccc accgctcccc ctccgcgccc caactcccag cattgacctc       60
cccgctggca aggacagggc cgacgcggcg gctaacaagg ccgcggctgt gttcgacctg      120
cgccgggagc ccaagatccc ggagccattc ctgtggccgc acgaagaggc gcggccgacc      180
tcggccgcgg agctggaggt gccggtggtg gacgtgggcg tgctgcgcaa tggcgacggc      240
gcggggctcc gccgcgccgc ggcgcaagtg gcggcggcgt gcgcgacgca cgggttcttc      300
caggtgtgcg ggcacggcgt ggacgcggcg ctggggcgcg ccgcgctgga cggcgccagc      360
gacttcttcc ggctgccgct ggctgagaag cagcgggccc ggcgcgtccc cggcaccgtg      420
tgggtacacg agcgcgcacg ccgaccggtt cgcgtccaag ctcccctgga aggagaccct      480
gtccttcggc ttccacgacg gcgccgcggc gcccgtcgtc gtggactact tcaccggcac      540
cctcggccaa gatttcgagc cagtggggtg agtaaagaag aagatggcgc cgaatttaca      600
tttataagta ggaccagcag aagccctgc ccctgggggc cttagcattg cattcgactg       660
atgaatacgc atggcaggcg ggtgtaccag aggtactgcg aggagatgaa ggagctgtcg      720
ctgacgatca tggagctgct ggagctgagc ctgggcgtgg agcgcggcta ctaccgggag      780
ttcttcgagg acagccgctc catcatgcgg tgcaactact acccgccgtg cccggtgccg      840
gagcgcacgc tgggcacggg cccgcactgc gaccccacgg cgctgaccat cctcctgcag      900
gacgacgtcg gcgggctgga ggtcctggtg gacggcgagt ggcgccccgt ccggcccgtc      960
ccaggcgcca tggtcatcaa catcggcgac accttcatgg taacgaacga aagcgccggc     1020
tcctctgctt ttcttggcct ctttgtccct gccctgtgct gctgtgcata ttcattcatt     1080
cagttctctg tggggttttt ttttgttta attttttttt gggatcgtat ccagtgcaca      1140
agggccacgc cgtgcacaaa tgcacaaaac gaaatctggc cgtccatttt ccatccaacg     1200
acatgacggc gcggggggtt tttcacaaaa cagactcggc aagctacgga ggttgcggga     1260
gggttcatct gcatatttac gacggccgtt ggatggaaaa tggacggcca gatttcgttt     1320
tgtgtatttg tgcacggcgt ggcccttgtg cactggatac gatcccattt ttttttttgc     1380
cccgaatcct agtggaccta actgacagaa ttcagcacg cacacgtagg catgtcatgt       1440
agcagcactg cagtcgggtg cagtccagtc cagtcctgtc cagccgcgac actgtagtac     1500
atagcgatgc aacggagaca cgcgttggag ttggttccat ctcttctcgg cggccgtgcc     1560
gaggcttccg cggggaagct gcgacaacag aacggaccgc cggggtgggg caggcagcaa     1620
gctccctgtt ggcttgtgcc gttgcgcagc ggcgggtacc ggacaacgct ttcggcggcg     1680
gcgggcctcg tcggcttccc ctgttttttga tgccgcctct cggtgtccgg ggaccgggag     1740
gatcgatggg gcccgtgccg tctgatccgc cacgcgagcg gtcctatgcg atgcgccgca     1800
cgagcgcggg ggggccgtgg aacagtacac agctgggtca ctcactcact catcccgctg     1860
```

```
gttgtggctg cttggttgca acttggctcg gctgtctgtc tgttgccccc gccgcgtttt     1920
ctagccgttt ccgctttgct cgcggtttcg ctggcgatcc ggcacgcggc gcccacaccc     1980
ggggctggcc ccttggccga gtgggtggca ggcacttgca tgcatccggc cggtttcccg     2040
cgaccaagct ggcccgccgc aacaatgaga gtgagacgag actttgtgtc agtgtgtgta     2100
tgtacatgta tgtctgcgcg acagccctac cgtccgacac gatgattctt gtgcactgta     2160
ctgtactgta ctaactcccc ccaccccctc cggtatgtaa cgcatgccat atgcaggcgc     2220
tgtccaacgg gcggtacaag agctgcctgc accgcgcggt ggtgaaccgg cggcaggagc     2280
ggcaatcgct ggccttcttc ctgtgcccgc gcgaggaccg ggtggtgcgc ccgccggcca     2340
gcgccgcgcc gcggcagtac ccggacttca cctgggccga cctcatgcgc ttcacgcagc     2400
gccactaccg cgccgacacc cgcacgctgg acgccttcac ccgctggctc tcccacggcc     2460
cggcggcggc ggctccctgc acctaa                                           2486
```

<210> SEQ ID NO 212
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 212

```
atggacgcca gcccgacccc accgctcccc ctccgcgccc caactcccag cattgacctc       60
cccgctggca aggacagggc cgacgcggcg gctaacaagg ccgcggctgt gttcgacctg      120
cgccgggagc ccaagatccc ggagccattc ctgtggccgc acgaagaggc gcggccgacc      180
tcggccgcgg agctggaggt gccggtggtg gacgtgggcg tgctgcgcaa tggcgacggc      240
gcggggctcc gccgcgccgc ggcgcaagtg gcggcggcgt gcgcgacgca cgggttcttc      300
caggtgtgcg ggcacggcgt ggacgcggcg ctggggcgcg ccgcgctgga cggcgccagc      360
gacttcttcc ggctgccgct ggctgagaag cagcgggccc ggcgcgtccc cggcaccgtg      420
taccgggtac acgagcgcgc acgccgaccg gttcgcgtcc aagctcccct ggaaggagac      480
cctgtccttc ggcttccacg acggcgccgc ggcgcccgtc gtcgtggact acttcaccgg      540
caccctcggc caagatttcg agccagtggg gtgagtaaag aagaagatgg cgccgaattt      600
acatttataa gtaggaccag cagaagcccc tgcccctggg ggccttagca ttgcattcga      660
ctgatgaata cgcatggcag gcgggtgtac cagaggtact gcgaggagat gaaggagctg      720
tcgctgacga tcatggagct gctggagctg agcctgggcg tggagcgcgg ctactaccgg      780
gagttcttcg aggacagccg ctccatcatg cggtgcaact actacccgcc gtgcccggtg      840
ccggagcgca cgctgggcac gggcccgcac tgcgacccca cggcgctgac catcctcctg      900
caggacgacg tcggcgggct ggaggtcctg gtggacggcg agtggcgccc cgtccggccc      960 gtccaggcg ccatggtcat caacatcggc gacaccttca tggtaacgaa cgaaagcgcc      1020
ggctcctctg cttttcttgg cctctttgtc cctgccctgt gctgctgtgc atattcattc      1080
attcagttct ctgtggggtt ttttttttgt ttaatttttt tttgggatcg tatccagtgc      1140
acaagggcca cgccgtgcac aaatgcacaa aacgaaatct ggccgtccat tttccatcca      1200
acgacatgac ggcgcggggg gtttttcaca aaacagactc ggcaagctac ggaggttgcg      1260
ggagggttca tctgcatatt tacgacggcc gttggatgga aaatggacgg ccagatttcg      1320
ttttgtgtat ttgtgcacgg cgtggccctt gtgcactgga tacgatccca tttttttttt      1380
```

-continued

```
tgccccgaat cctagtggac ctaactggac agattacagc acgcacacgt aggcatgtca    1440
tgtagcagca ctgcagtcgg gtgcagtcca gtccagtcct gtccagccgc gacactgtag    1500
tacatagcga tgcaacggag acacgcgttg gagttggttc catctcttct cggcggccgt    1560
gccgaggctt ccgcggggaa gctgcgacaa cagaacggac cgccgggggt gggcaggcag    1620
caagctccct gttggcttgt gccgttgcgc agcggcgggt accggacaac gctttcggcg    1680
gcgcgcggcc tcgtcggctt cccctgtttt tgatgccgcc tctcggtgtc cggggaccgg    1740
gaggatcgat ggggcccgtg ccgtctgatc cgccacgcga gcggtcctat gcgatgcgcc    1800
gcacgagcgc gggggggccg tggaacagta cacagctggg tcactcactc actcatcccg    1860
ctggttgtgg ctgcttggtt gcaacttggc tcggctgtct gtctgttgcc cccgccgcgt    1920
tttctagccg tttccgcttt gctcgcggtt tcgctggcga tccggcacgc ggcgcccaca    1980
cccggggctg gccccttggc cgagtgggtg gcaggcactt gcatgcatcc ggccggtttc    2040
ccgcgaccaa gctggcccgc cgcaacaatg agagtgagac gagactttgt gtcagtgtgt    2100
gtatgtacat gtatgtctgc gcgacagccc taccgtccga cacgatgatt cttgtgcact    2160
gtactgtact gtactaactc cccccacccc ctccggtatg taacgcatgc catatgcagg    2220
cgctgtccaa cgggcggtac aagagctgcc tgcaccgcgc ggtggtgaac cggcggcagg    2280
agcggcaatc gctggccttc ttcctgtgcc cgcgcgagga ccgggtggtg cgcccgccgg    2340
ccagcgccgc gccgcggcag tacccggact tcacctgggc cgacctcatg cgcttcacgc    2400
agcgccacta ccgcgccgac acccgcacgc tggacgcctt cacccgctgg ctctcccacg    2460
gcccggcggc ggcggctccc tgcacctaa                                      2489
```

<210> SEQ ID NO 213
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 213

```
atggacgcca gcccgacccc accgctcccc ctccgcgccc caactcccag cattgacctc      60
cccgctggca aggacagggc cgacgcggcg gctaacaagg ccgcggctgt gttcgacctg     120
cgccgggagc ccaagatccc ggagccattc ctgtggccgc acgaagaggc gcggccgacc     180
tcggccgcgg agctggaggt gccggtggtg gacgtgggcg tgctgcgcaa tggcgacggc     240
gcggggctcc gccgcgccgc ggcgcaagtg gcggcggcgt gcgcgacgca cgggttcttc     300
caggtgtgcg ggcacggcgt ggacgcggcg ctggggcgcg ccgcgctgga cggcgccagc     360
gacttcttcc ggctgccgct ggctgagaag cagcgggccc ggcgcgtccc cggcaccgtg     420
ttccgggtac acgagcgcgc acgccgaccg gttcgcgtcc aagctcccct ggaaggagac     480
cctgtccttc ggcttccacg acggcgccgc ggcgcccgtc gtcgtggact acttcaccgg     540
caccctcggc caagatttcg agccagtggg gtgagtaaag aagaagatgg cgccgaattt     600
acatttataa gtaggaccag cagaagcccc tgcccctggg ggccttagca ttgcattcga     660
ctgatgaata cgcatggcag gcgggtgtac cagaggtact gcgaggagat gaaggagctg     720
tcgctgacga tcatggagct gctggagctg agcctgggcg tggagcgcgg ctactaccgg     780
gagttcttcg aggacagccg ctccatcatg cggtgcaact actacccgcc gtgcccggtg     840
ccggagcgca cgctgggcac gggcccgcac tgcgacccca cggcgctgac catcctcctg     900
caggacgacg tcggcgggct ggaggtcctg gtggacggcg agtggcgccc cgtccggccc     960
```

-continued

```
gtcccaggcg ccatggtcat caacatcggc gacaccttca tggtaacgaa cgaaagcgcc      1020
ggctcctctg cttttcttgg cctctttgtc cctgccctgt gctgctgtgc atattcattc      1080
attcagttct ctgtggggtt ttttttttgt ttaattttt tttgggatcg tatccagtgc      1140
acaagggcca cgccgtgcac aaatgcacaa aacgaaatct ggccgtccat tttccatcca      1200
acgacatgac ggcgcggggg gttttcaca aaacagactc ggcaagctac ggaggttgcg      1260
ggagggttca tctgcatatt tacgacggcc gttggatgga aaatggacgg ccagatttcg      1320
ttttgtgtat ttgtgcacgg cgtggccctt gtgcactgga tacgatccca tttttttttt      1380
tgccccgaat cctagtggac ctaactggac agattacagc acgcacacgt aggcatgtca      1440
tgtagcagca ctgcagtcgg gtgcagtcca gtccagtcct gtccagccgc gacactgtag      1500
tacatagcga tgcaacggag acacgcgttg gagttggttc catctcttct cggcggccgt      1560
gccgaggctt ccgcggggaa gctgcgacaa cagaacggac cgccgggggt gggcaggcag      1620
caagctccct gttggcttgt gccgttgcgc agcggcgggt accggacaac gctttcggcg      1680
gcgcgcggcc tcgtcggctt cccctgtttt tgatgccgcc tctcggtgtc cggggaccgg      1740
gaggatcgat ggggcccgtg ccgtctgatc cgccacgcga gcggtcctat gcgatgcgcc      1800
gcacgagcgc ggggggggccg tggaacagta cacagctggg tcactcactc actcatcccg      1860
ctggttgtgg ctgcttggtt gcaacttggc tcggctgtct gtctgttgcc cccgccgcgt      1920
tttctagccg tttccgcttt gctcgcggtt tcgctggcga tccggcacgc ggcgcccaca      1980 cccgggggctg gccccttggc cgagtggggtg gcaggcactt gcatgcatcc ggccggtttc      2040
ccgcgaccaa gctggcccgc cgcaacaatg agagtgagac gagactttgt gtcagtgtgt      2100
gtatgtacat gtatgtctgc gcgacagccc taccgtccga cacgatgatt cttgtgcact      2160
gtactgtact gtactaactc cccccacccc ctccggtatg taacgcatgc catatgcagg      2220
cgctgtccaa cgggcggtac aagagctgcc tgcaccgcgc ggtggtgaac cggcggcagg      2280
agcggcaatc gctggccttc ttcctgtgcc cgcgcgagga ccgggtggtg cgcccgccgg      2340
ccagcgccgc gccgcggcag tacccggact tcacctgggc cgacctcatg cgcttcacgc      2400
agcgccacta ccgcgccgac acccgcacgc tggacgcctt caccgctgg ctctcccacg      2460 gccgggcggc ggcggctccc tgcacctaa                                      2489
```

```
<210> SEQ ID NO 214
<211> LENGTH: 2487
<212> TYPE: DNA
<213> ORGANISM: Artificial Sequence
<220> FEATURE:
<223> OTHER INFORMATION: mutant sequence by gene editing

<400> SEQUENCE: 214
atggacgcca gcccgacccc accgctcccc ctccgcgccc caactcccag cattgacctc        60
cccgctggca aggacagggc cgacgcggcg gctaacaagg ccgcggctgt gttcgacctg       120
cgccgggagc ccaagatccc ggagccattc ctgtggccgc acgaagaggc gcggccgacc       180
tcggccgcgg agctggaggt gccggtggtg gacgtgggcg tgctgcgcaa tggcgacggc       240
gcggggctcc gccgcgccgc ggcgcaagtg gcggcggcgt gcgcgacgca cgggttcttc       300
caggtgtgcg ggcacggcgt ggacgcggcg ctggggcgcg ccgcgctgga cggcgccagc       360
gacttcttcc ggctgccgct ggctgagaag cagcgggccc ggcgcgtccc cggcaccgtg       420
tccgggtaca cgagcgcgca cgccgaccgg ttcgcgtcca agctcccctg gaaggagacc       480
```

-continued

```
ctgtccttcg gcttccacga cggcgccgcg gcgcccgtcg tcgtggacta cttcaccggc     540
accctcggcc aagatttcga gccgtggggt gagtaaagaa gaagatggcg ccgaatttac     600
atttataagt aggaccagca gaagcccctg cccctggggg ccttagcatt gcattcgact     660
gatgaatacg catggcaggc gggtgtacca gaggtactgc gaggagatga aggagctgtc     720
gctgacgatc atggagctgc tggagctgag cctgggcgtg gagcgcggct actaccggga     780
gttcttcgag gacagccgct ccatcatgcg gtgcaactac tacccgccgt gcccggtgcc     840
ggagcgcacg ctgggcacgg gcccgcactg cgaccccacg gcgctgacca tcctcctgca     900
ggacgacgtc ggcgggctgg aggtcctggt ggacggcgag tggcgccccg tccggcccgt     960
cccaggcgcc atggtcatca acatcggcga caccttcatg gtaacgaacg aaagcgccgg    1020
ctcctctgct tttcttggcc tctttgtccc tgccctgtgc tgctgtgcat attcattcat    1080
tcagttctct gtggggtttt tttttttgttt aatttttttt tgggatcgta tccagtgcac    1140
aagggccacg ccgtgcacaa atgcacaaaa cgaaatctgg ccgtccattt tccatccaac    1200
gacatgacgg cgcgggggt tttttcacaaa acagactcgg caagctacgg aggttgcggg    1260
agggttcatc tgcatattta cgacggccgt tggatggaaa atggacggcc agatttcgtt    1320
ttgtgtattt gtgcacggcg tggcccttgt gcactggata cgatcccatt ttttttttttg    1380 ccccgaatcc tagtggacct aactggacag attacagcac gcacacgtag gcatgtcatg    1440
tagcagcact gcagtcgggt gcagtccagt ccagtcctgt ccagccgcga cactgtagta    1500
catagcgatg caacggagac acgcgttgga gttggttcca tctcttctcg gcggccgtgc    1560
cgaggcttcc gcggggaagc tgcgacaaca gaacggaccg ccgggggtgg gcaggcagca    1620
agctccctgt tggcttgtgc cgttgcgcag cggcgggtac cggacaacgc tttcggcggc    1680
gcgcggcctc gtcggcttcc cctgtttttg atgccgcctc tcggtgtccg gggaccggga    1740
ggatcgatgg ggcccgtgcc gtctgatccg ccacgcgagc ggtcctatgc gatgcgccgc    1800
acgagcgcgg gggggccgtg gaacagtaca cagctgggtc actcactcac tcatcccgct    1860
ggttgtggct gcttggttgc aacttggctc ggctgtctgt ctgttgcccc cgccgcgttt    1920
tctagccgtt ccgcctttgc tcgcggtttc gctggcgatc cggcacgcgg cgcccacacc    1980
cggggctggc cccttggccg agtgggtggc aggcacttgc atgcatccgg ccggtttccc    2040
gcgaccaagc tggcccgccg caacaatgag agtgagacga gactttgtgt cagtgtgtgt    2100
atgtacatgt atgtctgcgc gacagcccta ccgtccgaca cgatgattct tgtgcactgt    2160
actgtactgt actaactccc cccacccct ccggtatgta acgcatgcca tatgcaggcg    2220
ctgtccaacg ggcggtacaa gagctgcctg caccgcgcgg tggtgaaccg gcggcaggag    2280
cggcaatcgc tggccttctt cctgtgcccg cgcgaggacc gggtggtgcg cccgccggcc    2340
agcgccgcgc cgcggcagta cccggacttc acctgggccg acctcatgcg cttcacgcag    2400
cgccactacc gcgccgacac ccgcacgctg gacgccttca cccgctggct ctcccacggc    2460
ccggcggcgg cggctccctg cacctaa                                        2487
```

<210> SEQ ID NO 215
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 215

```
atggacgcca gcccgacccc accgctcccc ctccgcgccc caactcccag cattgacctc     60
```

```
cccgctggca aggacagggc cgacgcggcg gctaacaagg ccgcggctgt gttcgacctg      120
cgccgggagc ccaagatccc ggagccattc ctgtggccgc acgaagaggc gcggccgacc      180
tcggccgcgg agctggaggt gccggtggtg gacgtgggcg tgctgcgcaa tggcgacggc      240
gcggggctcc gccgcgccgc ggcgcaagtg gcggcggcgt gcgcgacgca cgggttcttc      300
caggtgtgcg ggcacggcgt ggacgcggcg ctggggcgcg ccgcgctgga cggcgccagc      360
gacttcttcc ggctgccgct ggctgagaag cagcgggccc ggcgcgtccc cggcaccgtg      420
tccgggtaca cgagcgcgca cgccgaccgg ttcgcgtcca agctcccctg gaaggagacc      480
ctgtccttcg gcttccacga cggcgccgcg gcgcccgtcg tcgtggacta cttcaccggc      540
accctcggcc aagatttcga gccaagtggg gtgagtaaag aagaagatgg cgccgaattt      600
acatttataa gtaggaccag cagaagcccc tgcccctggg ggccttagca ttgcattcga      660
ctgatgaata cgcatggcag gcgggtgtac cagaggtact gcgaggagat gaaggagctg      720
tcgctgacga tcatggagct gctggagctg agcctgggcg tggagcgcgg ctactaccgg      780
gagttcttcg aggacagccg ctccatcatg cggtgcaact actacccgcc gtgcccggtg      840
ccggagcgca cgctgggcac gggcccgcac tgcgacccca cggcgctgac catcctcctg      900
caggacgacg tcggcgggct ggaggtcctg gtggacggcg agtggcgccc cgtccggccc      960
gtcccaggcg ccatggtcat caacatcggc gacaccttca tggtaacgaa cgaaagcgcc     1020
ggctcctctg cttttcttgg cctctttgtc cctgccctgt gctgctgtgc atattcattc     1080
attcagttct ctgtggggtt tttttttttgt ttaatttttt tttgggatcg tatccagtgc     1140
acaagggcca cgccgtgcac aaatgcacaa aacgaaatct ggccgtccat tttccatcca     1200
acgacatgac ggcgcggggg gttttttcaca aaacagactc ggcaagctac ggaggttgcg     1260
ggagggttca tctgcatatt tacgacggcc gttggatgga aaatggacgg ccagatttcg     1320
ttttgtgtat ttgtgcacgg cgtggccctt gtgcactgga tacgatccca tttttttttt     1380
tgccccgaat cctagtggac ctaactggac agattacagc acgcacacgt aggcatgtca     1440
tgtagcagca ctgcagtcgg gtgcagtcca gtccagtcct gtccagccgc gacactgtag     1500
tacatagcga tgcaacggag acacgcgttg gagttggttc catctcttct cggcggccgt     1560
gccgaggctt ccgcggggaa gctgcgacaa cagaacggac cgccgggggt gggcaggcag     1620
caagctccct gttggcttgt gccgttgcgc agcggcgggt accggacaac gctttcggcg     1680
gcgcgcggcc tcgtcggctt cccctgtttt tgatgccgcc tctcggtgtc cggggaccgg     1740
gaggatcgat ggggcccgtg ccgtctgatc cgccacgcga gcggtcctat gcgatgcgcc     1800
gcacgagcgc gggggggccg tggaacagta cacagctggg tcactcactc actcatcccg     1860
ctggttgtgg ctgcttggtt gcaacttggc tcggctgtct gtctgttgcc cccgccgcgt     1920
tttctagccg tttccgcttt gctcgcggtt tcgctggcga tccggcacgc ggcgcccaca     1980 cccgggggctg gccccttggc cgagtgggtg gcaggcactt gcatgcatcc ggccggtttc     2040
ccgcgaccaa gctggcccgc cgcaacaatg agagtgagac gagactttgt gtcagtgtgt     2100
gtatgtacat gtatgtctgc gcgacagccc taccgtccga cacgatgatt cttgtgcact     2160
gtactgtact gtactaactc ccccacccc ctccggtatg taacgcatgc catatgcagg     2220
cgctgtccaa cgggcggtac aagagctgcc tgcaccgcgc ggtggtgaac cggcggcagg     2280
agcggcaatc gctggccttc ttcctgtgcc cgcgcgagga ccgggtggtg cgcccgccgg     2340
ccagcgccgc gccgcggcag taccggact tcacctgggc cgacctcatg cgcttcacgc     2400
```

```
agcgccacta ccgcgccgac acccgcacgc tggacgcctt cacccgctgg ctctcccacg     2460
gcccggcggc ggcggctccc tgcacctaa                                        2489

<210> SEQ ID NO 216
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 216
atggacgcca gcccgacccc accgctcccc ctccgcgccc caactcccag cattgacctc       60
cccgctggca aggacagggc cgacgcggcg gctaacaagg ccgcggctgt gttcgacctg      120
cgccgggagc ccaagatccc ggagccattc ctgtggccgc acgaagaggc gcggccgacc      180
tcggccgcgg agctggaggt gccggtggtg gacgtgggcg tgctgcgcaa tggcgacggc      240
gcggggctcc gccgcgccgc ggcgcaagtg gcggcggcgt gcgcgacgca cgggttcttc      300
caggtgtgcg ggcacggcgt ggacgcggcg ctggggcgcg ccgcgctgga cggcgccagc      360
gacttcttcc ggctgccgct ggctgagaag cagcgggccc ggcgcgtccc cggcaccgtg      420
tccgggtaca cgagcgcgca cgccgaccgg ttcgcgtcca agctcccctg gaaggagacc      480
ctgtccttcg gcttccacga cggcgccgcg gcgcccgtcg tcgtggacta cttcaccggc      540
accctcggcc aagatttcga gccacgtggg gtgagtaaag aagaagatgg cgccgaattt      600
acatttataa gtaggaccag cagaagcccc tgcccctggg ggccttagca ttgcattcga      660
ctgatgaata cgcatggcag gcgggtgtac cagaggtact gcgaggagat gaaggagctg      720
tcgctgacga tcatggagct gctggagctg agcctgggcg tggagcgcgg ctactaccgg      780
gagttcttcg aggacagccg ctccatcatg cggtgcaact actacccgcc gtgcccggtg      840
ccggagcgca cgctgggcac gggcccgcac tgcgacccca cggcgctgac catcctcctg      900
caggacgacg tcggcgggct ggaggtcctg gtggacggca gtggcgcccc cgtccggccc      960
gtcccaggcg ccatggtcat caacatcggc gacaccttca tggtaacgaa cgaaagcgcc     1020
ggctcctctg cttttcttgg cctctttgtc cctgccctgt gctgctgtgc atattcattc     1080
attcagttct ctgtggggtt ttttttttgt ttaatttttt tttgggatcg tatccagtgc     1140
acaagggcca cgccgtgcac aaatgcacaa aacgaaatct ggccgtccat tttccatcca     1200
acgacatgac ggcgcggggg gttttcaca aaacagactc ggcaagctac ggaggttgcg      1260
ggagggttca tctgcatatt tacgacggcc gttggatgga aaatggacgg ccagatttcg     1320
ttttgtgtat ttgtgcacgg cgtggccctt gtgcactgga tacgatccca tttttttttt     1380
tgccccgaat cctagtggac ctaactggac agattacagc acgcacacgt aggcatgtca     1440
tgtagcagca ctgcagtcgg gtgcagtcca gtccagtcct gtccagccgc gacactgtag     1500
tacatagcga tgcaacggag acacgcgttg gagttggttc catctcttct cggcggccgt     1560
gccgaggctt ccgcggggaa gctgcgacaa cagaacggac cgccggggt gggcaggcag      1620 caagctccct gttggcttgt gccgttgcgc agcggcgggt accggacaac gctttcggcg     1680
gcgcgcggcc tcgtcggctt cccctgtttt tgatgccgcc tctcggtgtc cggggaccgg     1740
gaggatcgat ggggcccgtg ccgtctgatc cgccacgcga gcggtcctat gcgatgcgcc     1800
gcacgagcgc ggggggggccg tggaacagta cacagctggg tcactcactc actcatcccg     1860
ctggttgtgg ctgcttggtt gcaacttggc tcggctgtct gtctgttgcc cccgccgcgt     1920
tttctagccg tttccgcttt gctcgcggtt tcgctggcga tccggcacgc ggcgcccaca     1980
```

```
cccgggggctg gccccttggc cgagtgggtg gcaggcactt gcatgcatcc ggccggtttc      2040
ccgcgaccaa gctggcccgc cgcaacaatg agagtgagac gagactttgt gtcagtgtgt      2100
gtatgtacat gtatgtctgc gcgacagccc taccgtccga cacgatgatt cttgtgcact      2160
gtactgtact gtactaactc cccccacccc ctccggtatg taacgcatgc catatgcagg      2220
cgctgtccaa cgggcggtac aagagctgcc tgcaccgcgc ggtggtgaac cggcggcagg      2280
agcggcaatc gctggccttc ttcctgtgcc cgcgcgagga ccgggtggtg cgcccgccgg      2340
ccagcgccgc gccgcggcag tacccggact tcacctgggc cgacctcatg cgcttcacgc      2400
agcgccacta ccgcgccgac acccgcacgc tggacgcctt cacccgctgg ctctcccacg      2460
gcccggcggc ggcggctccc tgcacctaa                                        2489
```

<210> SEQ ID NO 217
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 217

```
atggacgcca gcccgacccc accgctcccc ctccgcgccc caactcccag cattgacctc        60
ccccgctggc aaggacaggg ccgacgcggc ggctaacaag gccgcggctg tgttcgacct       120
gcgccgggag cccaagatcc cggagccatt cctgtggccg cacgaagagg cgcggccgac       180
ctcggccgcg gagctggagg tgccggtggt ggacgtgggc gtgctgcgca atggcgacgg       240 cgcgggggctc cgccgcgccg cggcgcaagt ggcggcggcg tgcgcgacgc acgggttctt       300
ccaggtgtgc gggcacggcg tggacgcggc gctggggcgc gccgcgctgg acggcgccag       360
cgacttcttc cggctgccgc tggctgagaa gcagcgggcc cggcgcgtcc ccggcaccgt       420
gtccgggtac acgagcgcgc acgccgaccg gttcgcgtcc aagctcccct ggaaggagac       480
cctgtccttc ggcttccacg acggcgccgc ggcgcccgtc gtcgtggact acttcaccgg       540
caccctcggc caagatttcg agccagtggg gtgagtaaag aagaagatgg cgccgaattt       600
acatttataa gtaggaccag cagaagcccc tgcccctggg ggccttagca ttgcattcga       660
ctgatgaata cgcatggcag gcgggtgtac cagaggtact gcgaggagat gaaggagctg       720
tcgctgacga tcatggagct gctggagctg agcctgggcg tggagcgcgg ctactaccgg       780
gagttcttcg aggacagccg ctccatcatg cggtgcaact actacccgcc gtgcccggtg       840
ccggagcgca cgctgggcac gggcccgcac tgcgacccca cggcgctgac catcctcctg       900
caggacgacg tcggcgggct ggaggtcctg gtggacggcg agtggcgccc cgtccggccc       960 gtccaggcg ccatggtcat caacatcggc gacaccttca tggtaacgaa cgaaagcgcc       1020
ggctcctctg cttttcttgg cctctttgtc cctgccctgt gctgctgtgc atattcattc      1080
attcagttct ctgtggggtt ttttttttgt ttaatttttt tttgggatcg tatccagtgc      1140
acaagggcca cgccgtgcac aaatgcacaa aacgaaatct ggccgtccat tttccatcca      1200
acgacatgac ggcgcggggg gttttttcaca aaacagactc ggcaagctac ggaggttgcg      1260
ggagggttca tctgcatatt tacgacggcc gttggatgga aaatggacgg ccagatttcg      1320
ttttgtgtat ttgtgcacgg cgtggccctt gtgcactgga tacgatccca ttttttttttt      1380 tgccccgaat cctagtggac ctaactggac agattacagc acgcacacgt aggcatgtca      1440
tgtagcagca ctgcagtcgg gtgcagtcca gtccagtcct gtccagccgc gacactgtag      1500
```

-continued

```
tacatagcga tgcaacggag acacgcgttg gagttggttc catctcttct cggcggccgt    1560
gccgaggctt ccgcggggaa gctgcgacaa cagaacggac cgccgggggt gggcaggcag    1620
caagctccct gttggcttgt gccgttgcgc agcggcgggt accggacaac gctttcggcg    1680
gcgcgcggcc tcgtcggctt ccctgttttt tgatgccgcc tctcggtgtc cggggaccgg    1740
gaggatcgat ggggcccgtg ccgtctgatc cgccacgcga gcggtcctat gcgatgcgcc    1800
gcacgagcgc gggggggccg tggaacagta cacagctggg tcactcactc actcatcccg    1860
ctggttgtgg ctgcttggtt gcaacttggc tcggctgtct gtctgttgcc cccgccgcgt    1920
tttctagccg tttccgcttt gctcgcggtt tcgctggcga tccggcacgc ggcgcccaca    1980
cccggggctg gccccttggc cgagtgggtg gcaggcactt gcatgcatcc ggccggtttc    2040
ccgcgaccaa gctggcccgc cgcaacaatg agagtgagac gagactttgt gtcagtgtgt    2100
gtatgtacat gtatgtctgc gcgacagccc taccgtccga cacgatgatt cttgtgcact    2160
gtactgtact gtactaactc cccccacccc ctccggtatg taacgcatgc catatgcagg    2220
cgctgtccaa cgggcggtac aagagctgcc tgcaccgcgc ggtggtgaac cggcggcagg    2280
agcggcaatc gctggccttc ttcctgtgcc cgcgcgagga ccgggtggtg cgcccgccgg    2340
ccagcgccgc gccgcggcag tacccggact tcacctgggc cgacctcatg cgcttcacgc    2400
agcgccacta ccgcgccgac acccgcacgc tggacgcctt cacccgctgg ctctcccacg    2460
gcccggcggc ggcggctccc tgcacctaa                                      2489
```

```
<210> SEQ ID NO 218
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 218
tccccggcac cgtgtcgggt acacgagcgc                                        30
```

```
<210> SEQ ID NO 219
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 219
tccccggcac cgtgtgggta cacgagcgcg                                        30
```

```
<210> SEQ ID NO 220
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 220
tccccggcac cgtgttccgg gtacacgagc                                        30
```

```
<210> SEQ ID NO 221
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 221
```
gatccccgcg ccattctgtg gccgcaggaa                                    30

<210> SEQ ID NO 222
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 222
ccaggatttc gagccatggg gtaagtaagg                                    30

<210> SEQ ID NO 223
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 223
tcggccagga tttcgatggg gtaagtaagg t                                  31

<210> SEQ ID NO 224
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 224 ataccccac ccgccgacag cttccctgca ta                                  32

<210> SEQ ID NO 225
<211> LENGTH: 33
<212> TYPE: DNA
<213> ORGANISM: Artificial Sequence
<220> FEATURE:
<223> OTHER INFORMATION: mutant sequence by gene editing

<400> SEQUENCE: 225 ataccccac ccgccctgga cagcttccct gca                                 33

<210> SEQ ID NO 226
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 226 aaatacccc acccgggaca gcttccctgc at                                  32

<210> SEQ ID NO 227
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 227
cagcattgac ctcccacgct ggcaaggaca a                                  31

<210> SEQ ID NO 228
<211> LENGTH: 31
<212> TYPE: DNA

<213> ORGANISM: Artificial Sequence
<220> FEATURE:
<223> OTHER INFORMATION: mutant sequence by gene editing

<400> SEQUENCE: 228
cagcattgac ctcccccgct ggcaaggaca a                                                        31

<210> SEQ ID NO 229
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 229
ccggcgcgtc cccggcaccg tgtcgggtac acgagcgcgc acgccgaccg gttcgcggc        59

<210> SEQ ID NO 230
<211> LENGTH: 58
<212> TYPE: DNA
<213> ORGANISM: Artificial Sequence
<220> FEATURE:
<223> OTHER INFORMATION: mutant sequence by gene editing

<400> SEQUENCE: 230
ccggcgcgtc cccggcaccg tgtgggtaca cgagcgcgca cgccgaccgg ttcgcggc         58

<210> SEQ ID NO 231
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 231
ccggcgcgtc cccggcaccg tgttccgggt acacgagcgc gcacgccgac cggttcgcgg        60
c                                                                                        61

<210> SEQ ID NO 232
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 232
cgacctgcgc cgggagccca agatccccgc gccattctgt ggccgcagga agaggcgcg        59

<210> SEQ ID NO 233
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 233
ctacttcgtc ggcaccctcg gccaggattt cgagccatgg ggtaagtaag gtagtaaga        59

<210> SEQ ID NO 234
<211> LENGTH: 55
<212> TYPE: DNA
<213> ORGANISM: Artificial Sequence
<220> FEATURE:
<223> OTHER INFORMATION: mutant sequence by gene editing

<400> SEQUENCE: 234

-continued

```
ctacttcgtc ggcaccctcg gccaggattt cgatggggta agtaaggtag taaga          55

<210> SEQ ID NO 235
<211> LENGTH: 58
<212> TYPE: DNA
<213> ORGANISM: Artificial Sequence
<220> FEATURE:
<223> OTHER INFORMATION: mutant sequence by gene editing

<400> SEQUENCE: 235
gttacaaata cccccacccg ccgacagctt ccctgcatac ttgcagctcg cacatctc          58

<210> SEQ ID NO 236
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 236
gttacaaata cccccacccg ccctggacag cttccctgca tacttgcagc tcgcacatct          60
c                                                                        61

<210> SEQ ID NO 237
<211> LENGTH: 57
<212> TYPE: DNA
<213> ORGANISM: Artificial Sequence
<220> FEATURE:
<223> OTHER INFORMATION: mutant sequence by gene editing

<400> SEQUENCE: 237
gttacaaata cccccacccg ggacagcttc cctgcatact tgcagctcgc acatctc          57

<210> SEQ ID NO 238
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 238
tccgcgcccc cactcccagc cccagcattg acctcccacg ctggcaagga caaggccgac          60
g                                                                        61

<210> SEQ ID NO 239
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 239
tccgcgcccc cactcccagc cccagcattg acctccCccg ctggcaagga caaggccgac          60
g                                                                        61

<210> SEQ ID NO 240
<211> LENGTH: 60
<212> TYPE: DNA
<213> ORGANISM: Zea mays

<400> SEQUENCE: 240
ccggcgcgtc cccggcaccg tgtccgggta cacgagcgcg cacgccgacc ggttcgcggc          60
```

-continued

<210> SEQ ID NO 241
<211> LENGTH: 60
<212> TYPE: DNA
<213> ORGANISM: Zea mays

<400> SEQUENCE: 241
ccggcgcgtc cccggcaccg tgtccgggta cacgagcgcg cacgccgacc ggttcgcggc          60

<210> SEQ ID NO 242
<211> LENGTH: 60
<212> TYPE: DNA
<213> ORGANISM: Zea mays

<400> SEQUENCE: 242
ccggcgcgtc cccggcaccg tgtccgggta cacgagcgcg cacgccgacc ggttcgcggc          60

<210> SEQ ID NO 243
<211> LENGTH: 60
<212> TYPE: DNA
<213> ORGANISM: Zea mays

<400> SEQUENCE: 243
cgacctgcgc cgggagccca agatccccgc gccattcctg tggccgcagg aagaggcgcg          60

<210> SEQ ID NO 244
<211> LENGTH: 60
<212> TYPE: DNA
<213> ORGANISM: Zea mays

<400> SEQUENCE: 244
ctacttcgtc ggcaccctcg gccaggattt cgagccaatg gggtaagtaa ggtagtaaga          60

<210> SEQ ID NO 245
<211> LENGTH: 60
<212> TYPE: DNA
<213> ORGANISM: Zea mays

<400> SEQUENCE: 245
ctacttcgtc ggcaccctcg gccaggattt cgagccaatg gggtaagtaa ggtagtaaga          60

<210> SEQ ID NO 246
<211> LENGTH: 60
<212> TYPE: DNA
<213> ORGANISM: Zea mays

<400> SEQUENCE: 246
gttacaaata cccccacccg cccggacagc ttccctgcat acttgcagct cgcacatctc          60

<210> SEQ ID NO 247
<211> LENGTH: 60
<212> TYPE: DNA
<213> ORGANISM: Zea mays

<400> SEQUENCE: 247
gttacaaata cccccacccg cccggacagc ttccctgcat acttgcagct cgcacatctc          60

<210> SEQ ID NO 248
<211> LENGTH: 60
<212> TYPE: DNA
<213> ORGANISM: Zea mays

<400> SEQUENCE: 248
gttacaaata cccccacccg cccggacagc ttccctgcat acttgcagct cgcacatctc          60

<210> SEQ ID NO 249
<211> LENGTH: 60
<212> TYPE: DNA
<213> ORGANISM: Zea mays

<400> SEQUENCE: 249
tccgcgcccc cactcccagc cccagcattg acctccccgc tggcaaggac aaggccgacg       60

<210> SEQ ID NO 250
<211> LENGTH: 60
<212> TYPE: DNA
<213> ORGANISM: Zea mays

<400> SEQUENCE: 250
tccgcgcccc cactcccagc cccagcattg acctccccgc tggcaaggac aaggccgacg       60

<210> SEQ ID NO 251
<211> LENGTH: 2472
<212> TYPE: DNA
<213> ORGANISM: Artificial Sequence
<220> FEATURE:
<223> OTHER INFORMATION: mutant sequence by gene editing

<400> SEQUENCE: 251
atgaggccgc gcctccctcc aaatgttccc tccctgcctt cgtctttgtc gttgctcgca       60
aactccctgt cctcccctgt tacaaatacc cccacccgcc cggacagctt ccctgcatac      120
ttgcagctcg cacatctcat ggtgtcgcag gaacgacaag agccagctgt gcctagcagc      180
agcagcagca gcgccaagcg cgcagccacg tccatggacg ccagcccggc cccgccgctc      240
ctcctccgcg cccccactcc cagccccagc attgacctcc ccgctggcaa ggacaaggcc      300
gacgcggcgg ccagcaaggc cggcgcggcc gtgttcgacc tgcgccggga gcccaagatc      360
cccgcgccat cctgtgtgcc gcaggaagag gcgcggccgt cctcggccgc ggagctggag      420
gtgccgatgg tggacgtggg cgtgctgcgc aatggcgacc gcgcggggct gcggcgcgcc      480
gcggcgcagg tggccgcggc gtgcgcgacg cacgggttct tccaggtgtg cgggcacggc      540
gtggacgcgg cgctggggcg cgccgcgctg acggcgccca cgacttctt ccggctgccg      600 ctcgccgaga agcagcgcgc ccggcgcgtc cccggcaccg tgtcgggtac acgagcgcgc      660
acgccgaccg gttcgcggcc aagctcccct ggaaggagac cctgtcgttc ggctaccacg      720
acggcgccgc gtcgcctgtc gtcgtggact acttcgtcgg caccctcggc caggatttcg      780
agccaatggg gtaagtaagg tagtaagaag gagcgccggt ttacatttac cgcacgtcgg      840
cgtgcggtcg agtcgggact cgggagacgt atgaacccc gtcccgtccc atgcatgtgt      900
ggcaggtggg tgtaccagag gtactgcgag gagatgaagg agctgtcgct gacgatcatg      960
gagctgctgg agctgagcct gggcgtggag ctgcgcggct actaccggga gttcttcgag     1020
gacagccggt ccatcatgcg gtgcaactac tacccgccgt gcccggagcc ggagcgcacg     1080
ctgggcacgg gcccgcactg cgaccccacg gcgctcacca tcctcctgca ggacgacgtg     1140
ggcgggctgg aggtgctggt ggacggtgag tggcgccccg tccggccgt cccgggcgcc     1200 atggtcatca acatcggcga caccttcatg gtaacgaaac gaaagcgctc gctcctctgt     1260
tttccttggc cgctcttgtc ctgtgtgtat attcagttga gctctctctg tgctgttatt     1320
tcccgaatcc tagtggacct aaacgggcag gttattacag cacgcacacg taggcatgtc     1380
atgtagctag tacatacata gcgatgccga tgcaaatgca atagagacat gcgttcgagt     1440

```
tggttcctat ctcggcgggc tacggcaggt acacgcggcc gcggcgcgct ctctctagtc      1500
tatccgcggc cgcgcccagg ccgatcgagg cttccggggg agagttgcga caagagaacg      1560
gaccgagggg gtcggctagc ggtagcaagt tccctgttgg tttgtggcgt tggagcgttg      1620
cggagaggct tgcgcggcgg cggggacgtc gacggggacg tggcggggag acgatacgat      1680
gggtgccggg cagggcaacg ctttcggcgg gtggccgtgt ccaggtgcgc gcggccttgt      1740
cggtttcccc ctctcggtgt ccatggccga gaaatgggtc gacgaccgag accgacgctc      1800
ggtgcggcgc ccatcccgtc tgatccgccg cgccacgcga gcggccctat gcgatgccgc      1860
acgggcgcgg agggccgtcg cgcggagtat aatgtatagt atatagtaca aggttggttg      1920
gagtcgggtt gggttggatc gggtcaccgg tacgtggtgg ctgctgttgc ccccgccgtt      1980
tccgcttgca cttttgtcgc ggtttcgctg gcgatccggc acgcggcgcc cacaccacgc      2040
cggggctcca aacagctcgg gcccttggcc gtgtgggtgg caggcacttg cacgcgtccg      2100
gttgtcgcgg cctggcccgc cgccgggcgc accgcaacaa tgagacagcc cgacacgatg      2160
attcttgtgc actgtgctaa cccgcatgcc atgcaggcgc tgtcgaacgg gaggtacaag      2220
agctgcctgc accgcgcggt ggtgaaccag cggcgggcgc ggcggtcgct ggccttcttc      2280
ctgtgcccgc gcgaggaccg ggtggtgcgc ccgccggcca gtgctgcgcc gcggcgctac      2340
ccggacttca cctgggccga cctcatgcgc ttcacgcagc gccactaccg cgccgacacc      2400
cgcacgctgg acgccttcac ccgctggctc tcccacggcc cggcccaggc ggcggcgcct      2460
ccctgcacct ag                                                         2472
```

<210> SEQ ID NO 252
<211> LENGTH: 2471
<212> TYPE: DNA
<213> ORGANISM: Artificial Sequence
<220> FEATURE:
<223> OTHER INFORMATION: mutant sequence by gene editing

<400> SEQUENCE: 252

```
atgaggccgc gcctccctcc aaatgttccc tccctgcctt cgtctttgtc gttgctcgca        60
aactccctgt cctcccctgt tacaaatacc cccacccgcc cggacagctt ccctgcatac       120
ttgcagctcg cacatctcat ggtgtcgcag gaacgacaag agccagctgt gcctagcagc       180
agcagcagca gcgccaagcg cgcagccacg tccatggacg ccagcccggc cccgccgctc       240
ctcctccgcg cccccactcc cagccccagc attgacctcc ccgctggcaa ggacaaggcc       300
gacgcggcgg ccagcaaggc cggcgcggcc gtgttcgacc tgcgccggga gcccaagatc       360
cccgcgccat tcctgtggcc gcaggaagag gcgcggccgt cctcggccgc ggagctggag       420
gtgccgatgg tggacgtggg cgtgctgcgc aatggcgacc gcgcggggct gcggcgcgcc       480
gcggcgcagg tggccgcggc gtgcgcgacg cacgggttct tccaggtgtg cgggcacggc       540
gtggacgcgg cgctggggcg cgccgcgctg gacggcgcca gcgacttctt ccggctgccg       600
ctcgccgaga agcagcgcgc ccggcgcgtc cccggcaccg tgtgggtaca cgagcgcgca       660
cgccgaccgg ttcgcggcca agctcccctg gaaggagacc ctgtcgttcg gctaccacga       720
cggcgccgcg tcgcctgtcg tcgtggacta cttcgtcggc accctcggcc aggatttcga       780
gccaatgggg taagtaaggt agtaagaagg agcgccggtt tacatttacc gcacgtcggc       840
gtgcggtcga gtcgggactc gggagacgta tgaacccccg tcccgtccca tgcatgtgtg       900
gcaggtgggt gtaccagagg tactgcgagg agatgaagga gctgtcgctg acgatcatgg       960
agctgctgga gctgagcctg ggcgtggagc tgcgcggcta ctaccgggag ttcttcgagg      1020
```

-continued

```
acagccggtc catcatgcgg tgcaactact acccgccgtg cccggagccg gagcgcacgc      1080
tgggcacggg cccgcactgc gaccccacgg cgctcaccat cctcctgcag gacgacgtgg      1140
gcgggctgga ggtgctggtg gacggtgagt ggcgccccgt ccggcccgtc ccgggcgcca      1200
tggtcatcaa catcggcgac accttcatgg taacgaaacg aaagcgctcg ctcctctgtt      1260
ttccttggcc gctcttgtcc tgtgtgtata ttcagttgag ctctctctgt gctgttattt      1320
cccgaatcct agtggaccta aacgggcagg ttattacagc acgcacacgt aggcatgtca      1380
tgtagctagt acatacatag cgatgccgat gcaaatgcaa tagagacatg cgttcgagtt      1440
ggttcctatc tcggcgggct acggcaggta cacgcggccg cggcgcgctc tctctagtct      1500
atccgcggcc gcgcccaggc cgatcgaggc ttccggggga gagttgcgac aagagaacgg      1560
accgaggggg tcggctagcg gtagcaagtt ccctgttggt ttgtggcgtt ggagcgttgc      1620
ggagaggctt gcgcggcggc ggggacgtcg acggggacgt ggcggggaga cgatacgatg      1680
ggtgccgggc agggcaacgc tttcggcggg tggccgtgtc caggtgcgcg cggccttgtc      1740
ggtttccccc tctcggtgtc catggccgag aaatgggtcg acgaccgaga ccgacgctcg      1800
gtgcggcgcc catcccgtct gatccgccgc gccacgcgag cggccctatg cgatgccgca      1860
cgggcgcgga gggccgtcgc gcggagtata atgtatagta tatagtacaa ggttggttgg      1920
agtcgggttg ggttggatcg ggtcaccggt acgtggtggc tgctgttgcc cccgccgttt      1980
ccgcttgcac ttttgtcgcg gtttcgctgg cgatccggca cgcggcgccc acaccacgcc      2040
ggggctccaa acagctcggg cccttggccg tgtgggtggc aggcacttgc acgcgtccgg      2100
ttgtcgcggc ctggcccgcc gccgggcgca ccgcaacaat gagacagccc gacacgatga      2160
ttcttgtgca ctgtgctaac ccgcatgcca tgcaggcgct gtcgaacggg aggtacaaga      2220
gctgcctgca ccgcgcggtg gtgaaccagc ggcgggcgcg gcggtcgctg gccttcttcc      2280
tgtgcccgcg cgaggaccgg gtggtgcgcc cgccggccag tgctgcgccg cggcgctacc      2340
cggacttcac ctgggccgac ctcatgcgct tcacgcagcg ccactaccgc gccgacaccc      2400
gcacgctgga cgccttcacc cgctggctct cccacggccc ggcccaggcg gcggcgcctc      2460
cctgcaccta g                                                          2471
```

<210> SEQ ID NO 253
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 253

```
atgaggccgc gcctccctcc aaatgttccc tccctgcctt cgtctttgtc gttgctcgca        60
aactccctgt cctcccctgt tacaaatacc cccacccgcc cggacagctt ccctgcatac       120
ttgcagctcg cacatctcat ggtgtcgcag gaacgacaag agccagctgt gcctagcagc       180
agcagcagca gcgccaagcg cgcagccacg tccatggacg ccagcccggc cccgccgctc       240
ctcctccgcg cccccactcc cagccccagc attgacctcc ccgctggcaa ggacaaggcc       300
gacgcggcgc cagcaaggc cggcgcggcc gtgttcgacc tgcgccggga gcccaagatc       360
cccgcgccat tcctgtggcc gcaggaagag gcgcggccgt cctcggccgc ggagctggag       420
gtgccgatgg tggacgtggg cgtgctgcgc aatggcgacc gcgcggggct gcggcgcgcc       480
gcggcgcagg tggccgcggc gtgcgcgacg cacgggttct tccaggtgtg cgggcacggc       540
```

-continued

```
gtggacgcgg cgctggggcg cgccgcgctg gacggcgcca gcgacttctt ccggctgccg      600
ctcgccgaga agcagcgcgc ccggcgcgtc cccggcaccg tgttccgggt acacgagcgc      660
gcacgccgac cggttcgcgg ccaagctccc ctggaaggag accctgtcgt tcggctacca      720
cgacggcgcc gcgtcgcctg tcgtcgtgga ctacttcgtc ggcaccctcg gccaggattt      780
cgagccaatg gggtaagtaa ggtagtaaga aggagcgccg gtttacattt accgcacgtc      840
ggcgtgcggt cgagtcggga ctcgggagac gtatgaaccc ccgtcccgtc ccatgcatgt      900
gtggcaggtg ggtgtaccag aggtactgcg aggagatgaa ggagctgtcg ctgacgatca      960
tggagctgct ggagctgagc ctgggcgtgg agctgcgcgg ctactaccgg gagttcttcg     1020
aggacagccg gtccatcatg cggtgcaact actacccgcc gtgcccggag ccggagcgca     1080
cgctgggcac gggcccgcac tgcgacccca cggcgctcac catcctcctg caggacgacg     1140
tgggcgggct ggaggtgctg gtggacggtg agtggcgccc cgtccggccc gtcccgggcg     1200
ccatggtcat caacatcggc gacaccttca tggtaacgaa acgaaagcgc tcgctcctct     1260
gttttccttg gccgctcttg tcctgtgtgt atattcagtt gagctctctc tgtgctgtta     1320
tttcccgaat cctagtggac ctaaacgggc aggttattac agcacgcaca cgtaggcatg     1380
tcatgtagct agtacataca tagcgatgcc gatgcaaatg caatagagac atgcgttcga     1440
gttggttcct atctcggcgg gctacggcag gtacacgcgg ccgcggcgcg ctctctctag     1500
tctatccgcg gccgcgccca ggccgatcga ggcttccggg ggagagttgc gacaagagaa     1560
cggaccgagg gggtcggcta gcggtagcaa gttccctgtt ggtttgtggc gttggagcgt     1620
tgcggagagg cttgcgcggc ggcggggacg tcgacgggga cgtggcgggg agacgatacg     1680
atgggtgccg ggcagggcaa cgctttcggc gggtggccgt gtccaggtgc gcgcggcctt     1740
gtcggtttcc ccctctcggt gtccatggcc gagaaatggg tcgacgaccg agaccgacgc     1800
tcggtgcggc gcccatcccg tctgatccgc cgcgccacgc gagcggccct atgcgatgcc     1860
gcacgggcgc ggagggccgt cgcgcggagt ataatgtata gtatatagta caaggttggt     1920
tggagtcggg ttgggttgga tcgggtcacc ggtacgtggt ggctgctgtt gccccgccg      1980 tttccgcttg cactttgtc gcggtttcgc tggcgatccg gcacgcggcg cccacaccac     2040
gccggggctc caaacagctc gggcccttgg ccgtgtgggt ggcaggcact tgcacgcgtc     2100
cggttgtcgc ggcctggccc gccgccgggc gcaccgcaac aatgagacag cccgacacga     2160
tgattcttgt gcactgtgct aacccgcatg ccatgcaggc gctgtcgaac gggaggtaca     2220
agagctgcct gcaccgcgcg gtggtgaacc agcggcgggc gcggcggtcg ctggccttct     2280
tcctgtgccc gcgcgaggac cgggtggtgc gcccgccggc cagtgctgcg ccgcggcgct     2340
acccggactt cacctgggcc gacctcatgc gcttcacgca gcgccactac cgcgccgaca     2400
cccgcacgct ggacgccttc acccgctggc tctcccacgg cccggcccag gcggcggcgc     2460
ctccctgcac ctag                                                      2474
```

<210> SEQ ID NO 254
<211> LENGTH: 2472
<212> TYPE: DNA
<213> ORGANISM: Artificial Sequence
<220> FEATURE:
<223> OTHER INFORMATION: mutant sequence by gene editing

<400> SEQUENCE: 254

```
atgaggccgc gcctccctcc aaatgttccc tccctgcctt cgtctttgtc gttgctcgca       60
aactccctgt cctccctgt tacaaatacc cccaccgcc cggacagctt ccctgcatac         120
```

```
ttgcagctcg cacatctcat ggtgtcgcag gaacgacaag agccagctgt gcctagcagc      180
agcagcagca gcgccaagcg cgcagccacg tccatggacg ccagcccggc cccgccgctc      240
ctcctccgcg cccccactcc cagccccagc attgacctcc ccgctggcaa ggacaaggcc      300
gacgcggcgg ccagcaaggc cggcgcggcc gtgttcgacc tgcgccggga gcccaagatc      360
cccgcgccat tctgtggccg caggaagagg cgcggccgtc ctcggccgcg gagctggagg      420
tgccgatggt ggacgtgggc gtgctgcgca atggcgaccg cgcggggctg cggcgcgccg      480
cggcgcaggt ggccgcggcg tgcgcgacgc acgggttctt ccaggtgtgc gggcacggcg      540
tggacgcggc gctggggcgc gccgcgctgg acggcgccag cgacttcttc cggctgccgc      600
tcgccgagaa gcagcgcgcc cggcgcgtcc ccggcaccgt gtccgggtac acgagcgcgc      660
acgccgaccg gttcgcggcc aagctcccct ggaaggagac cctgtcgttc ggctaccacg      720
acggcgccgc gtcgcctgtc gtcgtggact acttcgtcgg caccctcggc caggatttcg      780
agccaatggg gtaagtaagg tagtaagaag gagcgccggt ttacatttac cgcacgtcgg      840
cgtgcggtcg agtcgggact cgggagacgt atgaaccccc gtcccgtccc atgcatgtgt      900
ggcaggtggg tgtaccagag gtactgcgag gagatgaagg agctgtcgct gacgatcatg      960
gagctgctgg agctgagcct gggcgtggag ctgcgcggct actaccggga gttcttcgag     1020
gacagccggt ccatcatgcg gtgcaactac tacccgccgt gcccggagcc ggagcgcacg     1080
ctgggcacgg gcccgcactg cgacccccacg gcgctcacca tcctcctgca ggacgacgtg     1140
ggcgggctgg aggtgctggt ggacggtgag tggcgccccg tccggcccgt cccgggcgcc     1200
atggtcatca acatcggcga caccttcatg gtaacgaaac gaaagcgctc gctcctctgt     1260
tttccttggc cgctcttgtc ctgtgtgtat attcagttga gctctctctg tgctgttatt     1320
tcccgaatcc tagtggacct aaacgggcag gttattacag cacgcacacg taggcatgtc     1380
atgtagctag tacatacata gcgatgccga tgcaaatgca atagagacat gcgttcgagt     1440
tggttcctat ctcggcgggc tacggcaggt acacgcggcc gcggcgcgct ctctctagtc     1500
tatccgcggc cgcgcccagg ccgatcgagg cttccggggg agagttgcga caagagaacg     1560
gaccgagggg gtcggctagc ggtagcaagt tccctgttgg tttgtggcgt tggagcgttg     1620
cggagaggct tgcgcggcgg cggggacgtc gacggggacg tggcggggag acgatacgat     1680
gggtgccggg cagggcaacg ctttcggcgg gtggccgtgt ccaggtgcgc gcggccttgt     1740
cggtttcccc ctctcggtgt ccatggccga gaaatgggtc gacgaccgag accgacgctc     1800
ggtgcggcgc ccatcccgtc tgatccgccg cgccacgcga gcggccctat gcgatgccgc     1860
acgggcgcgg agggccgtcg cgcggagtat aatgtatagt atatagtaca aggttggttg     1920
gagtcgggtt gggttggatc gggtcaccgg tacgtggtgg ctgctgttgc cccgccgtt      1980 tccgcttgca cttttgtcgc ggtttcgctg gcgatccggc acgcggcgcc cacaccacgc     2040
cggggctcca aacagctcgg gcccttggcc gtgtgggtgg caggcacttg cacgcgtccg     2100
gttgtcgcgg cctggcccgc cgccgggcgc accgcaacaa tgagacagcc cgacacgatg     2160
attcttgtgc actgtgctaa cccgcatgcc atgcaggcgc tgtcgaacgg gaggtacaag     2220
agctgcctgc accgcgcgt ggtgaaccag cggcgggcgc ggcggtcgct ggccttcttc      2280
ctgtgcccgc gcgaggaccg ggtggtgcgc ccgccggcca gtgctgcgcc gcggcgctac     2340
ccggacttca cctgggccga cctcatgcgc ttcacgcagc gccactaccg cgccgacacc     2400
cgcacgctgg acgccttcac ccgctggctc tcccacggcc cggcccaggc ggcggcgcct     2460
```

-continued

```
ccctgcacct ag                                                      2472

<210> SEQ ID NO 255
<211> LENGTH: 2472
<212> TYPE: DNA
<213> ORGANISM: Artificial Sequence
<220> FEATURE:
<223> OTHER INFORMATION: mutant sequence by gene editing

<400> SEQUENCE: 255
atgaggccgc gcctccctcc aaatgttccc tccctgcctt cgtctttgtc gttgctcgca      60
aactccctgt cctcccctgt tacaaatacc cccacccgcc cggacagctt ccctgcatac     120
ttgcagctcg cacatctcat ggtgtcgcag gaacgacaag agccagctgt gcctagcagc     180
agcagcagca gcgccaagcg cgcagccacg tccatggacg ccagcccggc cccgccgctc     240
ctcctccgcg cccccactcc cagccccagc attgacctcc ccgctggcaa ggacaaggcc     300
gacgcggcgg ccagcaaggc cggcgcggcc gtgttcgacc tgcgccggga gcccaagatc     360
cccgcgccat tcctgtggcc gcaggaagag gcgcggccgt cctcggccgc ggagctggag     420
gtgccgatgg tggacgtggg cgtgctgcgc aatggcgacc gcgcggggct gcggcgcgcc     480
gcggcgcagg tggccgcggc gtgcgcgacg cacgggttct tccaggtgtg cgggcacggc     540
gtggacgcgg cgctggggcg cgccgcgctg gacggcgcca gcgacttctt ccggctgccg     600
ctcgccgaga agcagcgcgc ccggcgcgtc cccggcaccg tgtccgggta cacgagcgcg     660
cacgccgacc ggttcgcggc caagctcccc tggaaggaga ccctgtcgtt cggctaccac     720
gacggcgccg cgtcgcctgt cgtcgtggac tacttcgtcg gcaccctcgg ccaggatttc     780
gagccatggg gtaagtaagg tagtaagaag gagcgccggt ttacatttac cgcacgtcgg     840
cgtgcggtcg agtcgggact cgggagacgt atgaacccc gtcccgtccc atgcatgtgt     900
ggcaggtggg tgtaccagag gtactgcgag gagatgaagg agctgtcgct gacgatcatg     960
gagctgctgg agctgagcct gggcgtggag ctgcgcggct actaccggga gttcttcgag    1020
gacagccggt ccatcatgcg gtgcaactac tacccgccgt gcccggagcc ggagcgcacg    1080
ctgggcacgg gcccgcactg cgaccccacg gcgctcacca tcctcctgca ggacgacgtg    1140
ggcgggctgg aggtgctggt ggacggtgag tggcgccccg tccggcccgt cccgggcgcc    1200
atggtcatca acatcggcga caccttcatg gtaacgaaac gaaagcgctc gctcctctgt    1260
tttccttggc cgctcttgtc ctgtgtgtat attcagttga gctctctctg tgctgttatt    1320
tcccgaatcc tagtggacct aaacgggcag gttattacag cacgcacacg taggcatgtc    1380
atgtagctag tacatacata gcgatgccga tgcaaatgca atagagacat gcgttcgagt    1440
tggttcctat ctcggcgggc tacggcaggt acacgcggcc gcggcgcgct ctctctagtc    1500
tatccgcggc cgcgcccagg ccgatcgagg cttccggggg agagttgcga caagagaacg    1560
gaccgagggg gtcggctagc ggtagcaagt tccctgttgg tttgtggcgt tggagcgttg    1620
cggagaggct tgcgcggcgg cggggacgtc gacggggacg tggcggggag acgatacgat    1680
gggtgccggg cagggcaacg ctttcggcgg gtggccgtgt ccaggtgcgc gcggccttgt    1740
cggtttcccc ctctcggtgt ccatggccga gaaatgggtc gacgaccgag accgacgctc    1800
ggtgcggcgc ccatcccgtc tgatccgccg cgccacgcga gcggccctat gcgatgccgc    1860
acgggcgcgg agggccgtcg cgcggagtat aatgtatagt atatagtaca aggttggttg    1920
gagtcgggtt gggttggatc gggtcaccgg tacgtggtgg ctgctgttgc cccgccgtt    1980 tccgcttgca cttttgtcgc ggtttcgctg gcgatccggc acgcggcgcc cacaccacgc    2040
```

-continued

```
cggggctcca aacagctcgg gcccttggcc gtgtgggtgg caggcacttg cacgcgtccg      2100
gttgtcgcgg cctggcccgc cgccgggcgc accgcaacaa tgagacagcc cgacacgatg      2160
attcttgtgc actgtgctaa cccgcatgcc atgcaggcgc tgtcgaacgg gaggtacaag      2220
agctgcctgc accgcgcggt ggtgaaccag cggcgggcgc ggcggtcgct ggccttcttc      2280
ctgtgcccgc gcgaggaccg ggtggtgcgc ccgccggcca gtgctgcgcc gcggcgctac      2340
ccggacttca cctgggccga cctcatgcgc ttcacgcagc gccactaccg cgccgacacc      2400
cgcacgctgg acgccttcac ccgctggctc tcccacggcc cggcccaggc ggcggcgcct      2460
ccctgcacct ag                                                         2472
```

```
<210> SEQ ID NO 256
<211> LENGTH: 2468
<212> TYPE: DNA
<213> ORGANISM: Artificial Sequence
<220> FEATURE:
<223> OTHER INFORMATION: mutant sequence by gene editing

<400> SEQUENCE: 256
```

```
atgaggccgc gcctccctcc aaatgttccc tccctgcctt cgtctttgtc gttgctcgca        60
aactccctgt cctccctgt tacaaatacc cccacccgcc cggacagctt ccctgcatac        120
ttgcagctcg cacatctcat ggtgtcgcag gaacgacaag agccagctgt gcctagcagc       180
agcagcagca gcgccaagcg cgcagccacg tccatggacg ccagcccggc cccgccgctc       240
ctcctccgcg cccccactcc cagccccagc attgacctcc ccgctggcaa ggacaaggcc       300
gacgcggcgg ccagcaaggc cggcgcggcc gtgttcgacc tgcgccggga gcccaagatc       360
cccgcgccat tcctgtggcc gcaggaagag gcgcggccgt cctcggccgc ggagctggag       420
gtgccgatgg tggacgtggg cgtgctgcgc aatggcgacc gcgcggggct gcggcgcgcc       480
gcggcgcagg tggccgcggc gtgcgcgacg cacgggttct tccaggtgtg cgggcacggc       540
gtggacgcgg cgctggggcg cgccgcgctg gacggcgcca gcgacttctt ccggctgccg       600
ctcgccgaga agcagcgcgc ccggcgcgtc cccggcaccg tgtccgggta cacgagcgcg       660
cacgccgacc ggttcgcggc caagctcccc tggaaggaga ccctgtcgtt cggctaccac       720
gacggcgccg cgtcgcctgt cgtcgtggac tacttcgtcg gcaccctcgg ccaggatttc       780
gatggggtaa gtaaggtagt aagaaggagc gccggtttac atttaccgca cgtcggcgtg       840
cggtcgagtc gggactcggg agacgtatga accccgtcc cgtcccatgc atgtgtggca       900
ggtgggtgta ccagaggtac tgcgaggaga tgaaggagct gtcgctgacg atcatggagc       960
tgctggagct gagcctgggc gtggagctgc gcggctacta ccgggagttc ttcgaggaca      1020
gccggtccat catgcggtgc aactactacc cgccgtgccc ggagccggag cgcacgctgg      1080
gcacgggccc gcactgcgac cccacggcgc tcaccatcct cctgcaggac gacgtgggcg      1140
ggctggaggt gctggtggac ggtgagtggc ccccgtccg cccgtcccg ggcgccatgg       1200 tcatcaacat cggcgacacc ttcatggtaa cgaaacgaaa gcgctcgctc tctctgttttc     1260 cttggccgct cttgtcctgt gtgtatattc agttgagctc tctctgtgct gttatttccc      1320
gaatcctagt ggacctaaac gggcaggtta ttacagcacg cacacgtagg catgtcatgt      1380
agctagtaca tacatagcga tgccgatgca aatgcaatag agacatgcgt tcgagttggt      1440
tcctatctcg gcgggctacg gcaggtacac gcggccgcgg cgcgctctct ctagtctatc      1500
cgcggccgcg cccaggccga tcgaggcttc cgggggagag ttgcgacaag agaacggacc      1560
```

```
gaggggggtcg gctagcggta gcaagttccc tgttggtttg tggcgttgga gcgttgcgga      1620
gaggcttgcg cggcggcggg gacgtcgacg gggacgtggc ggggagacga tacgatgggt      1680
gccgggcagg gcaacgcttt cggcgggtgg ccgtgtccag gtgcgcgcgg ccttgtcggt      1740
ttccccctct cggtgtccat ggccgagaaa tgggtcgacg accgagaccg acgtcggtg       1800 cggcgcccat cccgtctgat ccgccgcgcc acgcgagcgg ccctatgcga tgccgcacgg      1860
gcgcggaggg ccgtcgcgcg gagtataatg tatagtatat agtacaaggt tggttggagt      1920
cgggttgggt tggatcgggt caccggtacg tggtggctgc tgttgcccc gccgtttccg       1980 cttgcacttt tgtcgcggtt tcgctggcga tccggcacgc ggcgcccaca ccacgccggg      2040
gctccaaaca gctcgggccc ttggccgtgt gggtggcagg cacttgcacg cgtccggttg      2100
tcgcggcctg gcccgccgcc gggcgcaccg caacaatgag acagcccgac acgatgattc      2160
ttgtgcactg tgctaacccg catgccatgc aggcgctgtc gaacgggagg tacaagagct      2220
gcctgcaccg cgcggtggtg aaccagcggc gggcgcggcg gtcgctggcc ttcttcctgt      2280
gcccgcgcga ggaccgggtg gtgcgcccgc cggccagtgc tgcgccgcgg cgctacccgg      2340
acttcacctg ggccgacctc atgcgcttca cgcagcgcca ctaccgcgcc gacacccgca      2400
cgctggacgc cttcacccgc tggctctccc acggcccggc ccaggcggcg gcgcctccct      2460
gcacctag                                                               2468
```

<210> SEQ ID NO 257
<211> LENGTH: 2471
<212> TYPE: DNA
<213> ORGANISM: Artificial Sequence
<220> FEATURE:
<223> OTHER INFORMATION: mutant sequence by gene editing

<400> SEQUENCE: 257

```
atgaggccgc gcctccctcc aaatgttccc tccctgcctt cgtctttgtc gttgctcgca       60
aactccctgt cctcccctgt tacaaatacc cccaccccgcc gacagcttcc ctgcatactt      120
gcagctcgca catctcatgg tgtcgcagga acgacaagag ccagctgtgc ctagcagcag       180
cagcagcagc gccaagcgcg cagccacgtc catggacgcc agcccggccc cgccgctcct       240
cctccgcgcc cccactccca gccccagcat tgacctcccc gctggcaagg acaaggccga       300
cgcggcggcc agcaaggccg gcgcggccgt gttcgacctg cgccgggagc ccaagatccc       360
cgcgccattc ctgtggccgc aggaagaggc gcggccgtcc tcggccgcgg agctggaggt       420
gccgatggtg gacgtgggcg tgctgcgcaa tggcgaccgc gcggggctgc ggcgcgccgc       480
ggcgcaggtg gccgcggcgt gcgcgacgca cgggttcttc caggtgtgcg ggcacggcgt       540
ggacgcggcg ctggggcgcg ccgcgctgga cggcgcccagc gacttcttcc ggctgccgct       600
cgccgagaag cagcgcgccc ggcgcgtccc cggcaccgtg tccgggtaca cgagcgcgca       660
cgccgaccgc ttcgcggcca agctcccctg gaaggagacc ctgtcgttcg gctaccacga       720
cggcgccgcg tcgcctgtcg tcgtggacta cttcgtcggc accctcggcc aggatttcga       780
gccaatgggg taagtaaggt agtaagaagg agcgccggtt tacatttacc gcacgtcggc       840
gtgcggtcga gtcgggactc gggagacgta tgaaccccg tcccgtccca tgcatgtgtg        900
gcaggtgggt gtaccagagg tactgcgagg agatgaagga gctgtcgctg acgatcatgg       960
agctgctgga gctgagcctg ggcgtggagc tgcgcggcta ctaccgggag ttcttcgagg      1020
acagccggtc catcatgcgg tgcaactact acccgccgtg cccggagccg gagcgcacgc      1080
tgggcacggg cccgcactgc gaccccacgg cgctcaccat cctcctgcag gacgacgtgg      1140
```

```
gcgggctgga ggtgctggtg gacggtgagt ggcgccccgt ccggcccgtc ccgggcgcca    1200
tggtcatcaa catcggcgac accttcatgg taacgaaacg aaagcgctcg ctcctctgtt    1260
ttccttggcc gctcttgtcc tgtgtgtata ttcagttgag ctctctctgt gctgttattt    1320
cccgaatcct agtggaccta aacgggcagg ttattacagc acgcacacgt aggcatgtca    1380
tgtagctagt acatacatag cgatgccgat gcaaatgcaa tagagacatg cgttcgagtt    1440
ggttcctatc tcggcgggct acggcaggta cacgcggccg cggcgcgctc tctctagtct    1500
atccgcggcc gcgcccaggc cgatcgaggc ttccggggga gagttgcgac aagagaacgg    1560
accgaggggg tcggctagcg gtagcaagtt ccctgttggt ttgtggcgtt ggagcgttgc    1620
ggagaggctt gcgcggcggc ggggacgtcg acggggacgt ggcggggaga cgatacgatg    1680
ggtgccgggc agggcaacgc tttcggcggg tggccgtgtc caggtgcgcg cggccttgtc    1740
ggtttccccc tctcggtgtc catggccgag aaatgggtcg acgaccgaga ccgacgctcg    1800
gtgcggcgcc catcccgtct gatccgccgc gccacgcgag cggccctatg cgatgccgca    1860
cgggcgcgga gggccgtcgc gcggagtata atgtatagta tatagtacaa ggttggttgg    1920
agtcgggttg ggtggatcg ggtcaccggt acgtggtggc tgctgttgcc cccgccgttt    1980
ccgcttgcac ttttgtcgcg gtttcgctgg cgatccggca cgcggcgccc acaccacgcc    2040
ggggctccaa acagctcggg cccttggccg tgtgggtggc aggcacttgc acgcgtccgg    2100
ttgtcgcggc ctggcccgcc gccgggcgca ccgcaacaat gagacagccc gacacgatga    2160
ttcttgtgca ctgtgctaac ccgcatgcca tgcaggcgct gtcgaacggg aggtacaaga    2220
gctgcctgca ccgcgcggtg gtgaaccagc ggcgggcgcg gcggtcgctg gccttcttcc    2280
tgtgcccgcg cgaggaccgg gtggtgcgcc cgccggccag tgctgcgccg cggcgctacc    2340
cggacttcac ctgggccgac ctcatgcgct tcacgcagcg ccactaccgc gccgacaccc    2400
gcacgctgga cgccttcacc cgctggctct cccacggccc ggcccaggcg gcggcgcctc    2460
cctgcaccta g                                                        2471
```

<210> SEQ ID NO 258
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 258

```
atgaggccgc gcctccctcc aaatgttccc tccctgcctt cgtctttgtc gttgctcgca     60
aactccctgt cctcccctgt tacaaatacc cccacccgcc ctggacagct tccctgcata    120
cttgcagctc gcacatctca tggtgtcgca ggaacgacaa gagccagctg tgcctagcag    180
cagcagcagc agcgccaagc gcgcagccac gtccatggac gccagcccgg ccccgccgct    240
cctcctccgc gcccccactc ccagccccag cattgacctc cccgctggca aggacaaggc    300
cgacgcggcg gccagcaagg ccggcgcggc cgtgttcgac ctgcgccggg agcccaagat    360
ccccgcgcca ttcctgtggc cgcaggaaga ggcgcggccg tcctcggccg cggagctgga    420
ggtgccgatg tggacgtgg gcgtgctgcg caatggcgac cgcgcggggc tgcggcgcgc    480
cgcggcgcag gtggccgcgg cgtgcgcgac gcacgggttc ttccaggtgt gcgggcacgg    540
cgtggacgcg gcgctggggc gcgccgcgct ggacggcgcc agcgacttct tccggctgcc    600
gctcgccgag aagcagcgcg cccggcgcgt ccccggcacc gtgtccgggt acacgagcgc    660
```

-continued

```
gcacgccgac cggttcgcgg ccaagctccc ctggaaggag accctgtcgt tcggctacca      720
cgacggcgcc gcgtcgcctg tcgtcgtgga ctacttcgtc ggcaccctcg gccaggattt      780
cgagccaatg gggtaagtaa ggtagtaaga aggagcgccg gtttacattt accgcacgtc      840
ggcgtgcggt cgagtcggga ctcgggagac gtatgaaccc ccgtcccgtc ccatgcatgt      900
gtggcaggtg ggtgtaccag aggtactgcg aggagatgaa ggagctgtcg ctgacgatca      960
tggagctgct ggagctgagc ctgggcgtgg agctgcgcgg ctactaccgg gagttcttcg     1020
aggacagccg gtccatcatg cggtgcaact actacccgcc gtgcccggag ccggagcgca     1080
cgctgggcac gggcccgcac tgcgaccccca cggcgctcac catcctcctg caggacgacg     1140
tgggcgggct ggaggtgctg gtggacggtg agtggcgccc cgtccggccc gtcccgggcg     1200
ccatggtcat caacatcggc gacaccttca tggtaacgaa acgaaagcgc tcgctcctct     1260
gttttccttg gccgctcttg tcctgtgtgt atattcagtt gagctctctc tgtgctgtta     1320
tttcccgaat cctagtggac ctaaacgggc aggttattac agcacgcaca cgtaggcatg     1380
tcatgtagct agtacataca tagcgatgcc gatgcaaatg caatagagac atgcgttcga     1440
gttggttcct atctcggcgg gctacggcag gtacacgcgg ccgcggcgcg ctctctctag     1500
tctatccgcg gccgcgccca ggccgatcga ggcttccggg ggagagttgc gacaagagaa     1560
cggaccgagg gggtcggcta gcggtagcaa gttccctgtt ggtttgtggc gttggagcgt     1620
tgcggagagg cttgcgcggc ggcgggacg tcgacgggga cgtggcgggg agacgatacg     1680
atgggtgccg ggcagggcaa cgctttcggc gggtggccgt gtccaggtgc gcgcggcctt     1740
gtcggtttcc ccctctcggt gtccatggcc gagaaatggg tcgacgaccg agaccgacgc     1800
tcggtgcggc gcccatcccg tctgatccgc cgcgccacgc gagcggccct atgcgatgcc     1860
gcacgggcgc ggagggccgt cgcgcggagt ataatgtata gtatatagta caaggttggt     1920
tggagtcggg ttgggttgga tcgggtcacc ggtacgtggt ggctgctgtt gcccccgccg     1980
tttccgcttg cacttttgtc gcggtttcgc tggcgatccg gcacgcggcg cccacaccac     2040
gccggggctc caaacagctc gggcccttgg ccgtgtgggt ggcaggcact tgcacgcgtc     2100
cggttgtcgc ggcctggccc gccgccgggc gcaccgcaac aatgagacag cccgacacga     2160
tgattcttgt gcactgtgct aacccgcatg ccatgcaggc gctgtcgaac gggaggtaca     2220
agagctgcct gcaccgcgcg gtggtgaacc agcggcgggc gcggcggtcg ctggccttct     2280
tcctgtgccc gcgcgaggac cgggtggtgc gcccgccggc cagtgctgcg ccgcggcgct     2340
acccggactt cacctgggcc gacctcatgc gcttcacgca gcgccactac cgcgccgaca     2400
cccgcacgct ggacgccttc acccgctggc tctcccacgg cccggcccag gcggcggcgc     2460
ctccctgcac ctag                                                       2474
```

```
<210> SEQ ID NO 259
<211> LENGTH: 2470
<212> TYPE: DNA
<213> ORGANISM: Artificial Sequence
<220> FEATURE:
<223> OTHER INFORMATION: mutant sequence by gene editing

<400> SEQUENCE: 259
atgaggccgc gcctccctcc aaatgttccc tccctgcctt cgtctttgtc gttgctcgca       60
aactccctgt cctcccctgt tacaaatacc cccacccggg acagcttccc tgcatacttg      120
cagctcgcac atctcatggt gtcgcaggaa cgacaagagc cagctgtgcc tagcagcagc      180
agcagcagcg ccaagcgcgc agccacgtcc atggacgcca gcccggcccc gccgctcctc      240
```

-continued

```
ctccgcgccc ccactcccag ccccagcatt gacctccccg ctggcaagga caaggccgac      300
gcggcggcca gcaaggccgg cgcggccgtg ttcgacctgc gccgggagcc caagatcccc      360
gcgccattcc tgtggccgca ggaagaggcg cggccgtcct cggccgcgga gctggaggtg      420
ccgatggtgg acgtgggcgt gctgcgcaat ggcgaccgcg cggggctgcg gcgcgccgcg      480
gcgcaggtgg ccgcggcgtg cgcgacgcac gggttcttcc aggtgtgcgg gcacggcgtg      540
gacgcggcgc tggggcgcgc cgcgctggac ggcgccagcg acttcttccg gctgccgctc      600
gccgagaagc agcgcgcccg gcgcgtcccc ggcaccgtgt ccgggtacac gagcgcgcac      660
gccgaccggt tcgcggccaa gctcccctgg aaggagaccc tgtcgttcgg ctaccacgac      720
ggcgccgcgt cgcctgtcgt cgtggactac ttcgtcggca ccctcggcca ggatttcgag      780
ccaatggggt aagtaaggta gtaagaagga gcgccggttt acatttaccg cacgtcggcg      840
tgcggtcgag tcgggactcg ggagacgtat gaacccccgt cccgtcccat gcatgtgtgg      900
caggtgggtg taccagaggt actgcgagga gatgaaggag ctgtcgctga cgatcatgga      960
gctgctggag ctgagcctgg gcgtggagct gcgcggctac taccgggagt tcttcgagga     1020
cagccggtcc atcatgcggt gcaactacta cccgccgtgc ccggagccgg agcgcacgct     1080
gggcacgggc ccgcactgcg accccacggc gctcaccatc ctcctgcagg acgacgtggg     1140
cgggctggag gtgctggtgg acggtgagtg gcgccccgtc cggcccgtcc cgggcgccat     1200
ggtcatcaac atcggcgaca ccttcatggt aacgaaacga aagcgctcgc tcctctgttt     1260
tccttggccg ctcttgtcct gtgtgtatat tcagttgagc tctctctgtg ctgttatttc     1320
ccgaatccta gtggacctaa acgggcaggt tattacagca cgcacacgta ggcatgtcat     1380
gtagctagta catacatagc gatgccgatg caaatgcaat agagacatgc gttcgagttg     1440
gttcctatct cggcgggcta cggcaggtac acgcggccgc ggcgcgctct ctctagtcta     1500
tccgcggccg cgcccaggcc gatcgaggct tccgggggag agttgcgaca agagaacgga     1560
ccgagggggt cggctagcgg tagcaagttc cctgttggtt tgtggcgttg gagcgttgcg     1620
gagaggcttg cgcggcggcg gggacgtcga cggggacgtg gcggggagac gatacgatgg     1680
gtgccgggca gggcaacgct ttcggcgggt ggccgtgtcc aggtgcgcgc ggccttgtcg     1740 gtttcccccct ctcggtgtcc atggccgaga aatgggtcga cgaccgagac cgacgctcgg     1800
tgcggcgccc atcccgtctg atccgccgcg ccacgcgagc ggccctatgc gatgccgcac     1860
gggcgcggag ggccgtcgcg cggagtataa tgtatagtat atagtacaag gttggttgga     1920
gtcgggttgg gttggatcgg gtcaccggta cgtggtggct gctgttgccc ccgccgtttc     1980
cgcttgcact tttgtcgcgg tttcgctggc gatccggcac gcggcgccca caccacgccg     2040
gggctccaaa cagctcgggc ccttggccgt gtgggtggca ggcacttgca cgcgtccggt     2100
tgtcgcggcc tggcccgccg ccgggcgcac cgcaacaatg agacagcccg acacgatgat     2160 tcttgtcac tgtgctaacc cgcatgccat gcaggcgctg tcgaacggga ggtacaagag      2220
ctgcctgcac cgcgcggtgg tgaaccagcg gcgggcgcgg cggtcgctgg ccttcttcct     2280
gtgcccgcgc gaggaccggg tggtgcgccc gccggccagt gctgcgccgc ggcgctaccc     2340
ggacttcacc tgggccgacc tcatgcgctt cacgcagcgc cactaccgcg ccgacacccg     2400
cacgctggac gccttcaccc gctggctctc ccacggcccg gcccaggcgg cggcgcctcc     2460
ctgcacctag                                                           2470
```

<210> SEQ ID NO 260

-continued

```
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 260
atgaggccgc gcctccctcc aaatgttccc tccctgcctt cgtctttgtc gttgctcgca      60
aactccctgt cctcccctgt tacaaatacc cccacccgcc cggacagctt ccctgcatac     120
ttgcagctcg cacatctcat ggtgtcgcag gaacgacaag agccagctgt gcctagcagc     180
agcagcagca gcgccaagcg cgcagccacg tccatggacg ccagcccggc cccgccgctc     240
ctcctccgcg cccccactcc cagccccagc attgacctcc cacgctggca aggacaaggc     300
cgacgcggcg gccagcaagg ccggcgcggc cgtgttcgac ctgcgccggg agcccaagat     360
ccccgcgcca ttcctgtggc cgcaggaaga ggcgcggccg tcctcggccg cggagctgga     420
ggtgccgatg gtggacgtgg gcgtgctgcg caatggcgac cgcgcggggc tgcggcgcgc     480
cgcggcgcag gtggccgcgg cgtgcgcgac gcacgggttc ttccaggtgt gcgggcacgg     540
cgtggacgcg gcgctggggc gcgccgcgct ggacggcgcc agcgacttct tccggctgcc     600
gctcgccgag aagcagcgcg cccggcgcgt ccccggcacc gtgtccgggt acacgagcgc     660
gcacgccgac cggttcgcgg ccaagctccc ctggaaggag accctgtcgt tcggctacca     720
cgacggcgcc gcgtcgcctg tcgtcgtgga ctacttcgtc ggcaccctcg gccaggattt     780
cgagccaatg gggtaagtaa ggtagtaaga aggagcgccg gtttacattt accgcacgtc     840
ggcgtgcggt cgagtcggga ctcgggagac gtatgaaccc ccgtcccgtc ccatgcatgt     900
gtggcaggtg ggtgtaccag aggtactgcg aggagatgaa ggagctgtcg ctgacgatca     960
tggagctgct ggagctgagc ctgggcgtgg agctgcgcgg ctactaccgg gagttcttcg    1020
aggacagccg gtccatcatg cggtgcaact actacccgcc gtgcccggag ccggagcgca    1080
cgctgggcac gggcccgcac tgcgaccccca cggcgctcac catcctcctg caggacgacg    1140
tgggcgggct ggaggtgctg gtggacggtg agtggcgccc cgtccggccc gtcccgggcg    1200
ccatggtcat caacatcggc gacacccttca tggtaacgaa acgaaagcgc tcgctcctct    1260
gttttccttg gccgctcttg tcctgtgtgt atattcagtt gagctctctc tgtgctgtta    1320
tttcccgaat cctagtggac ctaaacgggc aggttattac agcacgcaca cgtaggcatg    1380
tcatgtagct agtacataca tagcgatgcc gatgcaaatg caatagagac atgcgttcga    1440
gttggttcct atctcggcgg gctacggcag gtacacgcgg ccgcggcgcg ctctctctag    1500
tctatccgcg gccgcgccca ggccgatcga ggcttccggg ggagagttgc gacaagagaa    1560
cggaccgagg gggtcggcta gcggtagcaa gttccctgtt ggtttgtggc gttggagcgt    1620
tgcggagagg cttgcgcggc ggcggggacg tcgacgggga cgtggcgggg agacgatacg    1680
atgggtgccg ggcagggcaa cgctttcggc gggtggccgt gtccaggtgc gcgcggcctt    1740
gtcggtttcc ccctctcggt gtccatggcc gagaaatggg tcgacgaccg agaccgacgc    1800
tcggtgcggc gcccatcccg tctgatccgc cgcgccacgc gagcggccct atgcgatgcc    1860
gcacgggcgc ggagggccgt cgcgcggagt ataatgtata gtatatagta caaggttggt    1920
tggagtcggg ttgggttgga tcgggtcacc ggtacgtggt ggctgctgtt gcccccgccg    1980
tttccgcttg cacttttgtc gcggtttcgc tggcgatccg gcacgcgcg cccacaccac    2040 gccgggctc caaacagctc gggcccttgg ccgtgtgggt ggcaggcact tgcacgcgtc    2100
cggttgtcgc ggcctggccc gccgccgggc gcaccgcaac aatgagacag cccgacacga    2160
```

-continued

```
tgattcttgt gcactgtgct aacccgcatg ccatgcaggc gctgtcgaac gggaggtaca      2220
agagctgcct gcaccgcgcg gtggtgaacc agcggcgggc gcggcggtcg ctggccttct      2280
tcctgtgccc gcgcgaggac cgggtggtgc gcccgccggc cagtgctgcg ccgcggcgct      2340
acccggactt cacctgggcc gacctcatgc gcttcacgca gcgccactac cgcgccgaca      2400
cccgcacgct ggacgccttc acccgctggc tctcccacgg cccggcccag gcggcggcgc      2460
ctccctgcac ctag                                                        2474

<210> SEQ ID NO 261
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 261
atgaggccgc gcctccctcc aaatgttccc tccctgcctt cgtctttgtc gttgctcgca       60
aactccctgt cctcccctgt tacaaatacc cccacccgcc cggacagctt ccctgcatac      120
ttgcagctcg cacatctcat ggtgtcgcag gaacgacaag agccagctgt gcctagcagc      180
agcagcagca gcgccaagcg cgcagccacg tccatggacg ccagcccggc cccgccgctc      240
ctcctccgcg cccccactcc cagccccagc attgacctcc cccgctggca aggacaaggc      300
cgacgcggcg gccagcaagg ccggcgcggc cgtgttcgac ctgcgccggg agcccaagat      360
ccccgcgcca ttcctgtggc cgcaggaaga ggcgcggccg tcctcggccg cggagctgga      420
ggtgccgatg gtggacgtgg gcgtgctgcg caatggcgac cgcgcggggc tgcggcgcgc      480
cgcggcgcag gtggccgcgg cgtgcgcgac gcacgggttc ttccaggtgt gcgggcacgg      540
cgtggacgcg gcgctggggc gcgccgcgct ggacggcgcc agcgacttct tccggctgcc      600
gctcgccgag aagcagcgcg cccggcgcgt ccccggcacc gtgtccgggt acacgagcgc      660
gcacgccgac cggttcgcgg ccaagctccc ctggaaggag accctgtcgt tcggctacca      720
cgacggcgcc gcgtcgcctg tcgtcgtgga ctacttcgtc ggcaccctcg gccaggattt      780
cgagccaatg gggtaagtaa ggtagtaaga aggagcgccg gtttacattt accgcacgtc      840
ggcgtgcggt cgagtcggga ctcgggagac gtatgaaccc ccgtcccgtc ccatgcatgt      900
gtggcaggtg gtgtaccag aggtactgcg aggagatgaa ggagctgtcg ctgacgatca      960
tggagctgct ggagctgagc ctgggcgtgg agctgcgcgg ctactaccgg gagttcttcg     1020
aggacagccg gtccatcatg cggtgcaact actacccgcc gtgcccggag ccggagcgca     1080
cgctgggcac gggcccgcac tgcgacccca cggcgctcac catcctcctg caggacgacg     1140
tgggcggggc ggaggtgctg gtggacggtg agtggcgccc cgtccggccc gtcccgggcg     1200
ccatggtcat caacatcggc gacaccttca tggtaacgaa acgaaagcgc tcgctcctct     1260
gttttccttg gccgctcttg tcctgtgtgt atattcagtt gagctctctc tgtgctgtta     1320
tttcccgaat cctagtggac ctaaacgggc aggttattac agcacgcaca cgtaggcatg     1380
tcatgtagct agtacataca tagcgatgcc gatgcaaatg caatagagac atgcgttcga     1440
gttggttcct atctcggcgg gctacggcag gtacacgcgg ccgcggcgcg ctctctctag     1500
tctatccgcg gccgcgccca ggccgatcga ggcttccggg ggagagttgc gacaagagaa     1560
cggaccgagg gggtcggcta gcggtagcaa gttccctgtt ggtttgtggc gttggagcgt     1620
tgcggagagg cttgcgcggc ggcggggacg tcgacgggga cgtggcgggg agacgatacg     1680
```

-continued

```
atgggtgccg ggcagggcaa cgctttcggc gggtggccgt gtccaggtgc gcgcggcctt    1740
gtcggtttcc ccctctcggt gtccatggcc gagaaatggg tcgacgaccg agaccgacgc    1800
tcggtgcggc gcccatcccg tctgatccgc cgcgccacgc gagcggccct atgcgatgcc    1860
gcacgggcgc ggagggccgt cgcgcggagt ataatgtata gtatatagta caaggttggt    1920
tggagtcggg ttgggttgga tcgggtcacc ggtacgtggt ggctgctgtt gccccgccg    1980 tttccgcttg cacttttgtc gcggtttcgc tggcgatccg gcacgcggcg cccacaccac    2040
gccggggctc caaacagctc gggcccttgg ccgtgtgggt ggcaggcact tgcacgcgtc    2100
cggttgtcgc ggcctggccc gccgccgggc gcaccgcaac aatgagacag cccgacacga    2160
tgattcttgt gcactgtgct aacccgcatg ccatgcaggc gctgtcgaac gggaggtaca    2220
agagctgcct gcaccgcgcg gtggtgaacc agcggcgggc gcggcggtcg ctggccttct    2280
tcctgtgccc gcgcgaggac cgggtggtgc gcccgccggc cagtgctgcg ccgcggcgct    2340
acccggactt cacctgggcc gacctcatgc gcttcacgca gcgccactac cgcgccgaca    2400
cccgcacgct ggacgccttc acccgctggc tctcccacgg cccggcccag gcggcggcgc    2460
ctccctgcac ctag                                                       2474
```

METHODS AND COMPOSITIONS FOR INCREASING HARVESTABLE YIELD VIA EDITING GA20 OXIDASE GENES TO GENERATE SHORT STATURE PLANTS

CROSS-REFERENCE TO RELATED APPLICATIONS

This application is a U.S. National Stage of International Application No. PCT/US2019/018133, filed Feb. 15, 2019, which claims the benefit of U.S. Provisional Application No. 62/631,412, filed Feb. 15, 2018, and U.S. Provisional Application No. 62/631,416, filed Feb. 15, 2018, all of which are incorporated by reference in their entireties herein.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052058631SUBSEQLIST.TXT, date recorded: Jul. 10, 2023, size: 392,290 bytes).

BACKGROUND

The present disclosure relates to compositions and methods for improving traits, such as lodging resistance and increased yield in corn.

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, have not been realized through manipulation of the GA pathway. Indeed, some mutations in the GA pathway genes have been associated with various off-types in corn that are incompatible with yield, which has led researchers away from finding semi-dwarf, high-yielding corn varieties via manipulation of the GA pathway.

There continues to be a need in the art for the development of monocot or cereal crop plants, such as corn, having increased yield and/or resistance to lodging.

SUMMARY

In an aspect, the present disclosure provides a modified corn plant having a reduced plant height relative to a wild type control plant, and (i) an increased stem or stalk diameter relative to a wild type control plant, (ii) improved lodging resistance relative to a wild type control plant, or (iii) improved drought tolerance relative to a wild type control plant.

In an aspect, the present disclosure provides a modified corn plant, or plant part thereof, with a desirable semi-dwarf phenotype and having an intermediate plant height reduction. In another aspect, a modified corn plant with moderately reduced plant height can offer agronomic advantages over either unmodified plants with regular height or other modified plants that may exhibit a strong reduction in plant height.

In an aspect, the present disclosure provides a modified corn plant, or plant part thereof, comprising a mutant allele at GA20 oxidase_3 locus and a mutant allele at GA20 oxidase_5 locus, wherein at least one of the GA20 oxidase_3 and GA20 oxidase_5 loci comprises homozygous mutant alleles.

In another aspect, the present disclosure provides a modified corn plant, or plant part thereof, comprising a first homozygous mutation in one of GA20 oxidase_3 and GA20 oxidase_5 genes and further comprising a second heterozygous or homozygous mutation in the other one of the GA20 oxidase_3 and GA20 oxidase_5 genes.

In an aspect, the present disclosure provides a method of making a modified corn plant, or plant part thereof, comprising: (a) crossing a first corn plant comprising a mutant allele of the GA20 oxidase_3 locus with a second plant comprising a mutant allele of the GA20 oxidase_5 locus; and (b) selecting a progeny corn plant, or plant part thereof, from the cross in step (a) that is (i) homozygous for one or more mutant alleles of the GA20 oxidase_3 locus and heterozygous for a mutant allele of the GA20 oxidase_5 locus, or (ii) heterozygous for a mutant allele of the GA20 oxidase_3 locus and homozygous for one or more mutant alleles of the GA20 oxidase_5 locus.

In another aspect, the present disclosure provides a method of making a modified corn plant, or plant part thereof, comprising: (a) crossing a first corn plant comprising a mutant allele of the GA20 oxidase_3 locus and a mutant allele of the GA20 oxidase_5 locus with a second plant; and (b) selecting a progeny corn plant, or plant part thereof, from the cross in step (a) that is (i) homozygous for one or more mutant alleles of the GA20 oxidase_3 locus and heterozygous for a mutant allele of the GA20 oxidase_5 locus, or (ii) heterozygous for a mutant allele of the GA20 oxidase_3 locus and homozygous for one or more mutant alleles of the GA20 oxidase_5 locus.

BRIEF DESCRIPTION OF THE DRAWINGS

FIG. 1 shows plant heights of inbred mutant plants having edited mutant GA20 oxidase_3 and/or GA20 oxidase_5 genes in comparison to inbred wild-type control plants and plants expressing a GA20 oxidase suppression construct.

DETAILED DESCRIPTION

To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, "locus" is a chromosomal locus or region where a polymorphic nucleic acid, trait determinant, gene, or marker is located. A "locus" can be shared by two homologous chromosomes to refer to their corresponding locus or region. As used herein, "allele" refers to an alternative nucleic acid sequence of a gene or at a particular locus (e.g., a nucleic acid sequence of a gene or locus that is different than other alleles for the same gene or locus). Such an allele can be considered (i) wild-type or (ii) mutant if one or more mutations or edits are present in the nucleic acid sequence of the mutant allele relative to the wild-type allele. A mutant allele for a gene may have a reduced or eliminated activity or expression level for the gene relative to the wild-type allele. For diploid organisms such as corn, a first allele can occur on one chromosome, and a second allele can occur at the same locus on a second homologous chromosome. If one allele at a locus on one chromosome of a plant is a mutant allele and the other corresponding allele on the homologous chromosome of the plant is wild-type, then the plant is described as being heterozygous for the mutant allele. However, if both alleles at a locus are mutant alleles, then the plant is described as being homozygous for the mutant alleles. A plant homozygous for mutant alleles at a locus may comprise the same mutant allele or different mutant alleles if heteroallelic or biallelic.

As used herein, a "wild-type gene" or "wild-type allele" refers to a gene or allele having a sequence or genotype that is most common in a particular plant species, or another sequence or genotype with natural variations, polymorphisms, or other silent mutations relative to the most common sequence or genotype that do not significantly impact the expression and activity of the gene or allele. Indeed, a "wild-type" gene or allele contains no variation, polymorphism, or any other type of mutation that substantially affects the normal function, activity, expression, or phenotypic consequence of the gene or allele.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" may also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity may be adjusted upwards to correct for the conservative nature of the non-identical substitution(s). Sequences that differ by such conservative substitutions are said to have "sequence similarity" or "similarity." Thus, "percent similarity" or "percent similar" as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pair-wise or multiple sequence alignment algorithms and programs are known in the art, such as ClustalW, or Basic Local Alignment Search Tool® (BLAST®), etc., that may be used to compare the sequence identity or similarity between two or more nucleotide or protein sequences. Although other alignment and comparison methods are known in the art, the alignment between two sequences (including the percent identity ranges described above) may be as determined by the ClustalW or BLAST® algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity may be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences may be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more GA oxidase gene(s) relative to a wild-type or control plant, plant seed, plant part, plant cell, and/or plant genome, such as via a genome editing event or mutation affecting (e.g., reducing or eliminating) the expression level or activity of one or more endogenous GA3 and/or GA20 oxidase genes. Indeed, the term "modified" may further refer to a plant, plant seed, plant part, plant cell, and/or plant genome having one or more mutations affecting expression of one or more endogenous GA oxidase genes, such as one or more endogenous GA3 and/or GA20 oxidase genes, introduced through chemical mutagenesis, transposon insertion or excision, or any other known mutagenesis technique, or introduced through genome editing. For clarity, therefore, a modified plant, plant seed, plant part, plant cell, and/or plant genome includes a mutated and/or edited plant, plant seed, plant part, plant cell, and/or plant genome having a modified expression level, expression pattern, and/or coding sequence of one or more GA oxidase gene(s) relative to a wild-type or control plant, plant seed, plant part, plant cell, and/or plant genome. Modified plants may be homozygous or heterozygous for any given mutation or edit, and/or may be bi-allelic at a GA oxidase gene locus. A modified plant is bi-allelic for a GA oxidase gene if each copy of the GA oxidase gene is modified by a different allele (i.e., different mutation(s) and/or edit(s)), wherein each allele lowers the expression level and/or activity of the GA oxidase gene. Modified plants or seeds may contain various molecular changes that affect expression of GA oxidase gene(s), such as GA3 and/or GA20 oxidase gene(s), including genetic and/or epigenetic modifications. Modified plants, plant parts, seeds, etc., may have been subjected to mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more GA oxidase genes. A modified seed provided herein may give rise to a modified plant provided herein. A modified plant, plant seed, plant part, plant cell, or plant genome provided herein may comprise a recombinant DNA construct or vector or genome edit as provided herein. A "modified plant product" may be any product made from a modified plant, plant part, plant cell, or plant chromosome provided herein, or any portion or component thereof.

As used herein, the term "homozygous" refers to a genotype comprising two identical alleles at a given locus in a diploid genome, or a genotype comprising two non-identical mutant alleles at a given locus in a diploid genome. The latter genotype comprising two non-identical mutant alleles is also referred to as being heteroallelic or transheterozygous, or as a heteroallelic combination. As used herein, "heterozygous" describes a genotype comprising a mutant allele and a wild-type allele at a given locus in a diploid genome.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a genome editing event(s) affecting one or more GA oxidase genes. For example, a control plant may be an inbred line that is the same as the inbred line used to make the modified plant, or a control plant may be the product of the same hybrid cross of inbred parental lines as the modified plant, except for the absence in the control plant of any genome editing event(s) affecting one or more GA oxidase genes. Similarly, an unmodified control plant refers to a plant that shares a substantially similar or essentially identical genetic background as a modified plant, but without the one or more engineered changes to the genome (e.g., transgene, mutation or edit) of the modified plant. For purposes of comparison to a modified plant, plant seed, plant part, plant cell and/or plant genome, a "wild-type plant" (or likewise a "wild-type" plant seed, plant part, plant cell and/or plant genome) refers to a non-transgenic and non-genome edited control plant, plant seed, plant part, plant cell and/or plant genome. As used herein, a "control" plant, plant seed, plant part, plant cell and/or plant genome may also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, a "target site" for genome editing refers to the location of a polynucleotide sequence within a plant genome that is bound and cleaved by a site-specific nuclease introducing a double stranded break (or single-stranded nick) into the nucleic acid backbone of the polynucleotide sequence and/or its complementary DNA strand. A target site may comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. A "target site" for a RNA-guided nuclease may comprise the sequence of either complementary strand of a double-stranded nucleic acid (DNA) molecule or chromosome at the target site. A site-specific nuclease may bind to a target site, such as via a non-coding guide RNA (e.g., without being limiting, a CRISPR RNA (crRNA) or a single-guide RNA (sgRNA) as described further below). A non-coding guide RNA provided herein may be complementary to a target site (e.g., complementary to either strand of a double-stranded nucleic acid molecule or chromosome at the target site). It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA may be tolerated. A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some embodiments a target region may be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region. Apart from genome editing, the term "target site" may also be used in the context of gene suppression to refer to a portion of a mRNA molecule (e.g., a "recognition site") that is complementary to at least a portion of a non-coding RNA molecule (e.g., a miRNA, siRNA, etc.) encoded by a suppression construct.

The co-pending PCT Application No. PCT/US2017/047405 and U.S. application Ser. No. 15/679,699, both filed on Aug. 17, 2017, are incorporated herein by reference in their entirety.

Most grain producing grasses, such as wheat, rice and sorghum, produce both male and female structures within each floret of the panicle (i.e., they have a single reproductive structure). However, corn or maize is unique among the grain-producing grasses in that it forms separate male (tassel) and female (ear) inflorescences. Corn produces completely sexually dimorphic reproductive structures by selective abortion of male organs (anthers) in florets of the ear, and female organs (ovules) in the florets of the tassel within early stages of development. Precisely regulated gibberellin synthesis and signaling is critical to regulation of this selective abortion process, with the female reproductive ear being most sensitive to disruptions in the GA pathway. Indeed, the "anther ear" phenotype is the most common reproductive phenotype in GA corn mutants.

In contrast to corn, mutations in the gibberellin synthesis or signaling pathways that led to the "Green Revolution" in wheat, rice and sorghum had little impact on their reproductive structures because these crop species do not undergo the selective abortion process of the grain bearing panicle during development, and thus are not sensitive to disruptions in GA levels. The same mutations have not been utilized in corn because disruption of the GA synthesis and signaling pathway has repeatedly led to dramatic distortion and masculinization of the ear ("anther ear") and sterility (disrupted anther and microspore development) in the tassel, in addition to extreme dwarfing in some cases. See, e.g., Chen, Y. et al., "The Maize DWARF1 Encodes a Gibberellin 3-Oxidase and Is Dual Localized to the Nucleus and Cytosol," *Plant Physiology* 166: 2028-2039 (2014). These GA mutant phenotypes (off-types) in corn led to significant reductions in kernel production and a reduction in yield. Furthermore, production of anthers within the ear increases the likelihood of fungal or insect infections, which reduces the quality of the grain that is produced on those mutant ears. Forward breeding to develop semi-dwarf lines of corn has not been successful, and the reproductive off-types (as well as the extreme dwarfing) of GA mutants have been challenging to overcome. Thus, the same mutations in the GA pathway that led to the Green Revolution in other grasses have not yet been successful in corn.

Despite these prior difficulties in achieving higher grain yields in corn through manipulation of the GA pathway, the present inventors have discovered a way to manipulate GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants may also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

According to embodiments of the present disclosure, modified corn plants are provided that have at least one beneficial agronomic trait and at least one female reproductive organ or ear that is substantially or completely free of off-types. The beneficial agronomic trait may include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. Off-types may include male (tassel or anther) sterility, reduced kernel or seed number, and/or the presence of one or more masculinized or male (or male-like) reproductive structures in the female organ or ear (e.g., anther ear) of the plant. A modified corn plant is provided herein that lacks significant off-types in the reproductive tissues of the plant. Such a modified corn plant may have a female reproductive organ or ear that appears normal relative to a control or wild-type plant. Indeed, modified corn plants are provided that comprise at least one reproductive organ or ear that does not have or exhibit, or is substantially or completely free of, off-types including male sterility, reduced kernel or seed number, and/or masculinized structure(s) in one or more female organs or ears. As used herein, a female organ or ear of a plant, such as corn, is "substantially free" of male reproductive structures if male reproductive structures are absent or nearly absent in the female organ or ear of the plant based on visual inspection of the female organ or ear at later reproductive stages. A female organ or ear of a plant, such as corn, is "completely free" of mature male reproductive structures if male reproductive structures are absent or not observed or observable in the female organ or ear of the plant, such as a corn plant, by visual inspection of the female organ or ear at later reproductive stages. A female organ or ear of a plant, such as corn, without significant off-types and substantially free of male reproductive structures in the ear may have a number of kernels or seeds per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the number of kernels or seeds per female organ or ear of a wild-type or control plant. Likewise, a female organ or ear of a plant, such as corn, without significant off-types and substantially free of male reproductive structures in the ear may have an average kernel or seed weight per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the average kernel or seed weight per female organ or ear of a wild-type or control plant. A female organ or ear of a plant, such as corn, that is completely free of mature male reproductive structures may have a number of kernels or seeds per female organ or ear of the plant that is about the same as a wild-type or control plant. In other words, the reproductive development of the female organ or ear of the plant may be normal or substantially normal. However, the number of seeds or kernels per female organ or ear may depend on other factors that affect resource utilization and development of the plant. Indeed, the number of kernels or seeds per female organ or ear of the plant, and/or the kernel or seed weight per female organ or ear of the plant, may be about the same or greater than a wild-type or control plant.

The plant hormone gibberellin plays an important role in a number of plant developmental processes including germination, cell elongation, flowering, embryogenesis and seed development. Certain biosynthetic enzymes (e.g., GA20 oxidase and GA3 oxidase) and catabolic enzymes (e.g., GA2 oxidase) in the GA pathway are critical to affecting active GA levels in plant tissues.

Several of the GA oxidases in cereal plants consist of a family of related GA oxidase genes. For example, corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1.

correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

A modified plant, plant part, cell, or explant provided herein may be of an elite variety or an elite line. An elite variety or an elite line refers to a variety that has resulted from breeding and selection for superior agronomic performance. A edited plant, cell, or explant provided herein may be a hybrid plant, cell, or explant. As used herein, a "hybrid" is created by crossing two plants from different varieties, lines, inbreds, or species, such that the progeny comprises genetic material from each parent. Skilled artisans recognize that higher order hybrids can be generated as well. For example, a first hybrid can be made by crossing Variety A with Variety B to create a A×B hybrid, and a second hybrid can be made by crossing Variety C with Variety D to create an C×D hybrid. The first and second hybrids can be further crossed to create the higher order hybrid (A×B)×(C×D) comprising genetic information from all four parent varieties.

Targeted mutations in the genome of a plant can be made by introducing a double strand break (DSB) or nick. According to this approach, mutations, such as deletions, insertions, inversions and/or substitutions may be introduced at a target site via imperfect repair of the DSB or nick to produce a knock-out or knock-down of a GA oxidase gene. Such mutations may be generated by imperfect repair of the targeted locus even without the use of a donor template molecule. A "knock-out" of a GA oxidase gene may be

TABLE 1

DNA and protein sequences by sequence identifier
for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

The genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 achieved by inducing a DSB or nick at or near the endogenous locus of the GA oxidase gene that results in non-expression of the GA oxidase protein or expression of a non-functional protein, whereas a "knock-down" of a GA oxidase gene may be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein. For example, the site of the DSB or nick within the endogenous locus may be in the upstream or 5' region of the GA oxidase gene (e.g., a promoter and/or enhancer sequence) to affect or reduce its level of expression. Similarly, such targeted knock-out or knock-down mutations of a GA oxidase gene may be generated with a donor template molecule to direct a particular or desired mutation at or near the target site via repair of the DSB or nick. The donor template molecule may comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene may be achieved by deleting or inverting at least a portion of the gene or by introducing a frame shift or premature stop codon into the coding sequence of the gene. A deletion of a portion of a GA oxidase gene may also be introduced by generating DSBs or nicks at two target sites and causing a deletion of the intervening target region flanked by the target sites.

A site-specific nuclease provided herein may be selected from the group consisting of a zinc-finger nuclease (ZFN), a meganuclease, an RNA-guided endonuclease, a TALE-endonuclease (TALEN), a recombinase, a transposase, or any combination thereof. See, e.g., Khandagale, K. et al., "Genome editing for targeted improvement in plants," *Plant Biotechnol Rep* 10: 327-343 (2016); and Gaj, T. et al., "ZFN, TALEN and CRISPR/Cas-based methods for genome engineering," *Trends Biotechnol.* 31(7): 397-405 (2013), the contents and disclosures of which are incorporated herein by reference. A recombinase may be a serine recombinase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombinase, and a Tnp1 recombinase. According to some embodiments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA transposase attached to a DNA binding domain provided herein is selected from the group consisting of a TALE-piggyBac and TALE-Mutator.

According to embodiments of the present disclosure, an RNA-guided endonuclease may be selected from the group consisting of Cast, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo) and homologs or modified versions thereof. According to some embodiments, an RNA-guided endonuclease may be a Cas9 or Cpf1 enzyme.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1. In another aspect, a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, an RNA-guided nuclease provided herein is selected from the group consisting of a Cas9 or a Cpf1. In another aspect, an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

For RNA-guided endonucleases, a guide RNA (gRNA) molecule is further provided to direct the endonuclease to a target site in the genome of the plant via base-pairing or hybridization to cause a DSB or nick at or near the target site. The gRNA may be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the plant genome, such as at or near a GA oxidase gene. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. See, e.g., Wu, X. et al., "Target specificity of the CRISPR-Cas9 system," *Quant Biol.* 2(2): 59-70 (2014), the content and disclosure of which is incorporated herein by reference. The genomic PAM sequence on the sense (+) strand adjacent to the target site (relative to the targeting sequence of the guide RNA) may comprise 5'-NGG-3'. However, the corresponding sequence of the guide RNA (i.e., immediately downstream (3') to the targeting sequence of the guide RNA) may generally not be complementary to the genomic PAM sequence. The guide RNA may typically be a non-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

In an aspect, the GA20 oxidase_3 gene is edited via a genome editing technique. For genome editing at or near the GA20 oxidase_3 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto). For genome editing at or near the GA20 oxidase_5 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto). As used herein, the term "consecutive" in reference to a polynucleotide or protein sequence means without deletions or gaps in the sequence.

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA20 oxidase_3 or GA20 oxidase_5 gene to mutate one or more promoter and/or regulatory sequences of the gene and affect or reduce its level of expression. For knockdown (and possibly knockout) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3096 of SEQ ID NO: 34, the nucleotide sequence range 3666-3775 of SEQ ID NO: 34, the nucleotide sequence range 4098-5314 of SEQ ID NO: 34, the nucleotide sequence range 5585-5800 of SEQ ID NO: 34, or the nucleotide sequence range 5801-8800 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3096, 3666-3775, 4098-5314, 5585-5800, 5801-8800, or 5585-8800 of SEQ ID NO: 34, or a sequence complementary thereto).

For knockdown (and possibly knockout) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3000 of SEQ ID NO: 35, the nucleotide sequence range 1-3000 of SEQ ID NO: 35, the nucleotide sequence range 3792-3906 of SEQ ID NO: 35, the nucleotide sequence range 4476-5197 of SEQ ID NO: 35, or the nucleotide sequence range 5860-8859 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3000, 3792-3906, 4476-5197, or 5860-8859 of SEQ ID NO: 35, or a sequence complementary thereto).

For knockout (and possibly knockdown) mutations through genome editing, an RNA-guided endonuclease may be targeted to a coding and/or intron sequence of a GA20 oxidase_3 or GA20 oxidase_5 gene to potentially eliminate expression and/or activity of a functional GA oxidase protein from the gene. However, a knockout of a GA oxidase gene expression may also be achieved in some cases by targeting the upstream and/or 5'UTR sequence(s) of the gene, or other sequences at or near the genomic locus of the gene. Thus, a knockout of a GA oxidase gene expression may be achieved by targeting a genomic sequence at or near the site or locus of a targeted GA20 oxidase_3 or GA20 oxidase_5 gene, an upstream or downstream sequence, such as a promoter and/or enhancer sequence, or an intron, 5'UTR, and/or 3'UTR sequence, of a GA20 oxidase_3 or GA20 oxidase_5 gene, as described above for knockdown of a GA20 oxidase_3 or GA20 oxidase_5 gene.

For knockout (and possibly knockdown) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3097-5584 of SEQ ID NO: 34, the nucleotide sequence range 3097-3665 of SEQ ID NO: 34, the nucleotide sequence range 3776-4097 of SEQ ID NO: 34, or the nucleotide sequence range 5315-5584 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 3097-5584, 3097-3665, 3097-3775, 3665-4097, 3776-4097, 3776-5314, 4098-5584, or 5315-5584 of SEQ ID NO: 34, or a sequence complementary thereto).

For knockout (and possibly knockdown) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3001-5473 of SEQ ID NO: 35, the nucleotide sequence range 3001-3791 of SEQ ID NO: 35, the nucleotide sequence range 3907-4475 of SEQ ID NO: 35, or the nucleotide sequence range 5198-5473 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 3001-5473, 3001-3791, 3001-3906, 3792-4475, 3907-4475, 3907-5197, 4476-5473, or 5198-5473 of SEQ ID NO: 35, or a sequence complementary thereto).

According to some embodiments, a guide RNA for targeting an endogenous GA20 oxidase_3 and/or GA20 oxidase_5 gene is provided, which may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167. According to some embodiments, a guide RNA for targeting both of the endogenous GA20 oxidase_3 and GA20 oxidase_5 genes is provided, which may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of SEQ ID NO: 34, and at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of SEQ ID NO: 35. According to some embodiments, a guide RNA for targeting both of the endogenous GA20 oxidase_3 and GA20 oxidase_5 genes is provided, which may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 158-167.

In addition to the guide sequence, a guide RNA may further comprise one or more other structural or scaffold sequence(s), which may bind or interact with an RNA-guided endonuclease. Such scaffold or structural sequences may further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

According to some embodiments, recombinant DNA constructs and vectors are provided comprising a polynucleotide sequence encoding a site-specific nuclease, such as a zinc-finger nuclease (ZFN), a meganuclease, an RNA-guided endonuclease, a TALE-endonuclease (TALEN), a recombinase, or a transposase, wherein the coding sequence is operably linked to a plant expressible promoter. For RNA-guided endonucleases, recombinant DNA constructs and vectors are further provided comprising a polynucleotide sequence encoding a guide RNA, wherein the guide RNA comprises a guide sequence of sufficient length having a percent identity or complementarity to a target site within the genome of a plant, such as at or near a targeted GA oxidase gene. According to some embodiments, a polynucleotide sequence of a recombinant DNA construct and vector that encodes a site-specific nuclease or a guide RNA may be operably linked to a plant expressible promoter, such as an inducible promoter, a constitutive promoter, a tissue-specific promoter, etc.

In an aspect, the present disclosure provides a modified corn plant, or plant part thereof, comprising a mutant allele at the GA20 oxidase_3 locus and a mutant allele at the GA20 oxidase_5 locus, wherein at least one of the GA20 oxidase_3 and GA20 oxidase_5 loci comprises homozygous mutant alleles. In another aspect, a modified corn plant comprises homozygous alleles at the GA20 oxidase_3 locus. In another aspect, a modified corn plant comprises homozygous alleles at the GA20 oxidase_5 locus. In a further aspect, only one of the GA20 oxidase_3 and GA20 oxidase_5 loci comprises homozygous alleles in a modified corn plant. In another aspect, a modified corn plant comprises homozygous alleles at both of the GA20 oxidase_3 and GA20 oxidase_5 loci. In another aspect, one or both of the GA20 oxidase_3 and GA20 oxidase_5 loci comprise a heteroallelic combination or two identical mutant alleles in a modified plant. In an aspect, a modified plant comprises a homozygous GA20 oxidase_3 locus comprising a heteroallelic combination of mutant alleles and a heterozygous GA20 oxidase_5 locus. In another aspect, a modified plant comprises a homozygous GA20 oxidase_3 locus comprising a heteroallelic combination of mutant alleles and a heterozygous GA20 oxidase_5 locus. In an aspect, a modified plant comprises a heterozygous GA20 oxidase_3 locus and a homozygous GA20 oxidase_5 locus comprising a heteroallelic combination of mutant alleles. In another aspect, a modified plant comprises a heterozygous GA20 oxidase_3 locus and a homozygous GA20 oxidase_5 locus comprising two identical mutant alleles.

In another aspect, the present disclosure provides a modified corn plant, or plant part thereof, comprising a first homozygous mutation in one of GA20 oxidase_3 and GA20 oxidase_5 genes and further comprising a second heterozygous or homozygous mutation in the other one of the GA20 oxidase_3 and GA20 oxidase_5 genes. In an aspect, a first homozygous mutation is in GA20 oxidase_3. In another aspect, a second mutation is heterozygous in GA20 oxidase_5. In an aspect, a first homozygous mutation is in GA20 oxidase_5. In another aspect, a second mutation is heterozygous in GA20 oxidase_3. In a further aspect, a first homozygous mutation comprises a heteroallelic combination of mutations or two identical mutant alleles in one of the GA20 oxidase_3 and GA20 oxidase_5 genes.

In an aspect, a GA20 oxidase_3 locus or gene comprises a sequence sharing at least 80%, at least 85%, at least 90%, at least 95%, at least 99%, or at least 99.5% sequence identity to SEQ ID No. 34 or 168. In an aspect, a GA20 oxidase_5 locus or gene comprises a sequence sharing at least 80%, at least 85%, at least 90%, at least 95%, at least 99%, or at least 99.5% sequence identity to SEQ ID No. 35 or 169.

In an aspect, a GA20 oxidase_3 or GA20 oxidase_5 mutation (mutant gene or mutant allele) comprises a mutation type selected from the group consisting of a nonsense mutation, a missense mutation, a frameshift mutation, and a splice-site mutation. In an aspect, a GA20 oxidase_3 or GA20 oxidase_5 mutation (or mutant allele) results in a truncated mRNA or polypeptide, or results in a non-translatable mRNA molecule. A missense mutation is a change in one DNA base pair that results in the substitution of one amino acid for another in the protein made by a gene. A nonsense mutation is also a change in one DNA base pair. Instead of substituting one amino acid for another, however, the altered DNA sequence prematurely signals the cell to stop building a protein. This type of mutation results in a shortened protein that may function improperly or not at all. A frameshift mutation occurs when the addition or loss of DNA bases changes a gene's reading frame. A frameshift mutation shifts the grouping of these bases and changes the code for amino acids. The resulting protein, even if made, is usually nonfunctional. Insertions, deletions, and duplications can all be frameshift mutations. In another aspect, a GA20 oxidase_3 or GA20 oxidase_5 mutation (mutant gene or mutant allele) can comprise a silent mutation which does not change an encoded amino acid sequence, but can affect mRNA transcript expression, stability or protein translation efficiency, or otherwise contribute to reduced enzyme activity, relative to a corresponding wild type GA20 oxidase_3 or GA20 oxidase_5 gene. In a further aspect, a GA20 oxidase_3 or GA20 oxidase_5 mutation (mutant gene or mutant allele) can comprise a mutation or edit at or around the TATA box or other promoter elements that affect gene transcription. In an aspect, a GA20 oxidase_3 mutation or allele in a modified corn plant is a recessive mutation or allele. In an aspect, a GA20 oxidase_3 mutation or allele in a modified corn plant is a dominant mutation or allele. In an aspect, a GA20 oxidase_5 mutation or allele in a modified corn plant is a recessive mutation or allele. In an aspect, a GA20 oxidase_5 mutation or allele in a modified corn plant is a dominant mutation or allele.

In an aspect, a GA20 oxidase_3 or GA20 oxidase_5 mutation (or mutant allele) comprises a mutation in a GA20 oxidase_3 or GA20 oxidase_5 sequence region selected from the group consisting of a promoter, 5' UTR, first exon, first intron, second exon, second intron, third exon, 3' UTR, and terminator. In an aspect, a GA20 oxidase_3 or GA20 oxidase_5 mutation (or mutant allele) comprises a mutation in the first or second exon of the GA20 oxidase_3 or GA20 oxidase_5 gene.

In an aspect, a mutant GA20 oxidase_3 or GA20 oxidase_5 allele exhibits an at least 30%, at least 40%, at least 50%, at least 60%, at least 70%, at least 80%, at least 90%, at least 95%, or 100% reduction of expression or enzymatic activity relative to an unmodified, wild-type GA20 oxidase_3 or GA20 oxidase_5 gene allele. In another aspect, a mutant GA20 oxidase_3 or GA20 oxidase_5 allele comprises a mutation in a sequence region selected from the group consisting of a promoter, 5' UTR, first exon, first intron, second exon, second intron, third exon, 3' UTR, terminator, and any combination thereof. In another aspect, a mutant GA20 oxidase_3 or GA20 oxidase_5 allele comprises one or more mutation types selected from the group consisting of a nonsense mutation, a missense mutation, a frameshift mutation, a splice-site mutation, and any combination thereof. In another aspect, a mutant GA20 oxidase_3 or GA20 oxidase_5 allele results in one or more of the following: a protein truncation, a non-translatable transcript, a non-functional protein, a premature stop codon, and any combination thereof. In another aspect, a mutant GA20 oxidase_3 or GA20 oxidase_5 allele comprises a mutation selected from the group consisting of a substitution, a deletion, an insertion, a duplication, and an inversion of one or more nucleotides relative to a wild-type GA20 oxidase_3 gene. In another aspect, a mutant GA20 oxidase_3 or GA20 oxidase_5 allele comprises one or more mutations in the first exon. In another aspect, a mutant GA20 oxidase_3 or GA20 oxidase_5 allele comprises one or more mutations in the second exon.

In an aspect, a modified corn plant, or plant part thereof, comprises a first mutation comprising one or more alleles, as a pair of two identical alleles or a heteroallelic combination, selected from the group consisting of: a deletion of 13 bases starting at 536; a deletion of base 542; an insertion of CC at base 542; a deletion of base 541; a deletion of 3 nt starting at base 540; a deletion of 2 bases starting at base 422; an insertion of an A at base 422; an insertion of a T at base 422; a deletion of base 564; an insertion of an A at base 564; an insertion of a C at base 565; and an insertion of a C at base 63; wherein the base numbering is based on SEQ ID No. 168 and counted from the first nucleotide of SEQ ID NO: 168 in the 5' to 3' direction. In another aspect, a modified corn plant, or plant part thereof, comprises a first mutation comprising one or more alleles, as a pair of two identical alleles or a heteroallelic combination, selected from the group consisting of: a deletion of base 644; a deletion of 2 bases starting at base 644; an insertion of a T at base 644; a deletion of base 372; a deletion of base 786; a deletion of 5 bases starting at base 786; a deletion of 2 bases starting at base 101; an insertion of a T at base base 102; a deletion of 3 bases starting at base 99; an insertion of an A at base 282; and an insertion of a C at base 282; wherein the base numbering is based on SEQ ID No. 169 and counted from the first nucleotide of SEQ ID NO: 169 in the 5' to 3' direction. In an aspect, a modified corn plant, or plant part thereof, comprises a first mutation identified by one or more of SEQ ID Nos.: 170 to 193 and 206 to 217 relative to the corresponding reference sequence in SEQ ID No: 168. In an aspect, a modified corn plant, or plant part thereof, comprises a first mutation identified by one or more of SEQ ID Nos.: 218 to 239 and 251 to 261 relative to the corresponding reference sequence in SEQ ID No: 169. In an aspect, the present disclosure provides a progeny plant of one or more plants listed in Table 5 or 6. In another aspect, also provided is a progeny plant of any one of plant Nos. 17 to 31 in Table 6. In a further aspect, a plant is provided from a cross or hybridization of one or more plants listed in Table 5 or 6.

In an aspect, a homozygous mutant GA20 oxidase_3 gene, a homozygous mutant GA20 oxidase_5 gene, or both comprise a mutation in a sequence region selected from the group consisting of promoter, 5' UTR, first exon, first intron, second exon, second intron, third exon, 3' UTR, terminator, and any combination thereof. In an aspect, a homozygous mutant GA20 oxidase_3 gene, a homozygous mutant GA20 oxidase_5 gene, or both comprise one or more mutation types selected from the group consisting of a nonsense mutation, a missense mutation, a frameshift mutation, a splice-site mutation, and any combination thereof. In an aspect, a homozygous mutant GA20 oxidase_3 gene, a homozygous mutant GA20 oxidase_5 gene, or both result in one or more of the following: a protein truncation, a non-translatable transcript, a non-functional protein, a premature stop codon, and any combination thereof. In an aspect, a homozygous mutant GA20 oxidase_3 gene, a homozygous mutant GA20 oxidase_5 gene, or both comprise a mutation selected from the group consisting of a substitution, a deletion, an insertion, a duplication, and an inversion of one or more nucleotides relative to a wild-type GA20 oxidase_3 gene. In an aspect, a mutant GA20 oxidase_3 gene, a homozygous mutant GA20 oxidase_5 gene, or both comprise a null allele.

In an aspect, a modified corn plant described here has a shorter plant height and/or improved lodging resistance relative to an unmodified control plant. In an aspect, a modified corn plant is at least 10%, at least 20%, at least 25%, at least 30%, at least 35%, or at least 40% shorter than an unmodified control plant. In another aspect, a modified corn plant has a stalk or stem diameter at one or more stem internodes is at least 5%, at least 10%, at least 15%, at least 20%, at least 25%, at least 30%, at least 35%, or at least 40% greater than the stalk or stem diameter at the same one or more internodes of an unmodified control plant. In an aspect, a modified corn plant has a stalk or stem diameter at one or more of the first, second, third, and/or fourth internode below the ear is at least 5%, at least 10%, at least 15%, at least 20%, at least 25%, at least 30%, at least 35%, or at least 40% greater than the same internode of an unmodified control plant. In another aspect, the level of one or more active GAs in at least one internode tissue of the stem or stalk of a modified corn plant is at least 5%, at least 10%, at least 15%, at least 20%, at least 25%, at least 30%, at least 35%, or at least 40% lower than the same internode tissue of an unmodified control plant. In an aspect, the level of one or more active GAs in at least one internode tissue of the stem or stalk of a modified corn plant is lower than the same internode tissue of an unmodified control plant.

In another aspect, a modified corn plant does not have any significant off-types in at least one female organ or ear. In an aspect, a modified corn plant exhibits essentially no reproductive abnormality. In a further aspect, an off-type or reproductive abnormality is selected from the group consisting of male (tassel or anther) sterility, reduced kernel or seed number, and the presence of one or more masculinized or male (or male-like) reproductive structures in the female organ or ear (e.g., anther ear).

In another aspect, a modified corn plant comprises one or more traits, relative to an unmodified control plant, selected from the group consisting of shorter plant height, increased stalk/stem diameter, improved lodging resistance, reduced green snap, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, and increased prolificacy.

In an aspect, a modified corn plant is an inbred. In another aspect, a modified corn plant is a hybrid. In an aspect, a modified corn plant is a plant modified by a targeted genome editing technique.

According to some embodiments, a recombinant DNA construct or vector may comprise a first polynucleotide sequence encoding a site-specific nuclease and a second polynucleotide sequence encoding a guide RNA that may be introduced into a plant cell together via plant transformation techniques. Alternatively, two recombinant DNA constructs or vectors may be provided including a first recombinant DNA construct or vector and a second DNA construct or vector that may be introduced into a plant cell together or sequentially via plant transformation techniques, wherein the first recombinant DNA construct or vector comprises a polynucleotide sequence encoding a site-specific nuclease and the second recombinant DNA construct or vector comprises a polynucleotide sequence encoding a guide RNA. According to some embodiments, a recombinant DNA construct or vector comprising a polynucleotide sequence encoding a site-specific nuclease may be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA may be introduced via plant transformation techniques into a plant cell that already comprises (or is transformed with) a recombinant DNA construct or vector comprising a polynucleotide sequence encoding a site-specific nuclease. According to yet further embodiments, a first plant comprising (or transformed with) a recombinant DNA construct or vector comprising a polynucleotide sequence encoding a site-specific nuclease may be crossed with a second plant comprising (or transformed with) a recombinant DNA construct or vector comprising a polynucleotide sequence encoding a guide RNA. Such recombinant DNA constructs or vectors may be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif The protein structure of the site-specific nuclease (or the fused/attached/tethered DNA binding domain) may target the site-specific nuclease to the target site. According to many of these embodiments, non-RNA-guided site-specific nucleases, such as recombinases, zinc finger nucleases (ZFNs), meganucleases, and TALENs, may be designed, engineered and constructed according to known methods to target and bind to a target site at or near the genomic locus of an endogenous GA oxidase gene of a corn plant, such as the GA20 oxidase_3 gene or the GA20 oxidase_5 gene in corn, to create a DSB or nick at such genomic locus to knockout or knockdown expression of the GA oxidase gene via repair of the DSB or nick. For example, an engineered site-specific nuclease, such as a recombinase, zinc finger nuclease (ZFN), meganuclease, or TALEN, may be designed to target and bind to (i) a target site within the genome of a plant corresponding to a sequence within SEQ ID NO: 34, or its complementary sequence, to create a DSB or nick at the genomic locus for the GA20 oxidase_3 gene, (ii) a target site within the genome of a plant corresponding to a sequence within SEQ ID NO: 35, or its complementary sequence, to create a DSB or nick at the genomic locus for the GA20 oxidase_5 gene, and/or (iii) a target site within the genome of a plant corresponding to a sequence within SEQ ID NO: 38, or its complementary sequence, to create a DSB or nick at the genomic locus for the GA20 oxidase_4 gene, which may then lead to the creation of a mutation or insertion of a sequence at the site of the DSB or nick, through cellular repair mechanisms, which may be guided by a donor molecule or template.

In an aspect, a targeted genome editing technique described herein may comprise the use of a recombinase. In some embodiments, a tyrosine recombinase attached, etc., to a DNA recognition domain or motif may be selected from the group consisting of a Cre recombinase, a Flp to recombinase, and a Tnp1 recombinase. In an aspect, a Cre recombinase or a Gin recombinase provided herein may be tethered to a zinc-finger DNA binding domain. The Flp-FRT site-directed recombination system may come from the 2μ plasmid from the baker's yeast *Saccharomyces cerevisiae*. In this system, Flp recombinase (flippase) may recombine sequences between flippase recognition target (FRT) sites. FRT sites comprise 34 nucleotides. Flp may bind to the "arms" of the FRT sites (one arm is in reverse orientation) and cleaves the FRT site at either end of an intervening nucleic acid sequence. After cleavage, Flp may recombine nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase may recombine a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger α-helix, which contribute to site-specific binding to the target site, can be changed and customized to fit specific target sequences. The other amino acids may form a consensus backbone to generate ZFNs with different sequence specificities. Methods and rules for designing ZFNs for targeting and binding to specific target sequences are known in the art. See, e.g., US Patent App. Nos. 2005/0064474, 2009/0117617, and 2012/0142062, the contents and disclosures of which are incorporated herein by reference. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs may be introduced as ZFN proteins, as polynucleotides encoding ZFN proteins, and/or as combinations of proteins and protein-encoding polynucleotides.

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also refers to one or both members of a pair of TALENs that work together to cleave DNA at the same site.

Transcription activator-like effectors (TALEs) can be engineered to bind practically any DNA sequence, such as at or near the genomic locus of a GA oxidase gene in a plant. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One.* 8: e82539). MutH is capable of introducing strand-specific nicks in DNA (see Gabsalilow et al. 2013. *Nucleic Acids Research.* 41: e83). TevI introduces double-stranded breaks in DNA at targeted sites (see Beurdeley et al., 2013. *Nature Communications.* 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39: e82; and tale-nt.cac.cornell.edu/about. In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation). See, e.g., US Patent App. Nos. 2011/0145940, 2011/0301073, and 2013/0117869, the contents and disclosures of which are incorporated herein by reference.

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase. As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant. An "edit" or "genomic edit" in the singular refers to one such targeted mutation, deletion, inversion, substitution or insertion, whereas "edits" or "genomic edits" refers to two or more targeted mutation(s), deletion(s), inversion(s), substitution(s) and/or insertion(s), with each "edit" being introduced via a targeted genome editing technique.

In an aspect, targeted gene editing approaches are used to modify the sequence of the promoter and/or regulatory region(s) of one or more of the GA20 oxidase_3 and/or GA20 oxidase_5 genes to knock-down or knock-out expression of these gene(s), such as through targeted deletions, insertions, mutations, or other sequence changes. Indeed, the promoter and/or regulatory region(s) or sequence(s), or the 5'-UTR, 3'UTR, and/or intron sequence(s), of one or more of the GA20 oxidase_3 and/or GA20 oxidase_5 genes may be largely deleted or mutated. Alternatively, all or a portion of the coding (exon), 5-UTR, 3'UTR, and/or intron sequence(s) of one or more of the GA20 oxidase_3 and/or GA20 oxidase_5 genes may be edited, deleted, mutated, or otherwise modified to knock-down or knock-out expression or activity of these gene(s). Such targeted modifications to the GA20 oxidase_3 and/or GA20 oxidase_5 gene loci may be achieved using any suitable genome editing technology known in the art, such as via repair of a double strand break (DSB) or nick introduced by a site-specific nuclease, such as, for example, a zinc-finger nuclease, an engineered or native meganuclease, a TALE-endonuclease, or an RNA-guided endonuclease (e.g., Cas9 or Cpf1). Such repair of the DSB or nick may introduce spontaneous or stochastic deletions, additions, mutations, etc., at the targeted site where the DSB or nick was introduced, or repair of the site may involve the use of a donor template molecule to direct or cause a preferred or specific deletion, addition, mutation, etc., at the targeted site.

For purposes of the present disclosure, a "plant" includes an explant, plant part, seedling, plantlet or whole plant at any stage of regeneration or development. As used herein, a "plant part" may refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure may be viable, nonviable, regenerable, and/or non-regenerable. A "propagule" may include any plant part that can grow into an entire plant.

According to some embodiments, a modified plant may be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified plant may be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre. As an example, corn plants may be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

According to embodiments of the present disclosure, a modified corn plant(s) is/are provided that comprise (i) a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or (ii) an average stem or stalk diameter of at least 18 mm, at least 18.5 mm, at least 19 mm, at least 19.5 mm, at least 20 mm, at least 20.5 mm, at least 21 mm, at least 21.5 mm, or at least 22 mm. Stated a different way, a modified corn plant(s) is/are provided that comprise a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or an average stem or stalk diameter that is greater than 18 mm, greater than 18.5 mm, greater than 19 mm, greater than 19.5 mm, greater than 20 mm, greater than 20.5 mm, greater than 21 mm, greater than 21.5 mm, or greater than 22 mm. Any such plant height trait or range that is expressed in millimeters (mm) may be converted into a different unit of measurement based on known conversions (e.g., one inch is equal to 2.54 cm or 25.4 millimeters, and millimeters (mm), centimeters (cm) and meters (m) only differ by one or more powers of ten). Thus, any measurement provided herein is further described in terms of any other comparable units of measurement according to known and established conversions. However, the exact plant height and/or stem diameter of a modified corn plant may depend on the environment and genetic background. Thus, the change in plant height and/or stem diameter of a modified corn plant may instead be described in terms of a minimum difference or percent change relative to a control plant. A modified corn plant may further comprise at least one ear that is substantially free of male reproductive tissues or structures or other off-types.

According to embodiments of the present disclosure, modified corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant may be substantially free of off-types, such as male reproductive tissues or structures in one or more ears of the modified corn plant.

According to embodiments of the present disclosure, modified corn plants are provided that have (i) a plant height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a wild-type or control plant, and/or (ii) a stem or stalk diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of the wild-type or control plant. According to embodiments of the present disclosure, a modified corn plant may have a reduced plant height that is no more than 20%, 25%, 30%, 35%, 40%, 45%, 50%, 55%, or 60% shorter than the height of a wild-type or control plant, and/or a stem or stalk diameter that is less than (or not more than) 10%, 15%, 20%, 25%, 30%, 35%, 40%, 45%, 50%, 55%, 60%, 65%, 70%, 75%, 80%, 85%, 90%, 95%, or 100% greater than the stem or stalk diameter of a wild-type or control plant. For example, a modified plant may have (i) a plant height that is at least 10%, at least 15%, or at least 20% less or shorter (i.e., greater than or equal to 10%, 15%, or 20% shorter), but not greater or more than 50% shorter, than a wild type or control plant, and/or (ii) a stem or stalk diameter that is that is at least 5%, at least 10%, or at least 15% greater, but not more than 30%, 35%, or 40% greater, than a wild type or control plant. For clarity, the phrases "at least 20% shorter" and "greater than or equal to 20% shorter" would exclude, for example, 10% shorter. Likewise for clarity, the phrases "not greater than 50% shorter", "no more than 50% shorter" and "not more than 50% shorter" would exclude 60% shorter; the phrase "at least 5% greater" would exclude 2% greater; and the phrases "not more than 30% greater" and "no more than 30% greater" would exclude 40% greater.

According to embodiments of the present disclosure, modified corn plants are provided that comprise a height between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the height of a wild-type or control plant, and/or a stem or stalk diameter that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, between 50% and 75%, between 8% and 20%, or between 8% and 15% greater than the stem or stalk diameter of the wild-type or control plant.

According to embodiments of the present disclosure, modified corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a wild-type or control plant. The "minus-2 internode" of a corn plant refers to the second internode below the ear of the plant, and the "minus-4 internode" of a corn plant refers to the fourth internode below the ear of the plant According to many embodiments, modified corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a wild-type or control plant.

According to embodiments of the present disclosure, modified corn plants are provided that comprise an ear weight (individually or on average) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the ear weight of a wild-type or control plant. A modified corn plant provided herein may comprise an ear weight that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75%, greater than the ear weight of a wild-type or control plant.

According to embodiments of the present disclosure, modified corn plants are provided that have a harvest index of at least 0.57, at least 0.58, at least 0.59, at least 0.60, at least 0.61, at least 0.62, at least 0.63, at least 0.64, or at least 0.65 (or greater). A modified corn plant may comprise a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. A modified corn plant may have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant may have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a wild-type or control plant.

According to embodiments of the present disclosure, modified corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant may have an increase in harvestable yield between 1 and 10, between 1 and 8, between 2 and 8, between 2 and 6, between 2 and 5, between 2.5 and 4.5, or between 3 and 4 bushels per acre. A modified corn plant may have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant may have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a wild-type or control plant.

According to embodiments of the present disclosure, a modified corn plant is provided that has a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a wild-type or control plant. A modified corn plant may have a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a wild-type or control plant. Further provided are populations of corn plants having increased lodging resistance and a reduced lodging frequency. Populations of modified corn plants are provided having a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a population of wild-type or control plants. A population of modified corn plants may comprise a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a population of wild-type or control plants, which may be expressed as an average over a specified number of plants or crop area of equal density.

According to embodiments of the present disclosure, modified corn plants are provided having a significantly reduced or decreased plant height (e.g., 2000 mm or less) and a significantly increased stem diameter (e.g., 18 mm or more), relative to a wild-type or control plant. According to these embodiments, the decrease or reduction in plant height and increase in stem diameter may be within any of the height, diameter or percentage ranges recited herein. Such modified corn plants having a reduced plant height and increased stem diameter relative to a wild-type or control plant may be transformed with a transcribable DNA sequence encoding a non-coding RNA molecule that targets at least one GA20 oxidase gene for suppression. Modified corn plants having a significantly reduced plant height and/or a significantly increased stem diameter relative to a wild-type or control plant may further have at least one ear that is substantially free of male reproductive tissues or structures and/or other off-types. Modified corn plants having a significantly reduced plant height and/or an increased stem diameter relative to a wild-type or control plant may have reduced activity of one or more GA20 oxidase and/or GA3 oxidase gene(s) in one or more tissue(s) of the plant, such as one or more vascular and/or leaf tissue(s) of the plant, relative to the same tissue(s) of the wild-type or control plant. According to many embodiments, modified corn plants may comprise at least one polynucleotide or transcribable DNA sequence encoding a non-coding RNA molecule operably linked to a promoter, which may be a constitutive, tissue-specific or tissue-preferred promoter, wherein the non-coding RNA molecule targets at least one GA20 oxidase for suppression as provided herein. The non-coding RNA molecule may be a miRNA, siRNA, or miRNA or siRNA precursor molecule. According to some embodiments, modified corn plants having a significantly reduced plant height and/or an increased stem diameter relative to a wild-type or control plant may further have an increased harvest index and/or increased lodging resistance relative to the wild-type or control plant.

Modified corn plants having a significantly reduced plant height and/or a significantly increased stem diameter relative to a wild-type or control plant may comprise a mutation (e.g., an insertion, deletion, substitution, etc.) in a GA oxidase gene introduced through a gene editing technology or other mutagenesis technique, wherein expression of the GA oxidase gene is reduced or eliminated in one or more tissues of the modified plant. Such modified corn plants having a reduced plant height and/or an increased stem diameter relative to a wild-type or control plant may further have an increased harvest index and/or increased lodging resistance relative to the wild-type or control plant. Such modified corn plants may be substantially free of off-types, such as male reproductive tissues or structures and/or other off-types in at least one ear of the modified plants. Plant mutagenesis techniques (excluding genome editing) may include chemical mutagenesis (i.e., treatment with a chemical mutagen, such as an azide, hydroxylamine, nitrous acid, acridine, nucleotide base analog, or alkylating agent—e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells may be subjected to mutagenesis. Treated plants may be reproduced to collect seeds or produce a progeny plant, and treated plant parts, plant tissues or plant cells may be developed or regenerated into plants or other plant tissues. Mutations generated with chemical or physical mutagenesis techniques may include a frameshift, missense or nonsense mutation leading to loss of function or expression of a targeted gene, such as a GA3 or GA20 oxidase gene.

One method for mutagenesis of a gene is called "TILL-ING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA oxidase gene may be used to identify whether a mutated plant has a mutation in the GA oxidase gene. Plants having mutations in the GA oxidase gene may then be tested for an altered trait, such as reduced plant height. Alternatively, mutagenized plants may be tested for an altered trait, such as reduced plant height, and then PCR amplification and sequencing of a nucleic acid sequence of a GA oxidase gene may be used to determine whether a plant having the altered trait also has a mutation in the GA oxidase gene. See, e.g., Colbert et al., 2001, *Plant Physiol* 126:480-484; and McCallum et al., 2000, Nature Biotechnology 18:455-457. TILL-ING can be used to identify mutations that alter the expression a gene or the activity of proteins encoded by a gene, which may be used to introduce and select for a targeted mutation in a GA oxidase gene of a corn plant.

Corn plants that have been subjected to a mutagenesis or genome editing treatment may be screened and selected based on an observable phenotype (e.g., any phenotype described herein, such as shorter plant height, increased stem/stalk diameter, etc.), or using a selection agent with a selectable marker (e.g., herbicide, etc.), a screenable marker, or a molecular technique (e.g., lower GA levels, lower GA oxidase transcript or protein levels, presence of transgene or transcribable sequence, etc.). Such screening and/or selecting techniques may be used to identify and select plants having a mutation in a GA oxidase gene that leads to a desirable plant phenotype.

According to embodiments of the present disclosure, a population of modified corn plants are provided, wherein the population of modified corn plants have an average plant height that is significantly less, and/or an average stem or stalk diameter that is significantly more, than a population of wild-type or control plants. The population of modified corn plants may share ancestry with a single modified corn plant. Modified corn plants within a population of modified corn plants may generally comprise at least one ear that is substantially free of male reproductive tissues or structures and/or other off-types. A population of modified corn plants may have increased lodging resistance on average or per number of plants or field area than a population of wild-type or control plants. The population of modified corn plants may have a lodging frequency that is at least 5%, at least 10%, at least 20%, at least 30%, at least 40%, at least 50%, at least 60%, at least 70% at least 80%, at least 90%, or 100% less (or lower) than a population of control corn plants. A population of modified corn plants may have a harvest index of at least 0.57 or greater.

According to embodiments of the present invention, modified corn plants are provided having a reduced gibberellin content (in active form) in at least the stem and internode tissue(s), such as the stem, internode, leaf and/or vascular tissue(s), as compared to the same tissue(s) of wild-type or control plants. According to many embodiments, modified corn plants are provided having a significantly reduced plant height and/or a significantly increased stem diameter relative to wild-type or control plants, wherein the modified corn plants further have significantly reduced or decreased level(s) of active gibberellins or active GAs (e.g., one or more of GA1, GA3, GA4, and/or GA7) in one or more stem, internode, leaf and/or vascular tissue(s), relative to the same tissue(s) of the wild-type or control plants. For example, the level of one or more active GAs in the stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn plant may comprise an active gibberellin (GA) level(s) (e.g., one or more of GA1, GA3, GA4, and/or GA7) in one or more stem, internode, leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or (or lower) than in the same tissue(s) of a wild-type or control corn plant. A modified corn plant having a reduced active gibberellin (GA) level(s) in one or more stem, internode, leaf and/or vascular tissue(s) may further be substantially free of off-types, such as male reproductive tissues or structures and/or other off-types in at least one ear of a modified corn plant.

According to embodiments of the present disclosure, modified corn plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified plants, as compared to the same tissue(s) of wild-type or control plants. According to many embodiments, a modified corn plant is provided comprising a significantly reduced plant height and/or a significantly increased stem diameter relative to wild-type or control plants, wherein the modified corn plant has a significantly reduced or eliminated expression level of one or more GA20 oxidase and/or GA3 oxidase gene transcript(s) and/or protein(s) in one or more tissues, such as one or more stem, internode, leaf and/or vascular tissue(s), of the modified plant, as compared to the same tissue(s) of a wild-type or control corn plant. For example, a modified corn plant has a significantly reduced or eliminated expression level of a GA20 oxidase_3 and/or GA20 oxidase_5 gene transcript(s) and/or protein(s), and/or a significantly reduced or eliminated expression level of a GA3 oxidase_1 and/or GA3 oxidase_2 gene transcript(s) and/or protein(s), in the whole modified plant, or in one or more stem, internode, leaf and/or vascular tissue(s) of the modified plant, as compared to the same tissue(s) of a wild-type or control plant. For example, the level of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn plant may comprise level(s) of one or more GA3 oxidase and/or GA20 oxidase gene transcript(s) and/or protein(s), or one or more GA oxidase (or GA oxidase-like) gene transcript(s) and/or protein(s), in the whole plant, or in one or more stem, internode, leaf and/or vascular tissue(s), that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or lower than in the same tissue(s) of a wild-type or control corn plant. A modified corn plant having a reduced or eliminated expression level of at least one GA20 oxidase and/or GA3 oxidase gene(s) in one or more tissue(s), may also be substantially free of off-types, such as male reproductive tissues or structures and/or other off-types in at least one ear of the modified corn plant.

Methods and techniques are provided for screening for, and/or identifying, cells or plants, etc., for the presence of targeted edits or transgenes, and selecting cells or plants comprising targeted edits or transgenes, which may be based on one or more phenotypes or traits, or on the presence or absence of a molecular marker or polynucleotide or protein sequence in the cells or plants. Nucleic acids can be isolated and detected using techniques known in the art. For example, nucleic acids can be isolated and detected using, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis. Any method known in the art may be used to screen for, and/or identify, cells, plants, etc., having a transgene or genome edit in its genome, which may be based on any suitable form of visual observation, selection, molecular technique, etc.

In some embodiments, methods are provided for detecting recombinant nucleic acids and/or polypeptides in plant cells. For example, nucleic acids may be detected using hybridization probes or through production of amplicons using PCR with primers as known in the art. Hybridization between nucleic acids is discussed in Sambrook et al. (1989, Molecular Cloning: A Laboratory Manual, 2nd Ed., Cold Spring Harbor Laboratory Press, Cold Spring Harbor, NY). Polypeptides can be detected using antibodies. Techniques for detecting polypeptides using antibodies include enzyme linked immunosorbent assays (ELISAs), Western blots, immunoprecipitations, immunofluorescence, and the like. An antibody provided herein may be a polyclonal antibody or a monoclonal antibody. An antibody having specific binding affinity for a polypeptide provided herein can be generated using methods known in the art. An antibody or hybridization probe may be attached to a solid support, such as a tube, plate or well, using methods known in the art.

Detection (e.g., of an amplification product, of a hybridization complex, of a polypeptide) can be accomplished using detectable labels that may be attached or associated with a hybridization probe or antibody. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified or edited plants or plant cells can be through any methodologies known to those skilled in the art of molecular biology. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina®, PacBio®, Ion Torrent™, etc.) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

EXAMPLES

Example 1. Phenotypic Observations of Corn Plants Having an Edited GA20 Oxidase_3 or GA20 Oxidase_5 Gene Several genome-edited mutations were created in the endogenous GA20 oxidase_3 and GA20 oxidase_5 genes in corn plants to test for the phenotypic effect of knocking out each of these genes. A series of ten single-chain guide RNA (sgRNAs) encoding targeting constructs were created for each of the GA20 oxidase_3 and GA20 oxidase_5 genes that target different positions along the genomic sequence for each gene. An additional series of ten sgRNAs were created that each target both of the GA20 oxidase_3 and GA20 oxidase_5 genes, at similar or different positions along the genomic sequence for each gene. Targeted genome edits were made by delivering the sgRNA along with expression of a Cas9 protein to corn explants to cause a DSB or nick to occur at or near the genomic target site for the gRNA, which may then be imperfectly repaired to introduce a mutation at or near the target site. The presence of a mutation was subsequently confirmed by RFLP analysis and/or sequencing of plants. Table 2 below provides a list of the guide RNA (gRNA) constructs that were tested, which may be used for genome editing of one or both of the GA20 oxidase_3 and GA20 oxidase_5 gene(s) with a RNA-guided endonuclease. These guide RNA constructs are generally designed to target the coding sequences of the GA20 oxidase_3 and/or GA20 oxidase_5 genes, but some of the joint targeting constructs may instead target a UTR sequence of one of the two genes. These gRNAs may be used with a suitable endonuclease to produce a double stranded break (DSB) or nick in the genome at or near the genomic target site of the respective gRNA, which may be imperfectly repaired to produce a mutation (e.g., an insertion, deletion, substitution, etc.). Plants homozygous for an edited GA20 oxidase_3 gene or homozygous for an edited GA20 oxidase_5 gene were generated from a few of the constructs (see bold text). Events were also generated from constructs targeting both genes for editing. For the constructs jointly targeting the GA20 oxidase_3 and GA20 oxidase_5 genes, the coding sequence (CDS) coordinates are provided in reference to one of the two genes as indicated in parenthesis. Table 2 further shows which constructs produced gene editing events, whether those events were homozygous or heterozygous in the R0 plants, and the ±numbers in parenthesis indicate the likely sequence change with the mutation (e.g., +1 means an insertion of 1 nucleotide, −1 means a deletion of 1 nucleotide, etc., and larger or more complicated Indels are labeled "del." or insert."). For joint targeting of GA20 oxidase_3 and GA20 oxidase_5 genes, the identity of the mutated gene is also provided in parenthesis. R0 plants homozygous for an edited GA20 oxidase_3 or GA20 oxidase_5 gene did not have an observable short stature, semi-dwarf phenotype and had a normal plant height relative to control plants (See constructs GA20 oxidase_3-D and GA20 oxidase_3-G, and constructs GA20 oxidase_5-B and GA20 oxidase_5-G in Table 2), indicating that knockout of only one of these genes is not sufficient to produce the semi-dwarf phenotype.

TABLE 2

| Guide RNAs (gRNAs) targeting GA20 oxidase_3 and GA oxidase_5 genes for editing. | | | |
|---|---|---|---|
| gRNA Gene Target | gRNA Targeting Sequence (SEQ ID NO) | Gene CDS coordinates | R0 Plants Generated |
| GA20 oxidase_3-A | 138 | 552-572 | — |
| GA20 oxidase_3-B | 139 | 879-899 | — |
| GA20 oxidase_3-C | 140 | 147-167 | — |
| GA20 oxidase_3-D | 141 | 526-546 | 1. homozygous (−1) |
| | | | 2. heterozygous (−1) |
| | | | 3. bi-allelic (−2, +1) |
| GA20 oxidase_3-E | 142 | 446-466 | — |
| GA20 oxidase_3-F | 143 | 2227-2247 | — |
| GA20 oxidase_3-G | 144 | 548-568 | 1. homozygous (+1) |
| | | | 2. heterozygous (−1) |
| | | | 3. bi-allelic (+1, −1) |
| GA20 oxidase_3-H | 145 | 547-567 | — |
| GA20 oxidase_3-I | 146 | 43-63 | — |
| GA20 oxidase_3-J | 147 | 548-567 | — |
| GA20 oxidase_5-A | 148 | 356-376 (+) | 1. heterozygous (−1) |
| GA20 oxidase_5-B | 149 | 99-119 | 1. homozygous (−1) |
| | | | 2. heterozygous (+1) |
| | | | 3. heterozygous (+1, −7) |
| | | | 4. heterozygous (−3, −1) |
| GA20 oxidase_5-C | 150 | 369-389 | — |
| GA20 oxidase_5-D | 151 | 48-68 | — |
| GA20 oxidase_5-E | 152 | 356-376 (−) | — |
| GA20 oxidase_5-F | 153 | 748-768 | 1. heterozygous (−1, +1) |
| GA20 oxidase_5-G | 154 | 770-790 | 1. homozygous (−1) |
| | | | 2. homozygous (−1) |
| GA20 oxidase_5-H | 155 | 10-30 | — |
| GA20 oxidase_5-I | 156 | 262-282 | — |
| GA20 oxidase_5-J | 157 | 768-788 | — |
| GA20 oxidase_3/5-A | 158 | 290 . . . 310 (GA20 Ox_3) | — |
| GA20 oxidase_3/5-B | 159 | 289 . . . 309 (GA20 Ox_3) | — |
| GA20 oxidase_3/5-C | 160 | 270 . . . 290 (GA20 Ox_5) | — |

TABLE 2-continued

| | | | |
|---|---|---|---|
| Guide RNAs (gRNAs) targeting GA20 oxidase_3 and GA oxidase_5 genes for editing. | | | |
| gRNA Gene Target | gRNA Targeting Sequence (SEQ ID NO) | Gene CDS coordinates | R0 Plants Generated |
| GA20 oxidase_3/5-D | 161 | 49 . . . 69 (GA20 Ox_3) | — |
| GA20 oxidase_3/5-E | 162 | 265 . . . 285 (GA20 Ox_5) | 1. heterozygous (Ox5, +1) |
| GA20 oxidase_3/5-F | 163 | 419 . . . 439 (GA20 Ox_3) | 1. hetero (Ox3, +1, −1) hetero (Ox5, +1, del.) 2. hetero (Ox3, +1, del.) hetero (Ox5, +1) |
| GA20 oxidase_3/5-G | 164 | 110 . . . 130 (GA20 Ox 3) | — |
| GA20 oxidase_3/5-H | 165 | 634 . . . 654 (GA20 Ox_5) | — |
| GA20 oxidase_3/5-I | 166 | 98 . . . 118 (GA20 Ox_5) | — |
| GA20 oxidase_3/5-J | 167 | 517 . . . 537 (GA20 Ox_5) | — |

Example 2. Identification of Corn Plants Having Various Combinations of Edited GA20 Oxidase_3 and GA20 Oxidase_5 Mutant Alleles Corn plants were edited as described in Example 1 via a CRISPR/Cas9 based approach using guide RNAs (gRNAs) that target one of GA20 oxidase_3 and GA20 oxidase_5 genes specifically or target both of these two genes simultaneously (see Table 2). In total, 30 gRNA constructs were transformed into corn. Leaf samples from R0 plants were collected and analyzed for InDels by a Fragment Length Analysis (FLA) assay. Putative mutant alleles identified by FLA were sequenced using gene specific primers and standard deep sequencing protocols to confirmed the mutation(s). Table 3 provides a list of 12 edited mutant alleles in the GA20 oxidase_3 gene (ga20ox3-1 to ga20ox3-12) and their sequences. Table 4 provides a list of 11 edited mutant alleles in the GA20 oxidase_5 gene (ga20ox5-1 to ga20ox5-11) and their sequences. R0 plants with mutation(s) in either GA20 oxidase_3 or GA20 oxidase_5, or in both of those genes, were selfed to produce R1 plants.

R1 seeds from multiple R0 plants were planted and sampled again to confirm mutation(s) using FLA and standard sequencing protocols. Table 5 provides a list of R1 plants having mutations in GA20 oxidase_3, GA20 oxidase_5, or both genes. Table 5 also shows plant height and internode length (ear minus 2) of R1 plants measured at the R3 stage. Plant height were measured at R2/R3 growth stage from the soil line to the base of highest collared leaf. R1 plants that are homozygous or heterozygous for a mutation in the gene of interest (GA20 oxidase_3 and/or GA20 oxidase_5) were identified through sequencing and further selfed to produce R2 plants. Genotypes of the R2 plants were again determined by FLA and sequencing. Table 6 provides a list of R2 plants having mutations in GA20 oxidase_3, GA20 oxidase_5, or both genes, and their plant height at the R2/R3 stage. Table 6 also provides corresponding characterization of unedited reference control plants (wild-type inbred plants, shown as WT) and transgenic inbred corn plants having an artificial microRNA suppression construct targeting the GA20 oxidase_3 and GA20 oxidase_5 genes for suppression (SUP_GA20Ox3&Ox5 ("SUP_Ox3&Ox5")).

On average, R2 plants containing homozygous mutant alleles of both GA20 oxidase_3 and GA20 oxidase_5 genes (i.e., double homozygous) showed a semi-dwarf phenotype (about 27.5% reduction in plant height relative to control) with altered plant architecture similar to SUP_Ox3&Ox5 plants (comparing Homo_ox3/Homo_ox5 and SUP_Ox3&Ox5 plants in Table 7 and FIG. 1). Homozygous single ga20ox3 mutants and homozygous single ga20ox5 mutants exhibited a slight reduction (about 10-11%) in average plant height (at the R3 stage) relative to unedited reference control plants (WT inbred). In addition, corn plants with homozygous ga20ox3 mutations and heterozygous for a ga20ox5 mutation (i.e., Homo_ox3/Het_ox5 in Table 7 and FIG. 1) exhibited a moderate reduction (about 19.1%) in average plant height (at the R3 stage) relative to unedited reference control plants (WT inbred). Homo_ox3/Het_ox5 plants were slightly taller than double homozygous ga20ox3 ga20ox5 plants (Homo_ox3/Homo_ox5). Given that corn is a diploid organism, CRISPR-mediated gene editing can result in biallelic mutations in R0 plants (also known as a biallelic mutant combination or transheterozygous mutations). For simplicity, a biallelic mutant at a particular locus is treated as a homozygous mutant at that locus for genotype description and plant height calculation purposes. Detailed mutant genotypes (including biallelic mutants) are provided in Tables 18 and 19 for R1 and R2 generation plants, respectively. Both double homozygous ga20ox3/ga20ox5 mutants, and homozygous/heterozygous mutant combinations (e.g., Homo_ox3/Het_ox5 or Het_ox3/Homo_ox5) also resulted in shorter, semi-dwarf plants, although plant heights in homozygous/heterozygous mutant combinations were not reduced as much as the double homozygous ga20ox3/ga20ox5 mutant plants.

TABLE 3

A list of 12 edited mutant alleles in GA20 oxidase_3 (ga20ox3-1 to ga20ox3-12)
and their sequences. The gRNA IDs shown here correspond to those in Table 2.

| Gene Locus | Mutant allele | SEQ ID for Mutant Allele Sequence (~30 nt flanking edits) | SEQ ID for Mutant Allele Sequence (~60 nt flanking edits) | SEQ ID for Wild-type Reference Sequence (~60 nt flanking edits) | SEQ ID for Mutant Allele Sequence (genomic coding DNA) | Allele Description (EDIT @ genomic coding DNA coordinate, based on SEQ ID No. 168) | Edit Position | gRNA ID |
|---|---|---|---|---|---|---|---|---|
| GA20ox3 | ga20ox3-1 | 170 | 182 | 194 | 206 | Deletion of 13 bases starting at 536 | first exon | GA20ox3_d |
| GA20ox3 | ga20ox3-2 | 171 | 183 | 195 | 207 | Deletion of base 542 | first exon | GA20ox3_d |
| GA20ox3 | ga20ox3-3 | 172 | 184 | 196 | 208 | Insertion of CC at base 542 | first exon | GA20ox3_d |
| GA20ox3 | ga20ox3-4 | 173 | 185 | 197 | 209 | Deletion of base 541 | first exon | GA20ox3_d |
| GA20ox3 | ga20ox3-5 | 174 | 186 | 198 | 210 | Deletion of 3 nt starting at base 540 | first exon | GA20ox3_d |
| GA20ox3 | ga20ox3-6 | 175 | 187 | 199 | 211 | Deletion of 2 bases starting at base 422 | first exon | GA20ox3_5_f |
| GA20ox3 | ga20ox3-7 | 176 | 188 | 200 | 212 | Insertion of an A at base 422 | first exon | GA20ox3_5_f |
| GA20ox3 | ga20ox3-8 | 177 | 189 | 201 | 213 | Insertion of a T at base 422 | first exon | GA20ox3_5_f |
| GA20ox3 | ga20ox3-9 | 178 | 190 | 202 | 214 | Deletion of base 564 | first exon | GA20ox3_g |
| GA20ox3 | ga20ox3-10 | 179 | 191 | 203 | 215 | Insertion of an A at base 564 | first exon | GA20ox3_g |
| GA20ox3 | ga20ox3-11 | 180 | 192 | 204 | 216 | Insertion of a C at base 565 | first exon | GA20ox3_g |
| GA20ox3 | ga20ox3-12 | 181 | 193 | 205 | 217 | Insertion of a C at base 63 | first exon | GA20ox3_5_e |

TABLE 4

A list of 11 edited mutant alleles in GA20 oxidase_5 (ga20ox5-1 to ga20ox5-11)
and their sequences. The gRNA IDs shown here correspond to those in Table 2.

| Gene Locus | Mutant Allele | SEQ ID for Mutant Allele Sequence (~30 nt flanking edits) | SEQ ID for Mutant Allele Sequence (~60 nt flanking edits) | SEQ ID for Wild-type Reference Sequence (~60 nt flanking edits) | SEQ ID for Mutant Allele Sequence (genomic coding DNA) | Allele description (EDIT @ genomic coding DNA coordinate, based on SEQ ID No. 169) | Edit Position | gRNA ID |
|---|---|---|---|---|---|---|---|---|
| GA20ox5 | ga20ox5-1 | 218 | 229 | 240 | 251 | Deletion of base 644 | first exon | GA20ox3_5_f |
| GA20ox5 | ga20ox5-2 | 219 | 230 | 241 | 252 | Deletion of 2 bases starting at base 644 | first exon | GA20ox3_5_f |
| GA20ox5 | ga20ox5-3 | 220 | 231 | 242 | 253 | Insertion of a T at base 644 | first exon | GA20ox3_5_f |
| GA20ox5 | ga20ox5-4 | 221 | 232 | 243 | 254 | Deletion of base 372 | first exon | GA20ox5_a |
| GA20ox5 | ga20ox5-5 | 222 | 233 | 244 | 255 | Deletion of base 786 | first exon | GA2ox5_g |
| GA20ox5 | ga20ox5-6 | 223 | 234 | 245 | 256 | Deletion of 5 bases starting at base 786 | first exon | GA2ox5_g |
| GA20ox5 | ga20ox5-7 | 224 | 235 | 246 | 257 | Deletion of 2 bases starting at base 101 | first exon | GA20ox5_b |
| GA20ox5 | ga20ox5-8 | 225 | 236 | 247 | 258 | Insertion of a T at base base 102 | first exon | GA20ox5_b |
| GA20ox5 | ga20ox5-9 | 226 | 237 | 248 | 259 | Deletion of 3 bases starting at base 99 | first exon | GA20ox5_b |
| GA20ox5 | ga20ox5-10 | 227 | 238 | 249 | 260 | Insertion of an A at base 282 | first exon | GA20ox3_5_e |
| GA20ox5 | ga20ox5-11 | 228 | 239 | 250 | 261 | Insertion of a C at base 282 | first exon | GA20ox3_5_e |

TABLE 5

A list of R1 plants having mutations in GA20 oxidase_3, GA20 oxidase_5, or both genes.

| Plant No. | Plant Genotype | Plant Height (inches) | Internode Length (cm) | GA20ox3 Genotype | GA20ox5 Genotype | ga20ox3 Allele(s) | ga20ox5 Allele(s) | Gene-ration | gRNA |
|---|---|---|---|---|---|---|---|---|---|
| 1 | single homo ga20ox5 | 58.74 | 12 | WT | Biallelic deletion −1, deletion −5, | none | ga20ox5-6, ga20ox5-5 | R1 | GA20ox5_g |
| 2 | single homo ga20ox5 | 51.65 | 10 | WT | Biallelic deletion −1, deletion −5, | none | ga20ox5-6, ga20ox5-5 | R1 | GA20ox5_g |

TABLE 5-continued

A list of R1 plants having mutations in GA20 oxidase_3, GA20 oxidase_5, or both genes.

| Plant No. | Plant Genotype | Plant Height (inches) | Internode Length (cm) | GA20ox3 Genotype | GA20ox5 Genotype | ga20ox3 Allele(s) | ga20ox5 Allele(s) | Gene-ration | gRNA |
|---|---|---|---|---|---|---|---|---|---|
| 3 | single homo ga20ox5 | 57.49 | 10.5 | WT | Biallelic deletion −1, deletion −5, | none | ga20ox5-6, ga20ox5-5 | R1 | GA20ox5_g |
| 4 | single homo ga20ox5 | 68.27 | 13.8 | WT | Biallelic deletion −2, insertion +1, | none | ga20ox5-8, ga20ox5-7 | R1 | GA20ox5_b |
| 5 | single homo ga20ox5 | 56.89 | 11.3 | WT | Biallelic deletion −5, deletion −1, | none | ga20ox5-6, ga20ox5-5 | R1 | GA20ox5_g |
| 6 | hetero ga20ox3/ homo ga20ox5 | 53.7 | 10 | Het insertion +1, | Biallelic insertion +1, insertion +1, | ga20ox3-12 | ga20ox5-11, ga20ox5-10 | R1 | GA20ox3_5_e |
| 7 | homo ga20ox3/ hetero ga20ox5 | 53.9 | 9.5 | Biallelic insertion +1, insertion +1, | Het deletion −1, | ga20ox3-8, ga20ox3-7 | ga20ox5-1 | R1 | GA20ox3_5_f |
| 8 | homo ga20ox3/ hetero ga20ox5 | 56.69 | 10 | Biallelic deletion −2, insertion +1, | Het deletion −2, | ga20ox3-6, ga20ox3-8 | ga20ox5-2 | R1 | GA20ox3_5_f |
| 9 | homo ga20ox3/ hetero ga20ox5 | 49.09 | 9.5 | Biallelic insertion +1, deletion −2, | Het deletion −2, | ga20ox3-6, ga20ox3-8 | ga20ox5-2 | R1 | GA20ox3_5_f |
| 10 | homo ga20ox3/ hetero ga20ox5 | 54.96 | 10.3 | Biallelic insertion +1, deletion −2, | Het deletion −2, | ga20ox3-6, ga20ox3-8 | ga20ox5-2 | R1 | GA20ox3_5_f |
| 11 | homo ga20ox3/ hetero ga20ox5 | 47.13 | 9 | Homozygous insertion +1, | Het deletion −2, | ga20ox3-8 | ga20ox5-2 | R1 | GA20ox3_5_f |
| 12 | hetero ga20ox3/ hetero ga20ox5 | 53.31 | 10 | Het insertion +1, | Het deletion −5, | ga20ox3-10 | ga20ox5-6 | R1 | GA20ox3_g |
| 13 | homo ga20ox3/ hetero ga20ox5 | 56.57 | 11 | Biallelic insertion +1, insertion +1, | Het insertion +1, | ga20ox3-8, ga20ox3-7 | ga20ox5-3 | R1 | GA20ox3_5_f |
| 14 | homo ga20ox3/ hetero ga20ox5 | 49.57 | 8.1 | Biallelic insertion +1, insertion +1, | Het insertion +1, | ga20ox3-8, ga20ox3-7 | ga20ox5-3 | R1 | GA20ox3_5_f |
| 15 | homo ga20ox3/ hetero ga20ox5 | 53.35 | 9.1 | Biallelic insertion +1, insertion +1, | Het insertion +1, | ga20ox3-8, ga20ox3-7 | ga20ox5-3 | R1 | GA20ox3_5_f |
| 16 | homo ga20ox3/ hetero ga20ox5 | 59.41 | 9.6 | Biallelic insertion +1, insertion +1, | Het insertion +1, | ga20ox3-7, ga20ox3-8 | ga20ox5-3 | R1 | GA20ox3_5_f |
| 17 | homo ga20ox3/ hetero ga20ox5 | 60.75 | 11 | Biallelic insertion +1, insertion +1, | Het insertion +1, | ga20ox3-7, ga20ox3-8 | ga20ox5-3 | R1 | GA20ox3_5_f |
| 18 | single homo ga20ox5 | 51.54 | 10 | WT | Homozygous deletion −1, | none | ga20ox5-4 | R1 | GA20ox5_a |
| 19 | single homo ga20ox5 | 57.4 | 12.2 | WT | Homozygous deletion −1, | none | ga20ox5-4 | R1 | GA20ox5_a |
| 20 | single homo ga20ox5 | 58.9 | 11.5 | WT | Homozygous deletion −1, | none | ga20ox5-4 | R1 | GA20ox5_a |
| 21 | single homo ga20ox5 | 50.83 | 9 | WT | Homozygous deletion −1, | none | ga20ox5-5 | R1 | GA20ox5_g |
| 22 | single homo ga20ox5 | 55.08 | 10.5 | WT | Homozygous deletion −1, | none | ga20ox5-5 | R1 | GA20ox5_g |
| 23 | single homo ga20ox5 | 54.76 | 10 | WT | Homozygous deletion −1, | none | ga20ox5-5 | R1 | GA20ox5_g |
| 24 | single homo ga20ox5 | 56.54 | 10 | WT | Homozygous deletion −1, | none | ga20ox5-5 | R1 | GA20ox5_g |
| 25 | single homo ga20ox5 | 55.12 | 10.3 | WT | Homozygous deletion −1, | none | ga20ox5-5 | R1 | GA20ox5_g |
| 26 | single homo ga20ox5 | 55.47 | 9 | WT | Homozygous deletion −1, | none | ga20ox5-5 | R1 | GA20ox5_g |
| 27 | single homo ga20ox5 | 61.02 | 10 | WT | Homozygous deletion −1, | none | ga20ox5-5 | R1 | GA20ox5_g |
| 28 | single homo ga20ox5 | 48.62 | 7 | WT | Homozygous deletion −1, | none | ga20ox5-5 | R1 | GA20ox5_g |
| 29 | single homo ga20ox5 | 63.5 | 11.5 | WT | Homozygous deletion −1, | none | ga20ox5-5 | R1 | GA20ox5_g |
| 30 | single homo ga20ox5 | 60.28 | 10.5 | WT | Homozygous deletion −1, | none | ga20ox5-5 | R1 | GA20ox5_g |
| 31 | single homo ga20ox5 | 58.12 | 11.3 | WT | Homozygous deletion −1, | none | ga20ox5-5 | R1 | GA20ox5_g |
| 32 | single homo ga20ox5 | 51.89 | 12 | WT | Homozygous deletion −1, | none | ga20ox5-5 | R1 | GA20ox5_g |

TABLE 5-continued

A list of R1 plants having mutations in GA20 oxidase_3, GA20 oxidase_5, or both genes.

| Plant No. | Plant Genotype | Plant Height (inches) | Internode Length (cm) | GA20ox3 Genotype | GA20ox5 Genotype | ga20ox3 Allele(s) | ga20ox5 Allele(s) | Gene-ration | gRNA |
|---|---|---|---|---|---|---|---|---|---|
| 33 | single homo ga20ox5 | 70.08 | 14 | WT | Homozygous deletion −3, | none | ga20ox5-9 | R1 | GA20ox5_b |
| 34 | single homo ga20ox5 | 55.55 | 9.8 | WT | Homozygous insertion +1, | none | ga20ox5-10 | R1 | GA20ox3_5_e |
| 35 | not available | 59.57 | 10 | not available | not available | not available | not available | R1 | GA20ox3_d |
| 36 | not available | 67.28 | 13.3 | not available | not available | not available | not available | R1 | GA20ox3_g |
| 37 | not available | 56.54 | 9 | not available | not available | not available | not available | R1 | GA20ox3_d |
| 38 | not available | 63.74 | 11.5 | not available | not available | not available | not available | R1 | GA20ox3_g |
| 39 | single homo ga20ox3 | 65.24 | 10 | Biallelic deletion −1, deletion −1, | WT | ga20ox3-4, ga20ox3-2 | none | R1 | GA20ox3_d |
| 40 | single homo ga20ox3 | 69.49 | 9.5 | Biallelic deletion −1, deletion −1, | WT | ga20ox3-2, ga20ox3-4 | none | R1 | GA20ox3_d |
| 41 | single homo ga20ox3 | 60.12 | 9 | Biallelic deletion −1, deletion −3, | WT | ga20ox3-5, ga20ox3-2 | none | R1 | GA20ox3_d |
| 42 | single homo ga20ox3 | 53.74 | 10 | Biallelic deletion −1, insertion +1, | WT | ga20ox3-10, ga20ox3-9 | none | R1 | GA20ox3_g |
| 43 | single homo ga20ox3 | 58.43 | 9.8 | Biallelic deletion −13, deletion −1, | WT | ga20ox3-1, ga20ox3-2 | none | R1 | GA20ox3_d |
| 44 | single homo ga20ox3 | 57.28 | 11.5 | Biallelic deletion −2, insertion +1, | WT | ga20ox3-8, ga20ox3-6 | none | R1 | GA20ox3_5_f |
| 45 | single homo ga20ox3 | 56.26 | 11.5 | Biallelic insertion +1, deletion −2, | WT | ga20ox3-8, ga20ox3-6 | none | R1 | GA20ox3_5_f |
| 46 | single homo ga20ox3 | 59.8 | 10.8 | Biallelic insertion +1, deletion −2, | WT | ga20ox3-8, ga20ox3-6 | none | R1 | GA20ox3_5_f |
| 47 | single hetero ga20ox3 | 54.45 | 11 | Het insertion +1, | WT | ga20ox3-8 | none | R1 | GA20ox3_5_f |
| 48 | single homo ga20ox3 | 52.68 | 9.5 | Homozygous deletion −1, | WT | ga20ox3-2 | none | R1 | GA20ox3_d |
| 49 | single homo ga20ox3 | 64.17 | 12 | Homozygous deletion −1, | WT | ga20ox3-2 | none | R1 | GA20ox3_d |
| 50 | single homo ga20ox3 | 56.97 | 11 | Homozygous deletion −1, | WT | ga20ox3-9 | none | R1 | GA20ox3_g |
| 51 | single homo ga20ox3 | 43.19 | 12.5 | Homozygous deletion −1, | WT | ga20ox3-9 | none | R1 | GA20ox3_g |
| 52 | single homo ga20ox3 | 58.94 | 11.3 | Homozygous deletion −1, | WT | ga20ox3-9 | none | R1 | GA20ox3_g |
| 53 | single homo ga20ox3 | 61.65 | 13 | Homozygous insertion +1, | WT | ga20ox3-8 | none | R1 | GA20ox3_5_f |
| 54 | single homo ga20ox3 | 60.91 | 11.5 | Homozygous insertion +1, | WT | ga20ox3-10 | none | R1 | GA20ox3_g |

TABLE 6

A list of R2 plants having edited alleles in GA20 oxidase_3, GA20 oxidase_5, or both genes. Plant No. 45 and 46 are considered outliers and not included for generating average plant height data shown in Table 7.

| Plant No. | Plant Genotype | Plant Height (inches) | GA20ox3 Genotype | GA20ox5 Genotype | ga20ox3 Allele(s) | ga20ox5 Allele | Generation | gRNA |
|---|---|---|---|---|---|---|---|---|
| 1 | homo ga20ox3/ hetero ga20ox5 | 45 | Biallelic +1 insertion | Heterozygous −1 deletion | ga20ox3-7, ga20ox3-8 | ga20ox5-1 | R2 | GA2ox3_5_f |
| 2 | homo ga20ox3/ heteroga20ox5 | 45.2 | homozygous +1 insertion | Heterozygous −1 deletion | ga20ox3-8 | ga20ox5-1 | R2 | GA2ox3_5_f |
| 3 | homo ga20ox3/ hetero ga20ox5 | 45 | Biallelic −2 deletion, +1 insertion | Heterozygous −2 deletion | ga20ox3-6, ga20ox3-8 | ga20ox5-2 | R2 | GA2ox3_5_f |
| 4 | homo ga20ox3/ hetero ga20ox5 | 42.8 | homozygous +1 insertion | Heterozygous −2 deletion | ga20ox3-8 | ga20ox5-2 | R2 | GA2ox3_5_f |
| 5 | homo ga20ox3/ hetero ga20ox5 | 45.2 | homozygous +1 insertion | Heterozygous −2 deletion | ga20ox3-8 | ga20ox5-2 | R2 | GA2ox3_5_f |
| 6 | homo ga20ox3/ hetero ga20ox5 | 48.8 | homozygous +1 insertion | Heterozygous −2 deletion | ga20ox3-8 | ga20ox5-2 | R2 | GA2ox3_5_f |

TABLE 6-continued

A list of R2 plants having edited alleles in GA20 oxidase_3, GA20 oxidase_5, or both genes. Plant No.
45 and 46 are considered outliers and not included for generating average plant height data shown in Table 7.

| Plant No. | Plant Genotype | Plant Height (inches) | GA20ox3 Genotype | GA20ox5 Genotype | ga20ox3 Allele(s) | ga20ox5 Allele | Generation | gRNA |
|---|---|---|---|---|---|---|---|---|
| 7 | homo ga20ox3/ hetero ga20ox5 | 51.8 | homozygous +1 insertion | Heterozygous −2 deletion | ga20ox3-8 | ga20ox5-2 | R2 | GA2ox3_5_f |
| 8 | homo ga20ox3/ hetero ga20ox5 | 45.4 | homozygous +1 insertion | Heterozygous −2 deletion | ga20ox3-8 | ga20ox5-2 | R2 | GA2ox3_5_f |
| 9 | homo ga20ox3/ hetero ga20ox5 | 47 | Homozygous −2 deletion | Heterozygous −2 deletion | ga20ox3-6 | ga20ox5-2 | R2 | GA2ox3_5_f |
| 10 | homo ga20ox3/ hetero ga20ox5 | 49.8 | Homozygous −2 deletion | Heterozygous −2 deletion | ga20ox3-6 | ga20ox5-2 | R2 | GA2ox3_5_f |
| 11 | single homo ga20ox5 | 52.4 | WT | Homozygous −1 deletion | none | ga20ox5-4 | R2 | GA2ox5_a |
| 12 | single homo ga20ox5 | 39.2 | WT | Homozygous −1 deletion | none | ga20ox5-4 | R2 | GA2ox5_a |
| 13 | single homo ga20ox5 | 53 | WT | Homozygous −1 deletion | none | ga20ox5-4 | R2 | GA2ox5_a |
| 14 | single homo ga20ox5 | 54 | WT | Homozygous −1 deletion | none | ga20ox5-4 | R2 | GA2ox5_a |
| 15 | single homo ga20ox5 | 53.8 | WT | Homozygous −1 deletion | none | ga20ox5-4 | R2 | GA2ox5_a |
| 16 | single homo ga20ox5 | 53.4 | WT | Homozygous −1 deletion | none | ga20ox5-4 | R2 | GA2ox5_a |
| 17 | Double homo | 45 | Biallelic +1 insertion | Homozygous +1 insertion | ga20ox3-7, ga20ox3-8 | ga20ox5-3 | R2 | GA2ox3_5_f |
| 18 | Double homo | 37 | homozygous +1 insertion | Homozygous −2 deletion | ga20ox3-8 | ga20ox5-2 | R2 | GA2ox3_5_f |
| 19 | Double homo | 39.2 | homozygous +1 insertion | Homozygous −2 deletion | ga20ox3-8 | ga20ox5-2 | R2 | GA2ox3_5_f |
| 20 | Double homo | 39.8 | homozygous +1 insertion | Homozygous −2 deletion | ga20ox3-8 | ga20ox5-2 | R2 | GA2ox3_5_f |
| 21 | Double homo | 40.8 | homozygous +1 insertion | Homozygous −2 deletion | ga20ox3-8 | ga20ox5-2 | R2 | GA2ox3_5_f |
| 22 | Double homo | 40.8 | homozygous +1 insertion | Homozygous −2 deletion | ga20ox3-8 | ga20ox5-2 | R2 | GA2ox3_5_f |
| 23 | Double homo | 41 | homozygous +1 insertion | Homozygous −2 deletion | ga20ox3-8 | ga20ox5-2 | R2 | GA2ox3_5_f |
| 24 | Double homo | 41.4 | homozygous +1 insertion | Homozygous −2 deletion | ga20ox3-8 | ga20ox5-2 | R2 | GA2ox3_5_f |
| 25 | Double homo | 41.8 | homozygous +1 insertion | Homozygous −2 deletion | ga20ox3-8 | ga20ox5-2 | R2 | GA2ox3_5_f |
| 26 | Double homo | 42 | homozygous +1 insertion | Homozygous −2 deletion | ga20ox3-8 | ga20ox5-2 | R2 | GA2ox3_5_f |
| 27 | Double homo | 42 | homozygous +1 insertion | Homozygous −2 deletion | ga20ox3-8 | ga20ox5-2 | R2 | GA2ox3_5_f |
| 28 | Double homo | 42.4 | homozygous +1 insertion | Homozygous −2 deletion | ga20ox3-8 | ga20ox5-2 | R2 | GA2ox3_5_f |
| 29 | Double homo | 43 | homozygous +1 insertion | Homozygous −2 deletion | ga20ox3-8 | ga20ox5-2 | R2 | GA2ox3_5_f |
| 30 | Double homo | 43.8 | homozygous +1 insertion | Homozygous −2 deletion | ga20ox3-8 | ga20ox5-2 | R2 | GA2ox3_5_f |
| 31 | Double homo | 46.2 | homozygous +1 insertion | Homozygous −2 deletion | ga20ox3-8 | ga20ox5-2 | R2 | GA2ox3_5_f |
| 32 | single homo ga20ox3 | 62 | Homozygous −1 deletion | WT | ga20ox3-9 | none | R2 | GA2ox3_g |
| 33 | single homo ga20ox3 | 39 | Homozygous −1 deletion | WT | ga20ox3-9 | none | R2 | GA2ox3_g |
| 34 | single homo ga20ox3 | 51 | Biallelic −2 deletion, +1 insertion | WT | ga20ox3-6, ga20ox3-8 | none | R2 | GA2ox3_5_f |
| 35 | single homo ga20ox3 | 52.8 | homozygous +1 insertion | WT | ga20ox3-8 | none | R2 | GA2ox3_5_f |
| 36 | single homo ga20ox3 | 59.4 | homozygous +1 insertion | WT | ga20ox3-8 | none | R2 | GA2ox3_5_f |
| 37 | single homo ga20ox3 | 46 | homozygous +1 insertion | WT | ga20ox3-8 | none | R2 | GA2ox3_5_f |
| 38 | single homo ga20ox3 | 52.8 | homozygous +1 insertion | WT | ga20ox3-8 | none | R2 | GA2ox3_5_f |
| 39 | single homo ga20ox3 | 51.4 | Homozygous −2 deletion | WT | ga20ox3-6 | none | R2 | GA2ox3_5_f |
| 40 | SUP_Ox3&Ox5 | 43.6 | WT | WT | None | none | n/a | none |
| 41 | SUP_Ox3&Ox5 | 43.8 | WT | WT | None | none | n/a | none |
| 42 | SUP_Ox3&Ox5 | 42.2 | WT | WT | None | none | n/a | none |
| 43 | WT | 56.4 | WT | WT | None | none | n/a | none |
| 44 | WT | 58.8 | WT | WT | None | none | n/a | none |

TABLE 6-continued

A list of R2 plants having edited alleles in GA20 oxidase_3, GA20 oxidase_5, or both genes. Plant No.
45 and 46 are considered outliers and not included for generating average plant height data shown in Table 7.

| Plant No. | Plant Genotype | Plant Height (inches) | GA20ox3 Genotype | GA20ox5 Genotype | ga20ox3 Allele(s) | ga20ox5 Allele | Generation | gRNA |
|---|---|---|---|---|---|---|---|---|
| 45 | Double homo | 61.8 | Biallelic −2 deletion, +1 insertion | Homozygous −2 deletion | ga20ox3-6 | ga20ox5-2 | R2 | GA2ox3_5_f |
| 46 | Double homo | 61.8 | Biallelic +1 insertion | Homozygous −1 deletion | ga20ox3-7, ga20ox3-8 | ga20ox5-1 | R2 | GA2ox3_5_f |

TABLE 7

R2/R3 stage plant height differences between greenhouse-grown
inbred gene-edited plants and reference control plants.

| Plant Genotype | Avg. Plant Height (inches) | Std. Dev | # of Plants | % Reduction |
|---|---|---|---|---|
| WT | 57.6 | 1.7 | 2 | 0 |
| Homo_ox3/WT_Ox5 | 51.8 | 7.2 | 8 | 10.1% |
| WT_Ox3/Homo_ox5 | 51.0 | 5.8 | 6 | 11.5% |
| Homo_ox3/Het_ox5 | 46.6 | 2.7 | 10 | 19.1% |
| Homo_ox3/Homo_ox5 | 41.7 | 2.3 | 17 | 27.5% |
| SUP_Ox3&Ox5 | 43.2 | 6.6 | 3 | 25.0% |

Example 3. Editing Both GA20 Oxidase_3 and
GA20 Oxidase_5 Reduces Active GA Levels in the
Plant R2 plants having edited alleles in GA20 oxidase_3, GA20 oxidase_5, or both genes were tested in the field along with transgenic inbred corn plants having an artificial microRNA suppression construct targeting the GA20 oxidase_3 and GA20 oxidase_5 genes for suppression (SUP_GA20Ox3&Ox5 ("SUP_Ox3&Ox5")). Various physiological traits were measured including plant height to ear node at R3, plant height to uppermost ligule, ear height, ear length, ear diameter, kernels/ear, kernels/unit area, single kernel weight, stalk diameter, and grain yield estimate. Plants containing homozygous mutant alleles of both GA20 oxidase_3 and GA20 oxidase_5 genes (i.e., double homozygous ga20ox3/ga20ox5 mutants) showed semi-dwarf phenotypes with altered plant architecture. Homozygous single ga20ox3 mutants and homozygous single ga20ox5 mutants showed slightly taller plant height than double homozygous ga20ox3/ga20ox5 mutants. Table 8 shows key traits with percent delta relative to wild type control plants without edited allele (i.e., percent difference compared to control).

In addition, top collared leaf at V8 was collected to measure the level of a panel of Gibberellic acid hormones through standard biochemical assays. Data indicate that at V8 growth stage, top collared leaf tissues of plants with both GA20ox3 and GA20ox5 edits have significantly lower levels of GA20, GA4 and GA1, but higher levels of GA53 compared to the wild type (control). Changes in GA hormone levels observed in tissues of plants with GA20ox3 and GA20ox5 edits were similar to those observed in transgenic SUP_Ox3&Ox5 plants (Table 9).

TABLE 8

Editing GA20 oxidase_3, GA20 oxidase_5, or both genes impacts various physiological
traits (shown as average percent difference relative to a wild-type control).

| | Percent_delta relative to WT control | | |
|---|---|---|---|
| Trait | Double homozygous ga20ox3/ga20ox5 (Plant # 18 through 31 in Table 6) | Homozygous single ga20ox5 (plant # 11 to 16 in Table 6) | Homozygous single ga20ox3 (plant # 32 and 33 in Table 6) |
| Plant Height to Ear Node R3 | −46.12 | −16.24 | −22.55 |
| Plant Height to Uppermost Ligulated Leaf R3 | −30.39 | −4.49 | −8.6 |
| Stalk Diameter Ear Minus Four R3 | −6.21 | −11.01 | −3.37 |
| Days to 50% Visible Silk R1 | −2.48 | −2.48 | −2.48 |
| Ear Diameter (imaging) R6 | −0.4 | −0.48 | −1.72 |
| Ear Length (imaging) R6 | −5.83 | −1.31 | −4.56 |
| Grain Yield Estimate R6 | −12.2 | −17.62 | −16.55 |
| Kernels per Ear R6 | −2.62 | −5.14 | −9.03 |
| Kernels per unit area | −10.59 | −7.08 | −11.15 |
| Single Kernel Weight R6 | −1.59 | −11.32 | −6.29 |

TABLE 9

Editing GA20 oxidase_3, GA20 oxidase_5, or both genes impacts GA hormonal levels (shown as Average Delta, i.e., difference in pmol GA/gram of tissue and (p-value), relative to a wild-type control). Average pmol GA/gram of tissue for wild-type hormonal levels also shown.

| Growth stage | Leaf type | Hormone type | Wild-type (average) | Homozygous single ga20ox3 (Average Delta) | Homozygous single ga20ox5 (Average Delta) | Double homozygous ga20ox3/ga20ox5 (Average Delta) | SUP_Ox3&Ox5 (Average Delta) |
|---|---|---|---|---|---|---|---|
| V8 | Leaf - top collared | GA12-pmole/g | 0.065 | 0.0250 (0.517) | 0.0007 (0.985) | 0.1382 (0.002) | 0.1726 (1.91E−4) |
| V8 | Leaf - top collared | GA1-pmole/g | 2.726 | 0.3236 (0.355) | 0.0984 (0.776) | −1.8405 (5.64E−5) | −1.4112 (7.41E−4) |
| V8 | Leaf - top collared | GA20-pmole/g | 2.025 | 0.6085 (0.017) | 0.6311 (0.014) | −1.8525 (4.85E−7) | −1.8446 (5.13E−7) |
| V8 | Leaf - top collared | GA34-pmole/g | 2.665 | −0.2339 (0.191) | −0.1940 (0.275) | 0.3424 (0.061) | 0.2456 (0.170) |
| V8 | Leaf - top collared | GA3-pmole/g | 0.200 | 0.1747 (0.006) | 0.2062 (0.002) | −0.0586 (0.312) | −0.03487 (0.544) |
| V8 | Leaf - top collared | GA4-pmole/g | 0.270 | −0.0734 (0.455) | 0.0169 (0.863) | −0.1473 (0.144) | −0.0842 (0.393) |
| V8 | Leaf - top collared | GA53-pmole/g | 0.355 | −0.0291 (0.893) | 0.1493 (0.492) | 0.9521 (3.77E−4) | 1.0875 (1.03E−4) |
| V8 | Leaf - top collared | GA8-pmole/g | 0.067 | 0.0066 (0.857) | −0.0063 (0.863) | −0.0065 (0.860) | 0.0393 (0.292) |
| V8 | Leaf - top collared | GA9-pmole/g | 1.894 | −1.0053 (0.034) | −0.5852 (0.201) | 2.5123 (1.48E−5) | 1.9821 (2.29E−4) |

Having described the present disclosure in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

What is claimed is:

1. A modified corn plant, or plant part thereof, comprising a mutant allele of a GA20 oxidase_3 gene at the GA20 oxidase_3 locus, wherein a wild-type allele of the GA20 oxidase_3 gene encodes a GA20 oxidase_3 protein comprising an amino acid sequence that is at least 95% identical to SEQ ID NO: 9, and a mutant allele of a GA20 oxidase_5 gene at the GA20 oxidase_5 locus, wherein a wild-type allele of the GA20 oxidase_5 gene encodes a GA20 oxidase_5 protein comprising an amino acid sequence that is at least 95% identical to SEQ ID NO: 15, and wherein (i) said modified corn plant is homozygous for the mutant allele at said GA20 oxidase_3 locus and is heterozygous for the mutant allele at said GA20 oxidase_5 locus, or (ii) said modified corn plant is heterozygous for the mutant allele at said GA20 oxidase_3 locus and is homozygous for the mutant allele at said GA20 oxidase_5 locus, and wherein said modified corn plant has a shorter plant height relative to a wild-type control plant.

2. The modified corn plant, or plant part thereof, of claim 1, wherein said modified corn plant is homozygous for the mutant allele at said GA20 oxidase_3 locus and is heterozygous for the mutant allele at said GA20 oxidase_5 locus, and wherein said GA20 oxidase_3 locus comprises a heteroallelic combination of mutant alleles or two identical mutant alleles.

3. The modified corn plant, or plant part thereof, of claim 1, wherein said modified corn plant is homozygous for the mutant allele at said GA20 oxidase_5 locus and is heterozygous for the mutant allele at said GA20 oxidase_3 locus, and wherein said GA20 oxidase_5 locus comprises a heteroallelic combination of mutant alleles or two identical mutant alleles.

4. The modified corn plant, or plant part thereof, of claim 1, wherein said mutant allele of the GA20 oxidase_3 gene or said mutant allele of said GA20 oxidase_5 gene exhibits an at least 50% reduction of expression or enzymatic activity relative to an unmodified, wild-type GA20 oxidase_3 or GA20 oxidase_5 gene allele.

5. The modified corn plant, or plant part thereof, of claim 1, wherein each mutant allele at the GA20 oxidase_3 locus comprises a mutation selected from the group consisting of a substitution, a deletion, an insertion, a duplication, and an inversion of one or more nucleotides relative to a wild-type GA20 oxidase_3 gene.

6. The modified corn plant, or plant part thereof, of claim 1, wherein each mutant allele at the GA20 oxidase_5 locus results in one or more of the following: a GA20 oxidase_5 protein truncation, a non-translatable GA20 oxidase_5 gene transcript, a non-functional GA20 oxidase_5 protein, a premature stop codon in the GA20 oxidase_5 gene, and any combination thereof.

7. The modified corn plant, or plant part thereof, of claim 1, wherein each mutant allele at the GA20 oxidase_5 locus comprises a mutation selected from the group consisting of a substitution, a deletion, an insertion, a duplication, and an inversion of one or more nucleotides relative to a wild-type GA20 oxidase_5 gene.

8. The modified corn plant, or plant part thereof, of claim 1, wherein said mutant allele of the GA20 oxidase_3 gene comprises a mutation selected from the group consisting of:

(a) a deletion of 13 bases starting at nucleotide base number 536;

(b) a deletion of nucleotide base number 542;

(c) an insertion of CC at nucleotide base number 542;

(d) a deletion of nucleotide base number 541;

(e) a deletion of 3 bases starting at nucleotide base number 540;

(f) a deletion of 2 bases starting at nucleotide base number 422;

(g) an insertion of an A at nucleotide base number 422;

(h) an insertion of a T at nucleotide base number 422;

(i) a deletion of nucleotide base number 564;

(j) an insertion of an A at nucleotide base number 564;

(k) an insertion of a C at nucleotide base number 565; and (l) an insertion of a C at nucleotide base number 63;

wherein said nucleotide base numbering is based on SEQ ID No. 168 and counted from the first nucleotide of SEQ ID NO: 168 in the 5' to 3' direction.

9. The modified corn plant, or plant part thereof, of claim 1, wherein said mutant allele of the GA20 oxidase_3 gene comprises a mutation identified by one or more of SEQ ID Nos: 170 to 193 and 206 to 217 relative to the corresponding reference sequence in SEQ ID No: 168.

10. The modified corn plant, or plant part thereof, of claim 1, wherein said mutant allele of the GA20 oxidase_5 gene comprises a mutation selected from the group consisting of:
  (a) a deletion of nucleotide base number 644;
  (b) a deletion of 2 bases starting at nucleotide base number 644;
  (c) an insertion of a T at nucleotide base number 644;
  (d) a deletion of nucleotide base number 372;
  (e) a deletion of nucleotide base number 786;
  (f) a deletion of 5 bases starting at nucleotide base number 786;
  (g) a deletion of 2 bases starting at nucleotide base number 101;
  (h) an insertion of a T at nucleotide base number 102;
  (i) a deletion of 3 bases starting at nucleotide base number 99;
  (j) an insertion of an A at nucleotide base number 282; and
  (k) an insertion of a C at nucleotide base number 282;
  wherein said base numbering is based on SEQ ID No. 169 and counted from the first nucleotide of SEQ ID NO: 169 in the 5' to 3' direction.

11. The modified corn plant, or plant part thereof, of claim 1, wherein said mutant allele of the GA20 oxidase_5 gene comprises a mutation identified by one or more of SEQ ID Nos: 218 to 239 and 251 to 261 relative to the corresponding reference sequence in SEQ ID No: 169.

12. The modified corn plant, or plant part thereof, of claim 1, wherein said modified corn plant has an improved lodging resistance relative to an unmodified control plant.

13. The modified corn plant, or plant part thereof, of claim 1, wherein said modified corn plant does not have any significant off-types in at least one female organ or ear.

14. A method of making a modified progeny corn plant, or plant part thereof, comprising:
  (a) crossing a first corn plant comprising a mutant allele of a GA20 oxidase_3 gene at the GA20 oxidase_3 locus, wherein a wild-type allele of the GA20 oxidase_3 gene encodes a GA20 oxidase_3 protein comprising an amino acid sequence that is at least 95% identical to SEQ ID NO: 9, with a second corn plant comprising a mutant allele of a GA20 oxidase_5 gene at the GA20 oxidase_5 locus, wherein a wild-type allele of the GA20 oxidase_5 gene encodes a GA20 oxidase_5 protein comprising an amino acid sequence that is at least 95% identical to SEQ ID NO: 15; and
  (b) selecting a progeny corn plant, or plant part thereof, from the cross in step (a) that is
    (i) homozygous for one or more mutant alleles at the GA20 oxidase_3 locus and heterozygous for a mutant allele at the GA20 oxidase_5 locus, or
    (ii) heterozygous for a mutant allele at the GA20 oxidase_3 locus and homozygous for one or more mutant alleles at the GA20 oxidase_5 locus,
    wherein the progeny corn plant has a shorter plant height relative to a wild-type control plant.

15. The method of claim 14, wherein the first corn plant is:
  (a1) homozygous for one or more mutant alleles at the GA20 oxidase_3 locus, or
  (b1) heterozygous for a mutant allele at the GA20 oxidase_3 locus; and wherein the second corn plant is:

(a2) homozygous for one or more mutant alleles at the GA20 oxidase_5 locus, or
  (b2) heterozygous for a mutant allele at the GA20 oxidase_5 locus.

16. The modified corn plant, or plant part thereof, of claim 1, wherein each mutant allele at the GA20 oxidase_3 locus results in one or more of the following: a GA20 oxidase_3 protein truncation, a non-translatable GA20 oxidase_3 gene transcript, a non-functional GA20 oxidase_3 protein, a premature stop codon in the GA20 oxidase_3 gene, and any combination thereof.

17. The modified corn plant, or plant part thereof, of claim 1, wherein said modified corn plant is at least 10% shorter than an unmodified control plant.

18. The modified corn plant, or plant part thereof, of claim 1, wherein said modified corn plant is at least 20% shorter than an unmodified control plant.

19. The modified corn plant, or plant part thereof, of claim 1, wherein said modified corn plant is at least 30% shorter than an unmodified control plant.

20. The modified corn plant, or plant part thereof, of claim 1, wherein the level of one or more active GAs in at least one internode tissue of the stem or stalk of said modified corn plant is lower than the same internode tissue of an unmodified control plant.

21. The modified corn plant, or plant part thereof, of claim 1, wherein said mutant allele of the GA20 oxidase_3 gene exhibits an at least 90% reduction of expression or enzymatic activity relative to an unmodified, wild-type GA20 oxidase_3 gene allele.

22. The modified corn plant, or plant part thereof, of claim 1, wherein said mutant allele of the GA20 oxidase_5 gene exhibits an at least 90% reduction of expression or enzymatic activity relative to an unmodified, wild-type GA20 oxidase_5 gene allele.

23. The modified corn plant, or plant part thereof, of claim 1, wherein the mutant allele of the GA20 oxidase_3 gene comprises a mutation relative to SEQ ID NO: 34.

24. The modified corn plant, or plant part thereof, of claim 1, wherein the mutant allele of the GA20 oxidase_3 gene comprises a mutation relative to SEQ ID NO: 168.

25. The modified corn plant, or plant part thereof, of claim 1, wherein the mutant allele of the GA20 oxidase_5 gene comprises a mutation relative to SEQ ID NO: 35.

26. The modified corn plant, or plant part thereof, of claim 1, wherein the mutant allele of the GA20 oxidase_5 gene comprises a mutation relative to SEQ ID NO: 169.

27. The plant part of the modified corn plant of claim 1, wherein the plant part is a corn plant organ or corn plant tissue of the modified corn plant.

28. The plant part of the modified corn plant of claim 1, wherein the plant part is a corn seed of the modified corn plant.

29. The method of claim 14, wherein the level of one or more active GAs in at least one internode tissue of the stem or stalk of said progeny corn plant is lower than the same internode tissue of an unmodified control plant.

30. The method of claim 14, wherein said mutant allele of the GA20 oxidase_3 gene exhibits an at least 90% reduction of expression or enzymatic activity relative to an unmodified, wild-type GA20 oxidase_3 gene allele.

31. The method of claim 14, wherein said mutant allele of the GA20 oxidase_5 gene exhibits an at least 90% reduction of expression or enzymatic activity relative to an unmodified, wild-type GA20 oxidase_5 gene allele.

32. The method of claim 14, wherein the mutant allele of the GA20 oxidase_3 gene comprises a mutation relative to SEQ ID NO: 34.

33. The method of claim 14, wherein the mutant allele of the GA20 oxidase_3 gene comprises a mutation relative to SEQ ID NO: 168.

34. The method of claim 14, wherein the mutant allele of the GA20 oxidase_5 gene comprises a mutation relative to SEQ ID NO: 35.

35. The method of claim 14, wherein the mutant allele of the GA20 oxidase_5 gene comprises a mutation relative to SEQ ID NO: 169.

36. The method of claim 15, wherein the first corn plant is homozygous for one or more mutant alleles of the GA20 oxidase_3 locus, and wherein said GA20 oxidase_3 locus comprises a heteroallelic combination of mutant alleles or two identical mutant alleles.

37. The method of claim 15, wherein the second corn plant is homozygous for one or more mutant alleles of the GA20 oxidase_5 locus, and wherein said GA20 oxidase_5 locus comprises a heteroallelic combination of mutant alleles or two identical mutant alleles.

38. The method of claim 15, wherein the first corn plant is:

(x1) homozygous for one or more mutant alleles of the GA20 oxidase_5 locus, (y1) heterozygous for a mutant allele of the GA20 oxidase_5 locus, or (z1) homozygous for a wild-type allele of the GA20 oxidase_5 locus; and wherein the second corn plant is:

(x2) homozygous for one or more mutant alleles of the GA20 oxidase_3 locus, or (y2) heterozygous for a mutant allele of the GA20 oxidase_3 locus, or (z2) homozygous for a wild-type allele of the GA20 oxidase_3 locus.

* * * * *